US012691143B2

(12) United States Patent　　　(10) Patent No.:　US 12,691,143 B2
Mouw et al.　　　　　　　　　　(45) Date of Patent:　Jul. 28, 2026

(54) METHOD FOR TREATING CANCER

(71) Applicants: THE CHILDREN'S MEDICAL CENTER CORPORATION, Boston, MA (US); DANA-FARBER CANCER INSTITUTE, INC., Boston, MA (US); DANISH CANCER SOCIETY, Copenhagen (DK)

(72) Inventors: Kent William Mouw, Newton, MA (US); Judit Borcsok, Copenhagen (DK); Zsofia Sztupinszki, Copenhagen (DK); Miklos Diossy, Copenhagen (DK); Zoltan Szallasi, Boston, MA (US)

(73) Assignees: THE CHILDREN'S MEDICAL CENTER CORPORATION; DANA-FARBER CANCER INSTITUTE, INC.; DANISH CANCER SOCIETY, Copenhagen (DK)

( * ) Notice: Subject to any disclaimer, the term of this patent is extended or adjusted under 35 U.S.C. 154(b) by 676 days.

(21) Appl. No.: 17/914,052

(22) PCT Filed: Mar. 25, 2021

(86) PCT No.: PCT/US2021/024171
§ 371 (c)(1),
(2) Date: Sep. 23, 2022

(87) PCT Pub. No.: WO2021/195390
PCT Pub. Date: Sep. 30, 2021

(65) Prior Publication Data
US 2023/0128143 A1　　Apr. 27, 2023

Related U.S. Application Data

(60) Provisional application No. 62/994,519, filed on Mar. 25, 2020.

(51) Int. Cl.
　　*A61K 33/243*　　(2019.01)
　　*A61K 31/122*　　(2006.01)
　　*A61K 45/06*　　(2006.01)
　　*A61P 35/00*　　(2006.01)

(52) U.S. Cl.
　　CPC .......... *A61K 33/243* (2019.01); *A61K 31/122* (2013.01); *A61K 45/06* (2013.01); *A61P 35/00* (2018.01)

(58) Field of Classification Search
None
See application file for complete search history.

(56) References Cited

U.S. PATENT DOCUMENTS

2018/0100197 A1　　4/2018　Knudsen
2019/0298679 A1 *　10/2019　Chen ................... A61K 31/436

OTHER PUBLICATIONS

Ibrahim, O. et al. Nucleotide excision repair is a predictor of early relapse in pediatric acute lymphoblastic leukemia. BMC Med Genomics, 2018, 11, 95 (Year: 2018).*
Rosell, R. et al. Nucleotide Excision Repair Pathways Involved in Cisplatin Resistance in Non-Small-Cell Lung Cancer. Cancer Control, 2003, 10, 4, 297-305 (Year: 2003).*
Ibrahim, O. et al. BMC Med Genomics, 2018, 11, 95 (Year: 2018).*
Rosell, R. et al. (Cancer Control, 2003, 10, 4, 297-305 (Year: 2003).*
Monroy, C. et al. Molecular Carcinogenesis 50:825-834 (2011) (Year: 2011).*
Barry, K. et al. Carcinogenesis vol. 33 No. 2 pp. 331-337, 2012 (Year: 2012).*
Paz-Elizur, T. et al. DNA Repair Biomarker for Lung Cancer Risk and its Correlation With Airway Cells Gene Expression. JNCI Cancer Spectr. Sep. 12, 2019;4(1):pkz067 (Year: 2019).*
Ibrahim et al., "Nucleotide excision repair is a predictor of early relapse in pediatric actue lymphoblastic leukemia." BMC Medical Geonomics 11(95): p. 1, col. 2, para 1-2; p. 9, col. 1, para 1 (Oct. 30, 2018).

* cited by examiner

*Primary Examiner* — Clinton A Brooks
*Assistant Examiner* — Nicola Maria Bauer
(74) *Attorney, Agent, or Firm* — NIXON PEABODY LLP; David S. Resnick; Ravinderjit S. Braich

(57) ABSTRACT

Provided herein are methods related to methods of predicting sensitivity to NER-targeting agents for the treatment of cancer. In one aspect, provided herein is a method for treating cancer in a subject) of at least 0.70 and the anti-cancer treatment comprises an alkylating chemotherapeutic agent.

24 Claims, 141 Drawing Sheets
Specification includes a Sequence Listing.

Irofulven
(6-hydroxymethylacylfulvene)

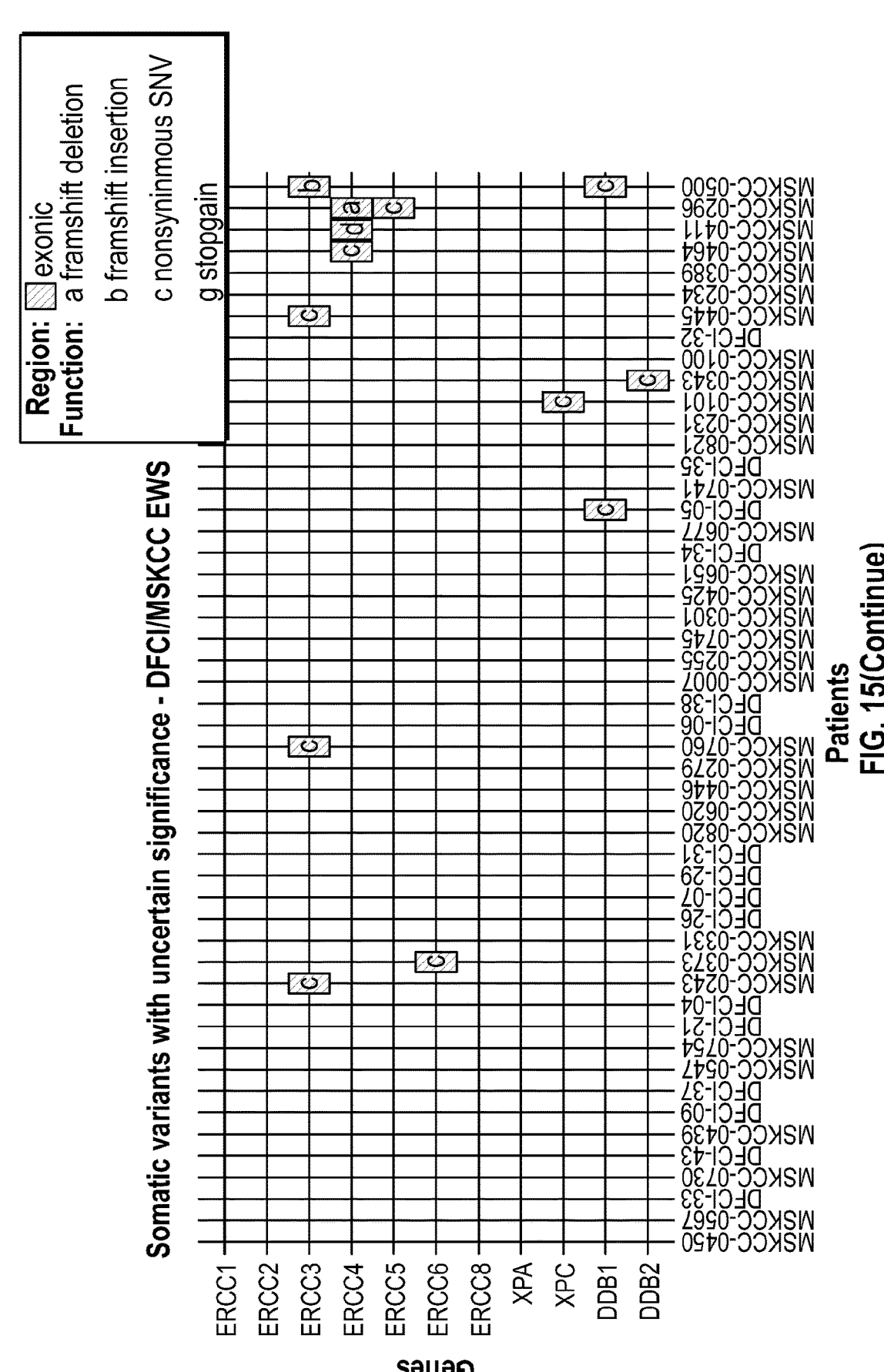
FIG. 15(Continue)

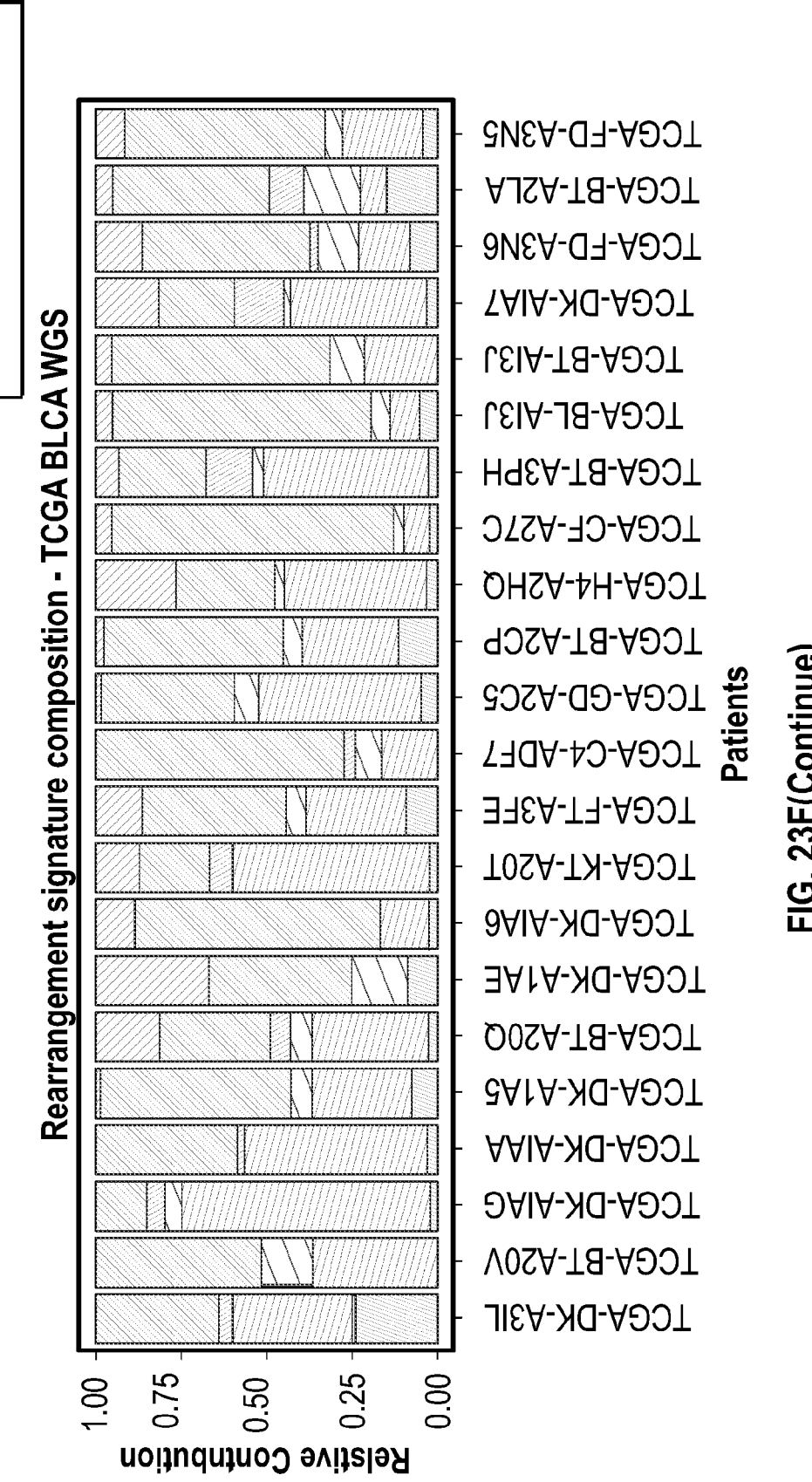
FIG. 23F(Continue)

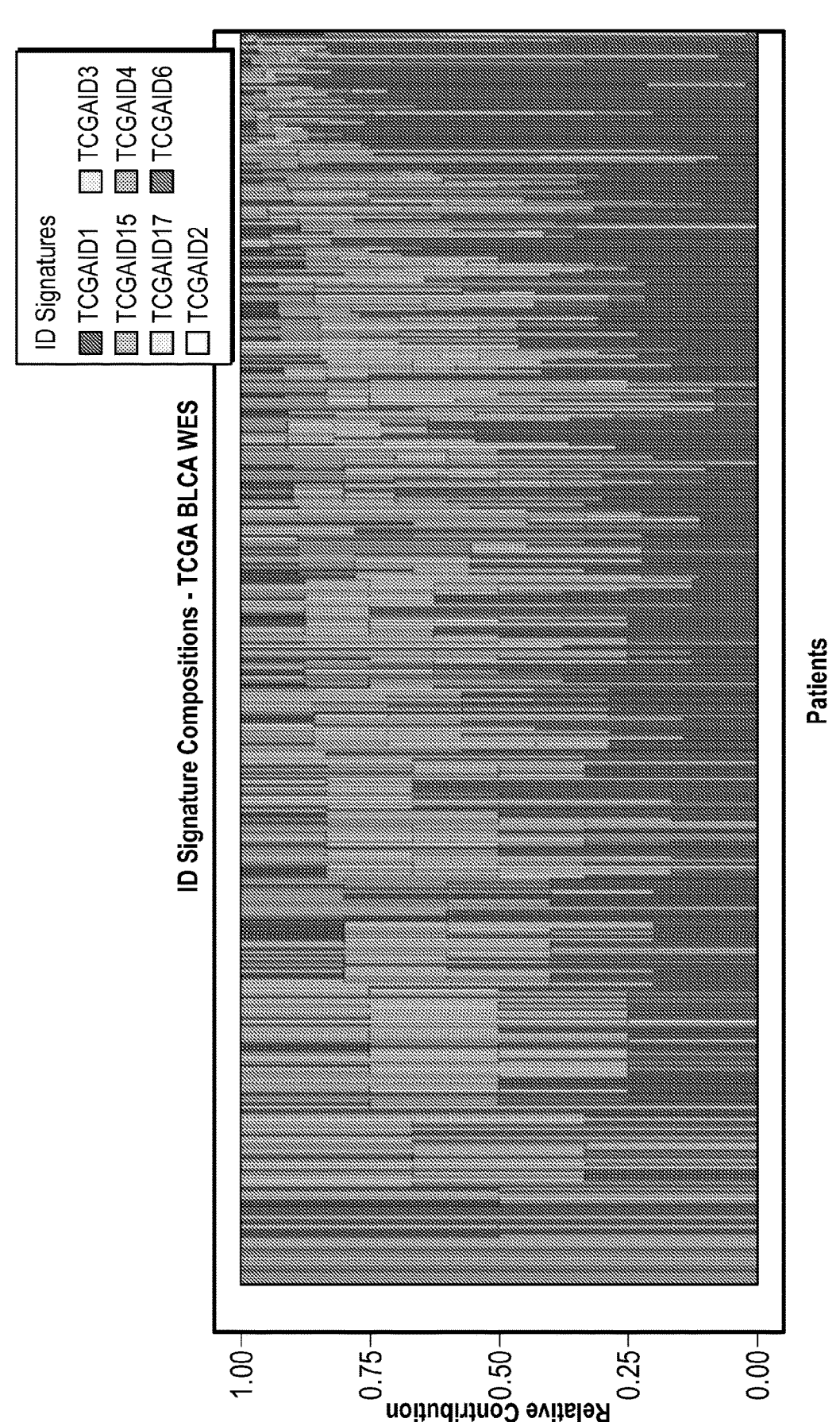
FIG. 26A (Continue)

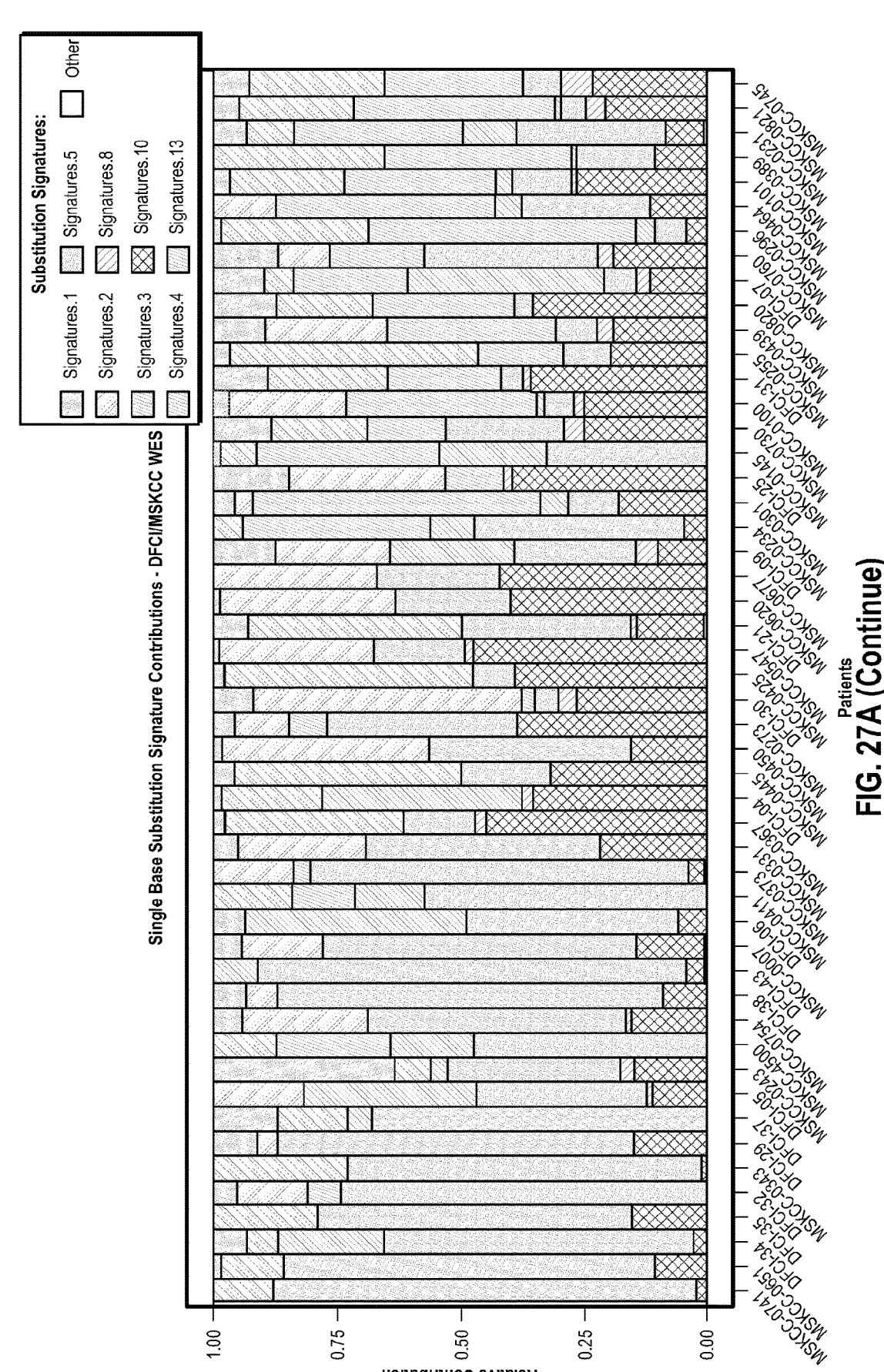
FIG. 27A (Continue)

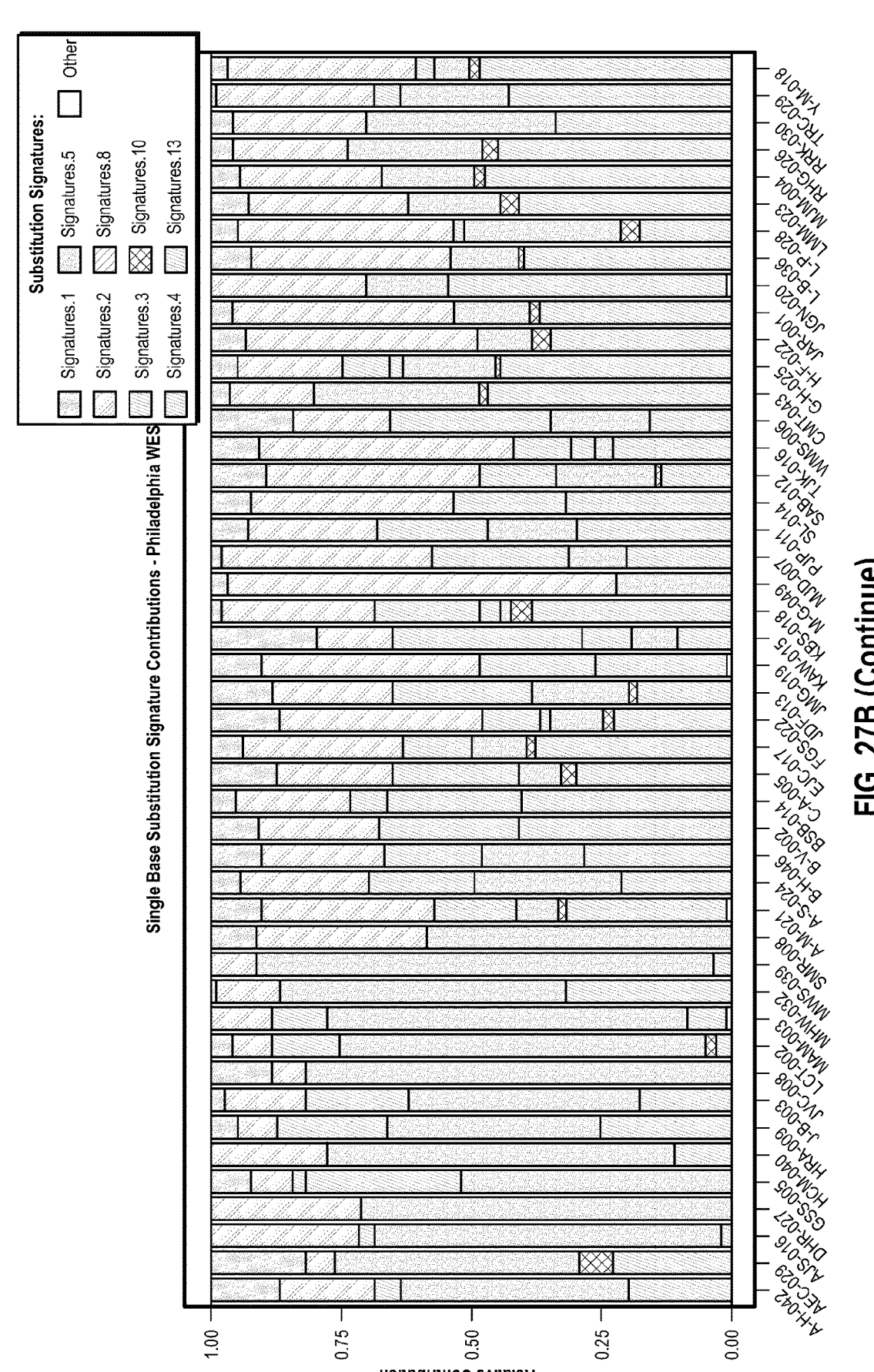
FIG. 27B (Continue)

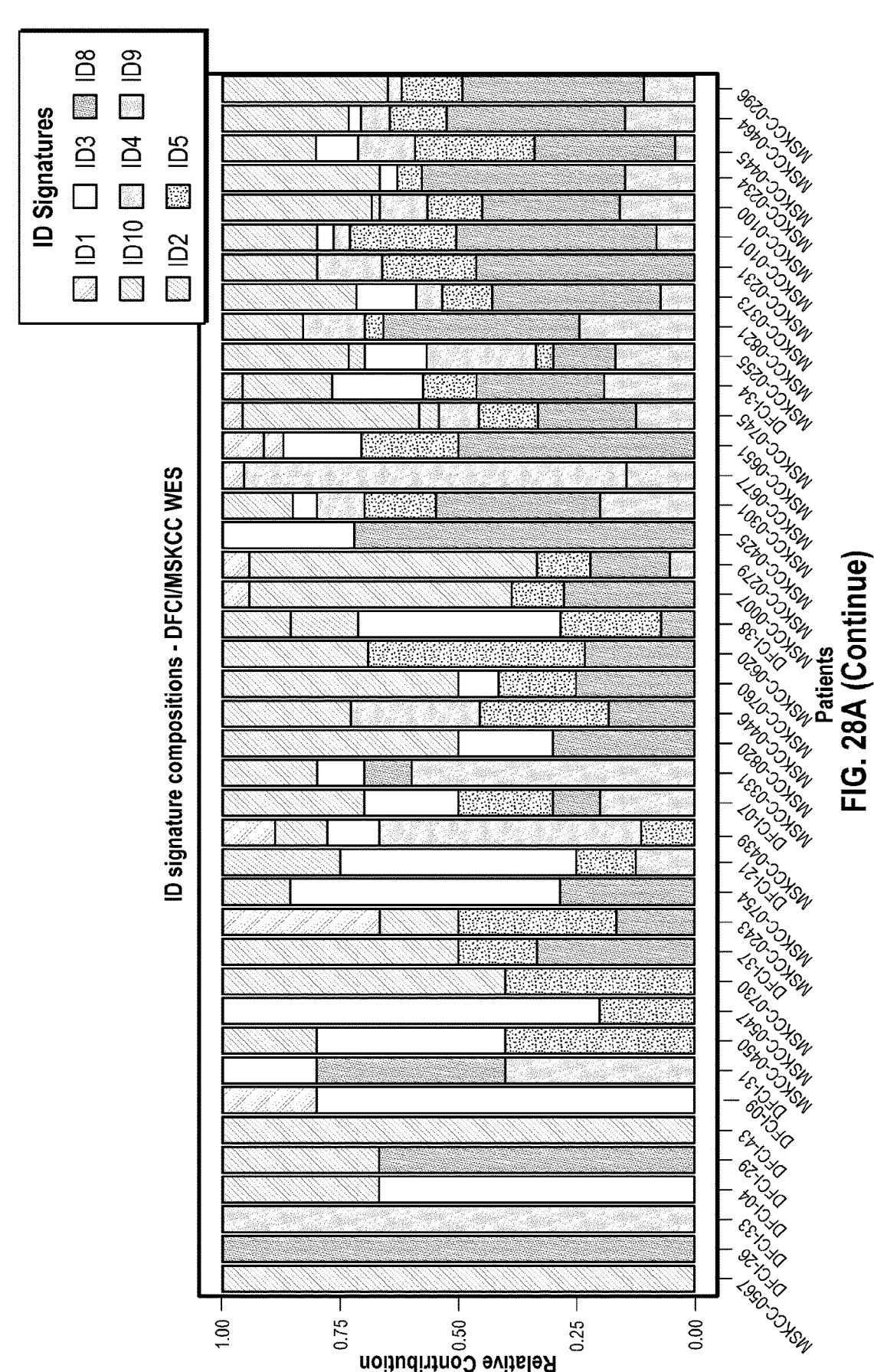
FIG. 28A (Continue)

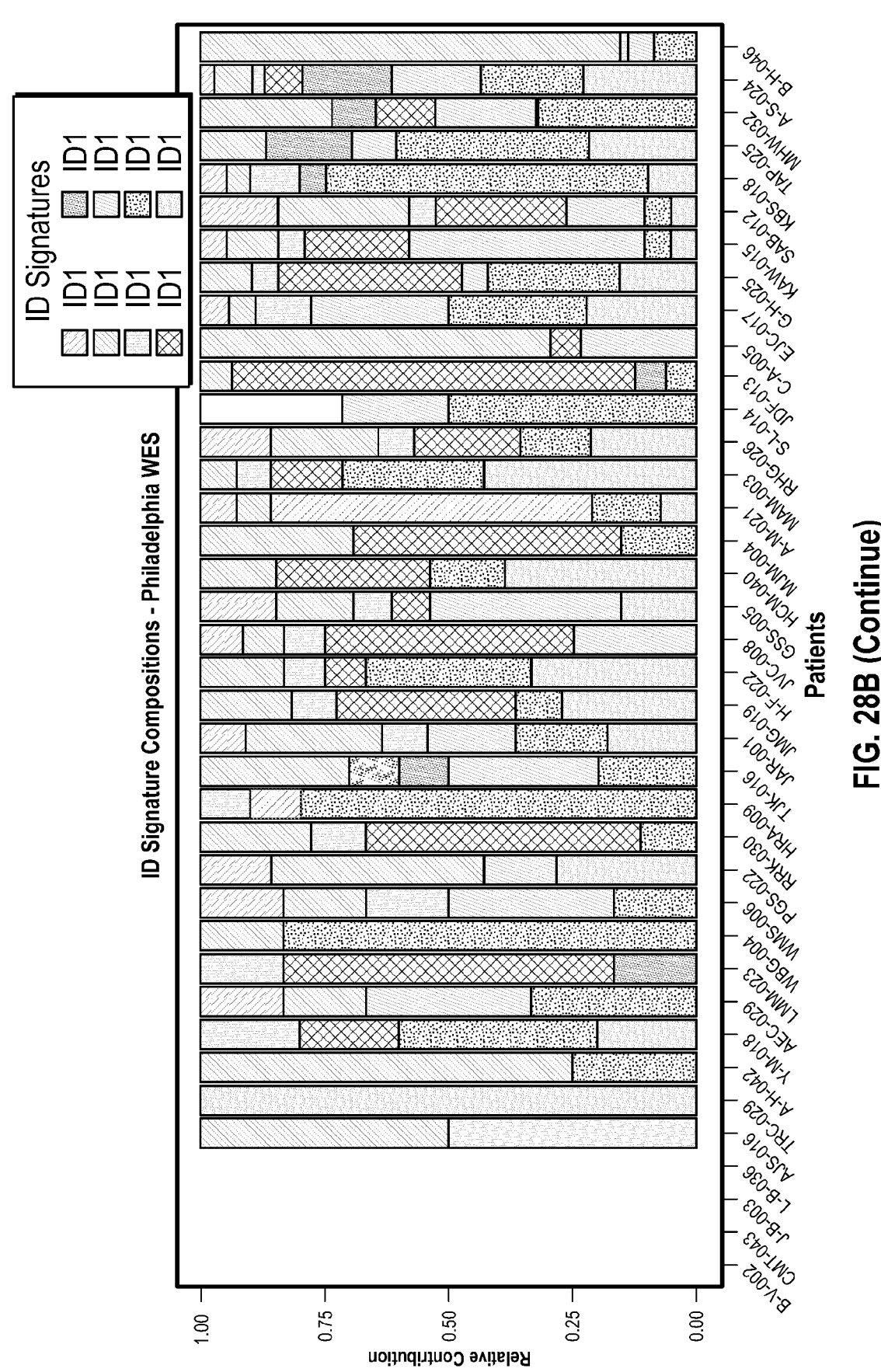
FIG. 28B (Continue)

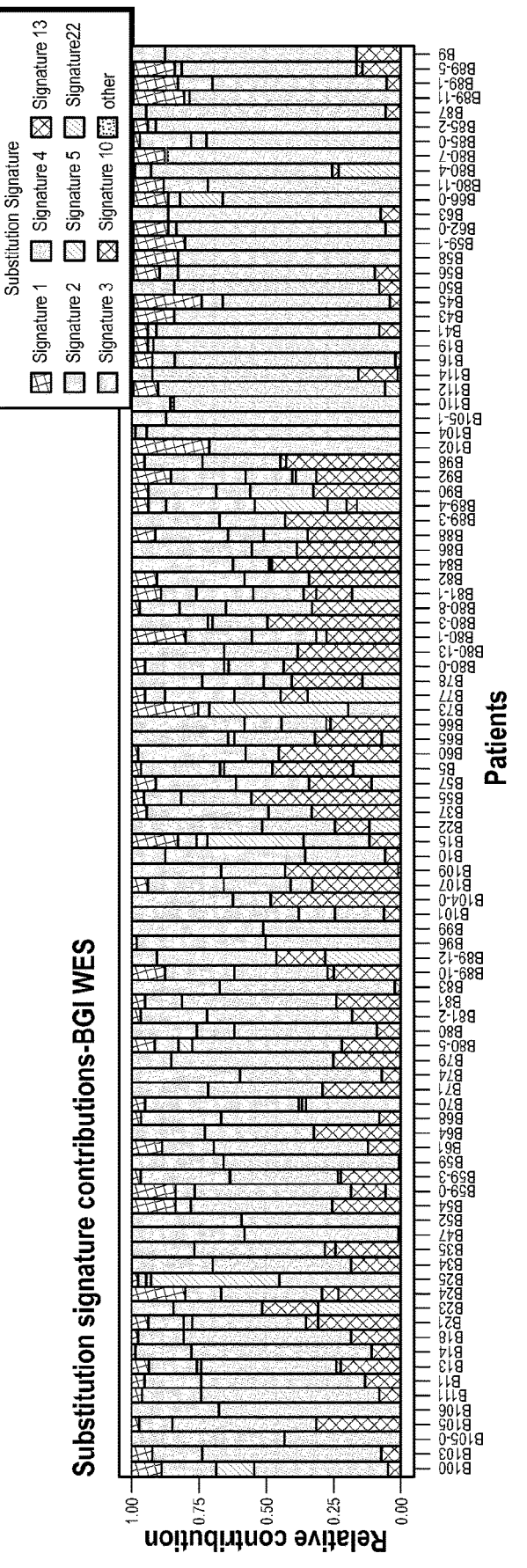
FIG. 29A (Continue)

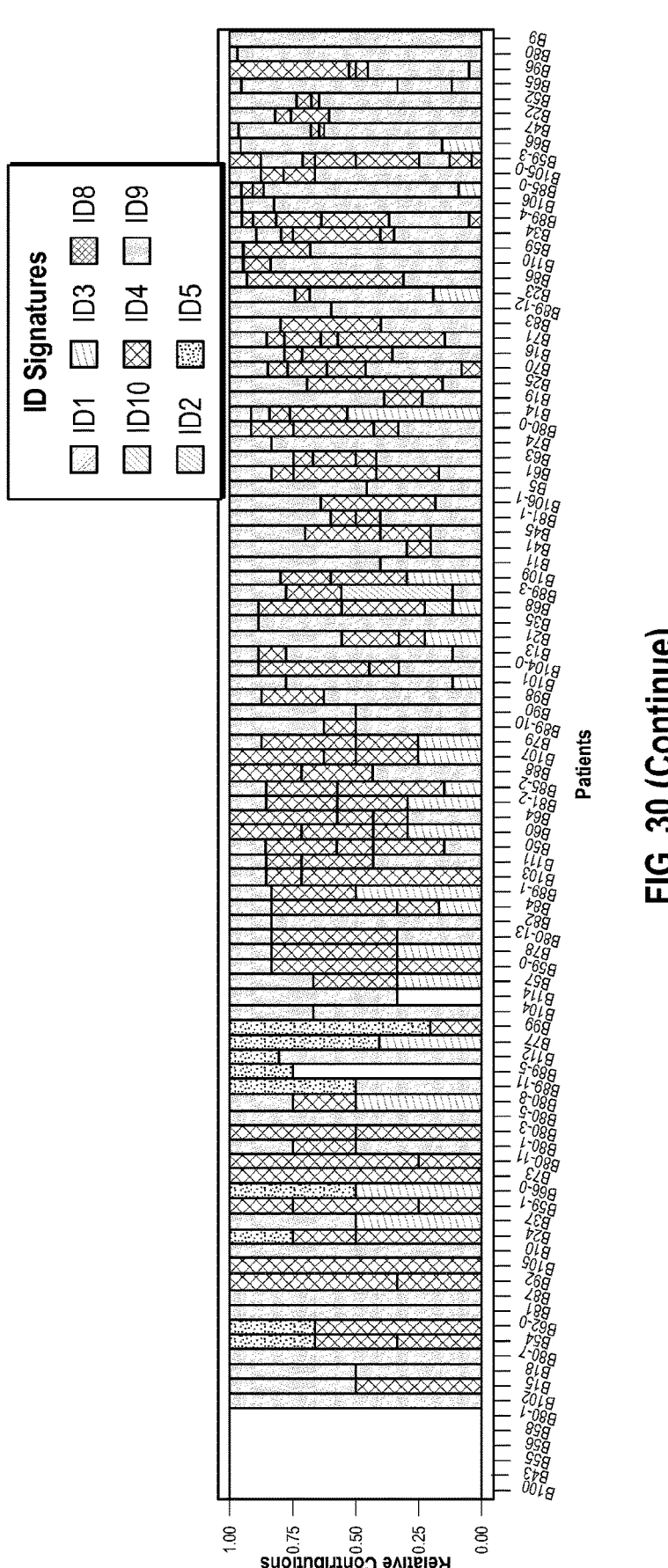
FIG. 30 (Continue)

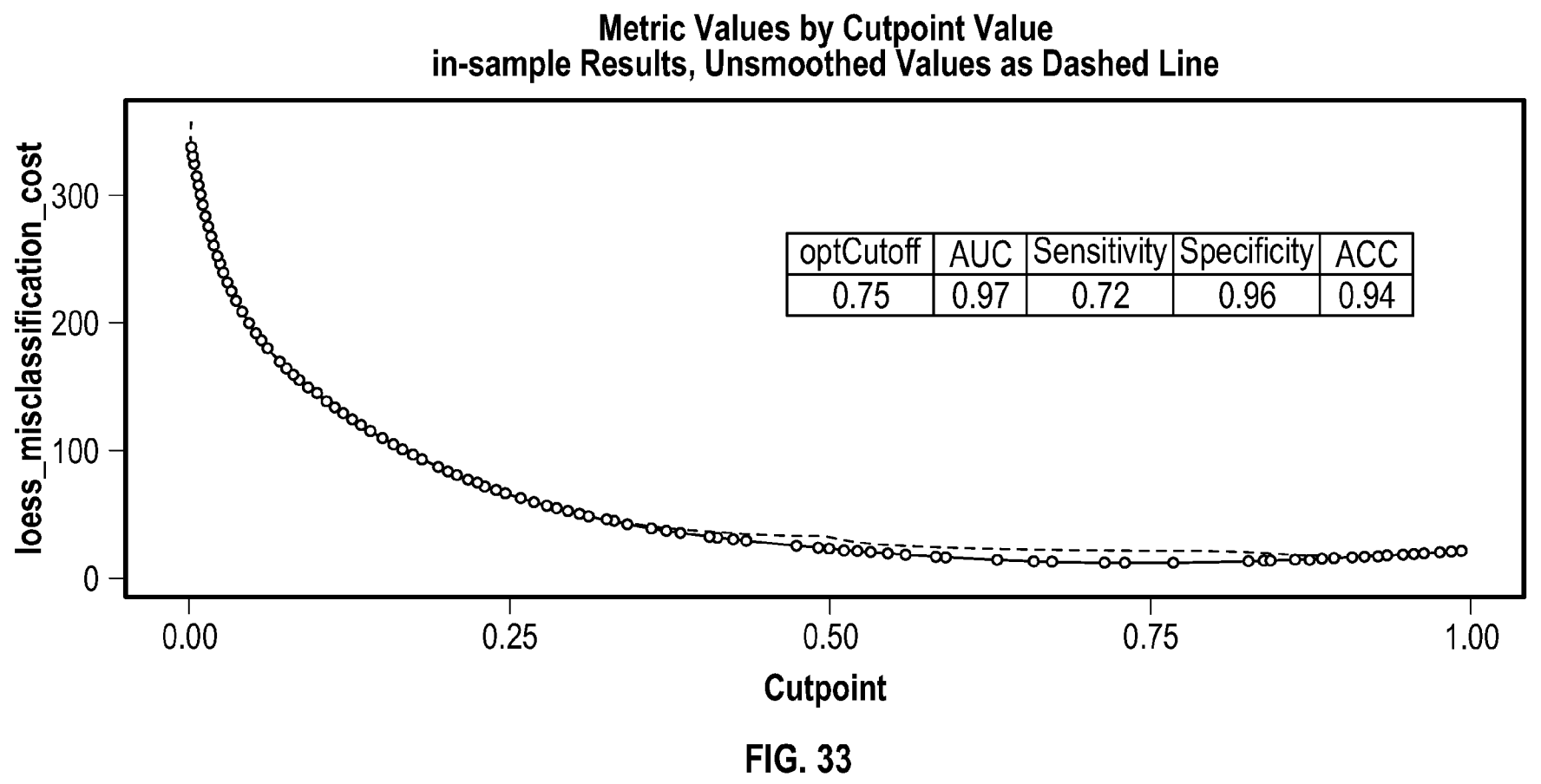

Metric Values by Cutpoint Value
in-sample Results, Unsmoothed Values as Dashed Line

| optCutoff | AUC | Sensitivity | Specificity | ACC |
|-----------|------|-------------|-------------|------|
| 0.75 | 0.97 | 0.72 | 0.96 | 0.94 |

Cutpoint loess_misclassification_cost

FIG. 33

DFCI/MSK cohort

Philadelphia Cohort

Philadelphia - BLCA Overall Survival

ERCC2 wild type
ERCC2 somatic mutant
+ NERDetect >= 0.33

HR = 0(0-Inf)
logrank P-value = 0.001

Survival Probability

Time [months]

Philadelphia - BLCA Overall Survival

ERCC2 wild type
ERCC2 somatic mutant

HR = 0(0-Inf)
logrank P-value = 0.005

Survival Probability

Time [months]

KU19-19 Xenografts

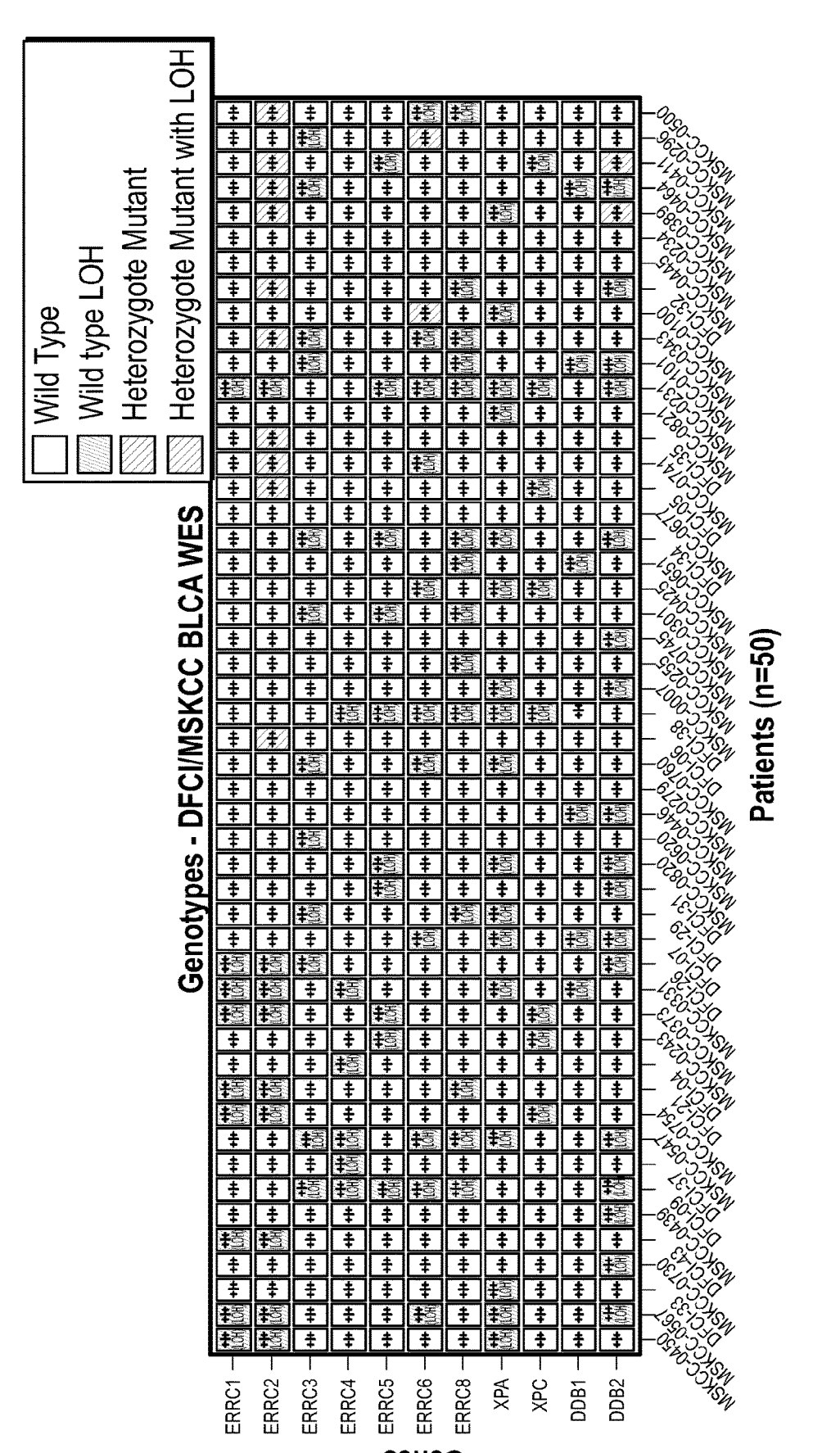
FIG. 40A (Continue)

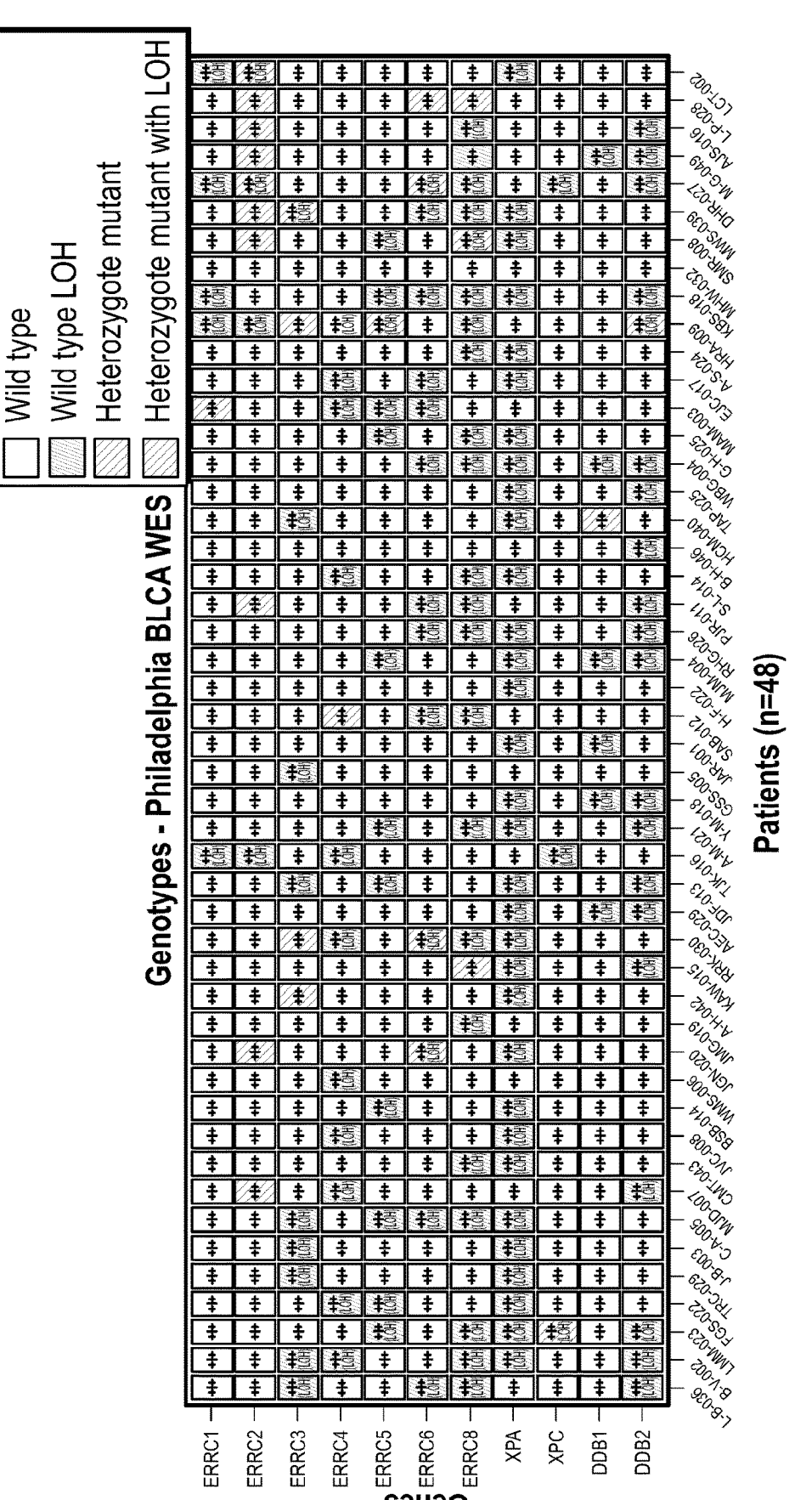
FIG. 40B (Continue)

ERCC2mut Scores - DFCI/MSKCC WES (all cases)

Legend:
- Nonresponder
- Responder
- * ERCC2 Somatic Mutant $P = 2.1 \times 10^{-4}$

|  | Nonresponder | Responder | Total |
|---|---|---|---|
| ERCC2mut >= 0.7 | 2 | 15 | 17 |
| ERCC2mut < 0.7 | 23 | 10 | 33 |
| Total | 25 | 25 | 50 |

PPV = 0.88          NPV = 0.7

ERCC2mut Score 1.00   0.75   0.50   0.25   0.00

Patients (n=50)

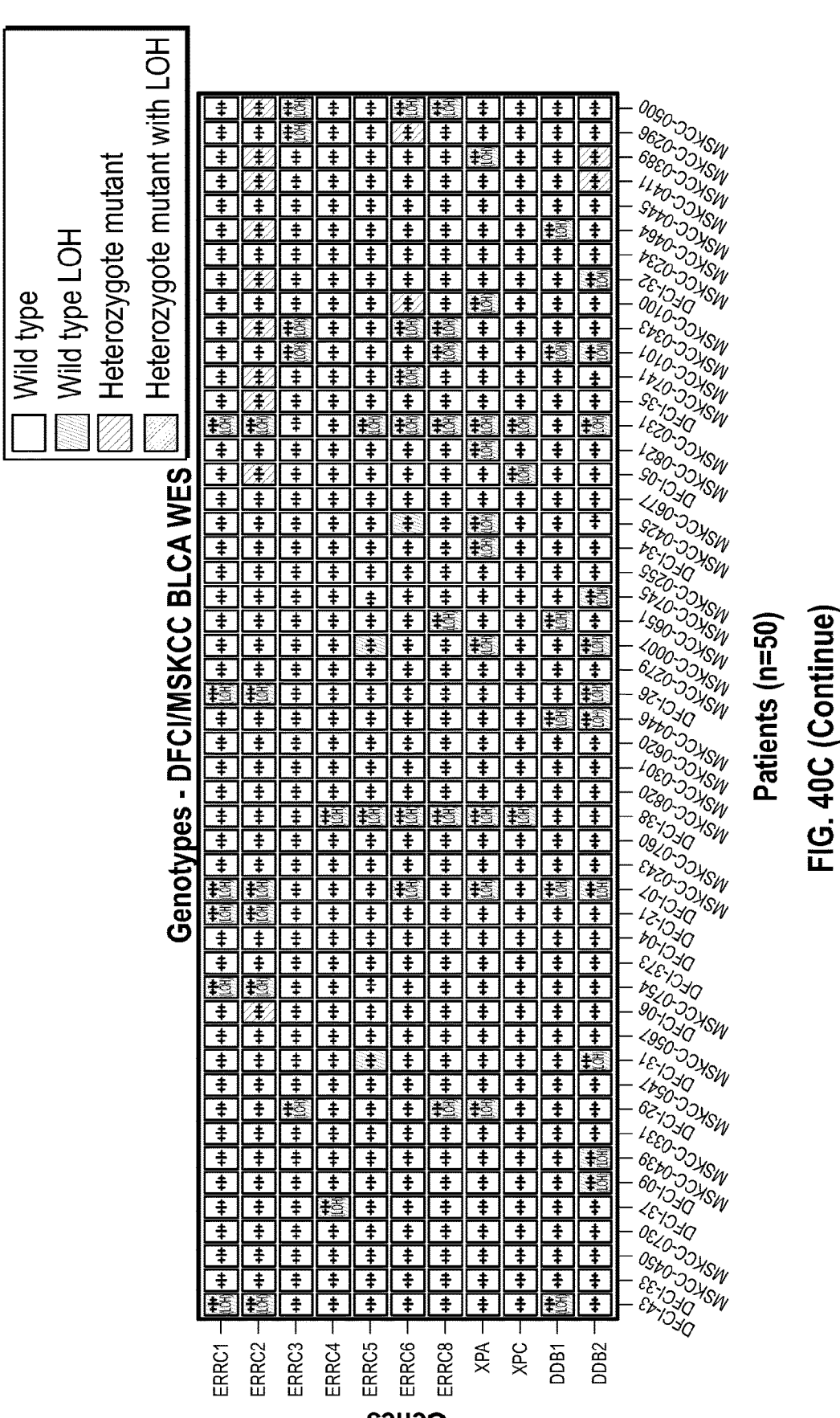
FIG. 40C (Continue)

Genotypes - Philadelphia BLCA WES

Patients (n=48)

FIG. 40D (Continue)

ERCC2mut Scores - DFCI/MSKCC WES (ERCC2 wild-type cases)

Overall Survival - DFCI/MSKCC WES (ERCC2 wild-type cases)

DFCI/MSK Cohort

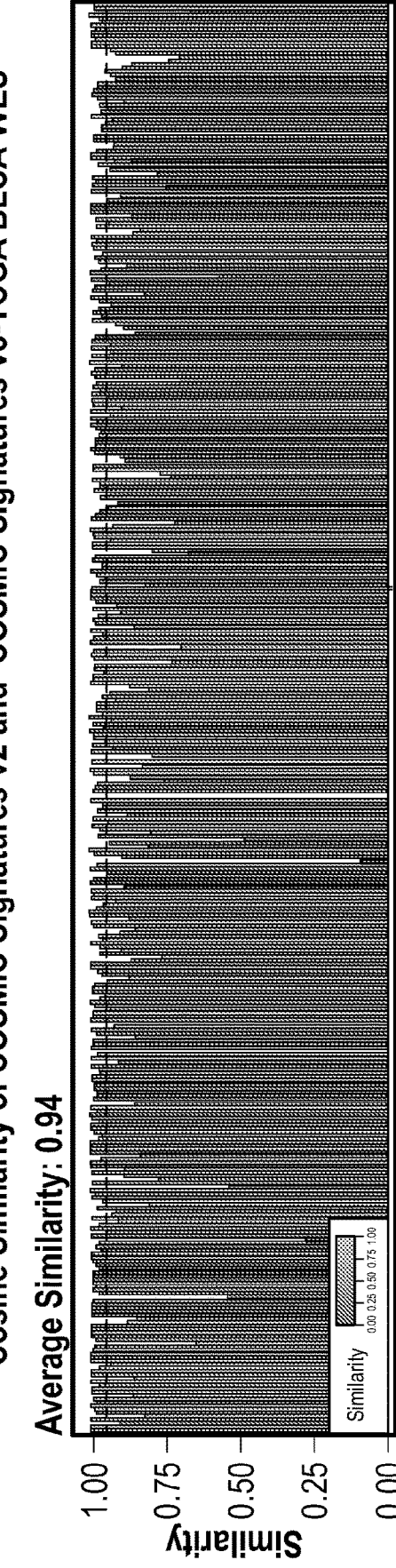
FIG. 53 (Continue)

```
                     SEQUENCE LISTING

<160> NUMBER OF SEQ ID NOS: 24

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
agguuaucuu ggaacuaaau gactt                                           25

<210> SEQ ID NO 2
<211> LENGTH: 27
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 2
aagucauuua guuccaagau aaccuug                                           27

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cugucaaccc ugauaucaac auuga                                            25

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucaauguuga uaucaggguu gacagaa                                          27

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
caagccagaa uacugcuaaa caaca                                            25

<210> SEQ ID NO 6
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uguuguuuag caguauucug gcuugaga                                         28

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggcaaccttc accatgacgc                                                  20

<210> SEQ ID NO 8
<211> LENGTH: 20
<212> TYPE: DNA
<213> ORGANISM: Artificial Sequence
<220> FEATURE:
```

<223> OTHER INFORMATION: Description of Artificial Sequence: Synthetic
     primer

<400> SEQUENCE: 8
gtgacatggc tggactcagg                                                20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
atcccgaaga acacccctc                                                 19

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
acagacactg tccctgctgg acatctaccc                                     30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
gggtagatgt ccagcaggga cagtgtctgt                                     30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
ttcaccatga cgctagcacg ggtctgcctc                                     30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13
gaggcagacc cgtgctagcg tcatggtgaa                                     30

<210> SEQ ID NO 14
<211> LENGTH: 73
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
taggatcctg gccagccggc ataacttcgt ataatgtatg ctatacgaag ttatggatct      60
gcgatcgctc cgg      73

<210> SEQ ID NO 15
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taggatcctg gccagccggc ataacttcgt atagcataca ttatacgaag ttataggcgg      60
ggaggcggcc caaagg      76

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtcctgctg agatccctcc      20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaggaaggag ggcggcccct t      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agcgtttcca gtctgtcatc a      21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcaatatcct cccgggtctc      20

<210> SEQ ID NO 20
<211> LENGTH: 8
<212> TYPE: PRT

-continued

```
<213> ORGANISM: Unknown
<220> FEATURE:
<223> OTHER INFORMATION: Description of Unknown:
      ERCC6 sequence

<400> SEQUENCE: 20

Gly Phe Lys Val Pro Gly Phe Leu
1               5

<210> SEQ ID NO 21
<211> LENGTH: 8
<212> TYPE: PRT
<213> ORGANISM: Homo sapiens

<400> SEQUENCE: 21

Gly Phe Lys Val Pro Gly Phe Leu
1               5

<210> SEQ ID NO 22
<211> LENGTH: 8
<212> TYPE: PRT
<213> ORGANISM: Mus sp.

<400> SEQUENCE: 22

Gly Phe Lys Val Pro Gly Phe Leu
1               5

<210> SEQ ID NO 23
<211> LENGTH: 8
<212> TYPE: PRT
<213> ORGANISM: Rattus sp.

<400> SEQUENCE: 23

Gly Phe Lys Val Pro Gly Phe Leu
1               5

<210> SEQ ID NO 24
<211> LENGTH: 8
<212> TYPE: PRT
<213> ORGANISM: Gallus gallus

<400> SEQUENCE: 24

Gly Phe Lys Val Pro Gly Phe Leu
1               5
```

METHOD FOR TREATING CANCER

CROSS-REFERENCE TO RELATED APPLICATIONS

This application is a 35 U.S.C. § 371 National Phase Entry Application of International Application No. PCT/US2021/024171, filed Mar. 25, 2021, which claims benefit under 35 U.S.C. § 119(e) of U.S. Provisional Application No. 62/994,519 filed Mar. 25, 2020 the contents of which are incorporated herein by reference in their entireties.

GOVERNMENT SUPPORT

This invention was made with Government support under Grant Number W81XWH-18-2-0056, awarded by the National Institutes of Health. The government has certain rights in the invention.

TECHNICAL FIELD

The technology described herein relates generally to methods of treating cancer and predicting outcome of anti-cancer treatment.

BACKGROUND

Platinum-based chemotherapy is a first-line treatment for several types of cancers, but only a subset of patients responds to therapy. With the determination of the human genome sequence and improvements in sequencing and bioinformatics technologies, systematic analyses of genetic alterations in human cancers have become possible. However, clinical interventions based upon this information have been severely hampered by the fact that often only a percentage of patients will respond favorably to a particular anti-cancer treatment. Medical oncologists currently cannot generally predict which patients will or will not respond to a proposed chemotherapeutic treatment. Accordingly, there is a great need in the art to identify patient responsiveness to particular anti-cancer therapies, in particular, cancers deficient in nucleotide excision repair (NER).

SUMMARY

The methods provided herein are based on the discovery that individual mutational signatures for NER deficiency can predict responsiveness of a cancer in a subject to anti-cancer agents independently of identifying specific chromosomal aberrations.

In one aspect, provided herein is a method for treating cancer in a subject. Generally, the method comprises administering an anti-cancer treatment to a subject in need thereof. The subject to be treated has a nucleotide excision repair (NER) deficiency score (NERDetect score, also referred to herein as ERCC2mut) of at least 0.70, for example at least 0.75. The anti-cancer treatment can be a chemotherapeutic agent. For example, the chemotherapeutic agent can be an alkylating chemotherapeutic agent.

In another aspect, provided herein is a method for selecting a subject for cancer treatment. The method comprises determining a NERDetect score and selecting the subject having a NERDetect score of at least 0.70, for example, at least 0.75. In some embodiments, the subject is selected for anti-cancer treatment with a chemotherapeutic agent. For example, the subject can be selected for treatment with an alkylating chemotherapeutic agent. In some embodiments, the method further comprises administering an anti-cancer treatment to the selected subjected.

In yet another aspect, provided herein is method of predicting responsiveness of a subject to anti-cancer treatment. The method comprises determining a NERDetect score and wherein a NERDetect score of at least 0.70, for example, at least 0.75 indicates the subject is responsive to anti-cancer treatment. In some embodiments, the subject is responsive to anti-cancer treatment with a chemotherapeutic agent. For example, the subject is responsive to treatment with an alkylating chemotherapeutic agent. In some embodiments, the method further comprises administering an anti-cancer treatment to subject.

NERDetect score is a summation of one or more mutational features of NER deficiency. In some embodiments, the mutational features of NER deficiency are selected from the following: (1) the number of mutations associated with a signature of insertions and deletions, e.g., an indel signature such as ID8 signature, ID2 signature and ID10 signature; (2) the number of deletions (1-50 bp); (3) the number of mutations associated with a signatures of single base substitutions (SBS), e.g., signature 5 (SBS5) and signature 2 (SBS2); (4) doublet base substitutions (DBS), e.g., DBS4; and (5) the ratio of the number of a certain type of base substitution on the transcribed and untranscribed strand, i.e., transcription strand bias ratio (TSB ratio) such as T>A, C>G and T>G.

Without wishing to be bound by a theory, the NERDetect score can predict outcome of anti-cancer therapy. Accordingly, also provided herein is method for predicting the outcome of anti-cancer treatment in a subject having or suspected of having cancer. Generally, the method comprises obtaining a biological sample from a subject and determining the mutational features of NER deficiency and summing the mutational features to obtain a NERDetect score. A NERDetect score of at least 0.70, for example, at least 0.75 indicates the subject is amenable to anti-cancer treatment. Thus, in some embodiments, the method further comprises administering an anti-cancer treatment to a subject determined to have a NERDetect score of at least 0.70, for example, at least 0.75. The anti-cancer treatment can be a chemotherapeutic agent, such as an alkylating chemotherapeutic agent.

In embodiments of the various aspects described herein, anti-cancer treatment can be chemotherapy, e.g., a chemotherapeutic agent such as an alkylating chemotherapeutic. In some embodiments of the various aspects described herein, the anti-cancer treatment comprises platinum-based chemotherapeutic agents. In some embodiments, anti-cancer treatment is cisplatin or irofulven.

In some embodiments of the various aspects described herein, cancer can be bladder cancer, breast cancer, lung cancer, ovarian cancer, thyroid cancer, pancreatic cancer, prostate cancer, uterine cancer, testicular cancer, gastric cancer, soft tissue and osteogenic sarcoma, neuroblastoma, Wim's tumor, malignant lymphoma (Hodgkin's and non-Hodgkin's lymphoma), acute myeloblastic leukemia (AML), acute lymphoblastic leukemia (ALL), Kaposi's sarcoma, Ewing's tumor, refractory multiple myeloma, colon cancer, or squamous cell carcinomas of the head, neck, cervix, melanoma, and vagina.

In some embodiments of the various aspects described herein, the biological sample can be selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow.

The methods provided herein can also be applied to any mutational signature extraction method, which includes but is not limited to, deconstructSigs, MutationalPatterns, Isomut, and Isomut2py.

BRIEF DESCRIPTION OF THE DRAWINGS

In FIGS. 1A-1D, distributions are displayed as ordered histograms (left) and bee-swarm plots (right). FIG. 1A. The distribution of the natural logarithm of the number of >5 bp deletions lacking flanking microhomology (TCGA.ID8). FIG. 1B. The distribution of the natural logarithm of the total number of 1-50 bp deletions. FIG. 1C. The distribution of the natural logarithm of the number of single base substitutions from COSMIC Signature 5. FIG. 1D. The distribution of the natural logarithm of the ratio of T>A single base substitutions on the transcribed and non-transcribed strand. FIG. 1E. Weights of the individual signature contributions and the intercept used to develop a NERDetect logistic regression model with LASSO ($\alpha$=1) regularization and $\lambda$=0.0293 regularization parameter. FIG. 1F. The composite NERDetect signature scores are strongly associated with ERCC2 mutation status in the TCGA bladder cancer cohort.

FIG. 2A: DFCI/MSK cohort (n=50). FIG. 2B: BGI cohort (n=98). FIG. 2C: FCCC cohort (n=48). P-values were calculated using the Fisher's exact test.

FIG. 3A. NERDetect scores for all cases in the DFCI/MSKCC (n=50). ERCC2 mutant cases are denoted by asterisks. FIG. 3B. NERDetect values for only the ERCC2 wild-type cases in the DFCI/MSKCC whole exome cohort (n=41). FIG. 3C. Overall survival for patients with WT ERCC2 tumors in the DFCI/MSK cohort. There is a trend towards improved survival for patients with NERDetect scores$\geq$0.75. FIG. 3D. NERDetect scores for all cases in the Philadelphia cohort (n=48). P-values were calculated by the Fisher's exact test.

FIG. 4A. Clonal populations of cells were cultured in parallel for multiple generations and single cells were then isolated, expanded, and harvested. KU19-19 (WT ERCC2), RT4 (WT ERCC2) and KE1 (derivative of KU19-19 with mutant ERCC2) are bladder cancer cell lines while TK6 (wild-type XPA) and XPA-deleted TK6 are lymphoblastoid cell lines. FIG. 4B. Whole genome sequencing and mutational signature analysis revealed significantly higher NERDetect scores in the NER-deficient KE1 and XPA KO lines compared to the NER-proficient cell lines.

FIG. 5A. Irofulven chemical structure. FIG. 5B. NER-deficient KE1

(ERCC2 mutant) and MDA-MB-468 (ERCC4 methylated) cell lines are significantly more sensitive to irofulven than their isogenic NER-proficient counterparts. FIG. 5C. Irofulven dose-response for KE1 (NER-deficient) xenografts. FIG. 5D. KE1 xenograft weights were significantly lower in irofulven-treated mice than in untreated mice.

FIG. 6A shows depletion of the TC-NER gene ERCC6 or the common NER gene ERCC3 results in significantly higher irofulven sensitivity compared to depletion of the GG-NER gene DDB2. FIGS. 6B-6C show that most bladder cancer cell lines are resistant to irofulven, with the exception of SW1710. Crystal violet staining demonstrates that most bladder cancer cell lines are resistant to irofulven, with the exception of SW1710 (FIG. 6C). FIG. 6D shows that SW1710 harbors an ERCC6 P500R missense mutation in a conserved region of the gene. FIG. 6E (top) shows that a cisplatin-resistant derivative of the NER-deficient MDA-MB-468 cell line remains sensitive to irofulven. FIG. 6E (bottom) shows an immunoblot showing that ERCC4 (XPF) protein expression remains absent in the cisplatin-resistant MDA-MB-468 line (lane 3), similar to the parental cisplatin-sensitive line (lane 2) and consistent with persistent NER deficiency. Lane 1 (positive control) shows an MDA-MB-468 line engineered to stably express wild-type ERCC4.

FIG. 33 shows the optimal cut-off value defined in the TCGA BLCA WES train-test set.

FIG. 36A shows the overall survival with and without somatic ERCC2 mutations (p-value=0.051). FIG. 36B shows the overall survival of patients with ERCC2 somatic mutation or high NERDetect score (≥0.75) and ERCC2 wild-type cases (p-value=0.007). FIG. 36C shows the overall survival of wild-type cases with high (≥0.75) and low (≤0.75) NERDetect score (p-value=0.062).

FIG. 37A shows the overall survival with and without somatic ERCC2 mutations (p-value=0.005). FIG. 37B shows the overall survival of patients with ERCC2 somatic mutation or NERDetect score≥0.33 and ERCC2 wild-type cases (p-value=0.001). FIG. 37C shows the overall survival of wild-type cases with NERDetect score≥0.33 and NERDetect score<0.33 (p-value=0.108).

FIG. 42A shows nine mutational features were significantly associated with ERCC2 mutation status in TCGA bladder cancer WES cohort and were used to develop the composite ERCC2mut score. FIG. 42B shows ERCC2mut signature scores are strongly associated with ERCC2 mutation status in TCGA bladder cancer cohort ($P<2.2\times10^{-16}$). A value of ≥0.70 maximally separates ERCC2-mutant from WT cases and is denoted by the horizontal dash-dotted line. In each validation cohort, ERCC2 mutants were highly enriched among patients with a high ERCC2mut score (≥0.70). FIG. 42C shows DFCI/MSKCC cohort (n=50), $P=3.3\times10^{-4}$. FIG. 42D shows BGI cohort (n=98), $P=7.5\times10^{-5}$. FIG. 42E shows Philadelphia cohort (n=48), $P=7.9\times10^{-4}$. P values were calculated using Fisher exact test.

FIG. 43A shows ERCC2mut signature scores for all cases in the DFCI/MSKCC cohort (n=50). ERCC2 mutant cases are denoted by asterisks. FIG. 43B shows ERCC2mut signature scores for all cases in the Philadelphia cohort (n=48). FIG. 43C shows ERCC2mut signature scores for WT ERCC2 cases in the DFCI/MSKCC cohort (n=41): high ERCC2mut signature scores (≥0.70) are significantly associated with cisplatin response (p=0.02). FIG. 43D shows overall survival (OS) for patients with WT ERCC2 tumors in the DFCI/MSK cohort. OS is significantly longer for WT ERCC2 patients with ERCC2mut signature scores≥0.70 (p=0.046). P-values were calculated by the Fisher's exact test.

FIG. 44A demonstrates separate clonal populations of NER-proficient KU19-19 or NER-deficient KE1 cells were cultured in parallel for ~30 generations and single cells were then isolated, expanded, and harvested. FIG. 44B demonstrates whole genome sequencing and mutational signature analysis revealed significantly higher ERCC2mut scores in the NER-deficient KE1 samples compared to the NER-proficient KU19-19 samples.

FIG. 45A shows overall survival with and without somatic ERCC2 mutations (p-value=0.051). FIG. 45B shows overall survival of patients with ERCC2 somatic mutation and/or high ERCC2mut score (≥0.7) and ERCC2 wild-type cases (p-value=0.005). FIG. 45C shows overall survival of wild-type cases with high (≥0.7) and low (<0.7) ERCC2mut score (p-value=0.046).

FIG. 46A shows overall survival with and without somatic ERCC2 mutations (p-value=0.005). FIG. 46B shows the overall survival of patients with ERCC2 somatic mutation and/or ERCC2mut score≥0.7 and ERCC wild-type cases (p-value=0.004). FIG. 46C shows the overall survival of wild-type cases with ERCCmut score≥0.7 and ERCCmut score<0.7 (p-value=0.004).

DETAILED DESCRIPTION

Figure 1A:
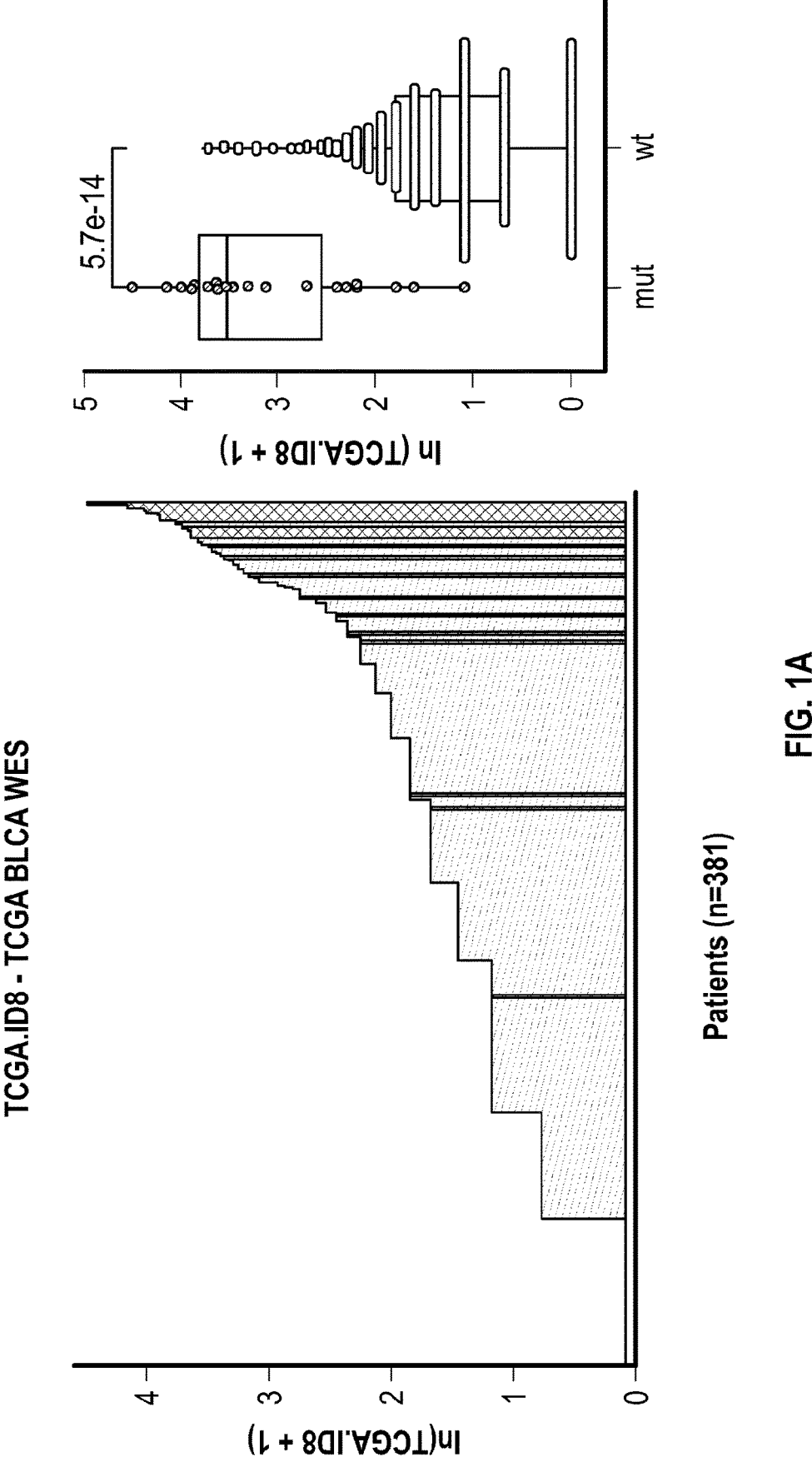
FIGS. 1A-1F shows the development of the NERDetect model. Four mutational signatures were significantly associated with ERCC2 helicase domain mutations in the TCGA bladder cancer cohort (panels A-D) and were used to construct the NERDetect model. ERCC2 mutant cases are shown in green and ERCC2 wild-type samples are shown in gray.

Cancer is a hyperproliferation of cells that exhibit a loss of normal cellular control that results in unregulated growth, lack of differentiation, local tissue invasion, and metastasis. The methods provided herein are directed at the treatment of tumors formed by cancer cells, such as solid tumors. These include carcinomas, sarcomas, lymphomas and myelomas, and bladder cancer. Leukemias, or cancers of blood cells, do not form solid tumors.

DNA repair pathway aberrations are common in tumor cells but are largely absent in normal cells. For example, nucleotide excision repair (NER) is a highly conserved DNA repair pathway that recognizes and repairs bulky intrastrand DNA adducts formed by genotoxic agents such as ultraviolet (UV) radiation and platinum chemotherapies. NER is initiated through two separate branches of lesion recognition: transcription coupled repair (TC-NER) is activated by RNA polymerase stalling at lesions in transcribed regions while global genome repair (GG-NER) is able to recognize lesions throughout the genome. Following lesion recognition, TC-NER and GG-NER converge on a common NER pathway that excises and replaces the damaged DNA strand in an error-free manner.

Sequencing and functional studies have revealed that NER pathway deficiency is present in a subset of tumors. Somatic missense mutations in ERCC2, a key NER gene that encodes a DNA helicase also known as XPD, are present in approximately 15% of muscle-invasive bladder tumors. ERCC2-mutated tumors display increased sensitivity to platinum-based therapy. Mutations in NER genes beyond ERCC2 also occur sporadically in bladder cancer and other tumor types, and these events also confer a therapeutically exploitable NER deficiency.

The mutations in an individual cancer genome may have been generated by multiple mutational processes, and thus incorporate multiple superimposed mutational signatures. Therefore, to systematically characterize the mutational processes that contribute to cancer, mathematical methods are used to decipher mutational signatures from somatic mutation catalogues, estimate the number of mutations that are attributable to each signature in individual samples and annotate each mutation class in each tumor with the probability that it arose from each signature.

For example, the mutational features of NER deficiency in cancer, are provided herein based on the analysis of bladder cancer whole genome and whole exome sequencing data sets to identify multiple types of mutational signatures catalogued in cancer, including SNVs, short indels, and large-scale rearrangements. In total, three mutational features of NER deficiency were significantly associated with ERCC2 mutations in the TCGA WES cohort and are discussed below.

Accordingly, the present invention relates generally to methods for treating cancer or predicting response of a cancer in a subject to anti-cancer therapies based upon a determination and analysis of a Nucleotide excision repair (NER) deficiency score, as referred to herein as NERDetect score. The methods provided herein can reliably identify NER deficiency from clinical tumor specimens.

NERDetect is a measurement predictive of responsiveness to anti-cancer therapies of a cancer in a subject. This utility of NERDetect is based upon the novel finding that the summation of individual mutational signatures can predict responsiveness of a cancer in a subject to anti-cancer agents independently of identifying specific chromosomal aberrations.

In one aspect, provided herein a method for treating a subject for cancer. Generally, the method comprises administering an anti-cancer treatment to a subject in need thereof, wherein the subject has a NERDetect score of at least 0.70. In various embodiments, the anti-cancer treatment comprises an alkylating chemotherapeutic agent.

Also provided herein is a method for predicting the outcome of anti-cancer treatment.

In some embodiments of the various aspects described herein, the method comprises obtaining and/or receiving results of a NERDetect score for the subject to be treated. For example, the method comprises obtaining/receiving results of an assay and determining the NERDetect score for the subject to be treated.

In some other embodiments of the various aspects described herein, the method comprises obtaining a biological sample from the subject and determining the NERDetect score. Methods of obtaining a sample from a subject is discussed further below.

Methods of Obtaining a Sample from a Subject

In some embodiments of any of the aspects, the methods provided herein comprise assaying a sample from the subject to determine the NERDetect score.

In some embodiments of any of the aspects, the assay is based upon nucleic acids obtained from a subject, biological sample, and/or control sample. In some embodiments of any of the aspects, the present invention encompasses several examples of a biological sample. Such samples can include "body fluids," which refer to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow.

In some embodiments, the sample is a tumor cell, a population of tumor cells, or a tumor. Methods that can be used to isolate tumor cells for use in the methods described herein are known in the art and/or provided herein. In general, the methods include acquisition of the tumor tissue, whether from a biopsy or from resected tumor tissue, followed by dissociation of the tumor tissue to a suspension of cells and placement of the cells in culture. The process is described for a number of different tumor types by, e.g., Kodack et al., *Cell Rep.* 2017 Dec. 12; 21(11): 3298-3309, which is incorporated herein by reference in its entirety. There are different approaches to isolate tumors in a tissue specific manner including, summarized in Table 1.

TABLE 1

Methodologies of tumor collection from different organs.

| Organ | Tumor specimen collection methods |
|---|---|
| Bladder | Transurethral resection of bladder tumor (TURBT). |
| Bone | Amputation |
| Brain | Craniotomy |
| Breast | Lumpectomy, wide local excision, Mastectomy—subcutaneous, Halsted radical, extended radical |
| Colon | Hemicolectomy—right or left and transverse colectomy |
| Kidney | Radical nephrectomy |
| Liver | Segmental or lobar resection |
| Lung | Thoracotomy, Lobectomy, Pneumonectomy |
| Prostate | Radical perineal prostatectomy, cystoprostatectomy, transurethral resection |

In some embodiments of any of the aspects, the methods and assays provided herein can further comprise a step of obtaining or having obtained a test sample from a subject. In some embodiments of any of the aspects, the subject can be a human subject. In some embodiments of any of the aspects, the subject can be a subject in need of treatment for cancer, e.g., bladder cancer, or a subject at risk of developing cancer. In some embodiments of any of the aspects, the subject has at least one symptom of cancer.

A subject can be any living organism in need of treatment for cancer. Such subjects include, but are not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult, child and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc.

In some embodiments, the subject is a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of cancer.

It is noted that a human subject can be of any age, gender, race or ethnic group, e.g., Caucasian (white), Asian, African, black, African American, African European, Hispanic, Middle eastern, etc.

In addition, the methods described herein can be used to treat domesticated animals and/or pets. A subject can be male or female. A subject can be one who has been previously diagnosed with or identified as suffering from a cancer. A subject need not have already undergone an anti-cancer treatment.

The test sample can be obtained by removing a sample from a subject, but can also be accomplished by using a previously isolated sample (e.g., isolated at a prior time point and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample is contained at room temperature (e.g., about 20° C.-25° C. or 68° F.-77° F.). In some embodiments of any of the aspects, the test sample is contained at about 4° C. or less. In some embodiments of any of the aspects, the test sample can be a frozen test sample, e.g., a frozen bodily fluid, e.g., contained at about 0° C. or less. The frozen sample can be thawed before employing the methods, assays, and kits described herein. After thawing, a frozen sample can be centrifuged before being subjected to the methods, compositions, assays and kits described herein.

In some embodiments of any of the aspects, the test sample is a clarified test sample, for example, by centrifugation and collection of a supernatant comprising the clarified test sample. In some embodiments of any of the aspects, the test sample is not a clarified test sample.

In some embodiments of any of the aspects, a test sample can be a pre-processed test sample, for example, supernatant or filtrate resulting from a treatment selected from the group consisting of centrifugation, filtration, thawing, purification, gravity or pulse-spinning, and any combinations thereof.

In some embodiments of any of the aspects, the test sample can be treated with a chemical and/or biological reagent. Chemical and/or biological reagents can be employed to protect and/or maintain the stability of the sample, including biomolecules (e.g., nucleic acids) therein, during processing.

In some embodiments of any of the aspects, a nucleic acid is isolated from the test sample. In some embodiments of any of the aspects, the methods and assays provided herein further comprise extracting, i.e., isolating/purifying the nucleic acid from the sample after a lysis step.

Furthermore, nucleic acid samples derived from cancerous and non-cancerous cells of a subject that can be used in the methods of the invention to determine the NERDetect score can be prepared by means well known in the art. For example, surgical procedures or needle biopsy aspiration can be used to collect cancerous samples from a subject. In some embodiments, it is important to enrich and/or purify the cancerous tissue and/or cell samples from the non-cancerous tissue and/or cell samples. In other embodiments, the cancerous tissue and/or cell samples can then be microdissected to reduce amount of normal tissue contamination prior to extraction of genomic nucleic acid or pre-RNA for use in the methods of the invention. In still another embodiment, the cancerous tissue and/or cell samples are enriched for cancer cells by at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range in between, in cancer cell content. Such enrichment can be accomplished according to methods well-known in the art, such as needle microdissection, laser microdissection, fluorescence activated cell sorting, and immunological cell sorting. In one embodiment, an automated machine performs the hyperproliferative cell enrichment to thereby transform the biological sample into a purified form enriched for the presence of hyperproliferative cells.

Collecting nucleic acid samples from non-cancerous cells of a subject can also be accomplished with surgery or aspiration. In surgical procedures where cancerous tissue is removed, surgeons often remove non-cancerous tissue and/or cell samples of the same tissue type of the cancer patient for comparison. Nucleic acid samples can be isolated from such non-cancerous tissue of the subject for use in the methods of the invention.

In certain embodiments of the methods of the invention, nucleic acid samples from non-cancerous tissues are not derived from the same tissue type as the cancerous tissue and/or cells sampled, and/or are not derived from the cancer patient. The nucleic acid samples from non-cancerous tissues may be derived from any non-cancerous and/or disease-free tissue and/or cells. Such non-cancerous samples can be collected by surgical or non-surgical procedures. In certain embodiments, non-cancerous nucleic acid samples are derived from tumor-free tissues. For example, non-cancerous samples may be collected from lymph nodes, peripheral blood lymphocytes, and/or mononuclear blood cells, or any subpopulation thereof. In a preferred embodiment, the non-cancerous tissue is not pre-cancerous tissue, e.g., it does not exhibit any indicia of a pre-neoplastic condition such as hyperplasia, metaplasia, or dysplasia.

In one embodiment, the nucleic acid samples used to compute NERDetect score are taken from at least 1, 2, 5, 10, 20, 30, 40, 50, 100, or 200 different organisms of that species.

According to certain aspects of the invention, nucleic acid "derived from" genomic DNA, as used in the methods of the invention can be fragments of genomic nucleic acid generated by restriction enzyme digestion and/or ligation to other nucleic acid, and/or amplification products of genomic nucleic acids, or pre-messenger RNA (pre-mRNA), amplification products of pre-mRNA, or genomic DNA fragments grown up in cloning vectors generated, e.g., by "shotgun" cloning methods. In certain embodiments, genomic nucleic acid samples are digested with restriction enzymes.

Though the nucleic acid sample need not comprise amplified nucleic acid, in some embodiments, the isolated nucleic acids can be processed in manners requiring and/or taking advantage of amplification. The genomic DNA samples of a subject optionally can be fragmented using restriction endonucleases and/or amplified prior to determining the NERDetect score. In one embodiment, the DNA fragments are amplified using polymerase chain reaction (PCR). Methods for practicing PCR are well known to those of skill in the art. One advantage of PCR is that small quantities of DNA can be used. For example, genomic DNA from a subject may be about 150 ng, 175, ng, 200 ng, 225 ng, 250 ng, 275 ng, or 300 ng of DNA.

Methods of Analyzing and Sequencing Nucleic Acids in a Sample

In some embodiments, the nucleic acids provided herein are sequenced and analyzed using methods known to those of skill in the art. Methods of evaluating a nucleic acid or set of nucleic acids in a sample for the mutational signatures provided herein include, but are not limited to, sequencing by hybridization (SBH), sequencing by ligation (SBL) (Shendure et al. (2005) Science 309: 1728), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT US05/27695), multiplex sequencing (U.S. Ser. No. 12/027,039, filed Feb. 6, 2008; Porreca et al (2007) Nat. Methods 4:931), polymerized colony (POLONY) sequencing (U.S. Pat. Nos. 6,432, 360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., using platforms such as Roche 454, Illumina Solexa, AB-SOLiD, Helicos, Polonator platforms and the like, can also be utilized. A variety of light-based sequencing technologies are known in the art (Landegren et al. (1998) *Genome Res.* 8:769-76; Kwok (2000) Pharmacogenomics 1:95-100; and Shi (2001) *Clin. Chem.* 47: 164-172). See also, e.g., see Shendure et al., *Nat. Biotechnol.* 2008, 26, 1135-1145, Science 2005, 309, 1728-1732, and *Nature* 2005, 437, 376-380, which are incorporated herein by reference in their entireties.

The nucleic acids (e.g., DNA) can be sequenced by any suitable method. For example, DNA to be sequenced is generally prepared by one of two approaches: first, for shotgun de novo sequencing, randomly fragmented DNA is cloned into a high-copy-number plasmid, which is then used to transform *Escherichia coli*; or second, for targeted resequencing, PCR amplification is carried out with primers that flank the target. The output of both approaches is an amplified template, either as many 'clonal' copies of a single plasmid insert present within a spatially isolated bacterial colony that can be picked, or as many PCR amplicons present within a single reaction volume. The sequencing biochemistry takes place in a 'cycle sequencing' reaction, in which cycles of template denaturation, primer annealing, and primer extension are performed. The primer is complementary to known sequence immediately flanking the region of interest. Each round of primer extension is stochastically terminated by the incorporation of fluorescently labeled dideoxynucleotides (ddNTPs). In the resulting mixture of end-labeled extension products, the label on the terminating ddNTP of any given fragment corresponds to the nucleotide identity of its terminal position. Sequence is determined by high-resolution electrophoretic separation of the single-stranded, end-labeled extension products in a capillary-based polymer gel. Laser excitation of fluorescent labels as fragments of discreet lengths exit the capillary, coupled to four-color detection of emission spectra, provides the readout that is represented in a Sanger sequencing 'trace'. Software translates these traces into DNA sequence, while also generating error probabilities for each base-call. The approach that is taken for subsequent analysis, for example, genome assembly or variant identification can depend on the genes being sequenced.

In some embodiments, the amplified DNA is shotgun sequenced. The number of reads can be at least 10,000, at least 1 million, at least 10 million, at least 100 million, or at least 1000 million. In another aspect, the number of reads can be from 10,000 to 100,000, or alternatively from 100, 000 to 1 million, or alternatively from 1 million to 10 million, or alternatively from 10 million to 100 million, or alternatively from 100 million to 1000 million. A "read" is a length of continuous nucleic acid sequence obtained by a sequencing reaction.

"Shotgun sequencing" refers to a method used to sequence a very large amount of DNA (such as the entire genome). In this method, the DNA to be sequenced is first shredded into smaller fragments which can be sequenced individually. The sequences of these fragments are then reassembled into their original order based on their overlapping sequences, thus yielding a complete sequence. "Shredding" of the DNA can be done using a number of different techniques including restriction enzyme digestion or mechanical shearing. Overlapping sequences are typically aligned by a computer suitably programmed. Methods and programs for shotgun sequencing a cDNA library are known in the art.

Using amplification, sequencing, and analysis methods provided herein, or amplification, sequencing and analysis methods known to those of skill in the art, each amplified portion of the genome is compared to a reference genome, such as a reference human genome such as described in International Human Genome Sequencing Consortium, *Nature* 431, 931-945 (2004), which is incorporated by reference in its entirety, and analyzed for single nucleotide polymorphisms (SNPs) associated with each portion. It is to be understood that the method may be applied to other genomes and that reference genomes are readily available to those of skill in the art. SNP analysis has been used to identify haplotypes, such as is described in H. C. Fan et al., *Nat. Biotech.* 29, 51-57 (2011) hereby, incorporated by reference in its entirety. Based on the sequence information and SNPs, the haplotype of single cells is constructed, such as for example, with a greater than 1000 kb haplotype block size. Accordingly, the haplotype of several or multiple single cells from the same individual can be compared to determine the complete haplotype of the individual.

In some embodiments, de-novo genome assembly methods are provided when a reference genome is not available from a species or when the sample has a complex structural variation as with some cancers. De-novo genome assembly is accomplished by assembling about 1000 kb blocks from each sub-genome portion (i.e., a portion of the genomic DNA extracted from a cell or the total genomic DNA) and then mapping blocks with one another. Methods of de-novo genome assembly are known and those principles may be applied to the present method of extracting DNA from a biological sample, for example, of the same cancer type, or the same subject, or another healthy subject, separating the extracted DNA into multiple portions, amplifying the multiple portions, sequencing the amplified DNA and comparing and analyzing the sequenced DNA to assembly the genome de novo, i.e. without a reference genome.

In some embodiments, the reference genome is the database of genotypes and phenotypes provided by International Cancer Genome Consortium (ICGC), National Center for Biotechnology Information (NCBI) and/or the cancer genome atlas (TCGA) available on the world wide web at http<dcc.icgc.org>, <ncbi.nlm.nih.gov/gap> and <portal-.gdc.cancer.gov>, respectively.

The reference genome provided herein can be used to determine mutation and copy number calling when compared with the nucleic acids assayed from the biological sample provided herein.

In certain embodiments of the methods of the invention, the nucleic acid from a subject is amplified using a single primer pair. For example, genomic DNA samples can be digested with restriction endonucleases to generate fragments of genomic DNA that are then ligated to an adaptor DNA sequence which the primer pair recognizes. In other embodiments of the methods of the invention, the nucleic acid of a subject is amplified using sets of primer pairs specific to a loci of interest, e.g., one or more mutational features of NER deficiency. Such sets of primer pairs each recognize genomic DNA sequences flanking particular loci of interest, e.g., one or more mutational features of NER deficiency. A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods and Applications, Academic Press Inc., San Diego, Calif. It will be apparent to one skilled in the art that controlled robotic systems are useful for isolating and amplifying nucleic acids and can be used.

In other embodiments, where genomic DNA of a subject is fragmented using restriction endonucleases and amplified prior to determining NERDetect score, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51).

In yet other embodiments, where the DNA of a subject is fragmented using restriction endonucleases and amplified prior to determining NERDetect score, the amplification comprises expressing a nucleic acid encoding a gene, or a gene and flanking genomic regions of nucleic acids, from the subject. RNA (pre-messenger RNA) that comprises the entire transcript including introns is then isolated and used in the methods of the invention to determine NERDetect score.

In certain embodiments, no amplification is required. In such embodiments, the genomic DNA, or pre-RNA, of a subject may be fragmented using restriction endonucleases or other methods. The resulting fragments may be hybridized to probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for sequencing. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

The nucleic acid samples derived from a subject used in the methods of the invention can be hybridized to arrays comprising probes (e.g., oligonucleotide probes) in order to identify informative loci of interest, e.g., one or more mutational features of NER deficiency. In preferred embodiments, the probes used in the methods of the invention comprise an array of probes that can be tiled on a DNA chip.

Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays.

The single-stranded synthetic oligodeoxyribonucleic acid DNA probes of an array may need to be denatured prior to contact with the nucleic acid samples from a subject, e.g., to remove hairpins or dimers which form due to self-complementary sequences.

Optimal hybridization conditions will depend on the length of the probes and type of nucleic acid samples from a subject. General parameters for specific (i.e., stringent) hybridization conditions for nucleic acids are described in Sambrook, J. et al., eds., 1989, Molecular Cloning: A Laboratory Manual, 2nd Ed., Cold Spring Harbor Laboratory Press, Cold Spring Harbor, N.Y., at pp. 9.47-9.51 and 11.55-11.61; Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization With Nucleic Acid Probes, Elsevier Science Publishers B. V. and Kricka, 1992, Nonisotopic DNA Probe Techniques, Academic Press, San Diego, Calif.

In some embodiments of the methods of the present invention, DNA arrays can be used to determine whether nucleic acid samples exhibit one or more mutational features of NER deficiency. Hybridization can be used to determine the presence or absence of heterozygosity. Various formats of DNA arrays that employ oligonucleotide "probes," (i.e., nucleic acid molecules having defined sequences) are well known to those of skill in the art.

Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways; of which several are described herein.

However, microarrays share certain characteristics. For example, they are reproducible, allowing multiple copies of a given array to be produced and easily compared with each other.

Preferably, the microarrays are made from materials that are stable under binding (e.g., nucleic acid hybridization) conditions. The microarrays are preferably small, e.g., between about 1 cm² and 25 cm², preferably about 1 to 3 cm². However, both larger and smaller arrays are also contemplated and may be preferable, e.g., for simultaneously evaluating a very large number of different probes.

Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. Using DNA array assays, complex mixtures of labeled nucleic acids, e.g., nucleic acid fragments derived from a restriction digestion of genomic DNA from non-cancerous tissue, can be analyzed.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules corresponding to each informative locus of interest (e.g., SNPs, RFLPs, STRs, etc.).

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA.

The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

The oligonucleotide probes may comprise DNA or DNA "mimics," e.g., derivatives and analogues. The oligonucleotide probes can be modified at the base moiety, at the sugar moiety, or at the phosphate backbone. Exemplary DNA mimics include, e.g., phosphorothioates. Further, a plurality of different oligonucleotides may be used that are complementary to the sequences of sample nucleic acids. For example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more different oligonucleotides can be used.

In certain embodiments, the assays can be performed using arrays suitable for use with molecular inversion probe protocols such as described by Wang et al. (2007) *Genome Biol.* 8, R246.

For oligonucleotide probes targeted at nucleic acid species of closely resembled (i.e., homologous) sequences, "cross-hybridization" among similar probes can significantly contaminate and confuse the results of hybridization measurements. Cross-hybridization is a particularly significant concern in the detection of SNPs since the sequence to be detected (i.e., the particular SNP) must be distinguished from other sequences that differ by only a single nucleotide. Cross-hybridization can be minimized by regulating either the hybridization stringency condition and/or during post-hybridization washings. Highly stringent conditions allow detection of allelic variants of a nucleotide sequence, e.g., about 1 mismatch per 10-30 nucleotides.

There is no single hybridization or washing condition which is optimal for all different nucleic acid sequences. For particular arrays of informative loci of interest, these conditions can be identical to those suggested by the manufacturer or can be adjusted by one of skill in the art.

In preferred embodiments, the probes used in the methods of the invention are immobilized (i.e., tiled) on a glass slide called a chip. For example, a DNA microarray can comprise a chip on which oligonucleotides (purified single-stranded DNA sequences in solution) have been robotically printed in an (approximately) rectangular array with each spot on the array corresponds to a single DNA sample which encodes an oligonucleotide. In summary the process comprises, flooding the DNA microarray chip with a labeled sample under conditions suitable for hybridization to occur between the slide sequences and the labeled sample, then the array is washed and dried, and the array is scanned with a laser microscope to detect hybridization. In certain embodiments there are at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 50,000, 60,000, 70,000, 80,000, 90,000, 100,000 or more or any range in between, of informative loci of interest for which probes appear on the array (with match/mismatch probes for a single locus of interest or probes tiled across a single locus of interest counting as one locus of interest). The maximum number of informative loci of interest being probed per array is determined by the size of the genome and genetic diversity of the subject's species. DNA chips are well known in the art and can be purchased in pre-fabricated form with sequences specific to particular species. In some embodiments, the Genome-Wide Human SNP Array 6.0™ and/or the 50K XbaI arrays (Affymetrix, Santa Clara, Calif.) are used in the methods of the invention. In other embodiments, SNPs and/or DNA copy number can be detected and quantitated using sequencing methods, such as "next-generation sequencing methods" as described further herein.

In some embodiments, nucleic acid samples derived from a subject are hybridized to the binding sites of an array described herein. In certain embodiments, nucleic acid samples derived from each of the two sample types of a subject (i.e., cancerous and non-cancerous) are hybridized to separate, though identical, arrays. In certain embodiments, nucleic acid samples derived from one of the two sample types of a subject (i.e., cancerous and non-cancerous) is hybridized to such an array, then following signal detection the chip is washed to remove the first labeled sample and reused to hybridize the remaining sample. In other embodiments, the array is not reused more than once. In certain embodiments, the nucleic acid samples derived from each of the two sample types of a subject (i.e., cancerous and non-cancerous) are differently labeled so that they can be distinguished. When the two samples are mixed and hybridized to the same array, the relative intensity of signal from each sample is determined for each site on the array, and any relative difference in abundance of an allele of informative loci of interest detected.

Signals can be recorded and, in some embodiments, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the array, a ratio of the emission of the two fluorophores can be calculated, which may help in eliminating cross hybridization signals to more accurately determining whether a particular SNP locus is heterozygous or homozygous.

In some embodiments, the nucleic acids samples, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, $^{32}P$ and $^{14}C$. Fluorescent molecules suitable for the present invention include, but are not limited to, fluorescein and its derivatives, rhodamine and its derivatives, Texas red, 5'-carboxy-fluorescein ("FAM"), 2', 7'-dimethoxy-4', 5'-dichloro-6-carboxy-fluorescein ("JOE"), N, N, N', N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto.

Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) *Genome Res.* 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) *Genome Res.* 6, 639-645. Alternatively, a fiber-optic bundle can be used such as that described by Ferguson et al. (1996) *Nat. Biotech.* 14, 1681-1684. The resulting signals can then be analyzed to determine the presence or absence of heterozygosity or homozygosity for informative loci of interest (e.g., SNPs, RFLPs, STRs, etc.) using computer software.

Some embodiments of the various aspects described herein comprise conducting an assay to determine the NER-Detect score. In some embodiments, the assay comprises one or more of whole genome sequencing, in situ hybridization, single nucleotide polymorphism (SNP) array, transcriptional arrays, array comparative genomic hybridization (aCGH), Southern blotting, molecular inversion probe (MIP). In some embodiments, the assay comprises next generation sequencing (NGS).

Methods of Determining the NERDetect Score

As used herein, the "NERDetect score" refers to a summation by logistic regression of one or more of the following mutational features of NER deficiency: (1) the number of mutations associated with a signature of insertions and deletions, e.g., an indel signature such as ID8 signature, ID2 signature and ID10 signature; (2) the number of deletions (1-50 bp); (3) the number of mutations associated with a signature of single base substitutions (SBS), e.g., signature 5 (SBS5), signature 2 (SBS2) and signature 40 (SBS40); (4) the number of mutations associated with a signature of doublet base substitutions (DBS), e.g., signature 4 (DBS4); and (4) the ratio of the number of a certain type of base substitution on the transcribed and untranscribed strand, i.e., transcription strand bias ratio (TSB ratio) such as T to A (T>A), C to G (C>G) and T to G (T>G). It is noted that the terms NERDetect score and ERCC2mut are used interchangeably herein.

In some embodiments of any one of the aspects, the NERDetect score is a summation by logistic regression of at least two, e.g., 2, 3, 4, 5, 6, 7, 8, 9 or 10 mutational features selected from the following:
  i. indel signature 8 (ID8);
  ii. indel signature 2 (ID2);
  iii. indel signature 10 (ID10);
  iv. single base substitutions signature 5 (SBS5);
  v. single base substitution signature 2 (SBS2);
  vi. single base substitution signature 40 (SBS40);
  vii. doublet base substitutions signature 4 (DBS4);
  viii. doublet base substitution signature 7 (DBS7);
  ix. TSB ratio T>A;
  x. TSB ratio C>G;
  xi. TSB ratio T>G; and
  xii. number of deletions (1-50 bp).

It is noted that the mutational features used in determining the NERDetect score can be based on any version of the Catalogue of Somatic Mutations in Cancer (COSMIC) Mutational Signatures. For example, the mutational features used in determining the NERDetect score can be selected from COSMIC version 1, COSMIC version 2, COSMIC version 3, or any combinations thereof. It is contemplated herein that the method of determining the NERDetect score can also be applied to any mutational signature extraction method, which includes but is not limited to, e.g., deconstructSigs, MutationalPatterns, Isomut, Isomut2py.

It is noted less than all 12 of the above discussed mutational features can be used in determining the NERDetect score. In other words, the NERDetect score can be determined using 1, 2, 3, 4, 5, 6, 7, 8, 9, 10, 11 or all 12 of the above discussed mutational features. In some embodiments, the NERDetect score can be determined using at least two of the above discussed mutational features. For example, the NERDetect score can be determined using at least ID8 and SBS5. In some embodiments, the NERDetect score can be determined using at least ID8, SBS5 and TSB ratio T>A. In some embodiments, the NERDetect score can be determined using at least ID8, ID10, DBS4, SBS2, SBS5, and TSB ratio C>G.

In some embodiments of any one of the aspects, the NERDetect score is determined using ID8, SBS5 and at least one additional mutational feature of NER deficiency. For example, the NERDetect score is determined using ID8, SBS5 and at least one, e.g., 2, 3, 4, 5, 6, 7, 8, 9 or 10 of ID2, ID10, SBS2, SBS40, DBS4, DBS7, TSB ratio T>A, TSB ratio C>G, TSB ratio T>G, and number of deletions (1-50 bp).

In some embodiments, the NERDetect score is determined using at least ID8, number of deletions (1-50 bp), SBS5, and transcription strand bias T>A.

In some embodiments, the NERDetect score is determined using at least ID8, ID2, ID10, SBS2, SBS5, DBS4, TSB ratio T>A, TSB ratio C>G, and TSB ratio T>G.

In some embodiments, the NERDetect score is determined using ID8, ID10, SBS2, SBS5, DBS4, DBS7, TSB ratio T>A and TSB ratio C>G.

In embodiments of the various aspects described herein, the mutational features of NER deficiency can be combined to calculate the NERDetect score according to the following formula:

$$p = \frac{1}{1 + e^{-(\beta_0 + \Sigma \beta_i x_i)}} \qquad \text{(Formula 1)}$$

where p is the NERDetect score, $\beta_o$ is the intercept, i is from 1 to the number of mutational features used, $\beta_i$ is the coefficient of the mutational feature and $x_i$ is a mutational feature of NER deficiency.

In some embodiments of any one the aspects, $\beta_o$ is −2.384. In some other embodiments of any one of the aspects, $\beta_o$ is −2.208. In yet some other embodiments, $\beta_o$ is −2.528.

In some embodiments of any one of the aspects, the coefficient for ID8 is 1.816. In some other embodiments, the coefficient for ID8 is 1.463. In yet some other embodiments, the coefficient for ID8 is 1.831

In some embodiments of any one of the aspects, the coefficient for SBS2 is 0.6159. In some other embodiments, the coefficient for SBS2 is 0.5.

In some embodiments of any one of the aspects, the coefficient for SBS5 is 0.5377. In some other embodiments, the coefficient for SBS5 is 0.4817. In yet some other embodiments, the coefficient for SBS5 is 0.2796.

In some embodiments of any one of the aspects, the coefficient for ID10 is 0.4609. In some other embodiments, the coefficient for ID10 is 0.1669.

In some embodiments of any one of the aspects, the coefficient for TSB ratio T>A is 0.1911. In some other embodiments, the coefficient for TSB ratio T>A is 0.3798.

In some embodiments of any one of the aspects, the coefficient for TSB ratio C>G is 0.2855. In some other embodiments, the coefficient for TSB ratio C>G is 0.06575.

In some embodiments of any one of the aspects, the coefficient for DBS4 is 0.2381. In some other embodiments, the coefficient for DBS4 is 0.4731.

In some embodiments of any one of the aspects, the coefficient for DBS7 is 0.08877.

In some embodiments of any one of the aspects, the coefficient for ID2 is 0.1688.

In some embodiments of any one of the aspects, the coefficient for TSB ratio T>G is 0.1272. In some other embodiments, the coefficient for TSB ratio T>G is 0.2633.

In some embodiments of any one of the aspects, the coefficient for the number of deletions (1-50 bp) is 0.254.

In some embodiments of any one of the aspects, the NERDetect score is determined using Formula 1 and at least ID8, number of deletions (1-50 bp), SBS5, and TSB ratio T>A, where the intercept ($\beta_o$) is −2.384, the coefficient of ID8 is 1.816, the coefficient for the number of deletions (1-50 bp) is 0.254, the coefficient for SBS5 is 0.5377 and the coefficient for the TSB ratio T>A is 0.1911.

In some embodiments of any one of the NERDetect score is determined using Formula 1 and at least ID8, SBS2, SBS5, ID10, TSB ratio T>A, TSB ratio C>G, DBS4, ID2 and TSB ratio T>G, where the intercept (po) is −2.208, the coefficient for ID8 is 1.463, the coefficient for SBS2 is 0.6159, the coefficient for SBS5 is 0.4817, the coefficient for ID10 is 0.4609, the coefficient for the TSB ratio T>A is 0.3798, the coefficient for the TSB ratio C>G is 0.2855, the coefficient for the DBS4 is 0.2381, the coefficient for the ID2 is 0.1688, and the coefficient for the TSB ratio T>G is 0.1272.

In some embodiments of any one of the NERDetect score is determined using Formula 1 and at least ID8, ID10, SBS2, SBS5, DBS4, DBS7, TSB ratio C>G, and TSB ratio T>G, where the intercept ($\beta_o$) is −2.528, the coefficient for ID8 is 1.831, the coefficient for ID10 is 0.1669, the coefficient for SBS2 is 0.5, the coefficient for SBS5 is 0.2796, the coefficient for DBS4 is 0.4731, the coefficient for DBS7 is 0.08877, the coefficient for the TSB ratio C>G is 0.06575 and the coefficient for the TSB ratio T>G is 0.2633.

Exemplary intercept ($\beta$) and coefficient values are also described in Tables 8, 12 and 13 in the Examples section.

In some embodiments of the various aspects described herein, the mutational features of NER deficiency can be combined to calculate the NERDetect score according to the following formula:

$$p = \frac{1}{1 + e^{-(\beta_0 + \beta_1 x_1 + \beta_2 x_2 + \beta_3 x_3 + \beta_4 x_4)}} \qquad \text{(Formula 2)}$$

where p is the NERDetect score, $\beta_o$ is the intercept, $\beta_1$, $\beta_2$, $\beta_3$, and $\beta_4$ are the coefficients of the mutational; features associated with NER deficiency, $x_1$, $x_2$, $x_3$, and $x_4$ are the above listed mutational features of NER deficiency.

In some embodiments of Formula 1, $x_1$ is the number of mutations associated with a signature of insertions and deletions, e.g., an indel signature such as ID8 signature; $x_2$ is the number of deletions (1-50 bp); $x_3$ is the number of mutations associated with a signature of single base substitutions or doublet base substitutions, e.g., COSMIC 5 signature; and $x_4$ is the ratio of the number of a certain type of base substitution on the transcribed and untranscribed strand, i.e., transcription strand bias such as T>A.

In some embodiments of the various aspects disclosed herein, $\beta_o$ is −2.384 in Formula 2. In some embodiments of the various aspects disclosed herein, $\beta_1$ is 1.816 in Formula 2. In some embodiments of the various aspects disclosed herein, $\beta_2$ is 0.254 in Formula 2. In some embodiments of the various aspects disclosed herein, $\beta_3$ is 0.5377 in Formula 2. In some embodiments of the various aspects disclosed herein, $\beta_4$ is 0.1911 in Formula 2.

In some preferred embodiments, $\beta_o$ is −2.384, $\beta_1$ is 1.816, $\beta_2$ is 0.254, $\beta_3$ is 0.5377 and $\beta_4$ is 0.1911 in Formula 2.

A NERDetect of at least 0.70, 0.75, 0.80, 0.85, 0.90, 0.95, 0.99 or more is predictive of response to an anti-cancer therapy (e.g., platinum based chemotherapeutics) of the cancer cell from which the assayed nucleic acid was derived.

In some embodiments of the various aspects described herein, the NERDetect score can be determined using a lasso logistic regression model that identifies the genomic features that distinguish between two categories of patient samples (subjects with cancers that have NER deficiency vs. subjects with cancers without NER deficiency). An exemplary regression model is provided in the working Examples.

Each mutational process in cancer can involve components of DNA damage or modification, DNA repair and DNA replication (which may be normal or abnormal), and generates a characteristic mutational signature that can include but is not limited to base substitutions, small insertions and deletions (indels), genome rearrangements and chromosome copy-number changes.

In some embodiments of any of the aspects, the total number of base pair deletions is used to determine the NERDetect score. Generally, the total number of 1-50 bp deletions indicates a deficiency in NER. Indels are described in detail, e.g., in Mills, R. E. (9 Aug. 2006). "An initial map of insertion and deletion (INDEL) variation in the human genome". *Genome Research*. 16 (9): 1182-1190, the contents of which is incorporated herein by reference in its entirety.

In some embodiments of any of the aspects, an indel score is used to determine the NERDetect score. Indels, also known as small insertions and deletions (ID) are defined as incorporation or loss of small fragments of DNA, of about 1 to about 50 base pairs.

In some embodiments of any of the aspects, the indel score is ID8. The indel signature "ID8" provided herein is characterized by >5 bp deletions that lack flanking micro-homology. The ID8 signatures can be determined from the sequencing data from the nucleic acids assayed according to the methods provided above. See, e.g., Alexandrov, L. B. et al. The Repertoire of Mutational Signatures in Human Cancer. *bioRxiv* 24, 322859 (2019), which is incorporated herein by reference in its entirety. Generally, ID8 signatures can involve double strand breaks by non-homologous DNA end-joining mechanisms but this is non-limiting.

Additional ID signatures are known in the art, e.g., available on the world wide web at cancer.sanger.ac.uk/cosmic/signatures/ID/index.tt.

In some embodiments of any of the aspects, the indel score used to determine NERDetect score is ID2. ID2 is composed predominantly of deletions of T at long (≥5 bp) mononucleotide repeats and is found in many cancer types.

In some embodiments of any of the aspects, the indel score is ID10. ID10 predominantly consists of ≥5 bp insertions at one-unit repeats.

In some embodiments of any of the aspects, single base substitution signatures are used to determine the NERDetect score. As used herein, "single base substitutions" or "SBS" or "single nucleotide variants" refer to a replacement of a certain nucleotide base with another nucleotide base. Considering the pyrimidines of the Watson-Crick base pairs, there are only six different possible substitutions: C>A, C>G, C>T, T>A, T>C, and T>G. SBS signatures are known in the art as described in Alexandrov et al. referenced herein and available on the world wide web at cancer.sanger.ac.uk/cosmic/signatures/SBS/index.tt.

In some embodiments of any of the aspects, the SBS signature used to determine the NERDetect score is a COSMIC 5 signature. Large-scale analyses of human tumor genome data across different cancer types have revealed 30 recurrent base substitution patterns, which are archived in the Catalogue of Somatic Mutations in Cancer (COSMIC) (available on the world wide web at cancer.sanger.ac.uk/cosmic/signatures). These mutational signatures are characterized by a specific contribution of 96 base substitution types with a certain sequence context. Some mutational signatures are linked to specific biological processes through association with exposure to carcinogens, such as tobacco smoke or the deficiency of DNA repair processes, such as nucleotide excision repair (NER). The COSMIC signature 5 that has been shown to correlate with ERCC2 mutation status in cancers. See, e.g., Kim, J. et al. "Somatic ERCC2 mutations are associated with a distinct genomic signature in urothelial tumors." *Nat. Genet.* 48, 600-606 (2016), which is incorporated herein by reference in their entirety. The COSMIC 5 signature can be trained on whole exome sequencing data or can be trained on whole genome sequencing data. It is noted that COSMIC 5 or COSMIC Signature 5 or Signature 5 refers to the same signature, i.e., Signature 5 from COSMIC v2. Signatures 5 COSMIC v2 was identified by Alexandrov et al., Nature, 2013.

In some embodiments of any of the aspects, the SBS Signature used to determine the NERDetect score is Signature 5*. Signature 5* is based on the association between somatic non-silent mutations in ERCC2 and activity of a specific mutational signature in three independent urothelial tumor cohorts. The signature is very similar to Signature 5 COSMIC v2 (although detected using a slightly different methodology applied to different datasets, hence called 'signature 5*' herein). Signature 5 is characterized by a broad pattern of base substitutions. Signature 5 can exhibit transcriptional strand bias for T>C substitutions at ApTpN context. The mutational profile of Signature 5* is described in further detail, e.g., in Kim J, et al. "*Nat Genet.* 2016; incorporated herein by reference above.

In some embodiments of any of the aspects, Signature 2 is used to determine the NERDetect score. Signature 2 has been found in 22 cancer types, but most commonly in cervical and bladder cancers. Signature 2 is described in further detail, e.g., in Kim J, et al. "*Nat Genet.* 2016; 48:600-6, referenced above.

In some embodiments of any of the aspects, doublet base substitution (DBS) signatures are used to determine the NERDetect score. In some embodiments, DBS 4 is used to determine the NERDetect score. As used herein "doublet base substitutions (DBS)" refer to the concurrent modification of two consecutive nucleotide bases. DBS signatures are common in most cancer types and are described in further detail e.g., in Alexandrov, L. B. et al. referenced above, which is incorporated herein by reference in its entirety. There is about 78 strand-agnostic DBS mutation types and 16 possible sources for doublet bases. Of these, AT, TA, CG, and GC are their own reverse complement. Of the various DBS signatures, DBS4 is dominated by GC>AA or TC>AA dinucleotide substitutions. The mutational profile of the DBS4 signature is known in the art, e.g., on the world wide web at cancer.sanger.ac.uk/cosmic/signatures/DBS/DBS4.tt.

In some embodiments, the NERDetect score is determined by transcriptional strand bias (TBS) of mutations. The transcriptional strand bias can be determined from the sequencing data from the nucleic acids assayed according to the methods provided herein. See e.g., Haradhvala, N. J. et al. Mutational Strand Asymmetries in Cancer Genomes Reveal Mechanisms of DNA Damage and Repair. *Cell* 164, 538-549 (2016) and Mugal C F et al., "Transcription-induced mutational strand bias and its effect on substitution rates in human genes." Mol Biol Evol. 2009 January; 26(1):131-42, the contents of each of which are incorporated herein by reference in their entireties.

It is noted that each of the mutational features provided herein can be independently associated with ERCC2 mutation status and therefore reflects distinct features of genomic instability induced by NER deficiency.

Methods of Diagnosing and Treating Cancer

The methods of the invention can be used to diagnose, treat and/or determine the phenotype of many different cancers. Specific examples of types of cancers include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

In some embodiments, the cancer is a bladder cancer. As used herein, the term "bladder cancer" refers to any cancer that affects the bladder of a subject.

The majority (>90%) of bladder cancers are transitional cell carcinomas (TCC) and arise from the urothelium. Other bladder cancer types include squamous cell carcinoma, adenocarcinoma, sarcoma, small cell carcinoma and secondary deposits from cancers elsewhere in the body. Approximately 30% of urothelial carcinomas invade the detrusor muscle of the bladder at presentation. These cancers are highly aggressive. The most invasive tumors may spread by way of the lymph and blood systems to invade bone, liver, and lungs and have high morbidity, see, e.g., Kaufman, D. S. *Ann Oncol* 17, v106-112 (2006), the contents of which is incorporated herein by reference in its entirety.

The symptoms and diagnosis of cancer, e.g., bladder cancer, can depend on the type and the stage of the cancer. A skilled physician can diagnose cancer in a subject by methods known in the art. For example, symptoms of bladder cancer in a subject can present as pain during urination, dark urine, blood in the urine, or frequent urination. Bladder cancer can be diagnosed by methods such as cystoscopy, biopsy, urine cytology, and medical imaging (e.g., CT scans, MRIs, etc.). While many urine-based tumor markers have been developed for detection and surveillance of bladder cancers and some of these are used in routine patient care (see, e.g., Lokeshwar, V. B. et al. Urology 66, 35-63 (2005); Friedrich, M. G. et al. BJU Int 92, 389-92 (2003); Ramakumar, S. et al. J Urol 161, 388-94 (1999); Sozen, S. et al. Eur Urol 36, 225-9 (1999); and Heicappell, R. et al. Urol Int 65, 181-4 (2000), the contents of each of which is incorporated herein by reference in their entireties), there is a need for methods of identifying and selecting patient that will respond to chemotherapeutic regimens and those that will require invasive procedures such and cystectomy (removal of the bladder).

Following cancer diagnosis, a subject may undergo an anti-cancer treatment or therapy. Non-limiting examples of anti-cancer therapies include tumor resection and removal, chemotherapy, radiation therapy, and/or any combination thereof. In general, chemotherapeutic agents include, but are not limited to an alkylating agent, mitotic inhibitors, antibiotics, antimetabolites, or anti-angiogenic agents, etc. Radiotherapy can also be used in combination with e.g., irradiation before or after administration an anti-cancer therapy provided herein, and can include, for example, the use of γ-irradiation, or microwaves to kill the cancer cells.

In certain embodiments, the invention provides methods for determining the phenotype of a cancer wherein the phenotype is response to therapy. The therapy may be any anti-cancer therapy including, but not limited to, chemotherapy, radiation therapy, immunotherapy, small molecule inhibitors, shRNA, hormonal, and combinations thereof.

The response to anti-cancer therapies relates to any response of the tumor to chemotherapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., J. Clin. Oncol. (2007) 25:4414-4422) or Miller-Payne score (Ogston et al., Breast (Edinburgh, Scotland) (2003) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

Additional criteria for evaluating the response to anti-cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to NERDetect scores that were determined prior to administration of any anti-cancer therapy. The outcome measurement may be pathologic response to therapy given in the neo-adjuvant setting. Alternatively, outcome measures, such as overall survival and disease-free survival can be monitored over a period of time for subjects following anti-cancer therapy for whom NERDetect scores are known. In certain embodiments, the same doses of anti-cancer agents are administered to each subject. In related embodiments, the doses administered are standard doses known in the art for anti-cancer agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. NERDetect score threshold values that correlate to outcome of an anti-cancer therapy can be determined using methods such as those described in the Examples section.

The methods provided herein can predict the responsiveness of a cancer to a treatment using the NERDetect score. Thus, in another aspect, provided herein is a method of selecting a subject for chemotherapeutic treatment, the method comprising:

In some embodiments of any of the aspects, the anti-cancer treatment is an agent or therapeutic. As used herein "anti-cancer agent" or "therapeutic" refers to any chemical or biological agent with therapeutic usefulness in the treatment of diseases characterized by abnormal cell growth. Such diseases include tumors, neoplasms and cancer as well as diseases characterized by hyperplastic growth. Examples of anti-cancer agents can include, e.g., chemotherapeutics, radiation therapy reagents, immunotherapies, targeted therapies, or hormone therapies.

In some embodiments, the anti-cancer treatment comprises an alkylating agent. In some embodiments, the alkylating chemotherapeutic agent is a platinum-based chemotherapeutic agent. In some embodiments, the platinum-based chemotherapeutic agent selected from the group consisting of cisplatin, carboplatin, dicycloplatin, eptaplatin, iproplatin, lobaplatin, miriplatin, nedaplatin, oxaliplatin, phenanthriplatin, picoplatin, satraplatin, triplatin teranitrate and any derivative thereof.

In some embodiments, the alkylating chemotherapeutic agent is selected from the group consisting of busulfan, carboplatin, carboquone, carmustine (BCNU), chlorambucil, cyclophosphamide, dacarbazine (DTIC; dimethyltriazenoimid-azolecarboxamide), hexamethylmelamine, ifosfamide, irofulven, lomustine, mechlorethamine, melphalan (L-sarcolysin), mitobronitol, nimustine, procarbazine, ranimustine, streptozocin (streptozotocin), temozolomide, thiotepa, trofosfamide, and any derivative thereof.

Figure 5A:
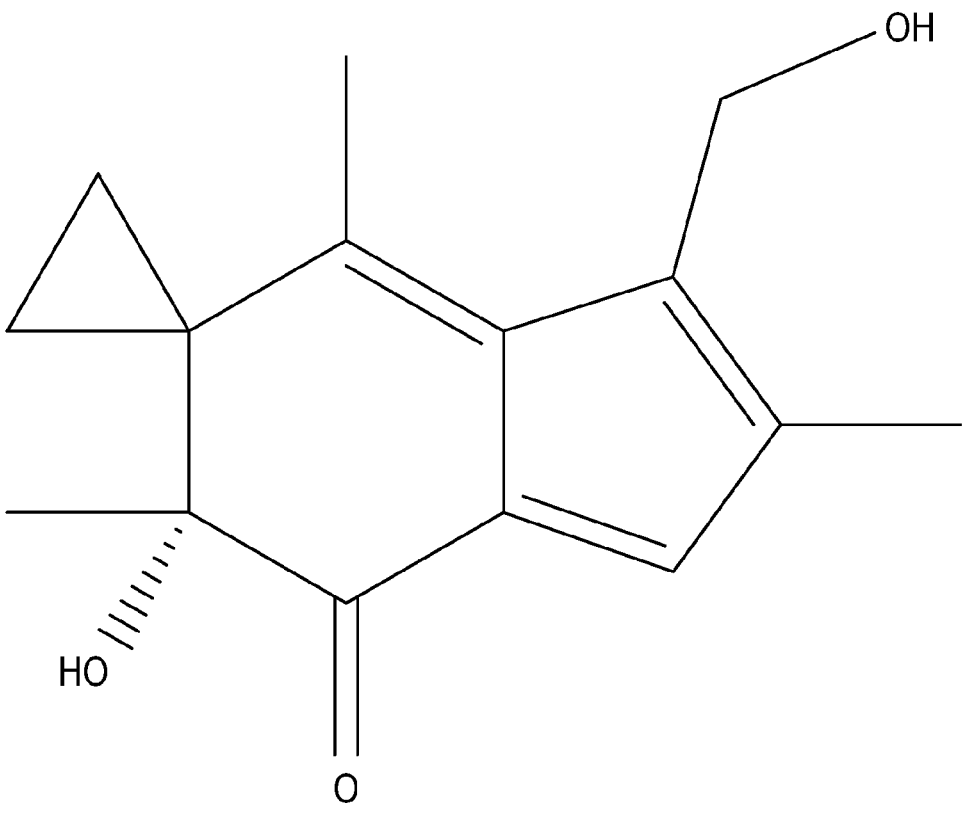
FIGS. 5A-5D demonstrate that NER-deficient cell lines are sensitive to irofulven in vitro and in vivo.

In some embodiments, the platinum-based chemotherapeutic agent is cisplatin. In some embodiments, the alkylating chemotherapeutic agent is irofulven or a derivative thereof. As used herein, the term "irofulven" refers to the compound having the chemical structure shown in FIG. 5A. Derivatives of irofulven are described, e.g., in US Patent Application No. 10,806,708 B2, the contents of which are incorporated herein by reference in its entirety.

The efficacy of anti-cancer therapies which damage DNA, as well as agents that take advantage of DNA repair defects but do not damage DNA themselves, as well as chemotherapy, is predicted according to the NERDetect score of a cancer in a subject according to the methods described herein.

In some embodiments, efficacy of chemotherapies is predicted. Chemotherapy includes the administration of a chemotherapeutic agent. Such a chemotherapeutic agent may be, but is not limited to, those selected from among the following groups of compounds: platinum compounds, alkylating agents, cytotoxic antibiotics, antimetabolites, antimitotic agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxel; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. The foregoing examples of chemotherapeutic agents are illustrative, and are not intended to be limiting.

In some embodiments, chemotherapy comprises an alkylating agent, i.e., an alkylating chemotherapeutic agent. As used herein, the term "alkylating chemotherapeutic agent" refers to an alkylating agent having anticancer activity, and the term "alkylating agent" herein generally refers to an agent giving an alkyl group in the alkylation reaction in which a hydrogen atom of an organic compound is substituted with an alkyl group. Exemplary alkylating agents include, but are not limited to, nitrogen mustards ethylenimines and methylmelamines, alkyl sulfonates, nitrosoureas, and triazenes.

In some preferred embodiments, chemotherapy comprises a platinum-based chemotherapeutic agent. Exemplary alkylating chemotherapeutic agents include, but are not limited to cisplatin, carboplatin, dicycloplatin, eptaplatin, iproplatin, lobaplatin, miriplatin, nedaplatin, oxaliplatin, phenanthriplatin, picoplatin, satraplatin, triplatin teranitrate and any derivative thereof. In some embodiments, chemotherapy is cisplatin. Other antineoplastic platinum coordination compounds are well known in the art, can be modified according to well-known methods in the art, and include the compounds disclosed in U.S. Pat. Nos. 4,996,337, 4,946,954, 5,091,521, 5,434,256, 5,527,905, and 5,633,243, all of which are incorporated herein by reference.

In some preferred embodiments, chemotherapy comprises an agent selected from the group consisting of busulfan, carboplatin, carboquone, carmustine (BCNU), chlorambucil, cyclophosphamide, dacarbazine (DTIC; dimethyltriazenoimid-azolecarboxamide), hexamethylmelamine, ifosfamide, irofulven, lomustine, mechlorethamine, melphalan (L-sarcolysin), mitobronitol, nimustine, procarbazine, ranimustine, streptozocin (streptozotocin), temozolomide, thiotepa, trofosfamide, and any derivative thereof. In some embodiments, chemotherapy is irofulven.

Anti-cancer therapies which damage DNA to a lesser extent than chemotherapy may have efficacy in subjects determined to have a NERDetect score of at least 0.70, 0.75, 0.80, 0.85, 0.90, 0.95, or 0.99. Examples of such therapies include radiation therapy, immunotherapy, hormone therapy, and gene therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be used in such therapies.

The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In one embodiment, anti-cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Some exemplary embodiments of the disclosure are described in the following numbered embodiments.

1. A method for treating cancer in a subject, the method comprising: administering an anti-cancer treatment to a subject in need thereof, wherein the subject has a nucleotide excision repair (NER) deficiency score (NERDetect score) of at least 0.70 and the anti-cancer treatment comprises an alkylating chemotherapeutic agent.

2. The method of paragraph 1, wherein the alkylating chemotherapeutic agent is a platinum-based chemotherapeutic agent.

3. The method of paragraph 2, wherein the platinum-based chemotherapeutic agent selected from the group consisting of cisplatin, carboplatin, dicycloplatin, eptaplatin, iproplatin, lobaplatin, miriplatin, nedaplatin, oxaliplatin, phenanthriplatin, picoplatin, satraplatin, triplatin teranitrate and any derivative thereof.

4. The method of paragraph 3, wherein the platinum-based chemotherapeutic agent is cisplatin.

5. The method of paragraph 1, wherein the alkylating chemotherapeutic agent is selected from the group consisting of busulfan, carboplatin, carboquone, cannustine (BCNU), chlorambucil, cyclophosphamide, dacarbazine (DTIC; dimethyltriazenoimid-azolecarboxamide), hexamethylmelamine, ifosfamide, irofulven, lomustine, mechlorethamine, melphalan (L-sarcolysin), mitobronitol, nimustine, procarbazine, ranimustine, streptozocin (streptozotocin), temozolomide, thiotepa, trofosfamide, and any derivative thereof.

6. The method of paragraph 4, wherein the alkylating chemotherapeutic agent is irofulven.

7. The method of any one of paragraphs 1-5, wherein the cancer is selected from the group consisting of bladder cancer, breast cancer, lung cancer, ovarian cancer, thyroid cancer, pancreatic cancer, prostate cancer, uterine cancer, testicular cancer, gastric cancer, soft tissue and osteogenic sarcomas, neuroblastoma, Wim's tumor, malignant lymphoma (Hodgkin's and non-Hodgkin's lymphoma), acute myeloblastic leukemia (AML), acute lymphoblastic leukemia (ALL), Kaposi's sarcoma, Ewing's tumor, refractory multiple myeloma, colon cancer, and squamous cell carcinomas of the head, neck, cervix, melanoma, and vagina.

8. The method of any one of paragraphs 1-7, wherein the subject is a mammal.

9. The method of any one of paragraphs 1-8, wherein the subject is human.

10. The method of any one of paragraphs 1-9, wherein the method further comprises administering an additional anti-cancer treatment.

11. The method of any one of paragraphs 1-10, wherein the subject has previously received an anti-cancer treatment.

12. The method of any one of paragraphs 1-0, wherein the subject has not previously received an anti-cancer treatment.

13. The method of any one of paragraphs 1-12, wherein the method further comprises receiving results of an assay indicating the subject has a NERDetect score of at least 0.70.

14. The method of any one of paragraphs 1-12, wherein the method further comprises obtaining results of an assay indicating the subject has a NERDetect score of at least 0.70.

15. The method of any one of paragraphs 1-12, wherein the method further comprises assaying a sample from the subject to determine the NERDetect score.

16. The method of paragraph 15, wherein the sample is selected from the group consisting of: cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow.

17. The method of paragraph 15 or 16, wherein the sample is obtained before the subject has received an anti-cancer treatment.

18. The method of paragraph 15 or 16, wherein the sample is obtained after the subject has received an anti-cancer treatment.

19. The method of any one of paragraphs 15-17, wherein the assay comprises detecting one or more of an indel signature ID8, an indel signature ID2, an indel signature ID10, a total number of 1-50 base pair deletions, a number of mutations associated with a signature of single base substitutions (SBS) signature 5 (COSIMIC signature 5 or Signature 5*), a number of mutations associated with a signature of single base substitutions signature 2 (SBS2), a number doublet base substitutions (DBS) signature 4 (DBS4), a transcriptional strand bias of one or more mutations, or any combination thereof.

20. The method of any one of paragraphs 15-19, wherein the assay comprises a step of extracting a nucleic acid from the sample.

21. The method of any one of paragraphs 15-20, wherein the assay comprises one or more of whole genome sequencing, in situ hybridization, single nucleotide polymorphism (SNP) array, transcriptional arrays, array comparative genomic hybridization (aCGH), Southern blotting, molecular inversion probe (MIP)

22. The method any one of paragraphs 15-20, wherein the assay comprises next generation (NGS) sequencing.

23. A method of selecting a subject for anti-cancer treatment, the method comprising: determining or obtaining a NERDetect score for the subject and selecting the subject having a NERDetect score of at least 0.70 for anti-cancer treatment.

24. A method of predicting a response to anti-cancer treatment in a subject, the method comprising determining or obtaining a NERDetect score for the subject and a NERDetect score of at least 0.70 indicates the subject is responsive to the anti-cancer treatment.

25. The method of paragraph 23 or 24, wherein the anti-cancer treatment is a chemotherapeutic agent.

26. The method of paragraph 23 or 24, wherein the anti-cancer treatment is an alkylating chemotherapeutic agent.

27. The method of paragraph 26, wherein the alkylating chemotherapeutic agent is a platinum-based chemotherapeutic agent.

28. The method of paragraph 27, wherein the platinum-based chemotherapeutic agent selected from the group consisting of cisplatin, carboplatin, dicycloplatin, eptaplatin, iproplatin, lobaplatin, miriplatin, nedaplatin, oxaliplatin, phenanthriplatin, picoplatin, satraplatin, triplatin teranitrate and any derivative thereof.

29. The method of paragraph 28, wherein the platinum-based chemotherapeutic agent is cisplatin.

30. The method of paragraph 26, wherein the alkylating chemotherapeutic agent is selected from the group consisting of busulfan, carboplatin, carboquone, carmustine (BCNU), chlorambucil, cyclophosphamide, dacarbazine (DTIC; dimethyltriazenoimid-azolecarboxamide), hexamethylmelamine, ifosfamide, irofulven, lomustine, mechlorethamine, melphalan (L-sarcolysin), mitobronitol, nimustine, procarbazine, ranimustine, streptozocin (streptozotocin), temozolomide, thiotepa, trofosfamide, and any derivative thereof.

31. The method of paragraph 30, wherein the alkylating chemotherapeutic agent is irofulven.

32. The method of paragraph 23 or 24, wherein the subject has or is suspected of having cancer.

33. The method of paragraph 32, wherein the cancer is selected from the group consisting of: bladder cancer, breast cancer, lung cancer, ovarian cancer, thyroid cancer, pancreatic cancer, prostate cancer, uterine cancer, testicular cancer, gastric cancer, soft tissue and osteogenic sarcoma, neuroblastoma, Wim's tumor, malignant lymphoma (Hodgkin's and non-Hodgkin's lymphoma), acute myeloblastic leukemia (AML), acute lymphoblastic leukemia (ALL), Kaposi's sarcoma, Ewing's tumor, refractory multiple myeloma, colon cancer, and squamous cell carcinomas of the head, neck, cervix, melanoma, and vagina.

34. The method of paragraph 23 or 24, wherein the subject is a mammal.

35. The method of paragraph 34, wherein the subject is human.

36. The method of paragraph 23 or 24, wherein the subject has previously received an anti-cancer treatment.

37. The method of paragraph 23 or 24, wherein the subject has not previously received an anti-cancer treatment.

38. The method of paragraph 23 or 24, wherein the method comprises receiving results of an assay indicating the subject has a NERDetect score of at least 0.70.

39. The method of paragraph 23 or 24, wherein the method comprises obtaining results of an assay indicating the subject has a NERDetect score of at least 0.70.

40. The method of paragraph 23 or 24, wherein the method further comprises assaying a sample from the subject to determine the NERDetect score.

41. The method of paragraph 40, wherein the sample is selected from the group consisting of: cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow.

42. The method of paragraph 40 or 41, wherein the sample is obtained before the subject has received an anti-cancer treatment.

43. The method of any one of paragraphs 40-42, wherein the sample is obtained after the subject has received an anti-cancer treatment.

44. The method of paragraph 40, wherein the assay comprises a step of extracting nucleic acid from the sample.

45. The method of paragraph 40, wherein the assay comprises one or more of whole genome sequencing, in situ hybridization, single nucleotide polymorphism (SNP) array, transcriptional arrays, array comparative genomic hybridization (aCGH), Southern blotting, molecular inversion probe (MIP)

46. The method of paragraph 40, wherein the assay comprises next generation (NGS) sequencing.

47. The method of paragraph 40 or 41, wherein the assay comprises detecting one or more of an indel signature ID8, an indel signature ID2, an indel signature ID10, a total number of 1-50 base pair deletions, a number of mutations associated with a signature of single base substitutions (SBS) signature 5 (COSIMIC signature 5 or Signature 5*), a number of mutations associated with a signature of single base substitutions signature 2 (SBS2), a number doublet base substitutions (DBS) signature 4 (DBS4), a transcriptional strand bias of one or more mutations, or any combination thereof.

Some Selected Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "cancer" refers to a hyperproliferation of cells that exhibit a loss of normal cellular control that results in unregulated growth, lack of differentiation, local tissue invasion, and metastasis. The methods provided herein are mainly directed at the treatment of solid tumors formed by cancer cells. These include carcinomas, sarcomas, lymphomas and myelomas, and bladder cancers. Leukemias, or cancers of blood cells, do not form solid tumors.

As used herein, the term "gene" refers to a region of genomic DNA associated with a given gene. For example, the region can be defined by a particular gene (such as protein coding sequence exons, intervening introns and associated expression control sequences) and its flanking sequence.

As used herein the term "chemotherapeutic agent" refers to any chemical or biological agent with therapeutic usefulness in the treatment of diseases characterized by abnormal cell growth by inhibiting a cellular activity upon which the cancer cell depends for continued survival and/or proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, 1131, 1125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

The term "sample" or "test sample" as used herein denotes a sample taken or isolated from a biological organism, e.g., a blood or plasma sample from a subject. In some embodiments of any of the aspects, the subject is the same subject to be treated, e.g., to be administered an anti-cancer therapy provided herein. In some embodiments of any of the aspects, the present invention encompasses several examples of a biological sample. In some embodiments of any of the aspects, cancer cells can be in a sample or isolated from a sample.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA.

As used herein, the term "administering," refers to the placement of an agent, anti-cancer treatment, or chemotherapeutic provided herein into a subject by a method or route which results in at least partial delivery of the agent at a desired site.

The terms "decrease", "reduced", "reduction", "to a lesser extent," or "inhibit" are all used herein to mean a decrease or lessening of a property, level, or other parameter by a statistically significant amount. In some embodiments, "reduced," "reduction," "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase," "increases," or "enhance" or "activate" or "to a greater extent" are all used herein to generally mean an increase of a property, level, or other parameter by a statistically significant amount; for the avoidance of any doubt, the terms "increased", "increase," "to a greater extent," "enhance" or "activate" can refer to an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, a "reference level" refers to the level of a marker or parameter in a normal, otherwise unaffected cell population or tissue (e.g., a cell, tissue, or biological sample obtained from a healthy subject, or a biological sample obtained from the subject at a prior time point, e.g., cell, tissue, or a biological sample obtained from a patient prior to being diagnosed with cancer).

As used herein, an "appropriate control" refers to an untreated, otherwise identical cell, subject, organism, or population (e.g., a cell, tissue, or biological sample that was not contacted by an agent or composition described herein) relative to a cell, tissue, biological sample, or population contacted or treated with a given treatment.

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Other embodiments of the present invention are described in the following Examples. The present invention is further illustrated by the following examples which should not be construed as further limiting.

EXAMPLES

Example 1: A Composite Mutational Signature of Nucleotide Excision Repair (NER) Deficiency Identifies Urothelial Tumors with Sensitivity to Ner-Targeted Agents Including Irofulven Cisplatin-based chemotherapy is a first-line treatment for muscle-invasive and metastatic urothelial cancer of the bladder, but only a subset of patients respond to therapy. Approximately 15% of bladder tumors have a somatic missense mutation in the nucleotide excision repair (NER) gene ERCC2, which confers increased sensitivity to cisplatin-based chemotherapy. However, reliable biomarkers beyond ERCC2 have not been identified.

Here, the inventors have developed and validated NER-Detect, a composite mutational signature of NER deficiency that is not only strongly correlated with ERCC2 mutation status, but is also associated with cisplatin response independent of ERCC2 status. The inventors show that NER gene inactivation is sufficient to drive the NERDetect mutational signature and also induces profound sensitivity to irofulven, an alkylating agent previously shown to have only modest activity in Phase I/II trials in biomarker-unselected populations. Together, these data provide a tool for identifying NER deficiency and platinum sensitivity in clinical samples and define a novel synthetic lethal relationship between NER deficiency and irofulven that may broaden therapy options for patients with bladder cancer.

Therapeutic approaches based on the principle of synthetic lethality are an attractive strategy for cancer treatment. Since DNA repair pathway aberrations are common in tumor cells but are largely absent in normal cells, agents that target DNA repair deficient cells may have a clinically exploitable therapeutic window. A successful example stemming from this principle is the development of PARP inhibitors for treatment of tumors with homologous recombination (HR) repair deficiency[1,2].

Nucleotide excision repair (NER) is a highly conserved DNA repair pathway that recognizes and repairs bulky intrastrand DNA adducts formed by genotoxic agents such as ultraviolet (UV) radiation and platinum chemotherapies[3]. NER is initiated through two separate branches of lesion recognition: transcription coupled repair (TC-NER) is activated by RNA polymerase stalling at lesions in transcribed regions while global genome repair (GG-NER) is able to recognize lesions throughout the genome. Following lesion recognition, TC-NER and GG-NER converge on a common NER pathway that excises and replaces the damaged DNA strand in an error-free manner.

Recently, sequencing and functional studies have revealed that NER pathway deficiency is present in a subset of tumors. Somatic missense mutations in ERCC2, a key NER gene that encodes the DNA helicase XPD, are present in approximately 10% of muscle-invasive bladder tumors (4). Although not strongly prognostic in patients treated without chemotherapy, ERCC2 mutations confer increased sensitivity to platinum-based chemotherapy (5-7), and mutations in ERCC2 and several other DNA repair genes (such as ATM, FANCC, and BRCA1/2) are being used as predictive biomarkers in several on-going clinical trials (8-10). Mutations in NER genes beyond ERCC2 also occur sporadically in bladder cancer and other tumor types, and it is possible that these events may also confer a therapeutically exploitable NER deficiency.

Cisplatin-based chemotherapy is a first-line treatment for muscle-invasive and metastatic urothelial cancer. Although 60-70% of patients have an initial response, resistance develops in the majority of patients (11). In addition, nearly half of all patients with urothelial cancer are ineligible for cisplatin-based chemotherapy due to medical comorbidities (12). Anti-PD1/PD-L1 agents are approved for cisplatin-ineligible or cisplatin-resistant patients; however, only ~20-30% of patients respond (13). Therefore, novel agents with activity in post-cisplatin and cisplatin-ineligible patient populations are needed.

Irofulven is a semi-synthetic DNA alkylating agent that is a derivative of the fungal product Illudin S (14). Irofulven-mediated DNA damage is not recognized by mismatch repair (MMR) or GG-NER, but instead activates TC-NER when the damage is encountered by RNA polymerase. Therefore, irofulven has been shown to have ~100-fold increased cytotoxic activity in non-tumor cell lines with a TC-NER or common NER pathway gene defect compared to the isogenic NER proficient line (15,16). Although well-tolerated, irofulven showed only modest clinical benefit as a single agent in Phase I/II clinical trials across a variety of tumor types (17-20). This apparent lack of efficacy may have occurred because NER deficiency is present in only a fraction of tumors, and these trials were conducted in biomarker-unselected populations.

Despite the potential clinical actionability of tumor NER deficiency, there are currently no functional or immunohistochemical (IHC) assays available to reliably identify NER deficiency from clinical specimens. An alternative approach to identify tumor NER deficiency is through the use of next-generation sequencing (NGS)-based mutational signatures. Because DNA repair deficiency is frequently associated with specific mutational patterns (signatures), the presence of a mutational signature can indicate a specific DNA repair deficiency, even in the absence of an obvious DNA repair gene alteration[9,10]. Such a strategy has been successfully employed to identify HR deficient cancer cases for the prioritization of PARP inhibitor and platinum-based therapy in breast and ovarian cancer[11,12]. For NER, a specific single nucleotide variation-based (SNV-based) mutation signature (signature 5*) has been associated with ERCC2 mutations in bladder tumors[10], but the signature was not independently associated with platinum response in tumors lacking an ERCC2 mutation.

To improve diagnostic utility, SNV signatures can be combined with other non-SNV based mutational features (such as short insertions/deletions [indels] or chromosomal rearrangements). These "composite" signatures may represent a more accurate measure of DNA repair deficiency, as has been demonstrated for HR deficiency[13]. The "HRDetect" composite signature combines six individual mutational features and was found to more accurately identify HR deficient tumors than any of the mutational features alone[13].

Accurate determination of tumor NER deficiency may become even more clinically relevant if therapeutic agents that specifically target NER deficient cancer cells are identified. Irofulven is an alkylating agent that demonstrates approximately 100-fold increased cytotoxic activity in non-tumor cell lines with a TC-NER or common NER pathway gene defect compared to the isogenic NER proficient line[14, 15]. Although well-tolerated, irofulven showed only modest clinical benefit as a single agent in Phase I/II clinical trials[16,17] However, this apparent lack of clinical efficacy may have occurred because the trials were not enriched for NER deficient cases due to an inability to prospectively predict tumor NER status. Therefore, a diagnostic mutational signature of NER deficiency could serve as a companion diagnostic for NER-targeting therapies such as irofulven. Here, the inventors derive and validate a composite mutational signature of NER deficiency in bladder cancer that is strongly associated with ERCC2 mutational status and also correlates with clinical response to platinum-based therapy in cases that lack an ERCC2 mutation.

Furthermore, the inventors have identified a novel synthetic lethal relationship between NER deficiency and irofulven sensitivity. The inventors show that inactivating mutations in genes of the TC-NER or common NER pathways are sufficient to drive irofulven sensitivity in vitro and in vivo, and the inventors demonstrate that acquired cisplatin resistance does not induce cross-resistance to irofulven. Finally, the inventors have defined a composite mutational signature of ERCC2 deficiency in bladder cancer that is strongly associated with cisplatin sensitivity, including in cases that lack an ERCC2 mutation. This mutational signature is therefore a useful tool to predict sensitivity to NER-targeting agents such as cisplatin and irofulven.

Materials and Methods

Patient Cohorts

In this study 632 whole genome (WGS) and whole exome sequenced (WES) pre-treatment samples were analyzed from four urothelial bladder tumor cohorts (Table 2).

TABLE 2

Summary of analyzer WGS and WES cohorts.

| Cohort | Sequencing type | Number of samples | Tissue source | Type | Therapy |
|---|---|---|---|---|---|
| TCGA | WGS | 23 | FF | MIBC | H |
| TCGA | WES | 412 | FF | MIBC | H |
| DFCI/MSKCC | WES | 50 | FF | MIBC | NACC |
| BGI | WES | 99 | FF | MIBC (62) NMIBC (37) | H |
| Philadelphia | WES | 48 | FFPE | MIBC | NACC |

Abbreviations:
FF—fresh frozen;
FFPE—formalin-fixed paraffin-embedded;
MIBC—muscle-invasive bladder cancer;
NMIBC—non-muscle-invasive bladder cancer;
NACC—neoadjuvant cisplatin-based chemotherapy;
H—heterogeneous therapy.

1. TCGA Cohort

The WGS normal and tumor bam files were downloaded from the ICGC data portal available on the world wide web at https://<dcc.icgc.org/>. The WES normal and tumor bam files, as well as the vcf files generated by MuTect2 were downloaded from the TCGA data portal available on the world wide web at https://<portal.gdc.cancer.gov/>.

2. DFCI/MSKCC and Philadelphia Cohorts

The normal and tumor bam files were downloaded from The database of Genotypes and Phenotypes (dbGaP) upon request (available on the world wide web at https://<www.ncbi.nlm.nih.gov/gap>) using the phs000771 accession code.

3. BGI Cohort

The normal and tumor fastq files were downloaded from the Sequence Read Archive (SRA) database (available on the world wide web at https://<www.ncbi.nlm.nih.gov/sra>) using the SRA063495 accession code. The details of the alignment process are described in Example 2.

The average coverage of the analyzed WGS and WES samples in each cohort is shown in FIGS. 7A-7B and FIGS. 8A-8C.

Mutation, Copy Number, and Structural Variant Calling

Germline variants were called with HaplotypeCaller in key NER-related genes, while somatic point mutations and indels were called with MuTect2 (GATK, v3.8). Germline and somatic mutations in key NER-related genes in each cohort are presented in FIGS. 9-16. The high fidelity of the reported variants was ensured by the application of additional hard filters in addition to the tools' default filters (Table 3 and Table 4).

TABLE 3

Additional germline mutation filtering
parameters applied in the cohorts.

| Cohort | TCGA WGS | TCGA WES | DFCI WES | MSKCC WES | BGI WES | Philadelphia WES |
|---|---|---|---|---|---|---|
| MQ | ≥50 | ≥50 | ≥30 | ≥30 | ≥30 | ≥30 |
| QUAL | ≥20 | ≥20 | ≥10 | ≥10 | ≥10 | ≥10 |
| DP | ≥15 | ≥15 | ≥15 | ≥15 | ≥10 | ≥10 |

TABLE 4

Additional somatic mutation filtering parameters applied in the cohorts.

| Cohort | TCGA WGS | TCGA WES | DFCI WES | MSKCC WES | BGI WES | Philadelphia WES |
|---|---|---|---|---|---|---|
| TLOD | ≥6 | ≥5 | ≥5 | ≥5 | ≥3 | ≥5 |
| NLOD | ≥3 | ≥5 | ≥5 | ≥5 | ≥3 | ≥5 |
| NORMAL.DEPTH | ≥15 | ≥10 | ≥10 | ≥15 | ≥10 | ≥10 |
| TUMOR.DEPTH | ≥20 | ≥10 | ≥15 | ≥20 | ≥10 | ≥10 |
| TUMOR.ALT | ≥5 | ≥5 | ≥5 | ≥5 | ≥3 | ≥5 |
| NORMAL.ALT | 0 | 0 | 0 | 0 | 0 | 0 |
| TUMOR.AF | ≥0.05 | ≥0.03 | ≥0.03 | ≥0.03 | ≥0.03 | ≥0.05 |

Figure 19A:
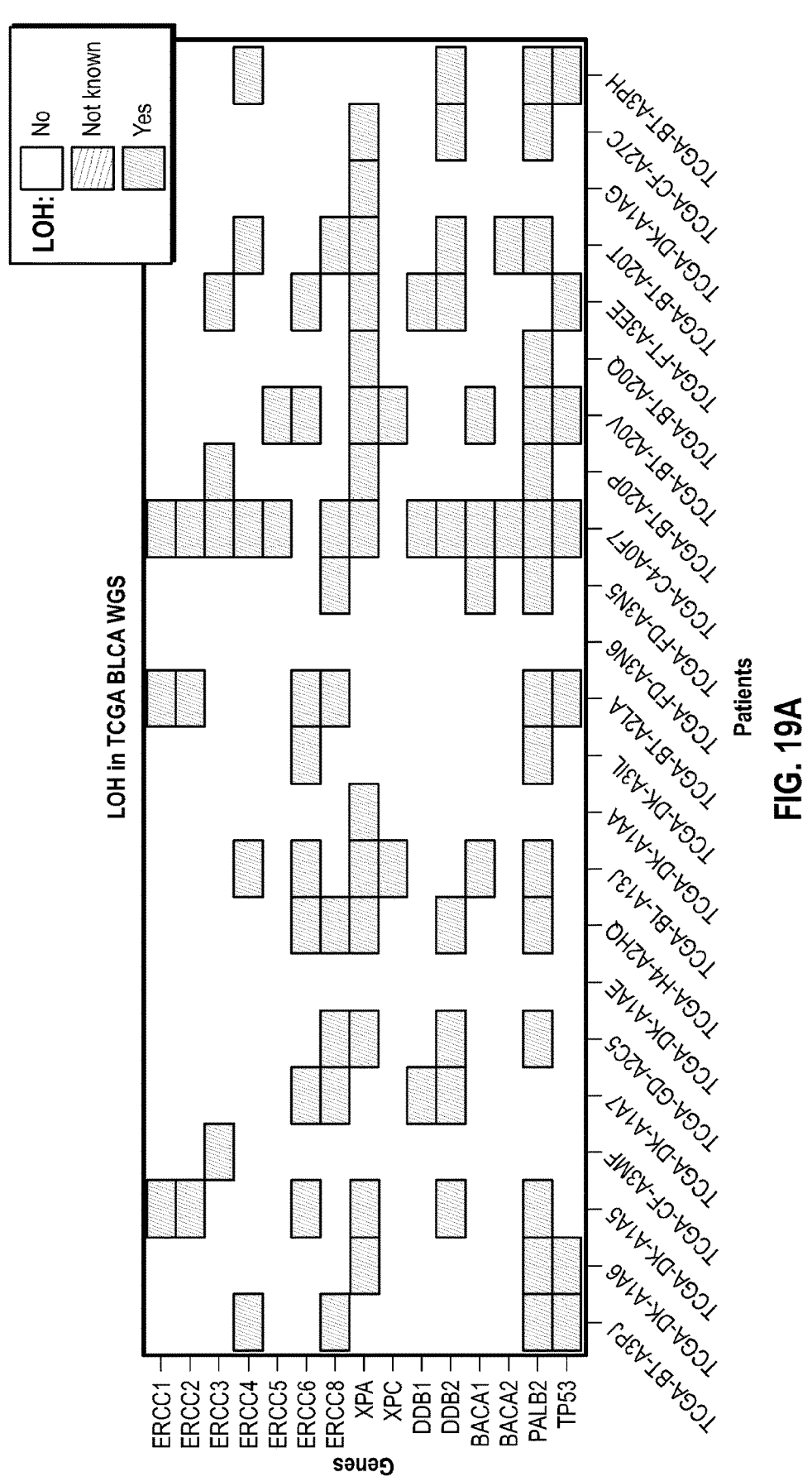
FIGS. 19A-19C show the estimated occurrence of LOH events in NER-related genes in the TCGA WGS (FIG. 19A), DFCI/MSKCC (FIG. 19B) and Philadelphia (FIG. 19C) WES cohorts.
Figure 19B:
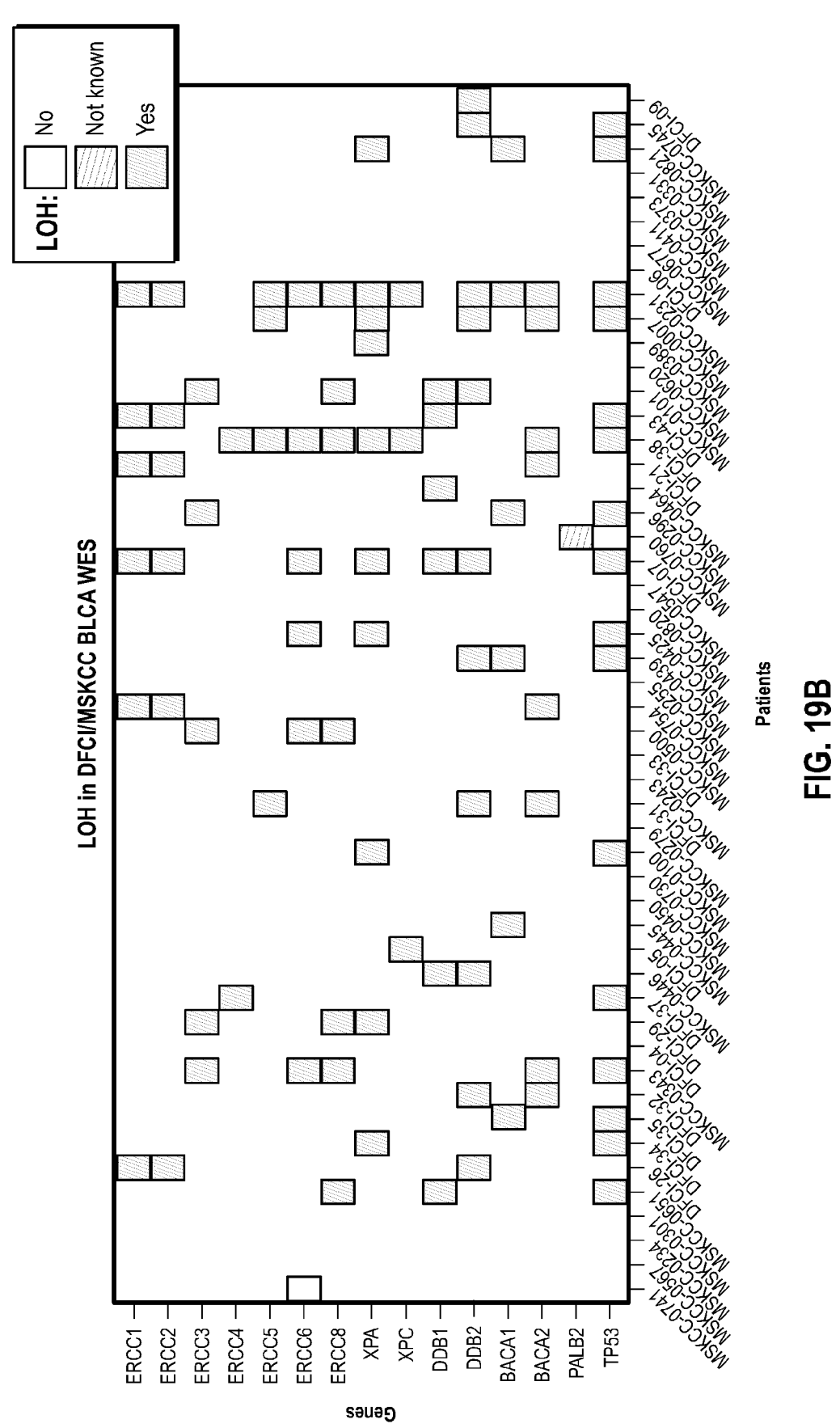
Figure 19C:
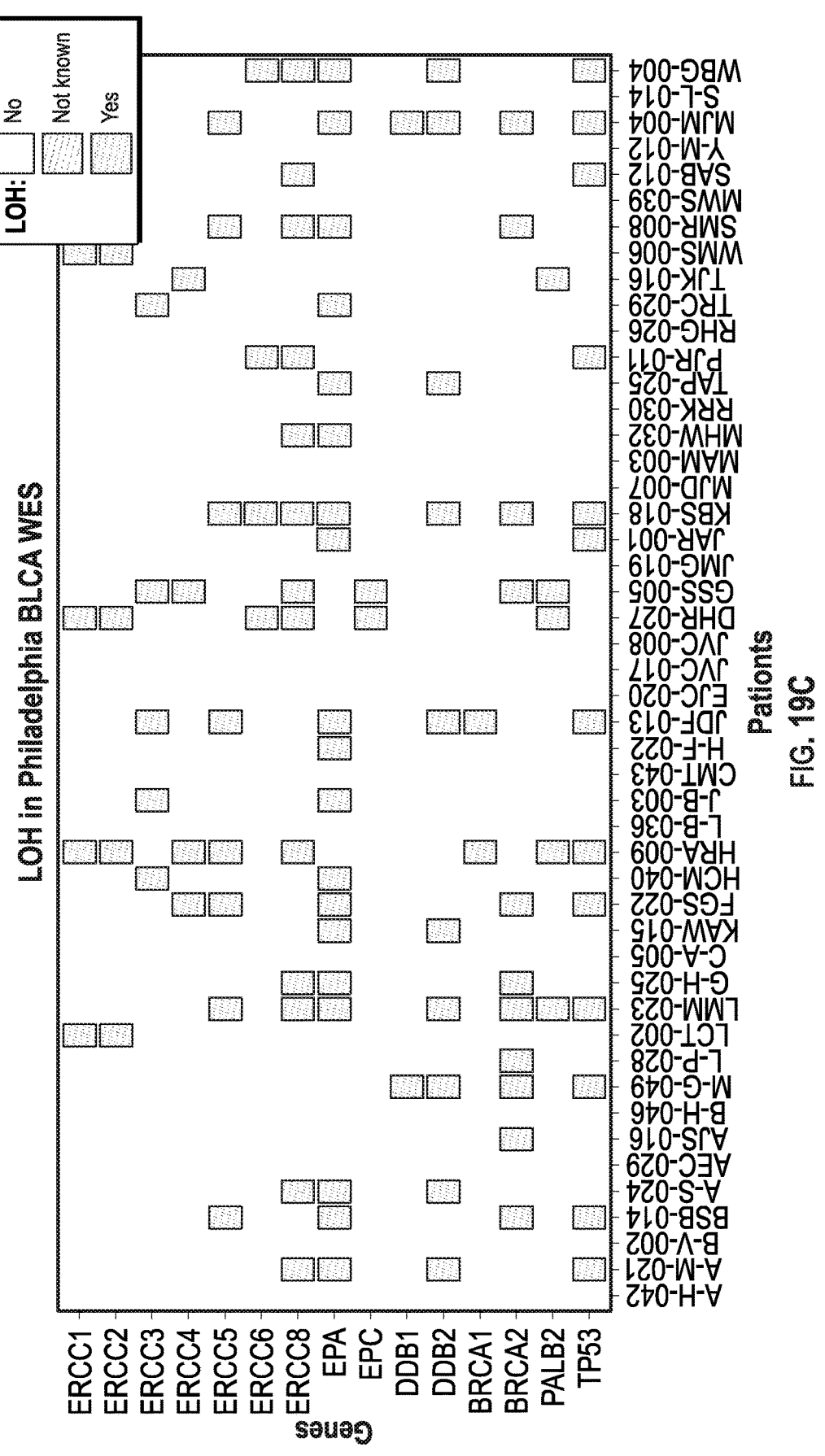
Figure 20:
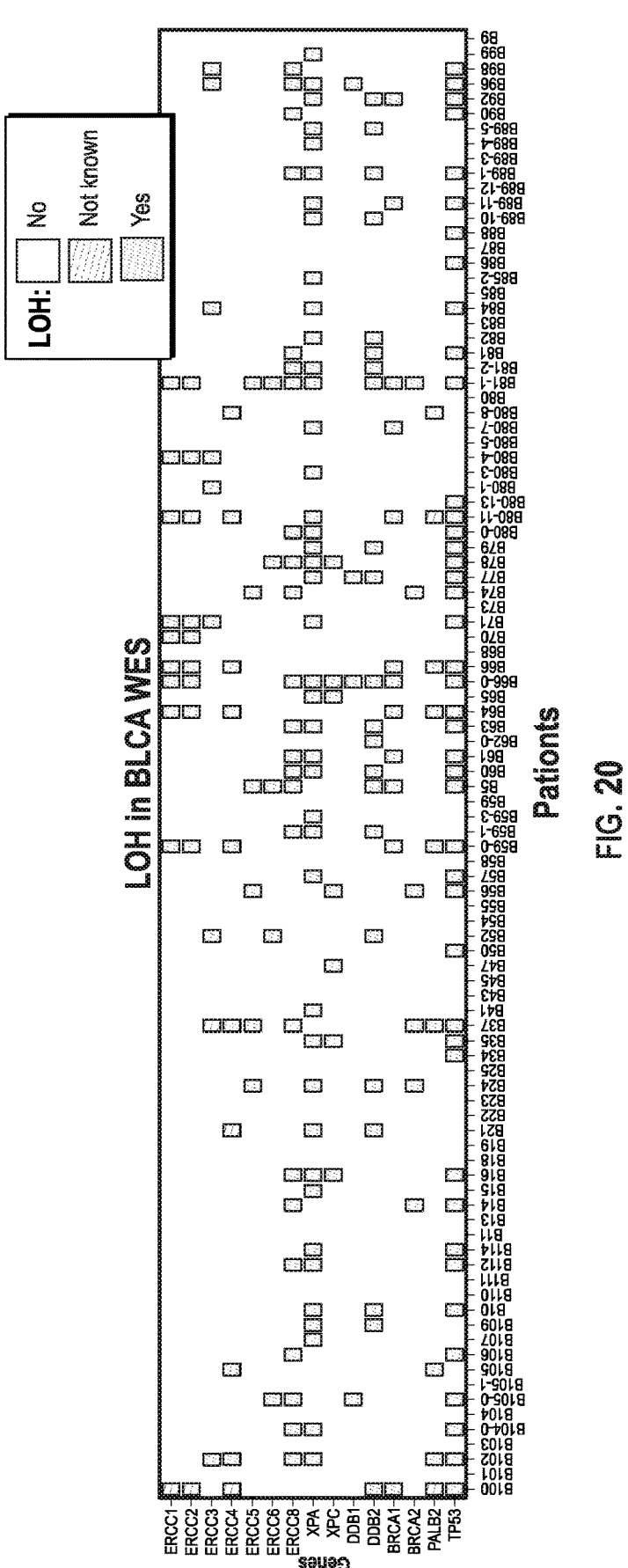
FIG. 20 shows (Top panel) the estimated occurrence of LOH events in NER-related genes in the BGI WES cohort. (Bottom panel): The estimated occurrence of LOH events in NER-related genes in the TCGA WES cohort.
Figure 20:
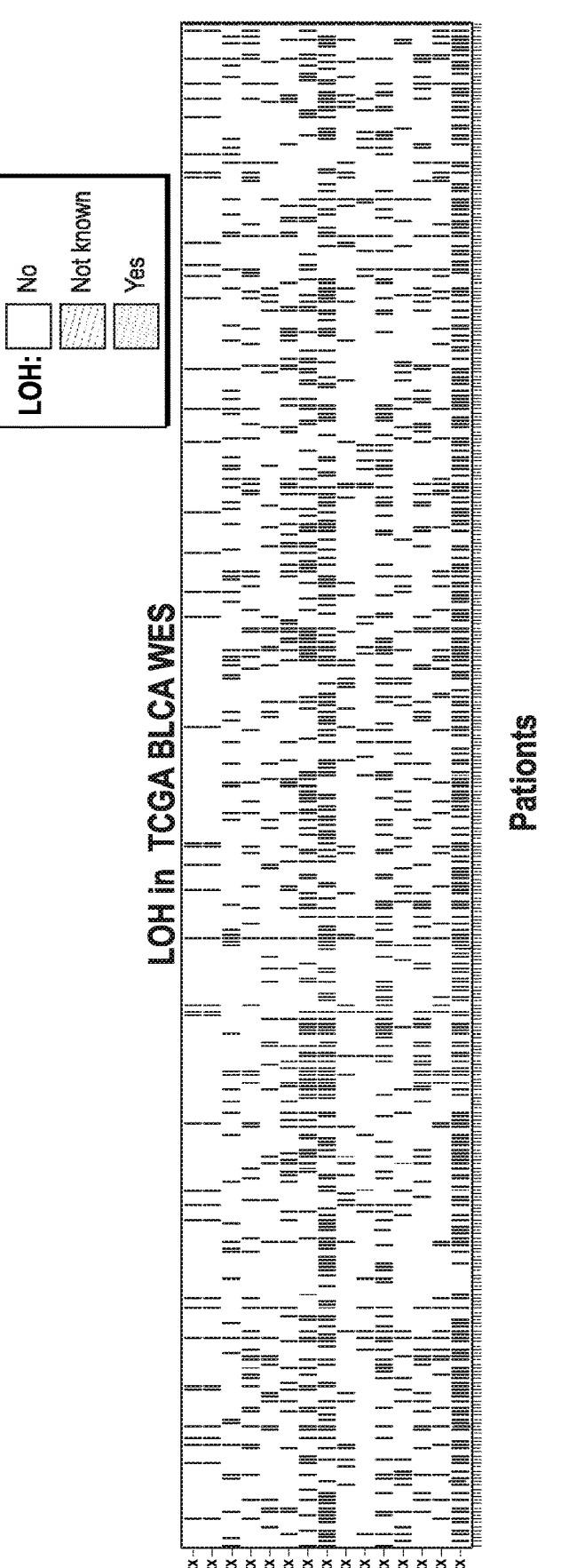
Figure 21A:
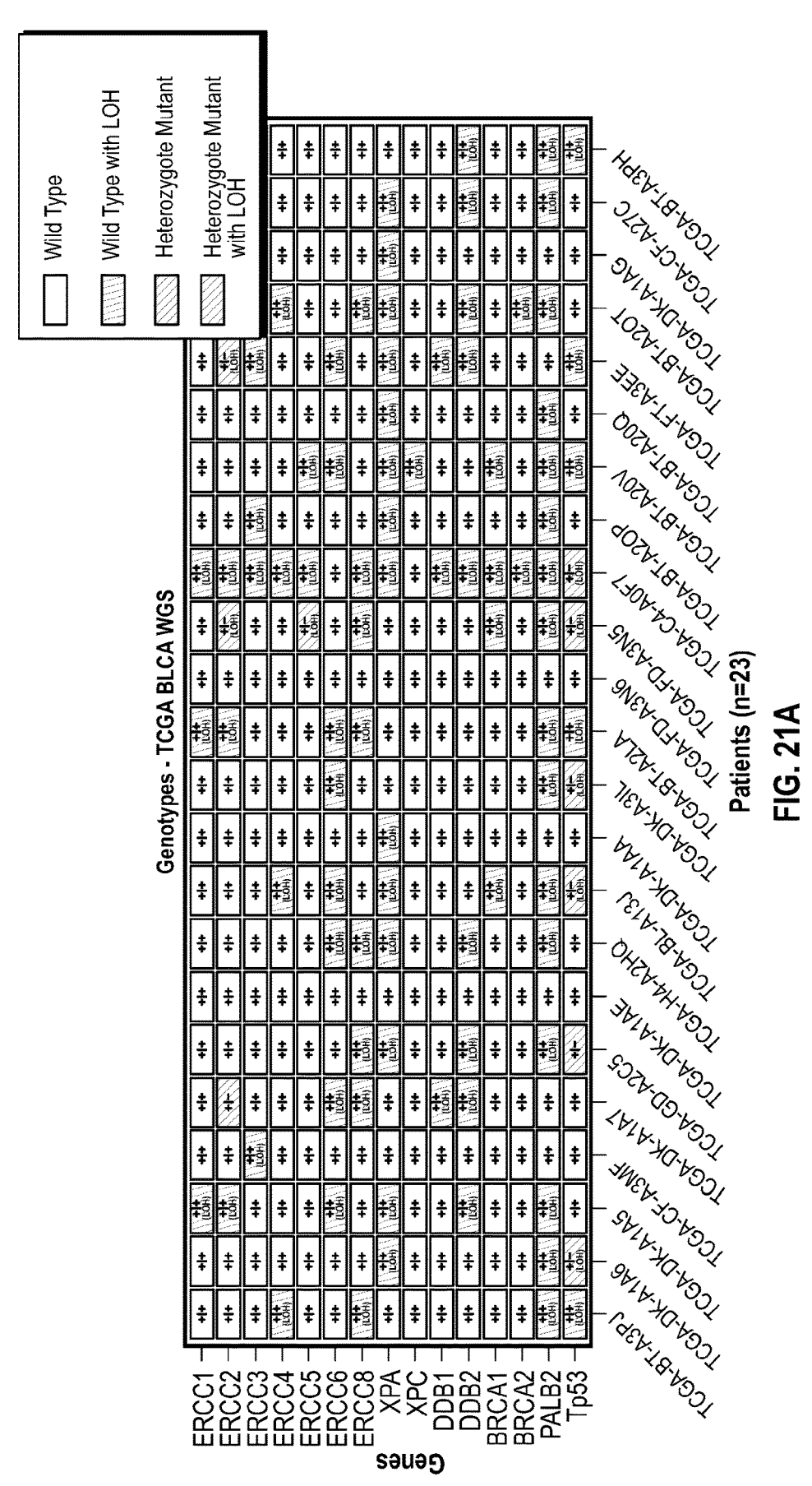
FIGS. 21A-21C show final genotypes of the patients in the TCGA WGS (FIG. 21A), DFCI/MSKCC (FIG. 21B) and Philadelphia WES (FIG. 21C) cohorts.
Figure 21B:
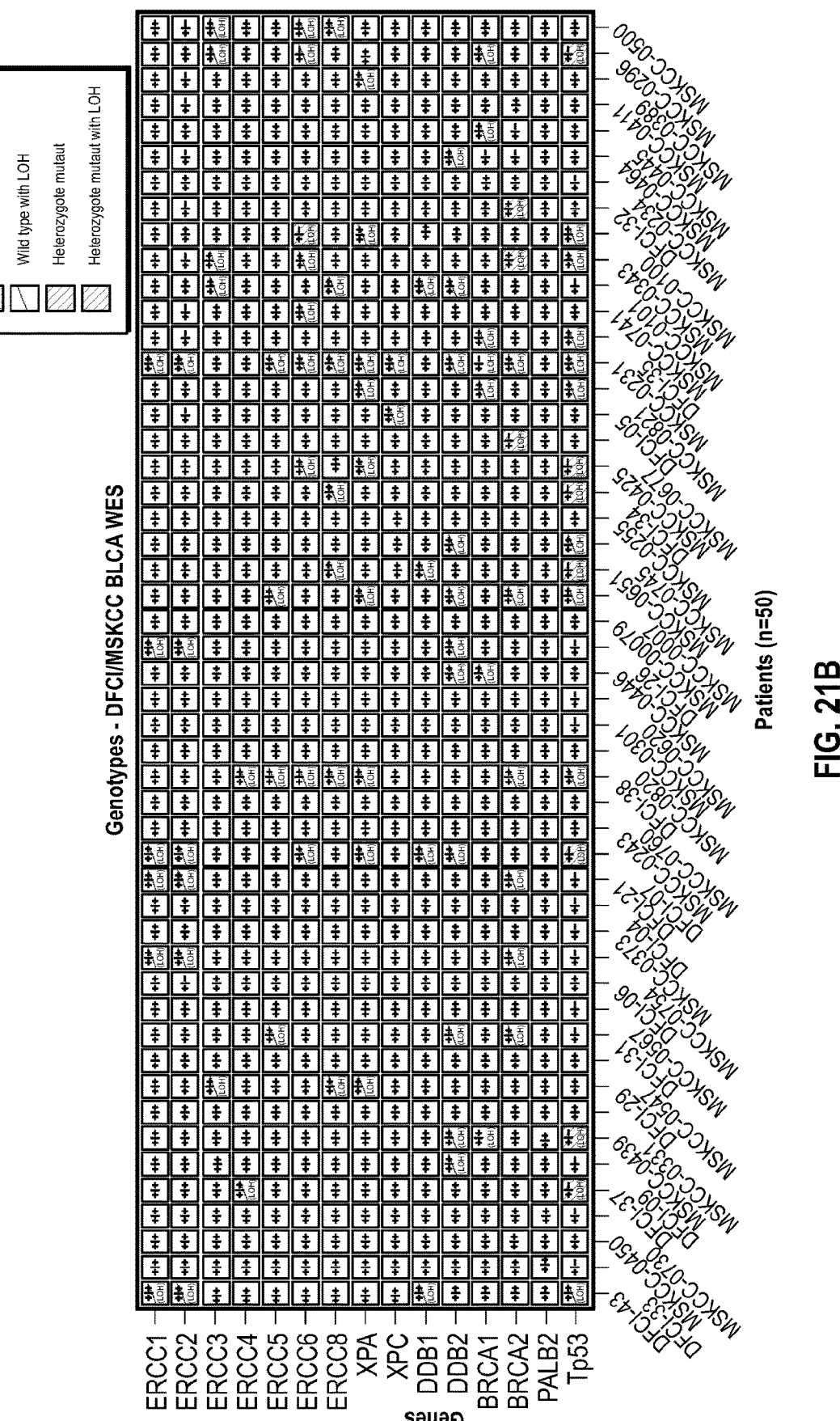
Figure 21C:
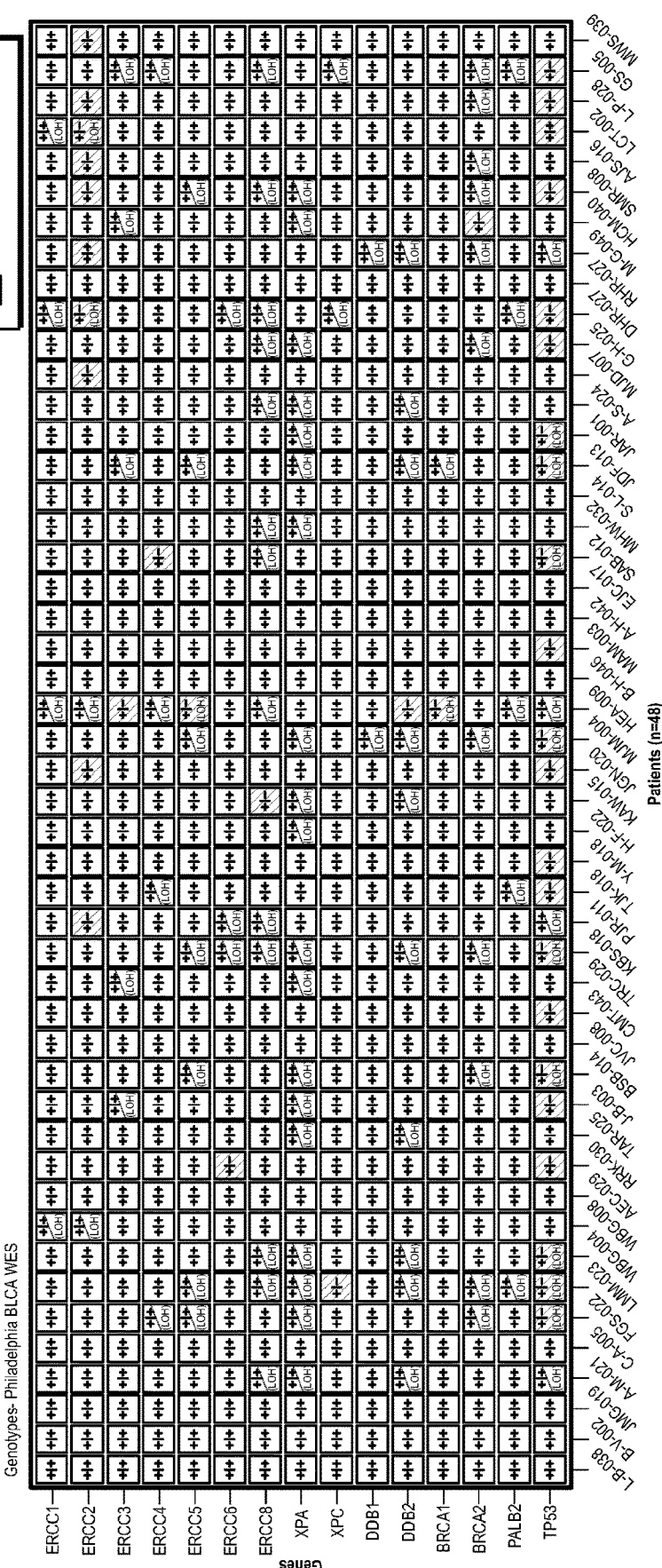
Figure 22:
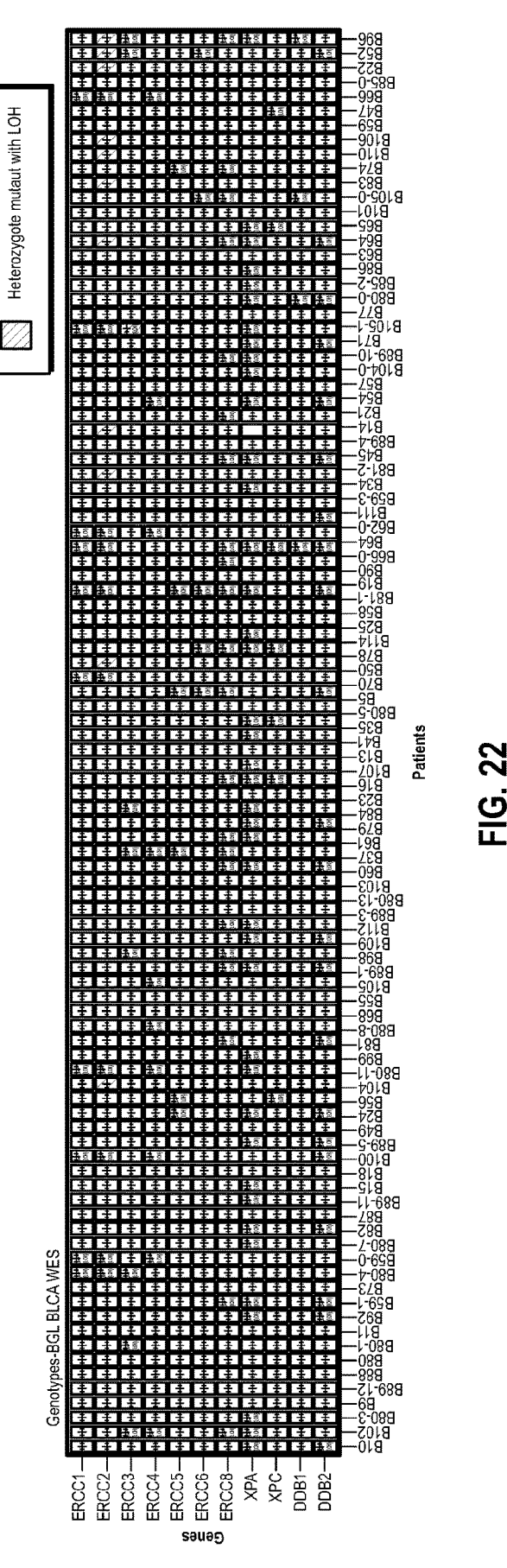
FIG. 22 shows final genotypes of the patients in the BGI WES cohort (TOP) and final genotypes of the patients in the TCGA WES cohort (Bottom).
Figure 22:
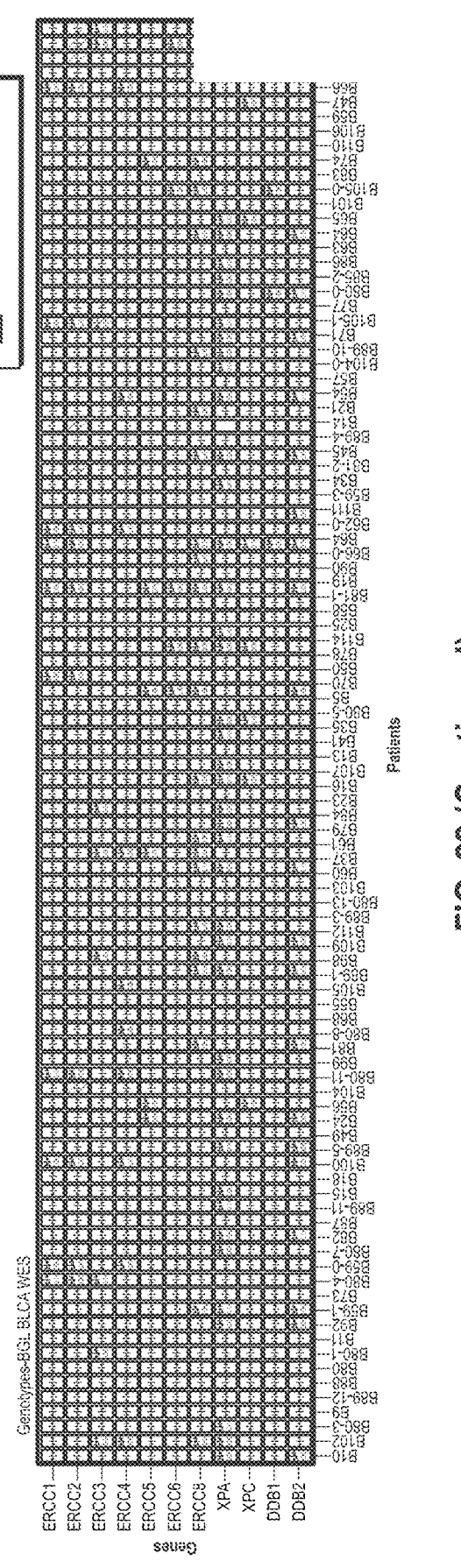
Figure 23A:
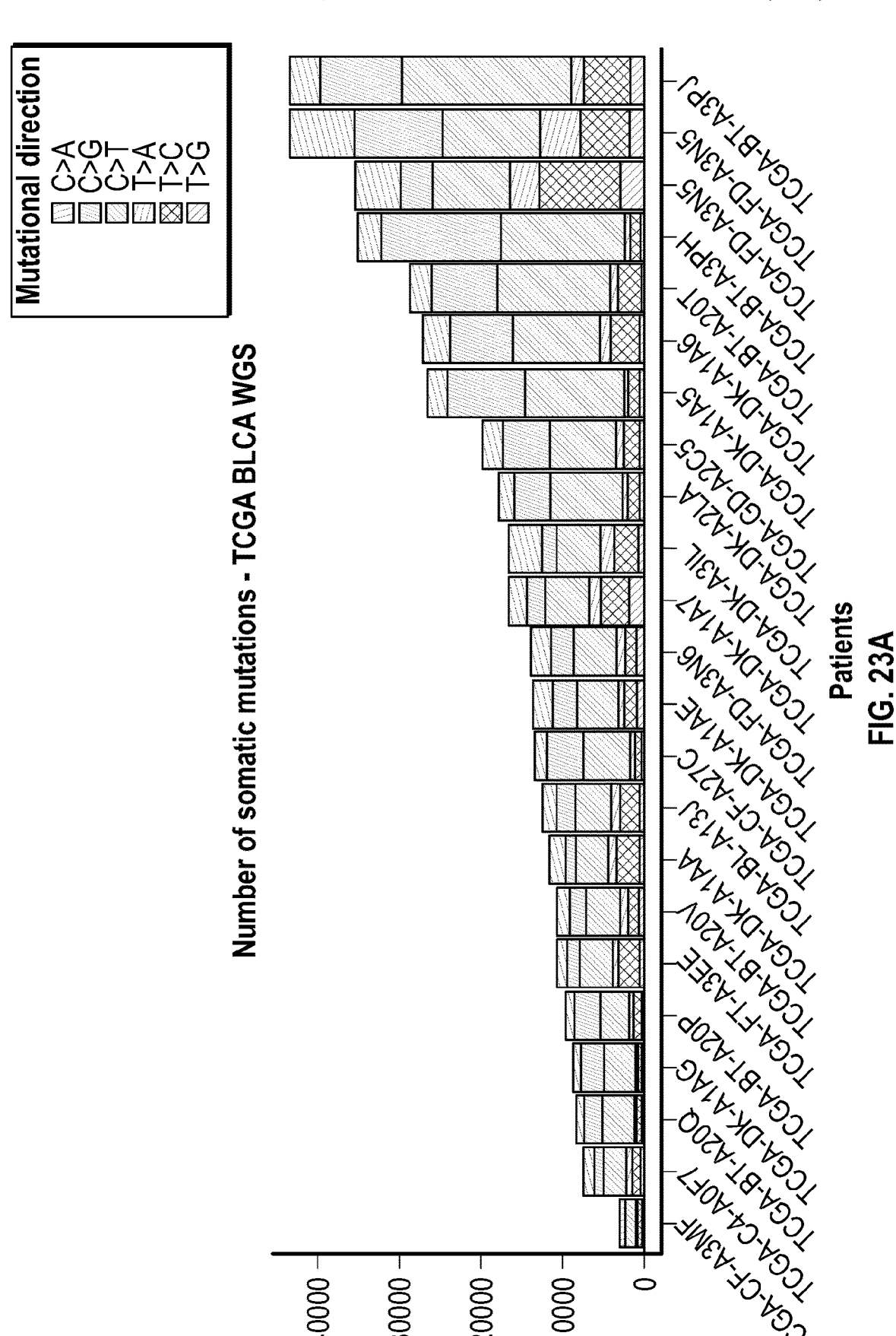
FIGS. 23A and 23C show the number of single base substitutions and the extracted single base substitution signatures in the TCGA BLCA WGS cohort.
Figure 23A:
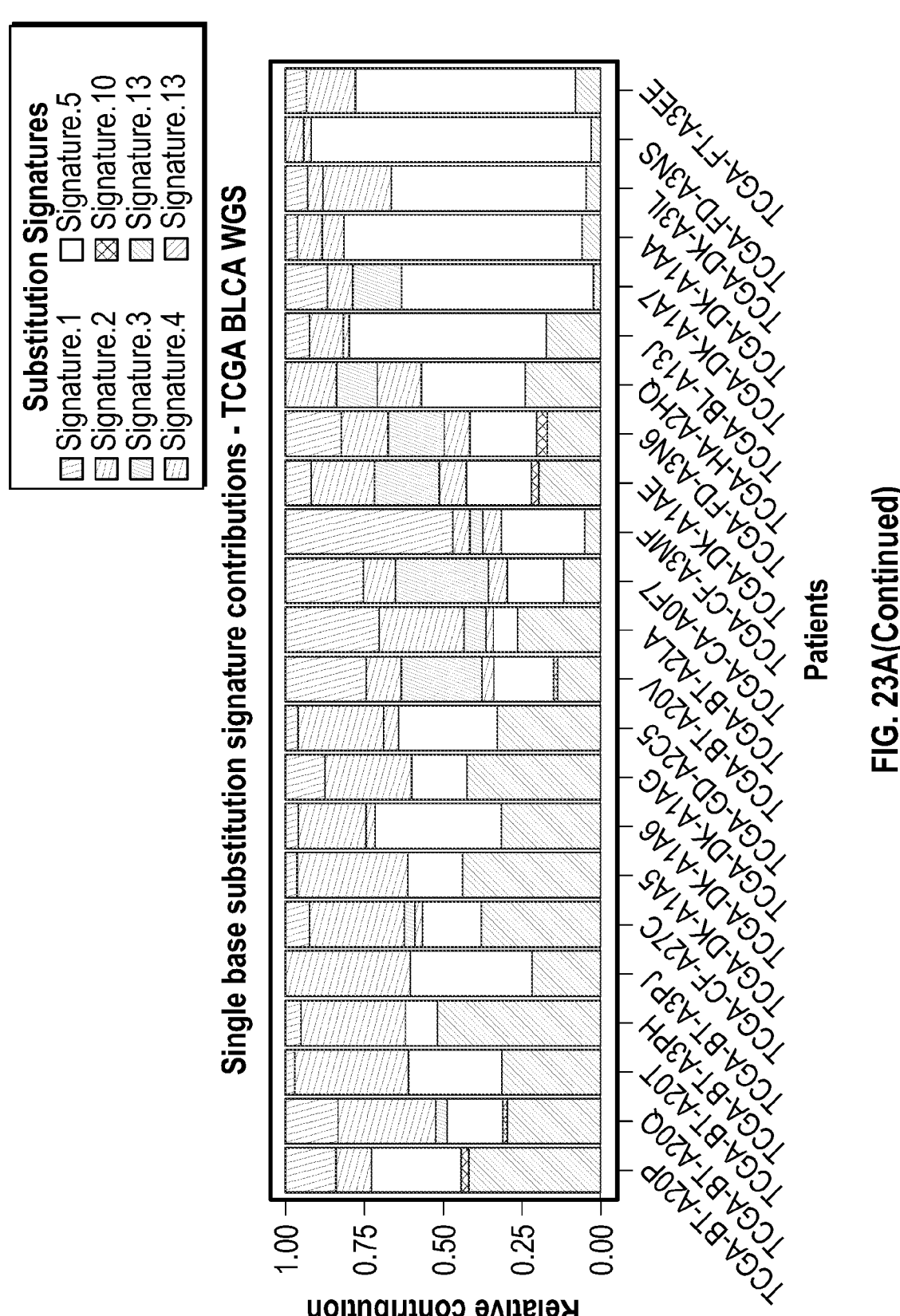
Figure 23B:
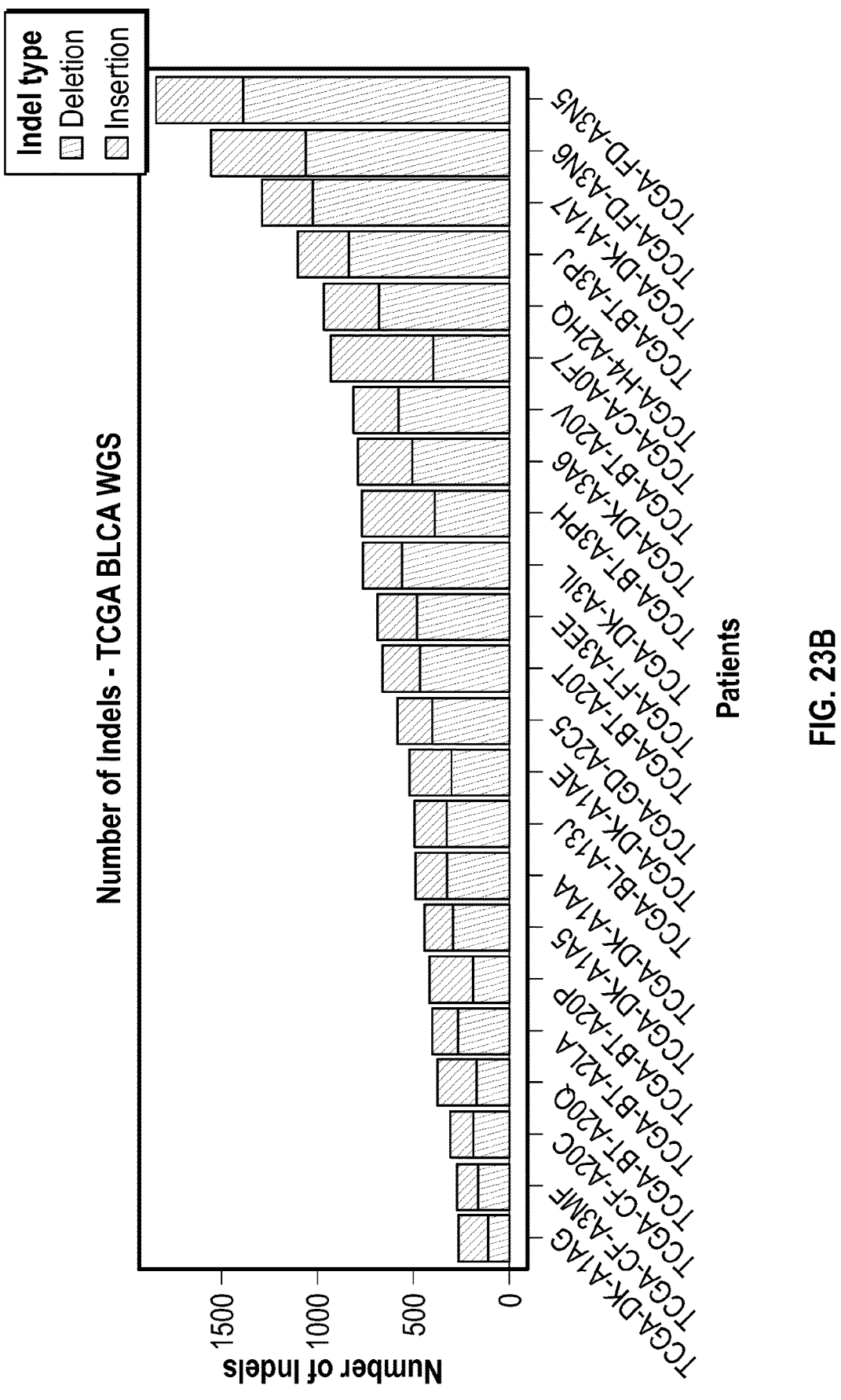
FIG. 23B and FIG. 23D show the number of indels and the extracted indel signatures in the TCGA BLCA WGS cohort. ERCC2 somatic mutants (TCGA-FT-A3EE, TCGA-DK-A1A7, TCGA-FD-A3N5) have elevated Signature 5 and ID8 contributions.
Figure 23B:
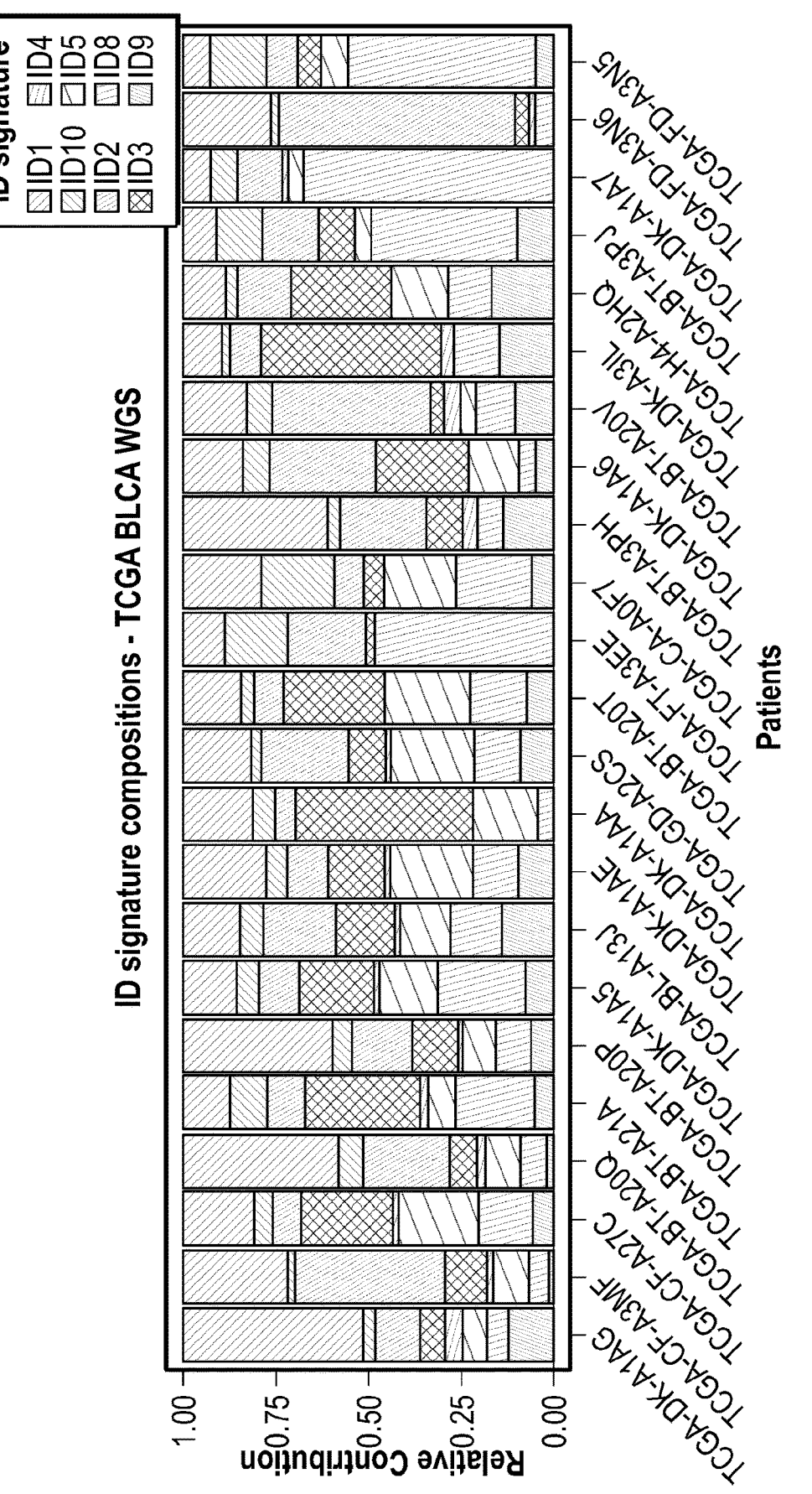
Figure 23C:
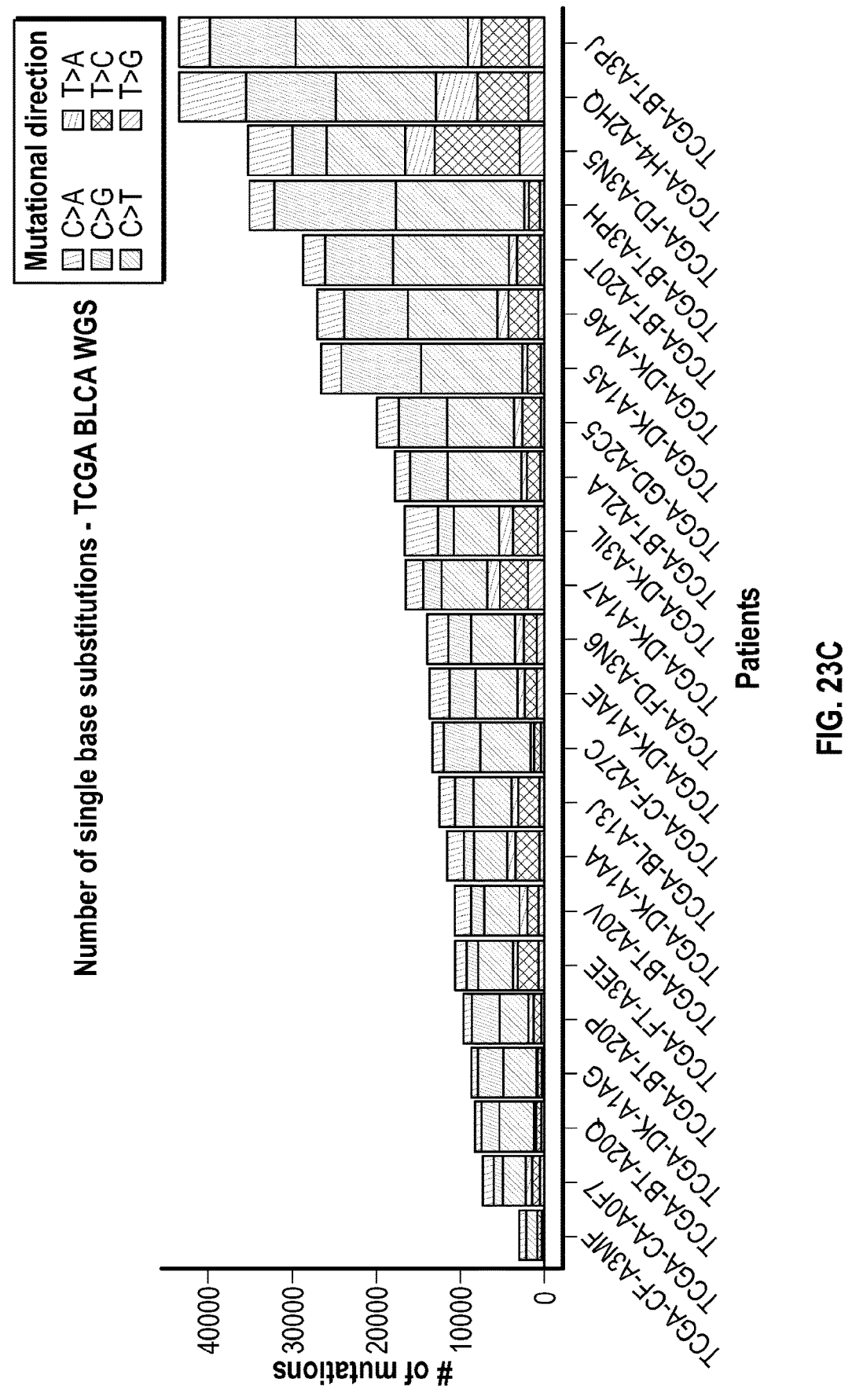
Figure 23C:
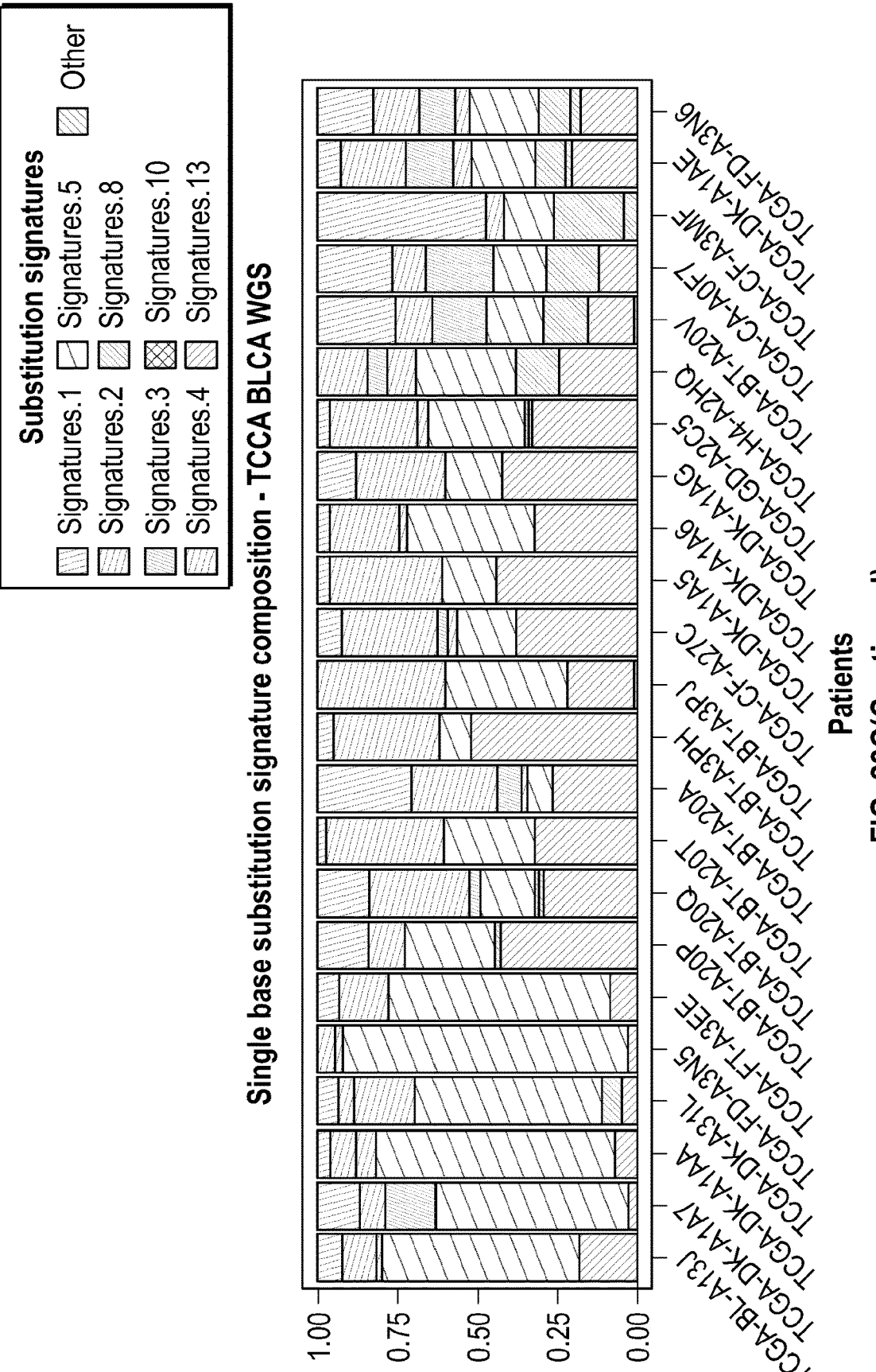
Figure 23D:
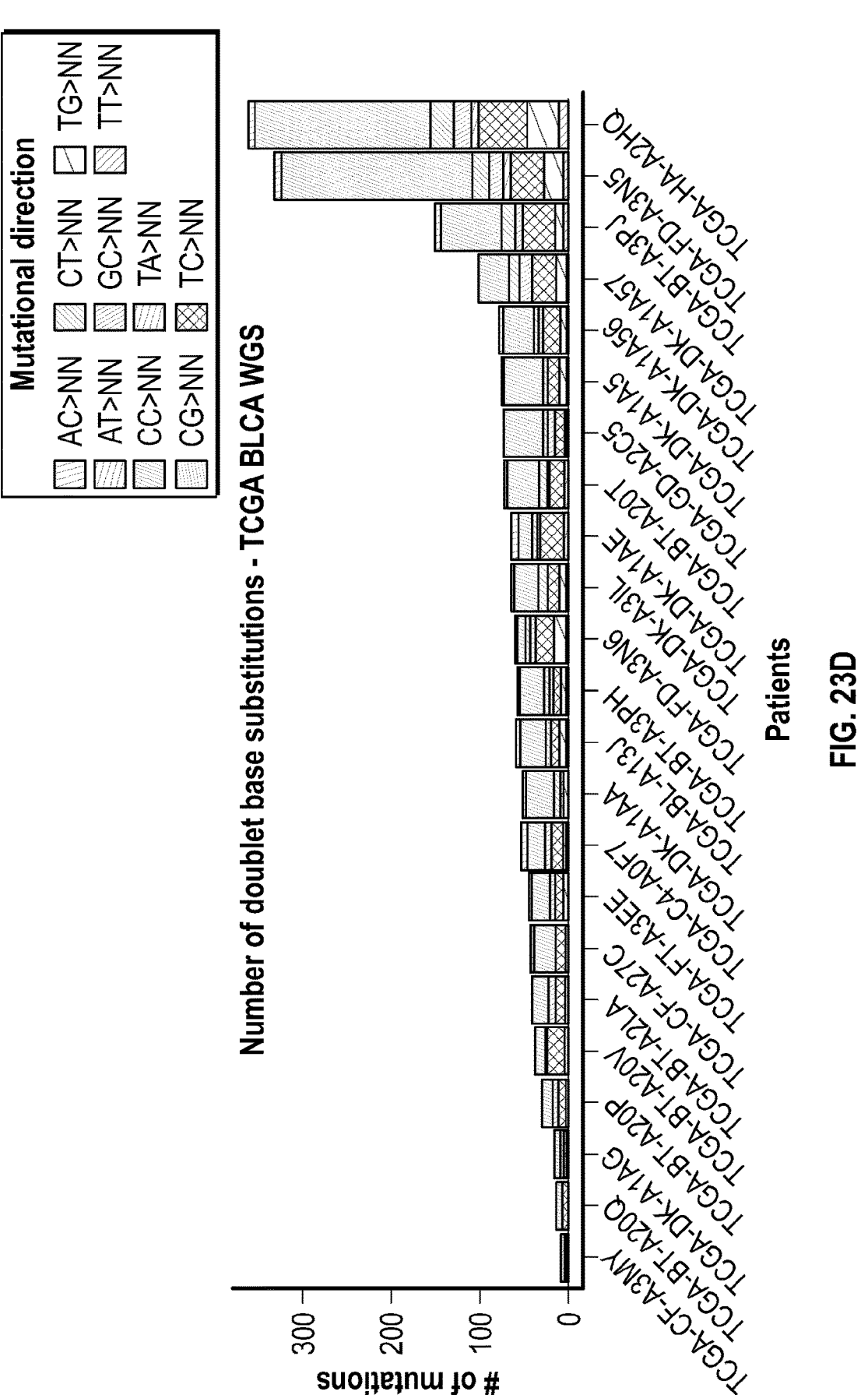
Figure 23D:
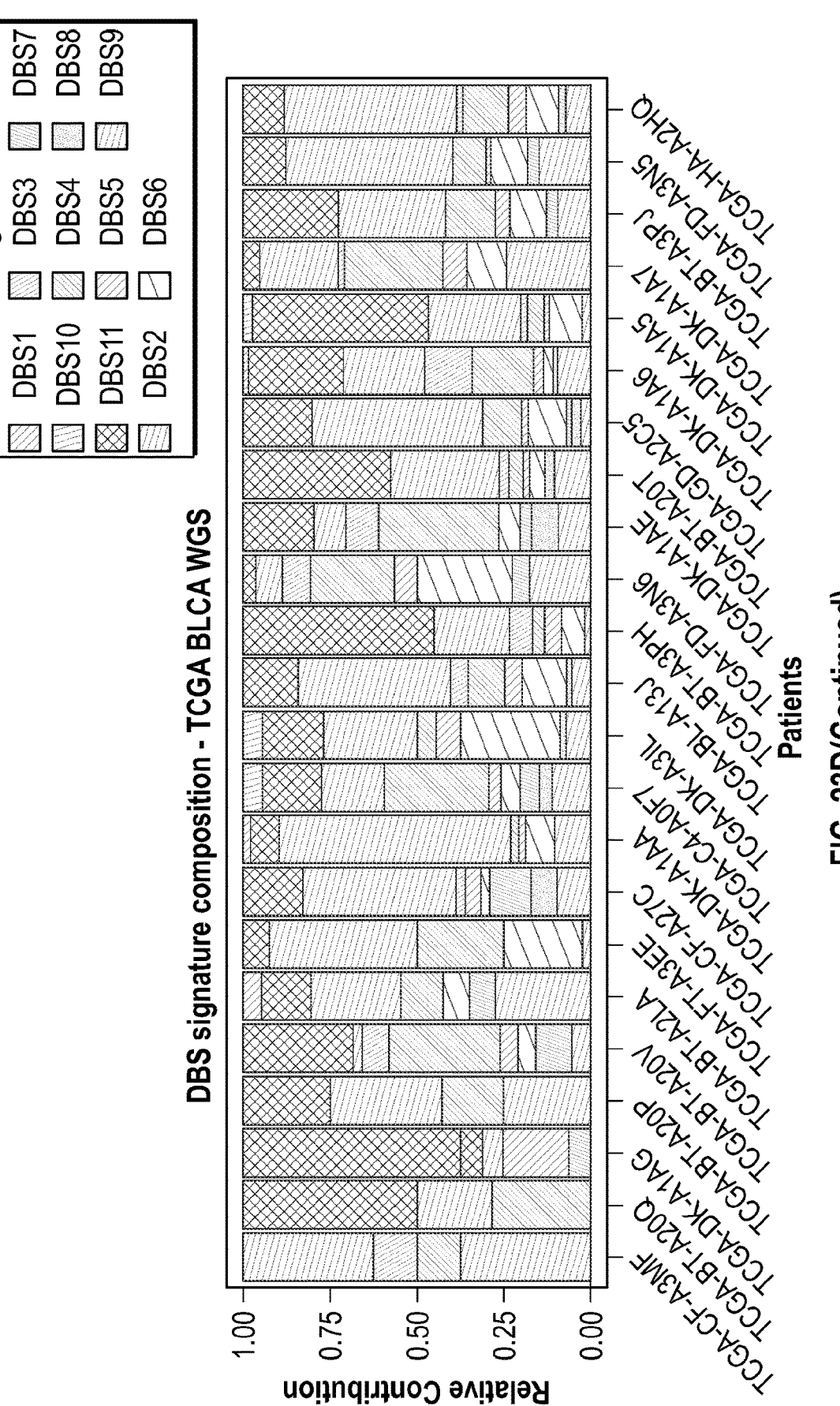
Figure 23E:
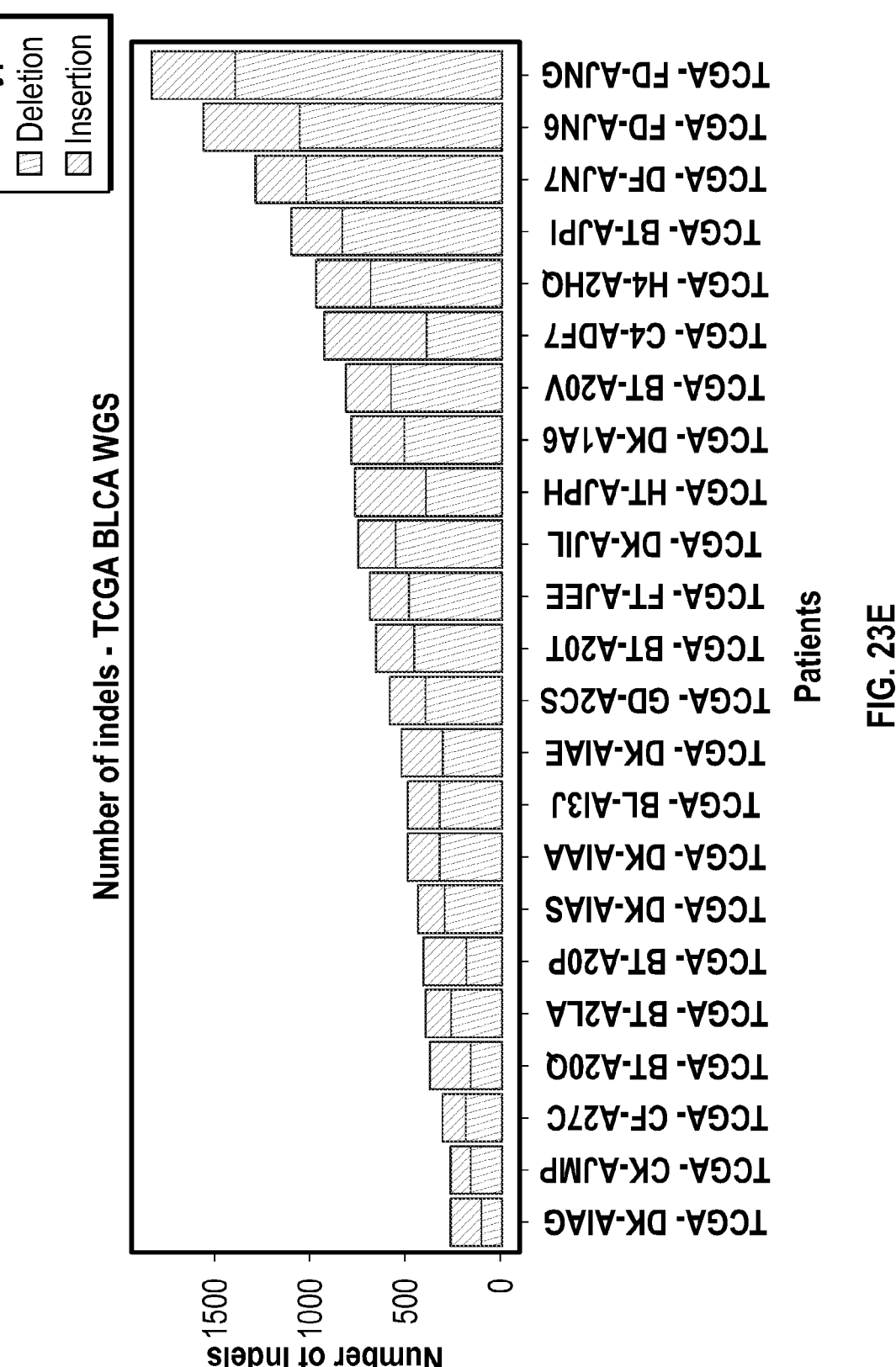
FIG. 23E shows TCGA BLCA WGS: number of insertions and deletions and the extracted ID signatures.
Figure 23E:
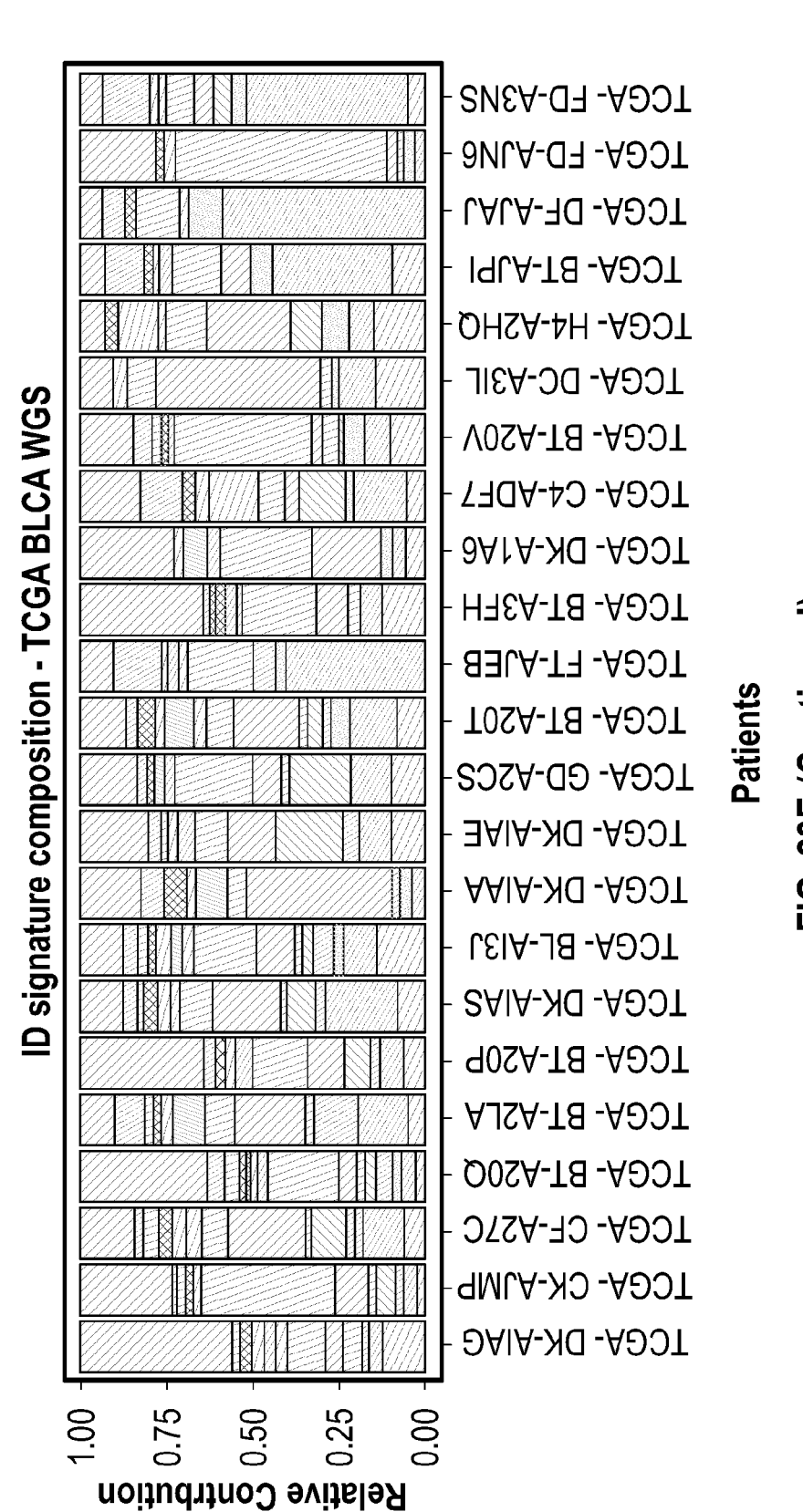
Figure 23F:
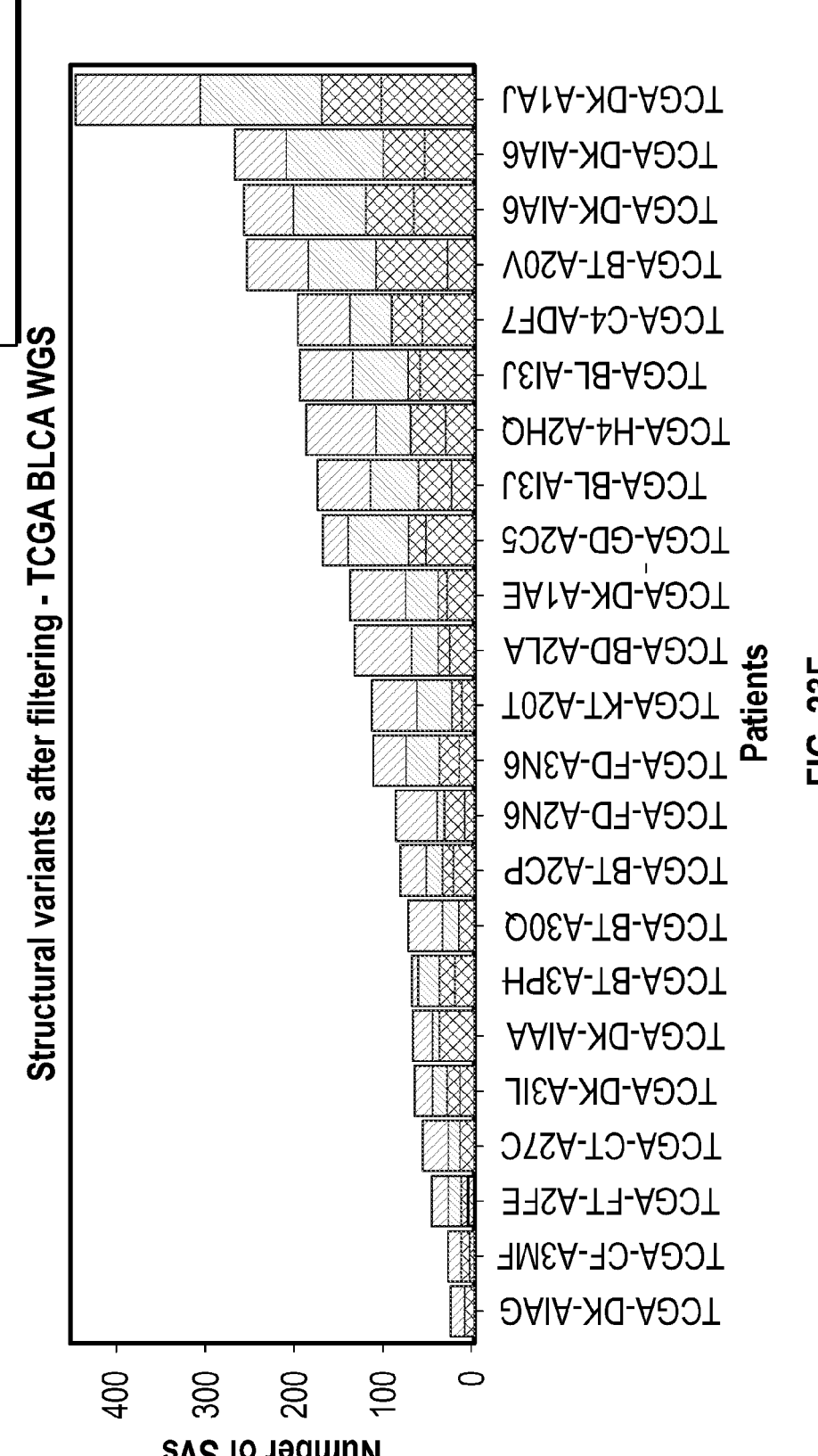
FIG. 23F shows the number of structural variants (after filtering) and the rearrangement signature composition of samples.
Figure 24:
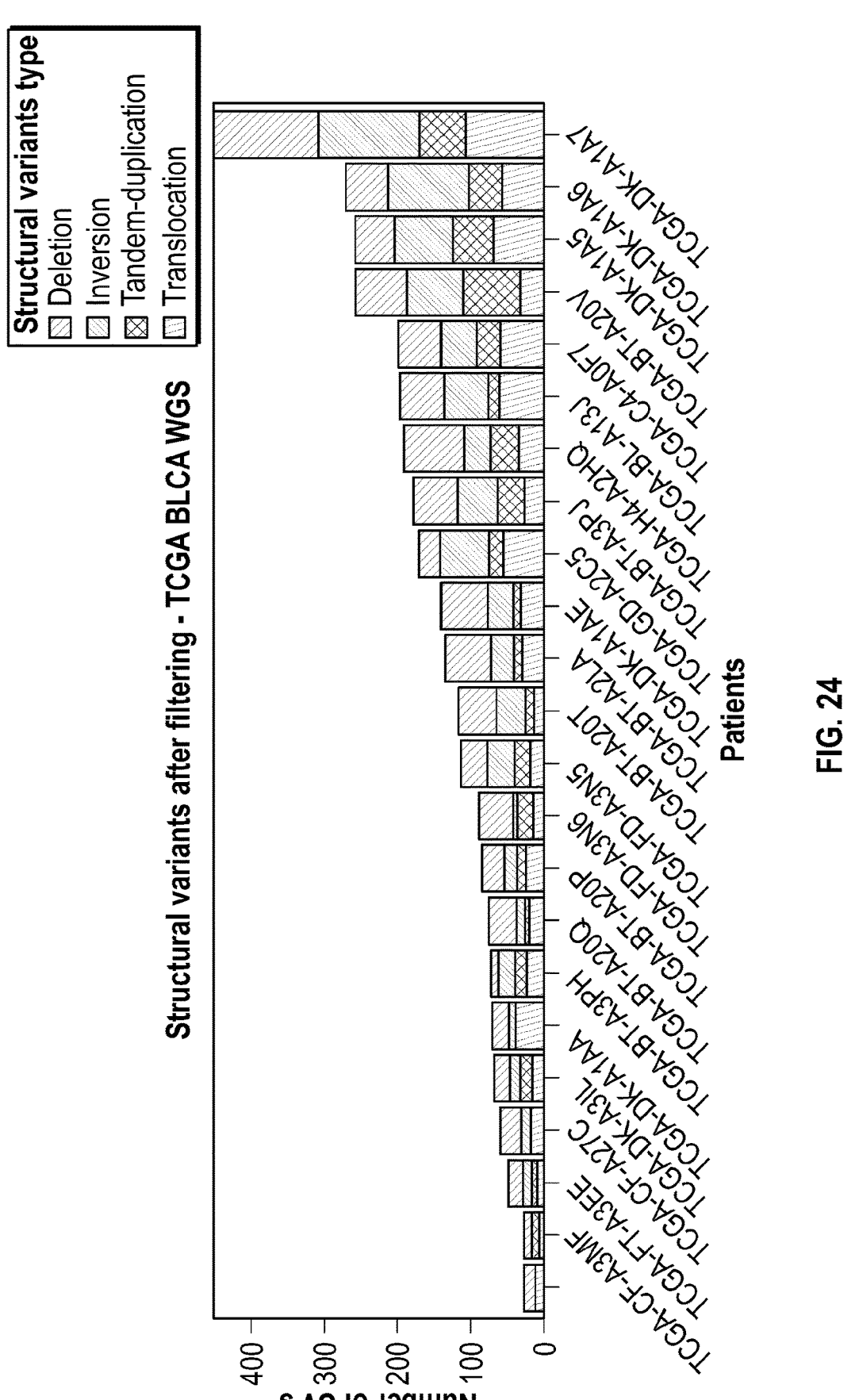
FIG. 24 shows the number of structural variants (after filtering) present in the TCGA BLCA WGS cohort (top panel). Bottom panel: Rearrangement signature composition of samples in the TCGA BLCA WGS cohort.
Figure 24:
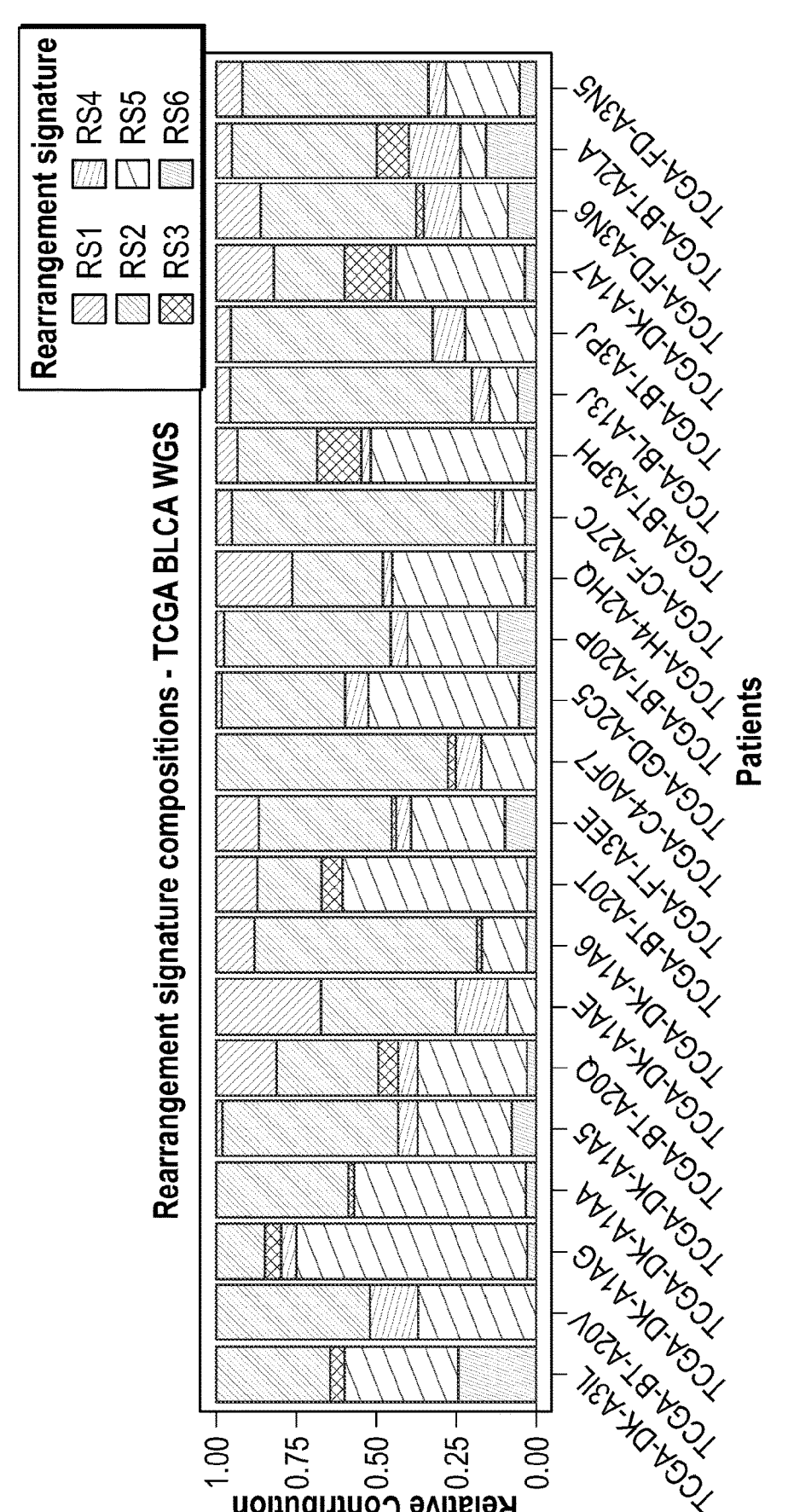
Figure 25A:
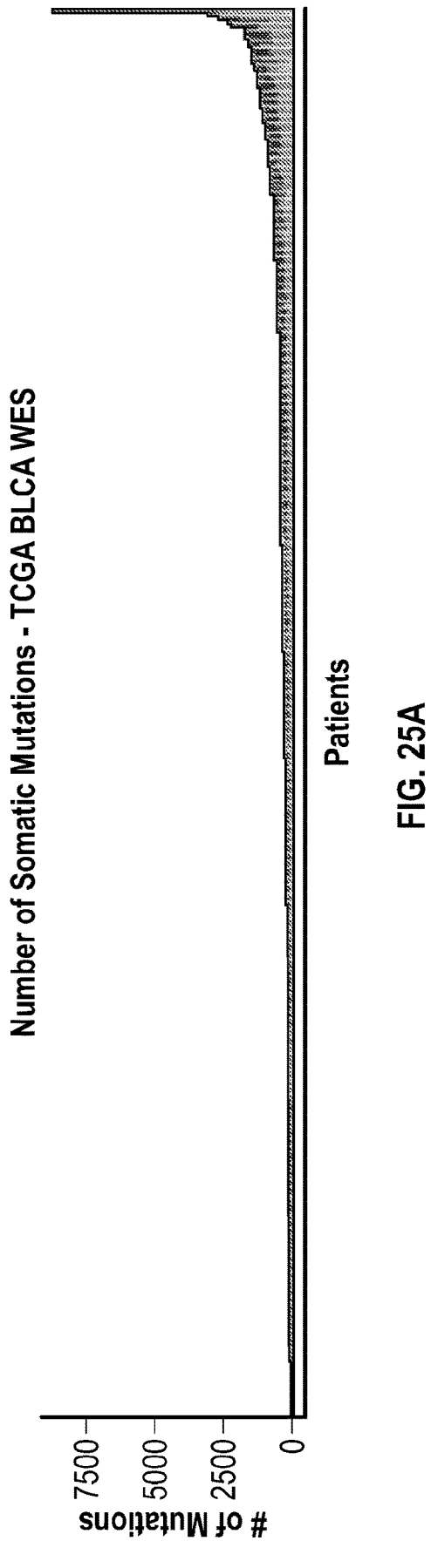
FIG. 25A shows the number of single base substitutions and the extracted single base substitution signatures in the TCGA BLCA WES cohort.
Figure 25A:
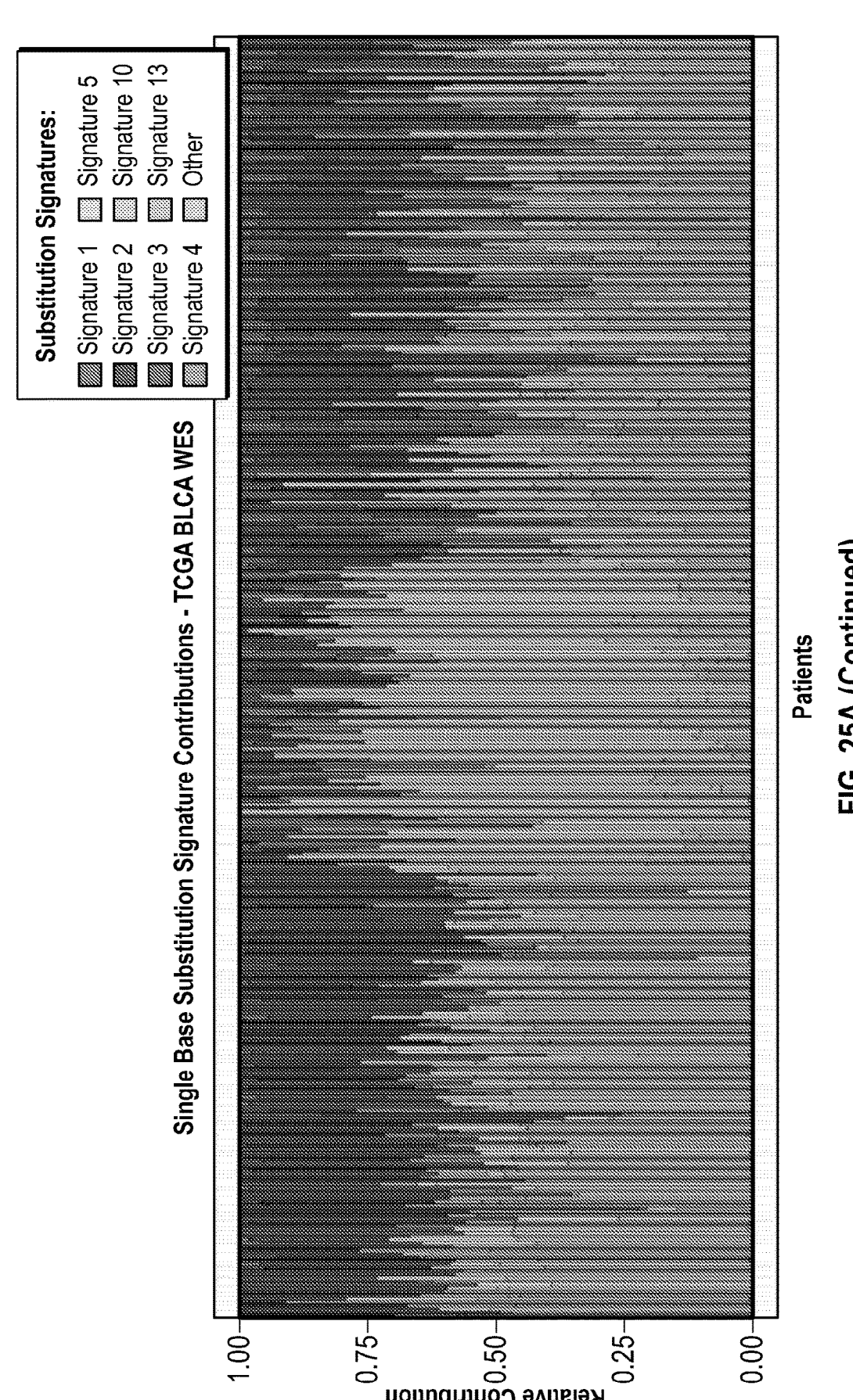
Figure 25B:
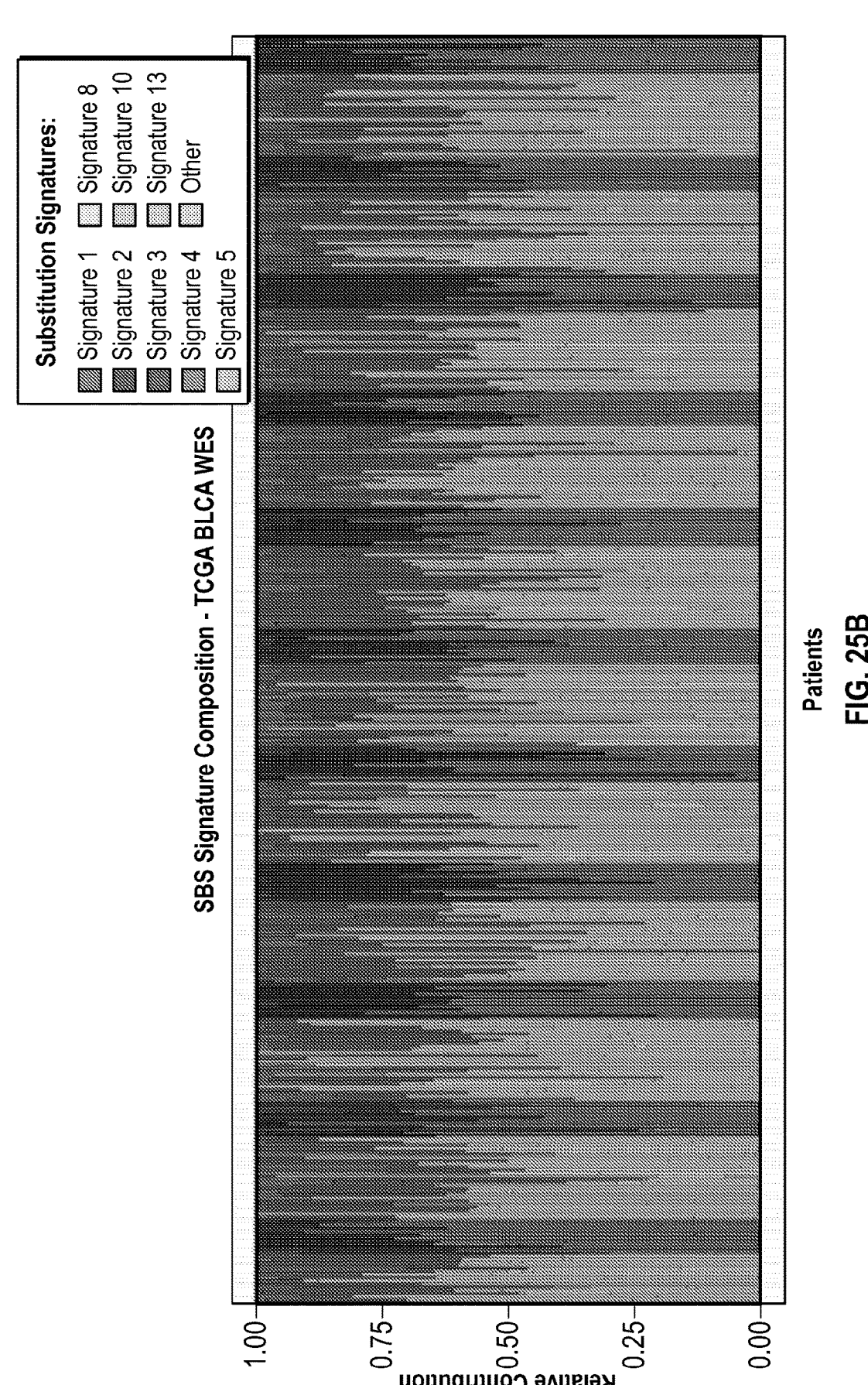
FIG. 25B shows TCGA BLCA WES: the extracted SBS signatures.
Figure 25C:
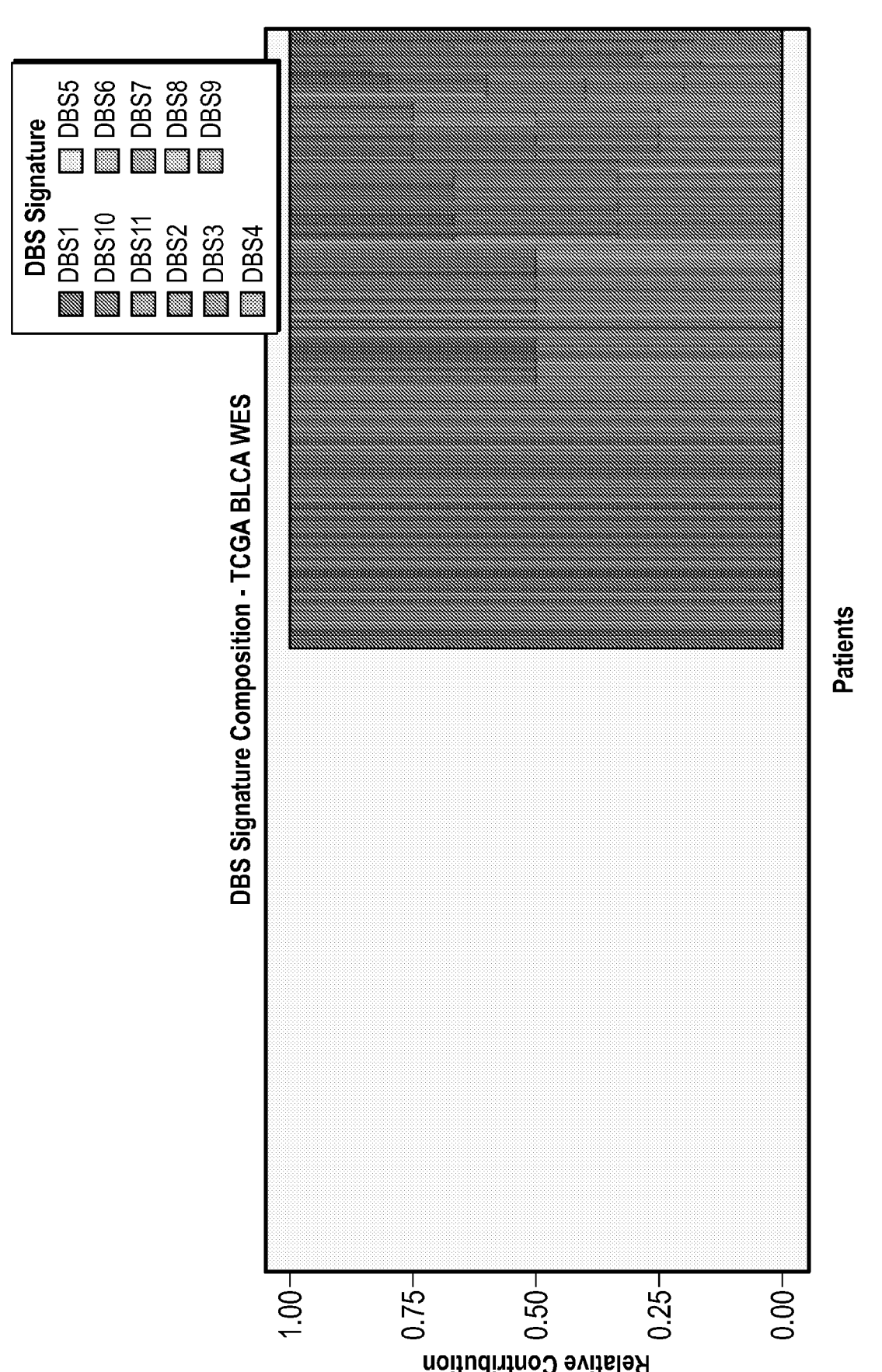
FIG. 25C shows TCGA BLCA WES: the extracted DBS signatures.

Allele-specific copy number profiles were estimated using Sequenza (27) (FIGS. 19-20). Germline and somatic mutations were annotated using InterVar (28) and the genotypes of the samples were determined (FIGS. 21-22). Structural variants were detected by BRASS (v6.0.0. available on the world-wide web at http://<github.com/cancerit/BRASS>). Further details are described in Example 2.

Mutational Signatures

Somatic single base substitution signatures were determined with the help of the deconstructSigs R package (29), using the COSMIC signatures as a mutational-process matrix (available on the world-wide web at <cancer.sanger.ac.uk/cosmic/signatures_v2>). Doublet base substitutions and indels in each sample were classified into a 78-dimensional doublet base substitution and an 83-dimensional indel catalog, respectively, with the help of the ICAMS R package (30), and the previously described matrices of doublet base substitution and indel signatures were used (31) in a non-negative least-squares problem to estimate the matrix of exposures to mutational processes. The extraction of rearrangement signatures was executed as described previously (32). The extracted single base substitution signatures, doublet base substitution signatures, indel signatures and rearrangement signatures are shown in FIGS. 23-30 and the cosine similarity between the single base substitution signature profiles of each sample is presented in FIGS. 52-53. Further details are provided in Examples 2 and 6.

Transcriptional Strand Bias

Transcriptional strand bias analysis was carried out using the MutationalPatterns R package (33), which identifies strand asymmetry in the reference frame of DNA transcription (34).

Cell Lines and Reagents

Bladder cancer cell lines were purchased from ATCC. The KE1 bladder cancer cell line is a derivative of KU19-19 in which an ERCC2 T484 mutation has been introduced by CRISPR/Cas9 gene editing as previously described (6). The MDA-MB-468 breast cancer cell line and its ERCC4-complemented derivative have been previously described (35). Small interfering RNAs (siRNAs) targeting specific NER genes as well as a non-targeting siRNA (siNTC) were purchased from Integrated DNA Technologies Inc. (Coralville, IA, USA; see Table 9 for sequences). Cells were seeded in 6-well plates and grown to 50% confluency. A transfection mixture containing siRNA diluted to a final concentration of 30 nM in Opti-MEM media containing Lipofectamine 3000 (Life Technologies; Carlsbad, CA) was then added to cells. After 48 hours, cells were trypsinized and re-aliquoted to separate wells and transfected with 15 nM siRNA for 24 hours immediately prior to viability assays performed as described below. To create the SW1710 ERCC2 P463L mutant cell line, a Cas9-encoding lentiviral vector as well as an sgRNA targeting the P463 codon were electroporated into SW1710 along with a donor template plasmid encoding the desired P463L codon change as well as a GFP reporter cassette. After 48 hours, GFP-positive cells were isolated by cell sorting and expanded. The presence of the P463L mutation was validated by Sanger sequencing followed by RT-PCR and targeted next-generation sequencing using the MSK-IMPACT assay. The sequences of sgRNA and PCR primers are listed in Table 10. Early-passage cells (≤6 passages) were used for all experiments and cell lines were tested monthly to confirm absence of mycoplasma. For additional details, see Example 2.

Cell Line Mutational Signatures

KU19-19 and KE1 cell populations were single cell sorted, and individual cells were expanded to create multiple populations of cells. Each population of KU19-19 or KE1 cells was propagated separately in culture for 30 days while maintaining the population above $1 \times 10^6$ cells at all times.

After 30 days, each population was single cell sorted and individual clones were grown to ~1×10⁶ cells. Cells were frozen, lysed, and genomic DNA was isolated. Whole genome sequencing (WGS) was performed at the Broad Institute to an average depth of 30×. Somatic mutations were called using IsoMut (36), single base substitution signatures, doublet base substitution signatures, and indel signatures were extracted as described in Example 2.

In Vitro Drug Sensitivity Assays

Cells were seeded in either 96-well (5,000 cells/well) or 24-well (20,000 cells/well) plates. The following day, irofulven and cisplatin stock solutions were serially diluted in media and added to cells. After 48 to 72 hours, media was removed and CellTiter-Glo® reagent (Promega; Madison, WI) was added. Plates were scanned using a luminescence microplate reader (BioTek). Survival at each drug concentration was plotted as a percentage of survival in drug-free media with error bars representing the standard deviation of at least three experiments.

For crystal violet imaging experiments, cells were seeded in 6-well plates (100,000-200,000 cells/well) with 15 nM siRNA transfection mixture (as detailed above). At 24 hours, fresh media containing irofulven or PBS was added and the cells were incubated for an additional 72 hours. Cells were then fixed in formalin solution for 30 minutes and stained with crystal violet prepared in equal volumes of methanol and water. Excess crystal violet was removed by washing with PBS, and plates were then dried and imaged.

Immunoblotting

Cells were lysed with ice-cold RIPA buffer supplemented with protease and phosphatase inhibitors (Roche). Samples were then sonicated and protein concentrations were determined using the Bradford assay. Sample buffer (Bio-Rad) was added and samples were then denatured at 90° C. for 10 mins. Samples were then loaded in NuPAGE™ protein gels (Thermo Fisher Scientific) and run at 90V for 2-3 hours. The gels were then transferred to nitrocellulose membranes at 30V overnight. Membranes were blocked for 30 mins in 5% milk in TBS buffer. Sections of the membrane corresponding to the appropriate molecular weights were stained overnight in primary antibodies prepared in 1% milk in TBST: XPF (1:700, clone D3G8C rabbit mAB, Cell Signaling); cleaved caspase 3 (1:1000, clone D175, rabbit mAB, Cell Signaling); total and cleaved PARP (1:1000, rabbit mAB, Cell Signaling); phospho-H2AX Ser139 (1:1000, clone JBW301 mouse mAB, Millipore); β-tubulin (1:1000, mouse mAB, Santa Cruz Technologies); Rpb1 CTD (1:1000, clone 4H8 Mouse mAb, Cell Signaling). A Licor Odyssey Infrared Imaging System was used for signal detection using IRDYE-conjugated secondary antibodies (LI-COR Biosciences).

Xenograft Studies

Six week old female athymic nude mice, NU/J (Stock No: 002019) were purchased from Jackson Laboratory (Bar Harbor, ME) and housed at the Dana-Farber Cancer Institute Animal Resources Facility. All animal experiments were performed in accordance with an IACUC-approved protocol. At 7-10 weeks of age, mice were anesthetized with isoflurane and subcutaneously injected on the left flank with 3 million KE1 or 1 million KU19-19 cells mixed 1:1 with Matrigel (BD Biosciences; Mississauga, ON) in PBS. Tumor size was measured with a digital caliper twice weekly and calculated using the formula: $(L \times W^2) \times \frac{1}{2}$. Drug treatments were administered when the average tumor volume reached a minimum of 100 mm³. Irofulven was prepared in PBS to a stock concentration of 200 µg/ml and was delivered intraperitoneally (IP) twice weekly at doses of 250 µg/kg, 500 µg/kg or 1 mg/kg for a total of 5 injections or until the tumor reached a pre-specified protocol endpoint. Control mice were injected with PBS alone. At the end of the experiment, mice were sacrificed and tumors were excised for tumor weight measurements and imaging.

ERCC2Mut Composite Mutational Signature

The inventors built a statistical model for detecting mutational features associated with ERCC2 mutation status. The classification model was trained on the TCGA BLCA WES data. The information gained from the extraction of signatures of single base substitutions, signatures of doublet base substitutions, signatures of indels and transcriptional strand bias was used to build a logistic regression model. The training set consisted of 28 ERCC2 somatic mutants and 367 wild-type samples (Table 11). The data were log-transformed and standardized. The detailed description of the model-building process is available in the Example 2.

Survival Analysis

Survival analysis is described in the Example 2.

Data Availability

The cell line WGS bam files were deposited at the European Nucleotide Archive (ENA) under the accession number PRJEB36417.

Results

The NERDetect Composite Mutational Signature is Strongly Associated with ERCC2 Mutation Status In Multiple Bladder Cancer Cohorts Characteristic single nucleotide variation (SNV)-based mutational signatures are often present in tumors harboring specific DNA repair defects such as HR- or mismatch repair (MMR)-deficiency[9]. For NER, an SNV-based mutational signature largely overlapping with COSMIC signature 5 was enriched in bladder tumors with a mutation in the NER gene ERCC2[10]. However, DNA repair pathway alterations are also known to induce other types of mutations, including short (1-20 bp) insertion/deletions (indels), which can be further categorized by the presence or absence of microhomology of the flanking sequence, and large-scale DNA rearrangements.

Figure 1B:
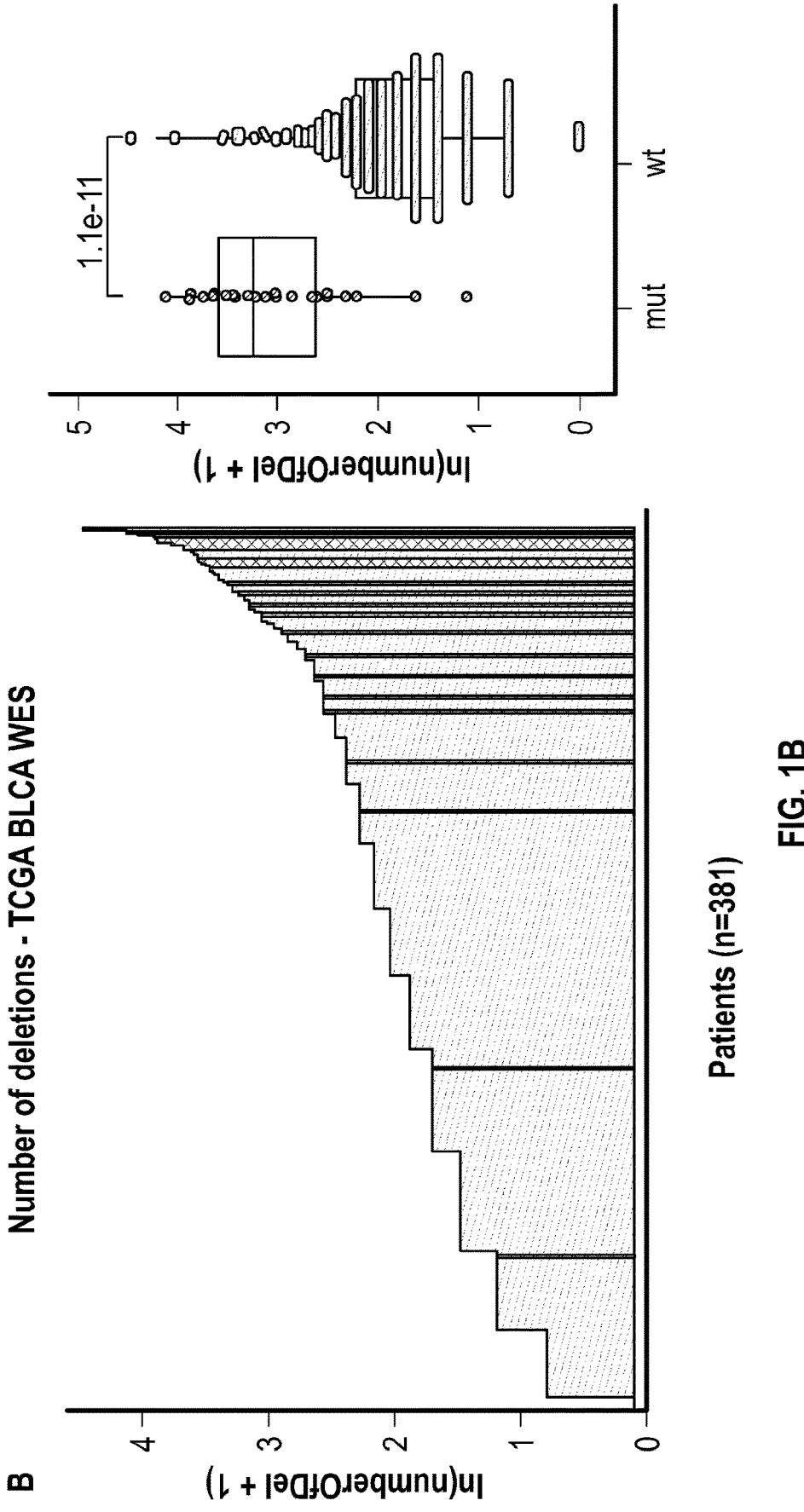
Figure 1C:
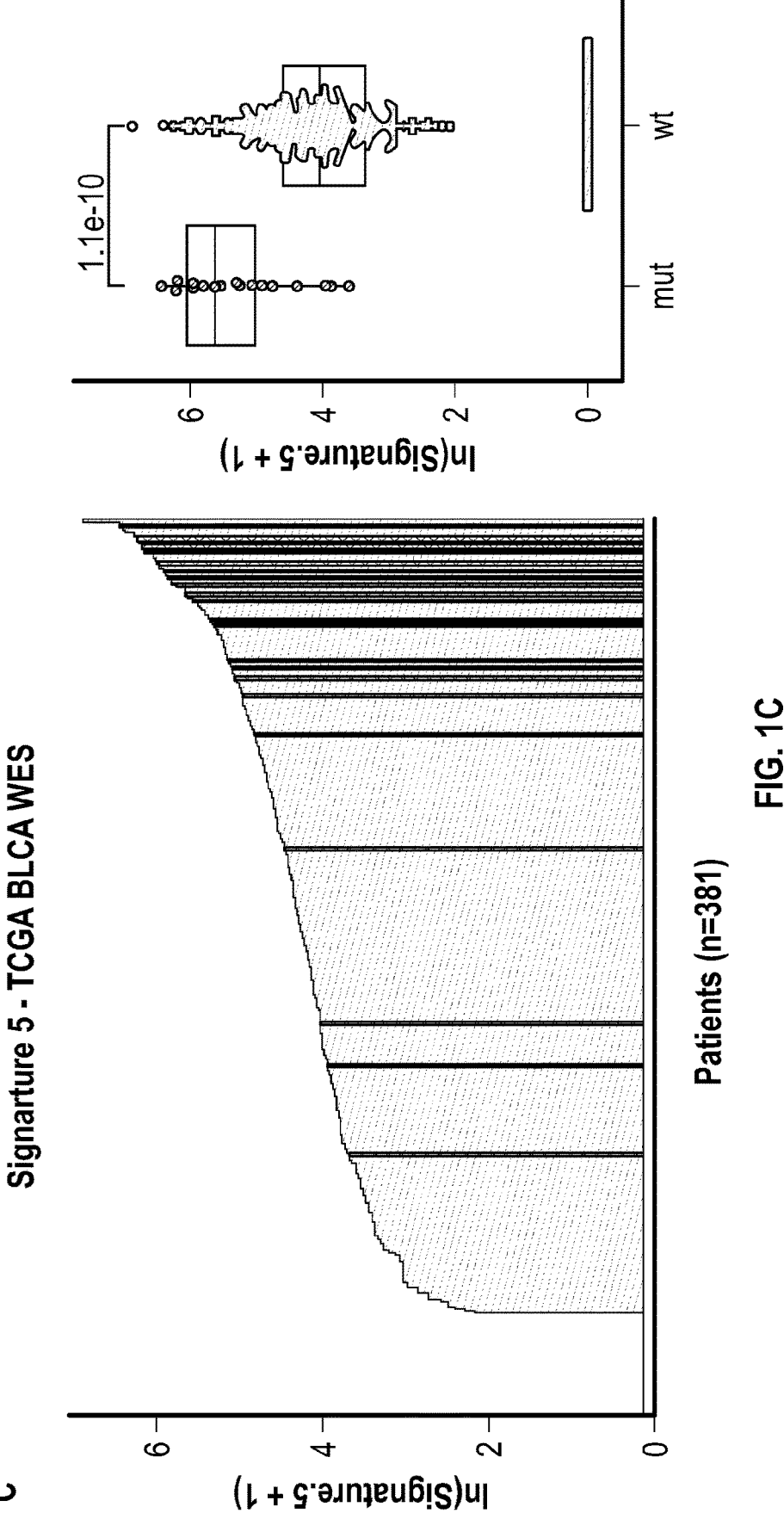
Figure 1D:
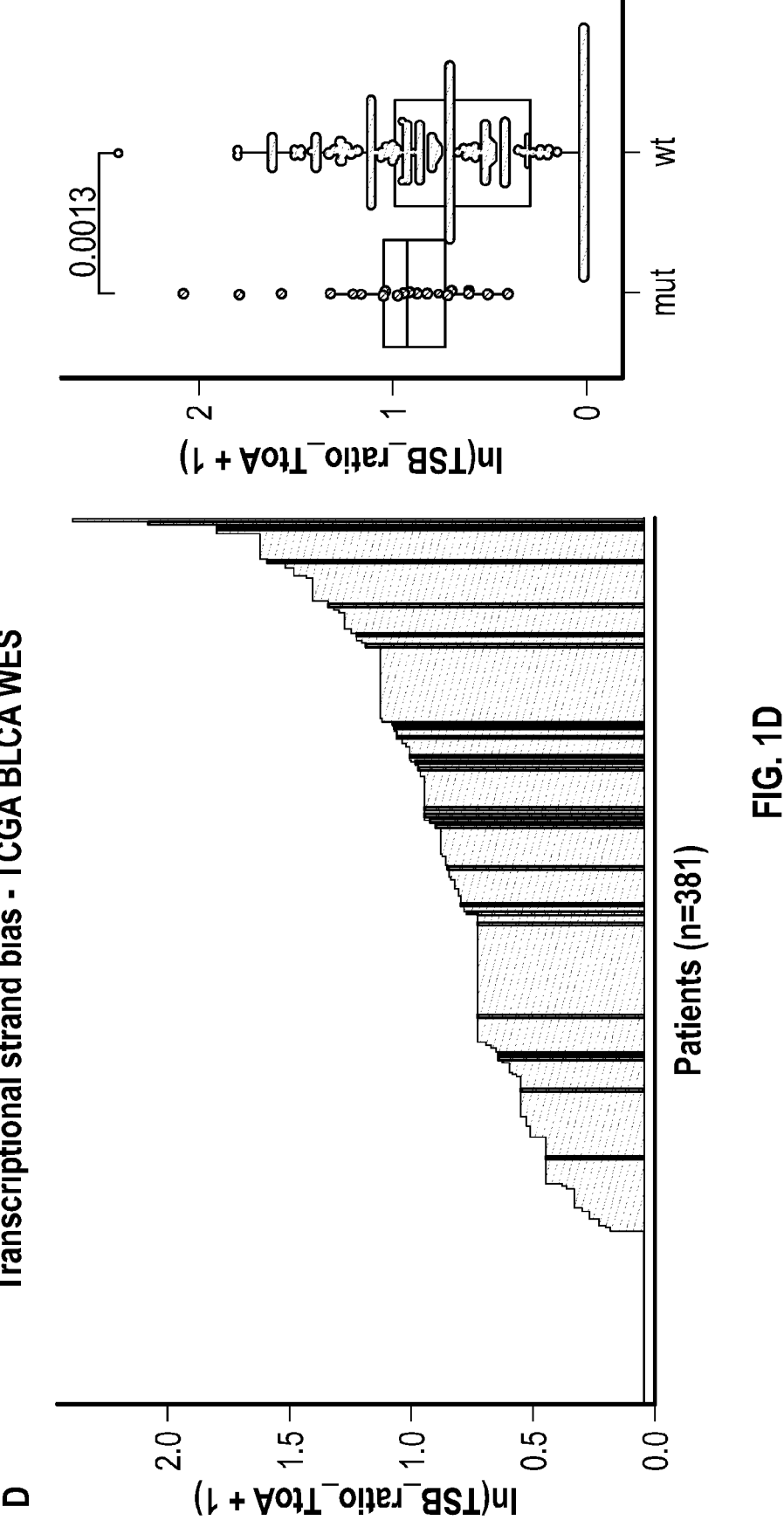

To further characterize the mutational features of NER deficiency in bladder cancer, we analyzed the TCGA bladder cancer whole genome and exome sequencing data sets[4] to identify multiple types of mutational signatures catalogued in cancer9, including SNVs, short indels, and large-scale rearrangements (FIGS. 42A-42E, see also Examples 2, 6, and 7). In total, four signatures were significantly associated with ERCC2 mutations in the TCGA WES cohort: (1) the indel signature "ID8" (as defined by the PCAWG Mutational Signatures Working Group[24]) characterized by >5 bp deletions that lack flanking microhomology (FIG. 1A; p-value=7.2×10⁻¹⁴, Wilcoxon test); (2) the total number of 1-50 bp deletions (FIG. 1B; p-value=1.6×10⁻¹¹); (3) COSMIC signature 5 that had been previously shown to correlate with ERCC2 status (FIG. 1C; p-value=9.2×10⁻¹¹); and (4) the transcriptional strand bias of mutations[25,26] (FIG. 1D; p-value=0.0015). Each of these mutational features was independently associated with ERCC2 mutation status and may therefore reflect distinct features of genomic instability induced by NER deficiency. Similar results were obtained in the subset of TCGA cases with available WGS data (Example 2).

Figure 1E:
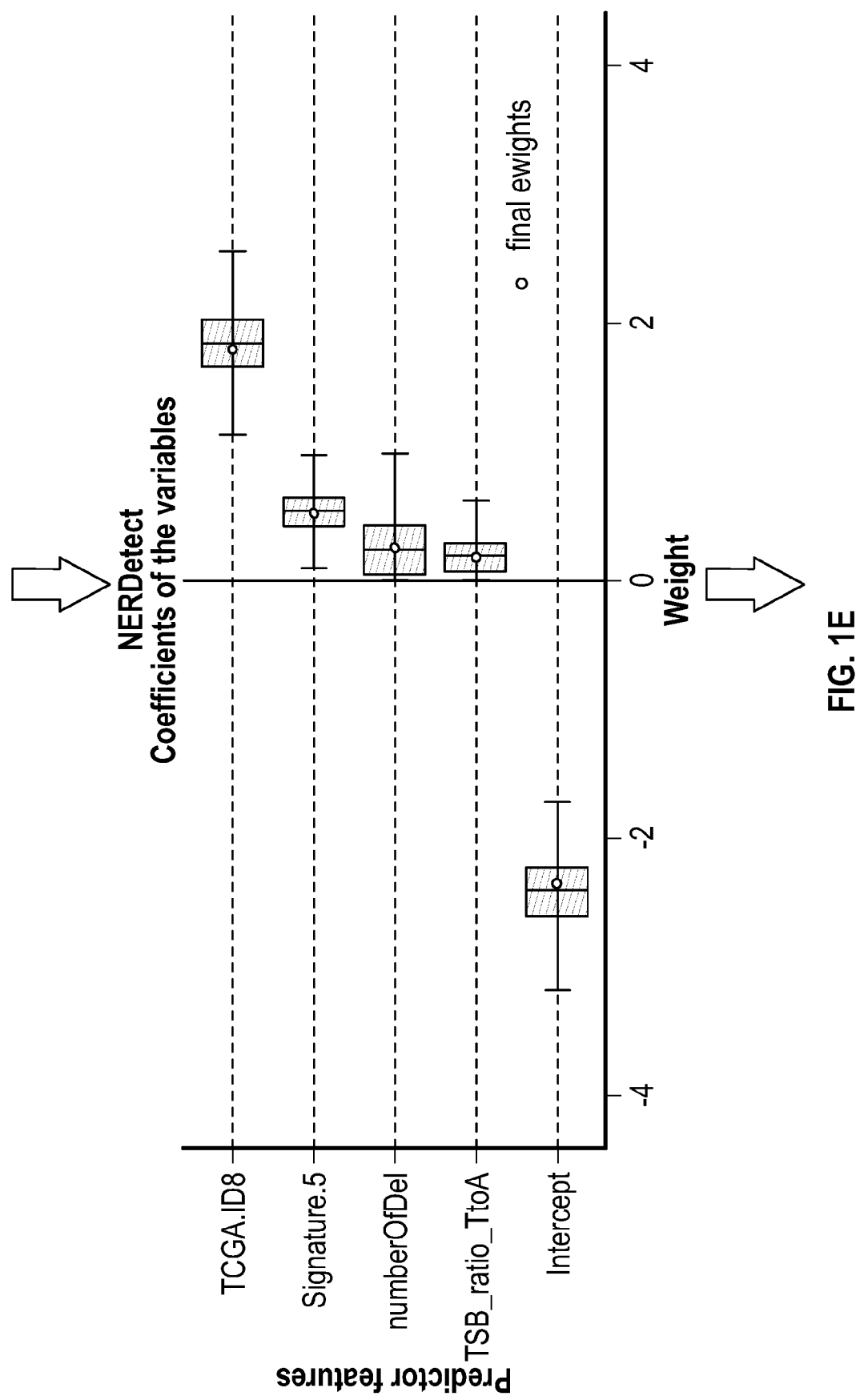
Figure 1F:
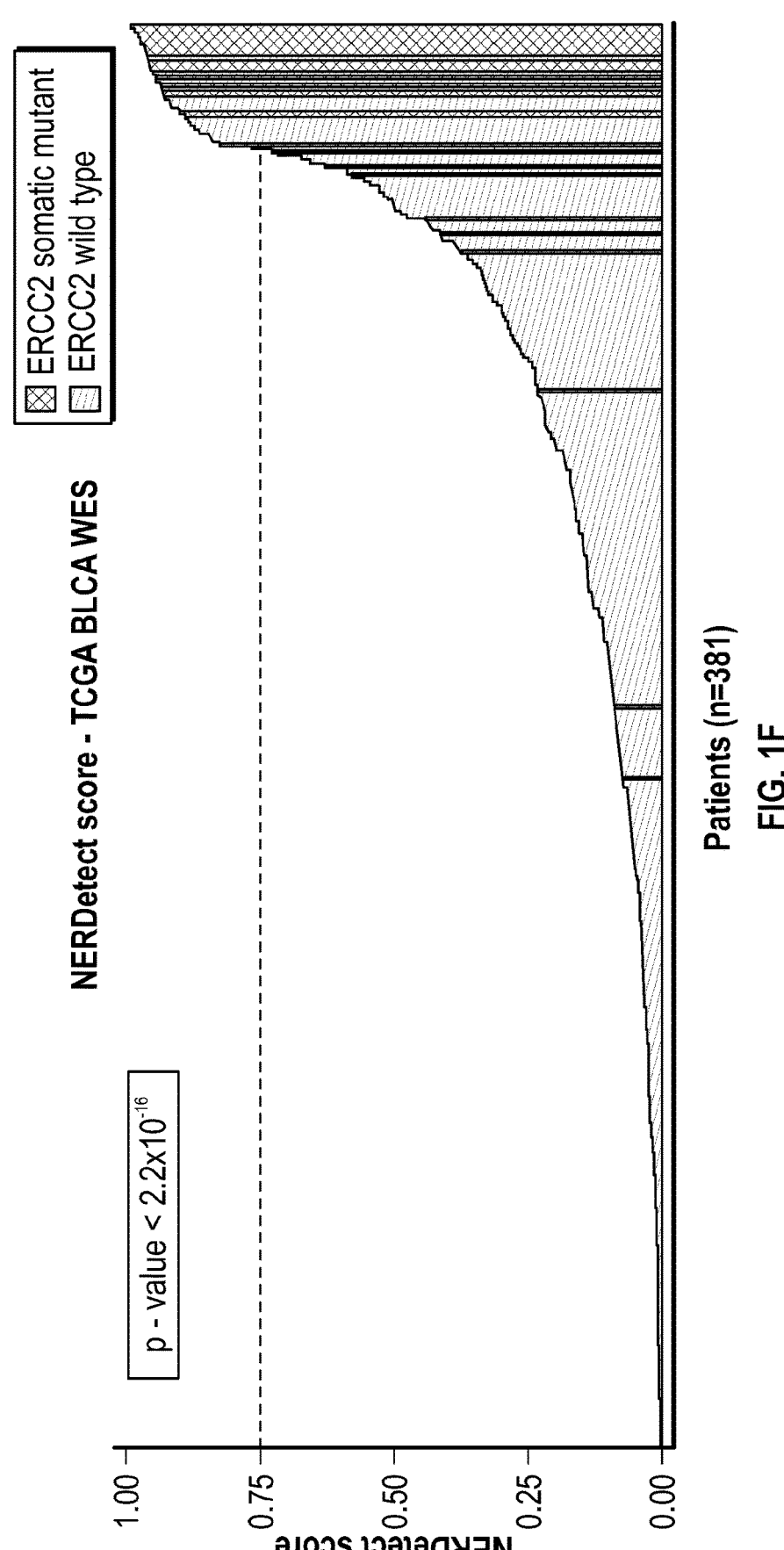

To further improve our ability to discriminate between NER proficient and deficient bladder cancer cases, we used the four mutational signatures that were each independently associated with ERCC2 mutation status to create a logistic regression-based classifier of NER deficiency (FIG. 1E; Example 2). This "NERDetect" classifier was trained on the TCGA WES bladder cancer cohort to distinguish between ERCC2 mutant and wild type (WT) cases, and ERCC2 mutants were highly enriched among cases with high NER-Detect scores (FIG. 1F; p=2.9×10$^{-16}$, Fisher's exact test). The composite NERDetect signature more accurately identified ERCC2 mutant cases than was previously possible using COSMIC 5 signature alone[10]: the NERDetect signature $AUC_{ROC}$ and $AUC_{PRC}$ were 0.97 and 0.75, respectively, compared to 0.91 and 0.37 with the COSMIC 5 signature (Example 2). By minimizing the cost of misclassification, we identified a threshold NERDetect score of ≥0.75 that best distinguished between ERCC2 mutant and WT cases in the TCGA WES cohort (Example 2).

Figure 2A:
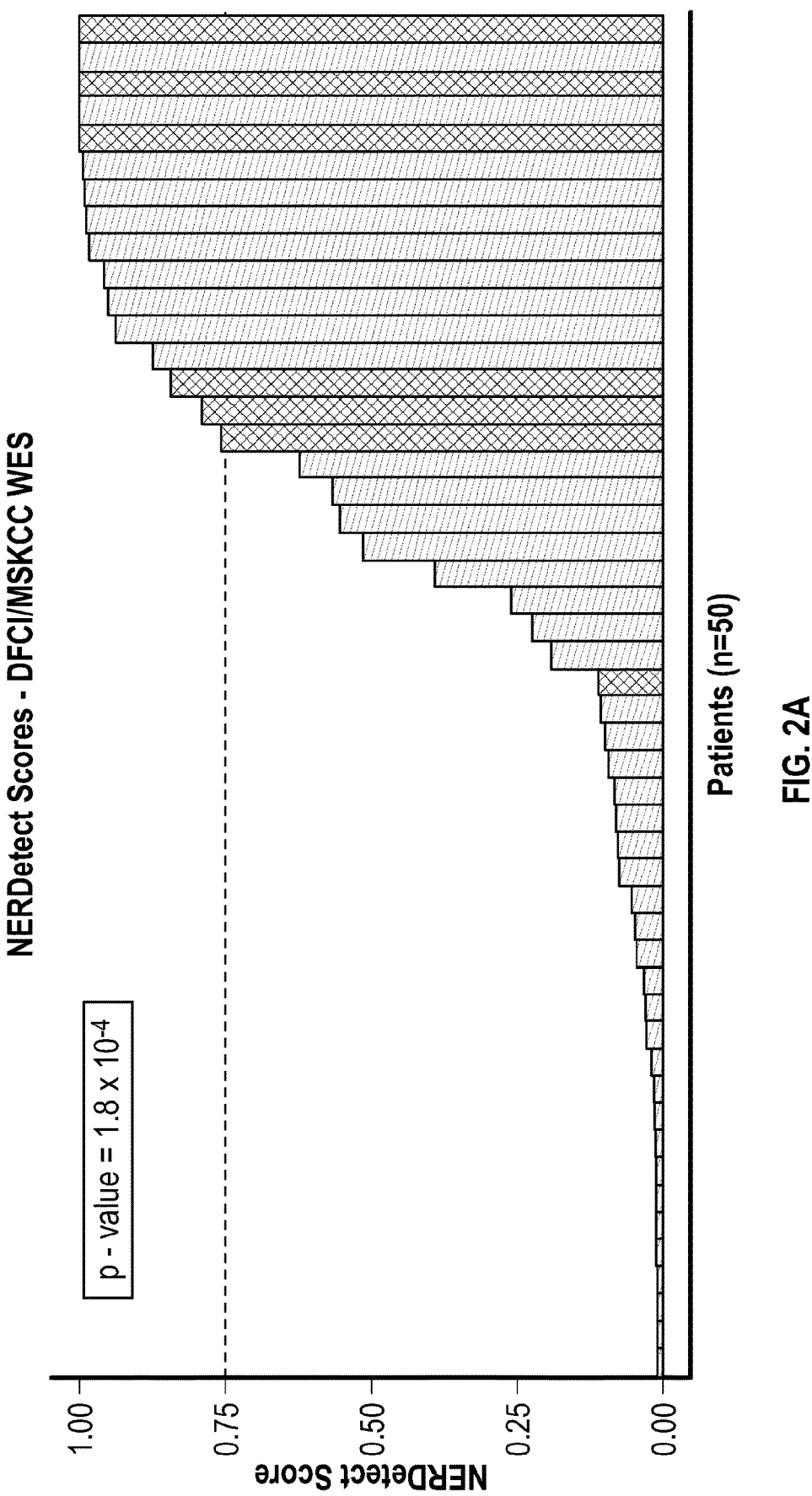
FIGS. 2A-2C show validation of the association between NERDetect scores and ERCC2 mutation status in three independent bladder cancer whole exome sequencing cohorts. Samples with an ERCC2 mutation are shown in green and ERCC2 wild-type samples are shown in gray. In each cohort, ERCC2 mutants are highly enriched among patients with a high NERDetect score ($\geq$0.75).
Figure 2B:
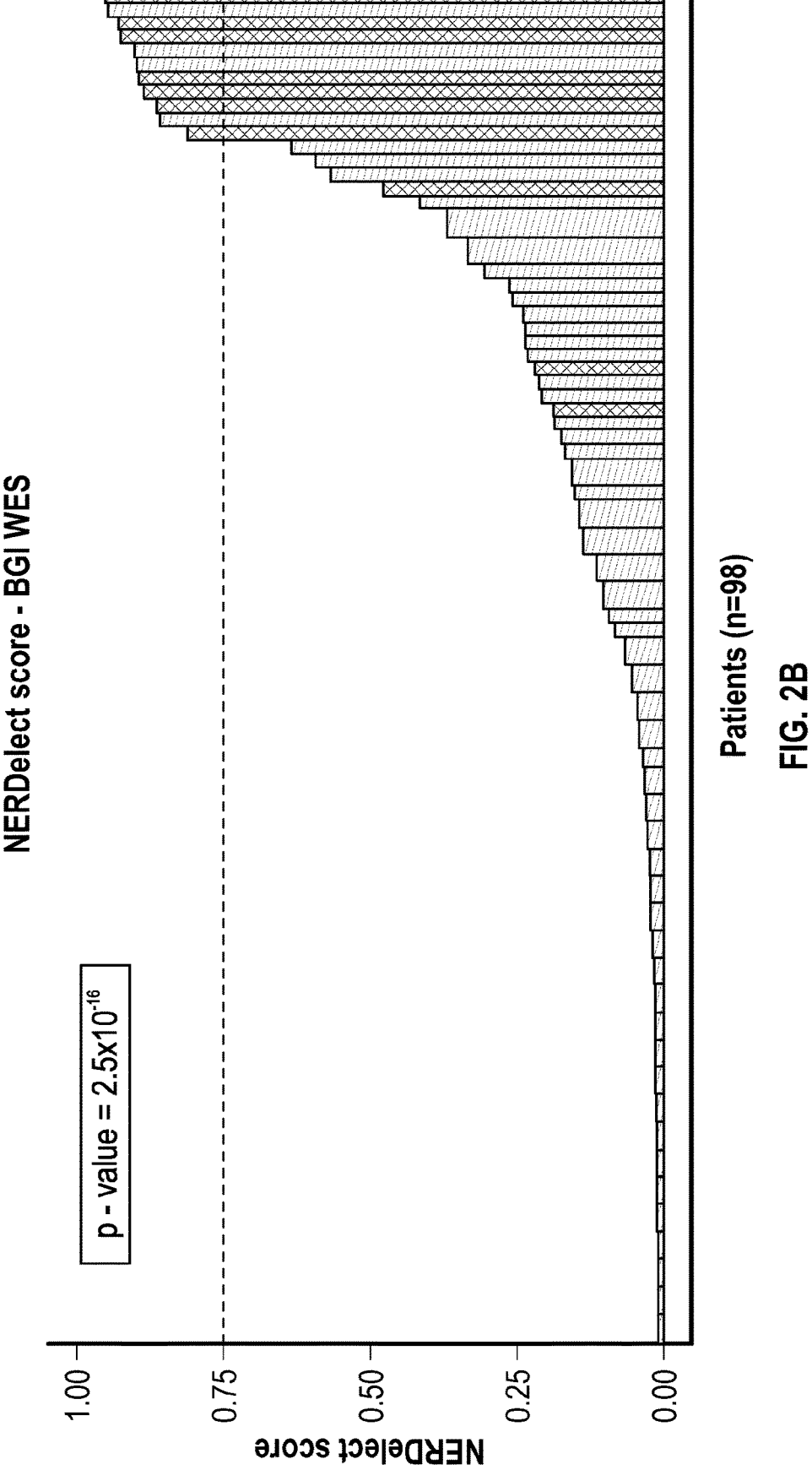
Figure 2C:
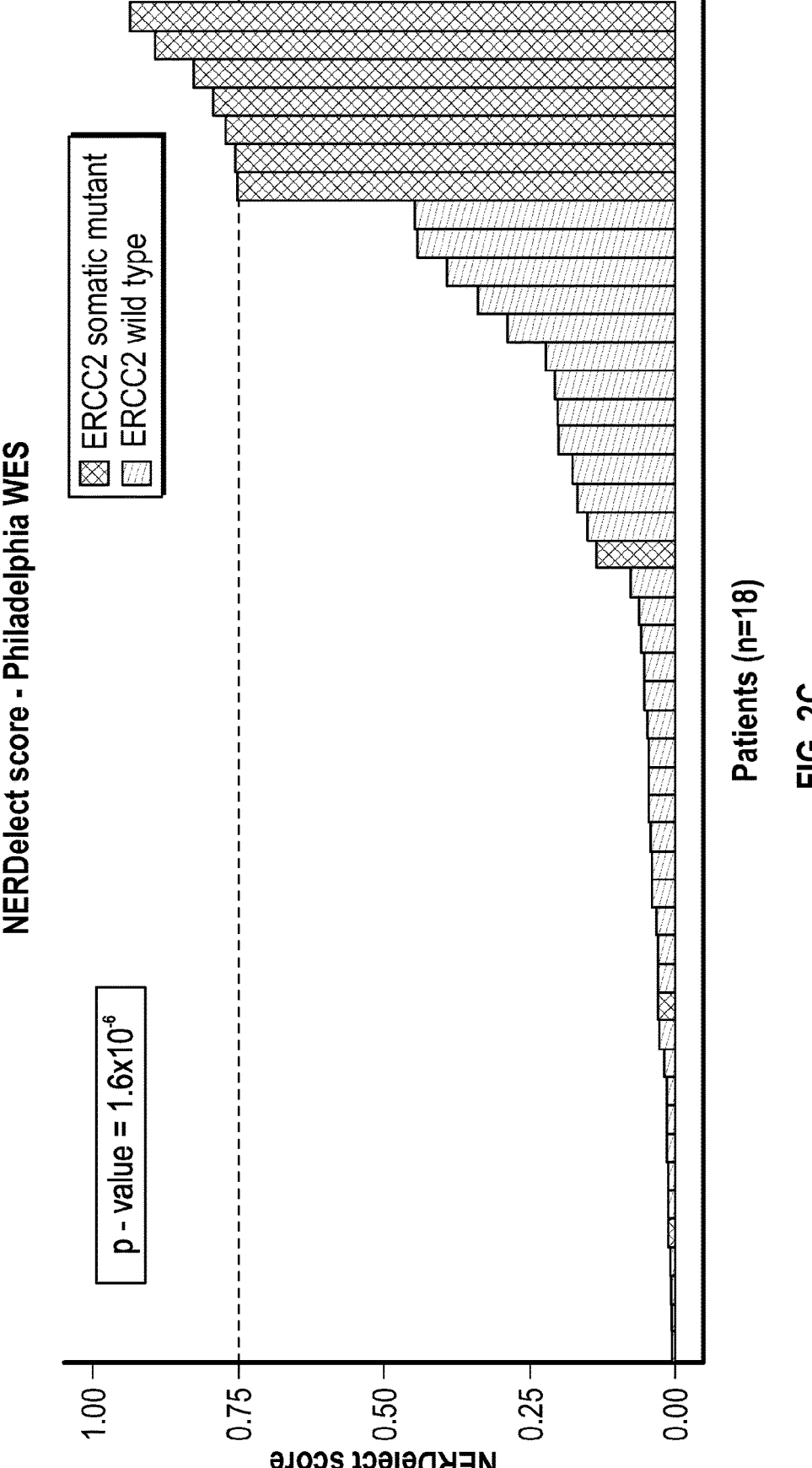

To validate the ability of the NERDetect classifier to discriminate between ERCC2 mutant and WT bladder tumors, we analyzed WES data from three additional independent bladder cancer cohorts[53,0,31]. The DFCI/MSK (n=50) and FCCC (n=48) cohorts are comprised of muscle-invasive bladder cancer patients who received neoadjuvant cisplatin-based chemotherapy followed by radical cystectomy, while the BGI cohort (n=98) included patients with MIBC or non-muscle-invasive bladder cancer. In each cohort, ERCC2 mutant cases were significantly associated with a NERDetect score≥0.75 (p=1.8×10$^4$ in the DFCI/MSKCC cohort, p=7.9×10$^4$ in the BGI cohort, and p=1.7×10$^{-5}$ in the FCCC cohort; Fisher's exact test; FIGS. 2A-2C, Example 2).

NERDetect Scores Correlate with Cisplatin Response Independent of ERCC2 Status

ERCC2 mutations are associated with complete pathologic response and improved survival in muscle-invasive bladder cancer patients treated with neoadjuvant cisplatin-based chemotherapy[6]. However, not all patients with complete response harbor an ERCC2 mutation; therefore, a tool to predict response in patients who lack an ERCC2 mutation could inform therapy selection. We hypothesized that tumors that are cisplatin sensitive but lack an ERCC2 mutation may harbor other genetic or epigenetic alterations that confer functional NER deficiency and increased NERDetect scores.

Figure 3A:
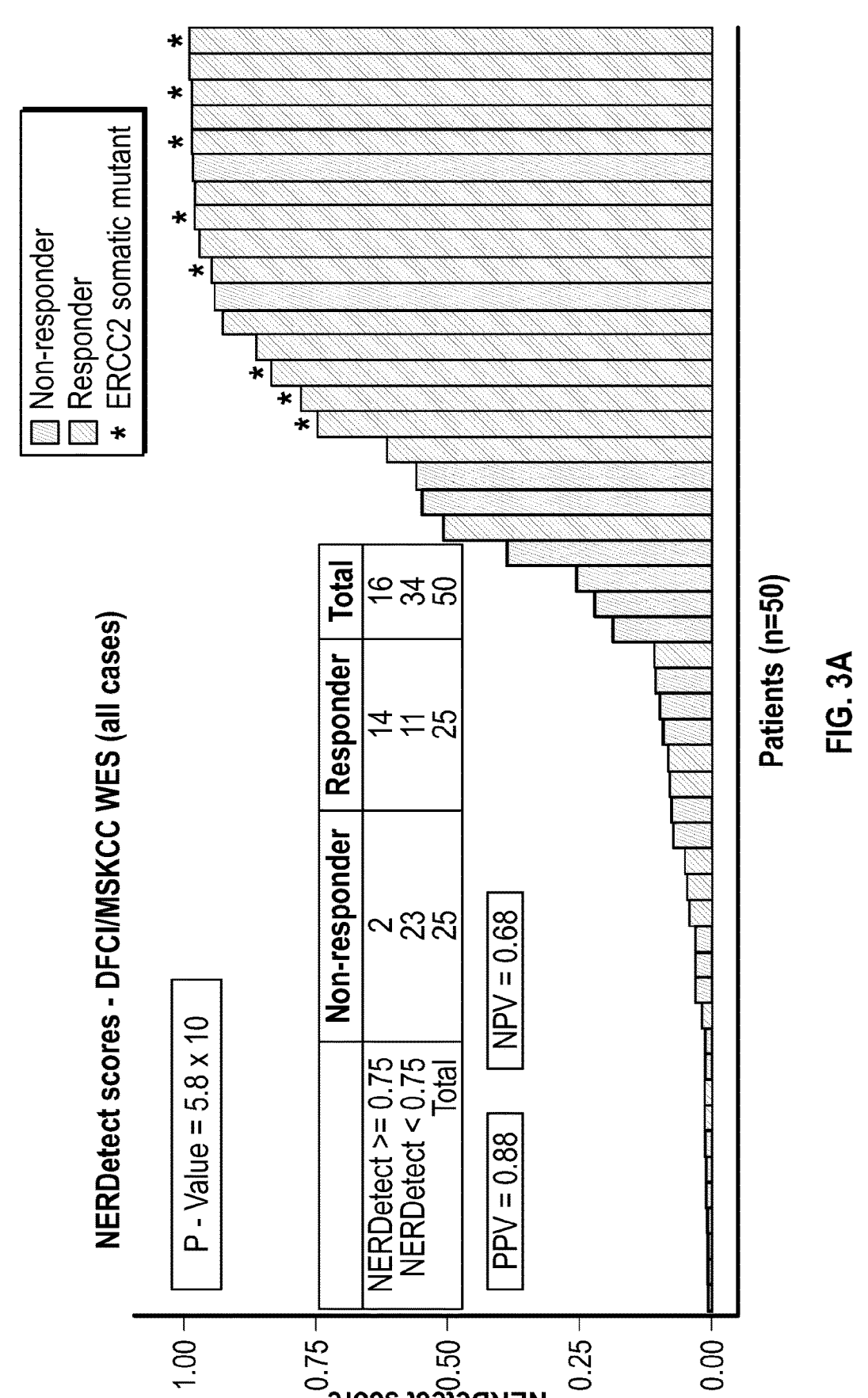
FIGS. 3A-3D show that NERDetect values are associated with cisplatin response independent of ERCC2 mutation status in the DFCI/MSK cohort. Cisplatin responders are colored gray and non-responders are in black.
Figure 3B:
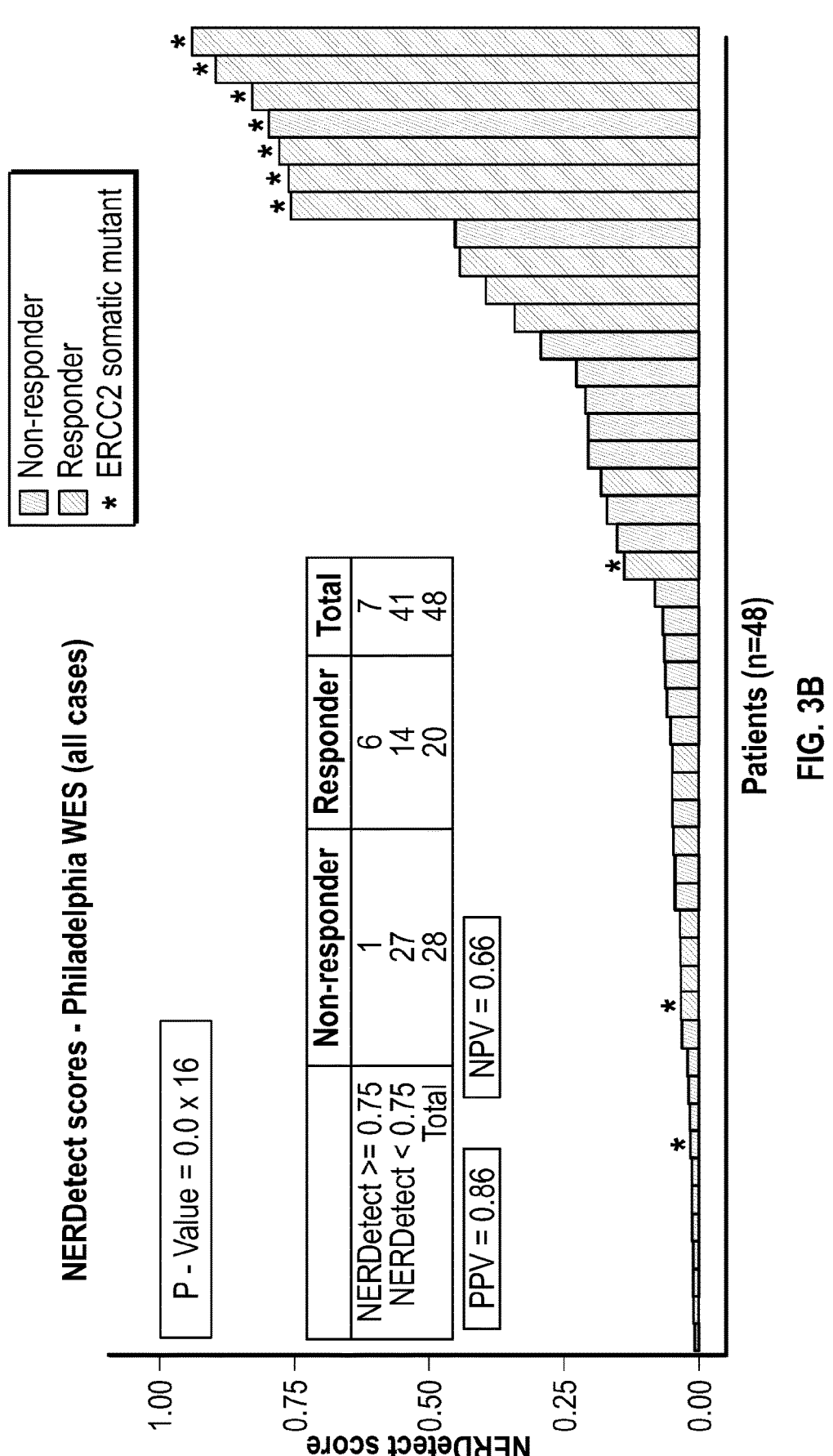

Patients in the DFCI/MSK and FCCC cohorts were treated with cisplatin-based chemotherapy followed by radical cystectomy, and cisplatin responders were defined as those that had no residual invasive disease on pathologic examination of the cystectomy specimen. The inventors found that NERDetect scores were strongly associated with cisplatin response in both the DFCI/MSK and FCCC cohorts (p<5.8×10$^{-4}$ and p=0.016, respectively; Fisher's exact test; FIGS. 3A-3B). For example, in the DFCI/MSKCC cohort, 14 of 16 cases (87%) with a NERDetect score 0.75 had a complete response versus only 11 of 34 (32%) cases with NERDetect score<0.75. In the FCCC cohort, six of seven cases (86%) with a NERDetect score≥0.75 had a complete response versus only 14 of 41 (34%) cases with NERDetect score<0.75. In both cohorts, overall survival was significantly longer in patients with higher NERDetect scores (Example 2, see also Example 4).

Next, analysis was restricted to patients without an ERCC2 mutation since this is the subset of patients for whom cisplatin response is currently most difficult to predict. Among the 41 WT ERCC2 cases in the DFCI/MSK cohort, 16 were cisplatin responders. There was a significant enrichment of cisplatin responders among the high NERDetect cases: six of the eight (75%) WT ERCC2 patients with NERDetect score≥0.75 in the DFCI/MSK cohort were responders vs only 10 of the 31 (32%) WT ERCC2 patients with NERDetect score<0.75 (p=0.04). In the FFPE-derived FCCC cohort, NERDetect scores were lower than in the other cohorts (which were derived from fresh frozen tissue), and there were no WT ERCC2 cases with NERDetect score≥0.75 (Example 2, Example 4). In both cohorts, there was a strong trend towards improved overall survival for WT ERCC2 patients with higher NERDetect scores (FIG. 4C; Example 2, Example 4). These data demonstrate that NERDetect scores are associated with cisplatin response independent of ERCC2 status, suggesting that cisplatin response is driven at least in part by relative NER deficiency in bladder tumors and that NERDetect scores may be useful in prioritizing patients for platinum or other NER-targeting agents.

NER Gene Inactivation is Sufficient to Induce the NERDetect Signature

Figure 4A:
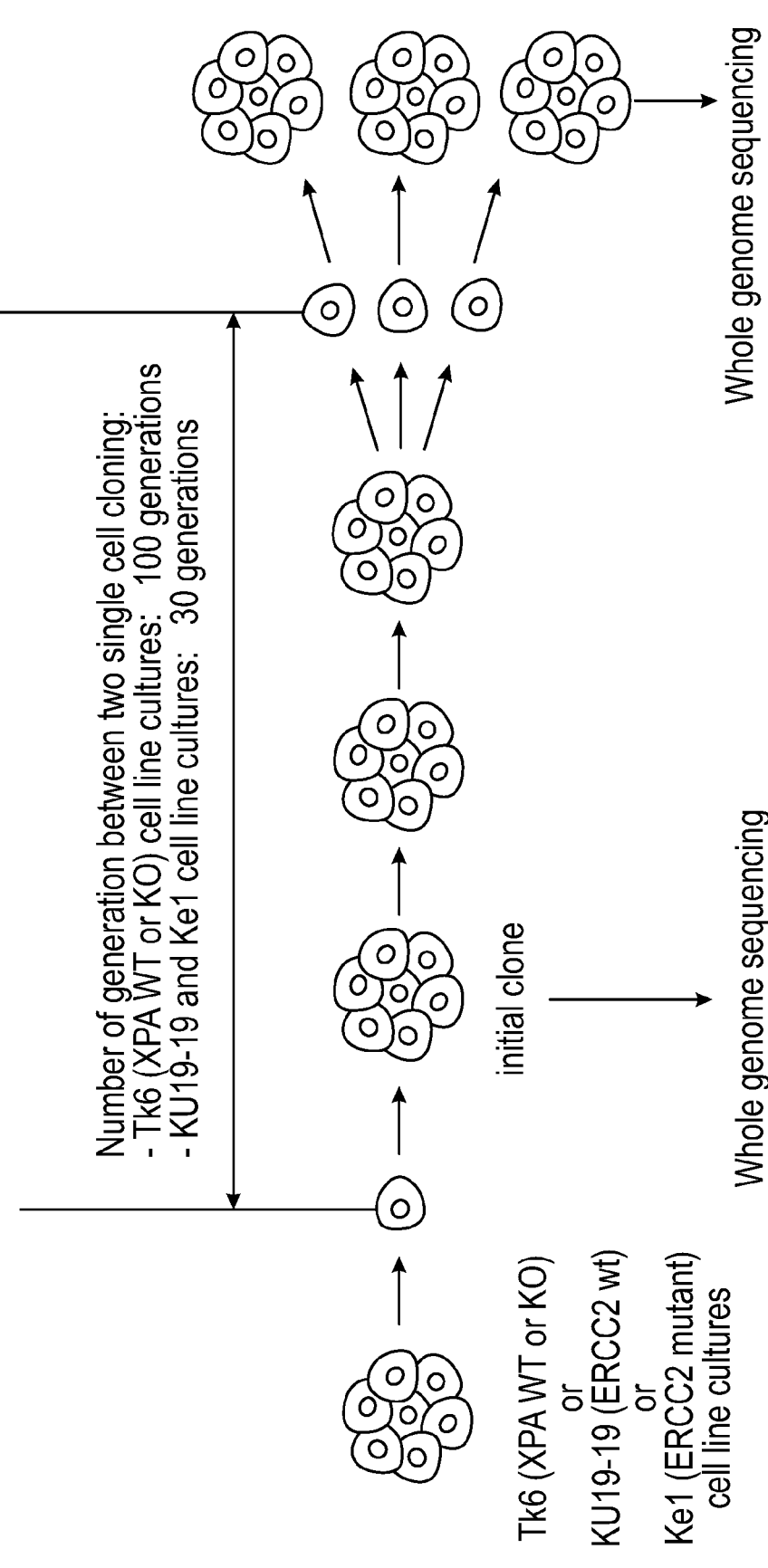
FIGS. 4A-4B show that NER deficiency drives the NER-Detect composite mutational signature.
Figure 4B:
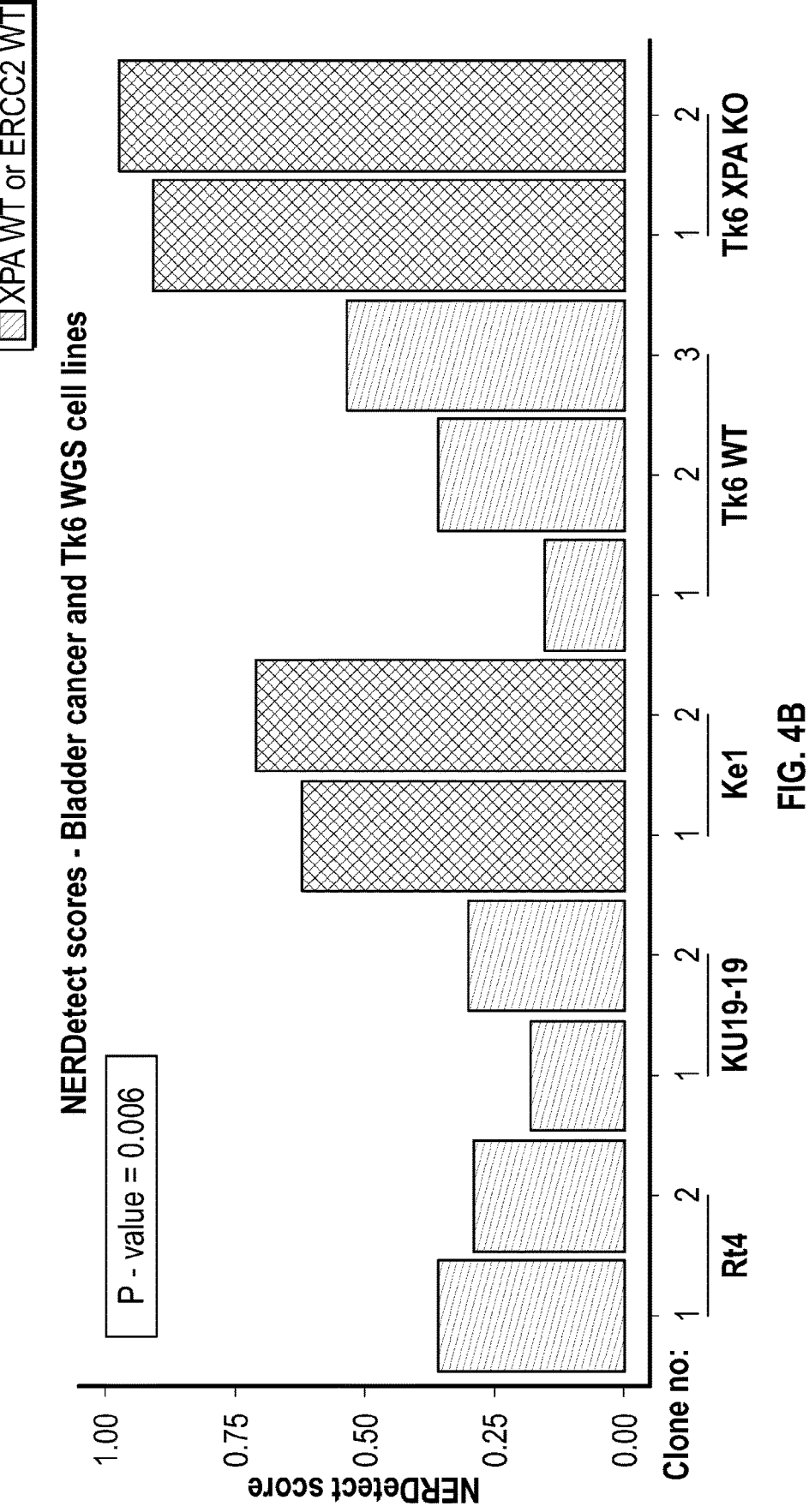

To further investigate the relationship between NER pathway activity and the NERDetect composite mutational signature, we tested if inactivation of a single NER gene was sufficient to generate the NERDetect signature. KU19-19 and RT4 are bladder cancer cell lines with no known NER pathway alterations while KE1 is a derivative of the KU 19-19 line that harbors an inactivating ERCC2 mutation introduced by CRISPR/Cas9 gene editing[6]. For each cell line, clonal populations were propagated in parallel for 30 days and single cells were isolated, expanded to ~1×10$^6$ cells, and harvested for genomic DNA isolation (FIG. 4A). Whole genome sequencing was performed from the 'parental' (P0) population as well as from at least two independent 'post-propagation' clonal populations. Mutations were called as previously described[29] and NERDetect scores were calculated for each sample (see Methods). We also performed a similar experiment in the NER-proficient human lymphoblast cell line TK6 as well as an XPA-deficient derivative of TK6 created by zinc finger nuclease editing[27]. XPA is a key NER factor involved in both TC-NER and GG-NER, and XPA-deficient TK6 cells are NER deficient. Although all cell lines acquired mutations that resulted in an increase in the NERDetect score, the NER-deficient KE1 and TK6 XPA KO cell lines had significantly higher NERDetect scores than the cell lines that lack any known NER pathway defect (p=0.006; FIG. 4B). These data demonstrate that NER deficiency created by loss of an NER gene is sufficient to induce the NERDetect composite mutational signature and further support a direct link between NERDetect score and cellular NER capacity.

Irofulven Kills NER Deficient Tumors In Vitro and In Vivo

Given that tumor NER deficiency drives sensitivity to platinum-based agents, we sought to determine if NER deficiency was also sufficient to confer sensitivity to other agents that create DNA damage typically repaired by the NER pathway. Irofulven is a DNA alkylating agent that creates lesions which do not distort the DNA helix and are thus not recognized by most DNA repair pathways, including the GG-NER pathway (FIG. 5A)[14]. However, when present in transcribed regions of the genome, irofulven lesions block RNA polymerase and activate TC-NER. Therefore, irofulven is highly toxic to cells from patients with inactivating mutations in a TC-NER or common NER gene[8,14].

Figure 5B:
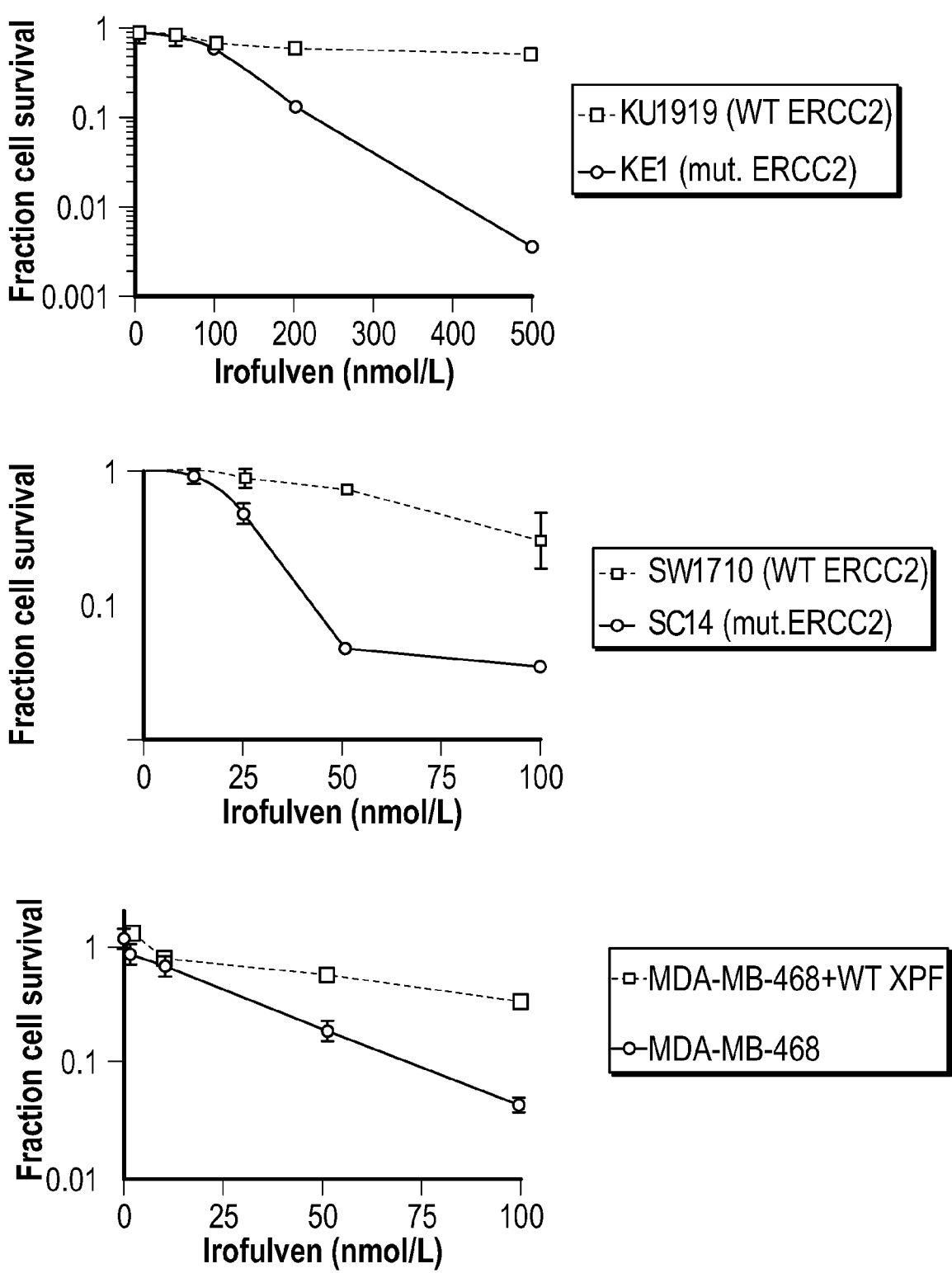

Given the activity of irofulven in TC-NER deficient non-tumor cells, we hypothesized that irofulven would also be toxic to tumor cells with loss-of-function of a TC-NER or common NER gene. We measured irofulven sensitivity of the NER-proficient KU19-19 bladder cancer cell line as well as its ERCC2-mutated derivative, KE1. While KU19-19 showed minimal sensitivity across the tested irofulven concentrations, the NER-deficient KE1 cell line was highly sensitive to irofulven (FIG. 5B).

We recently showed that the breast cancer cell line MDA-MB-468 is NER deficient due to epigenetic silencing of ERCC4, and that cisplatin sensitivity of the cell line could be rescued by re-expression of ERCC4[32]. We tested irofulven sensitivity of the parental MDA-MB-468 line as well as its ERCC4-complemented counterpart and again observed dramatically higher irofulven sensitivity in the NER-deficient cell line (FIG. 5B).

Figure 5C:
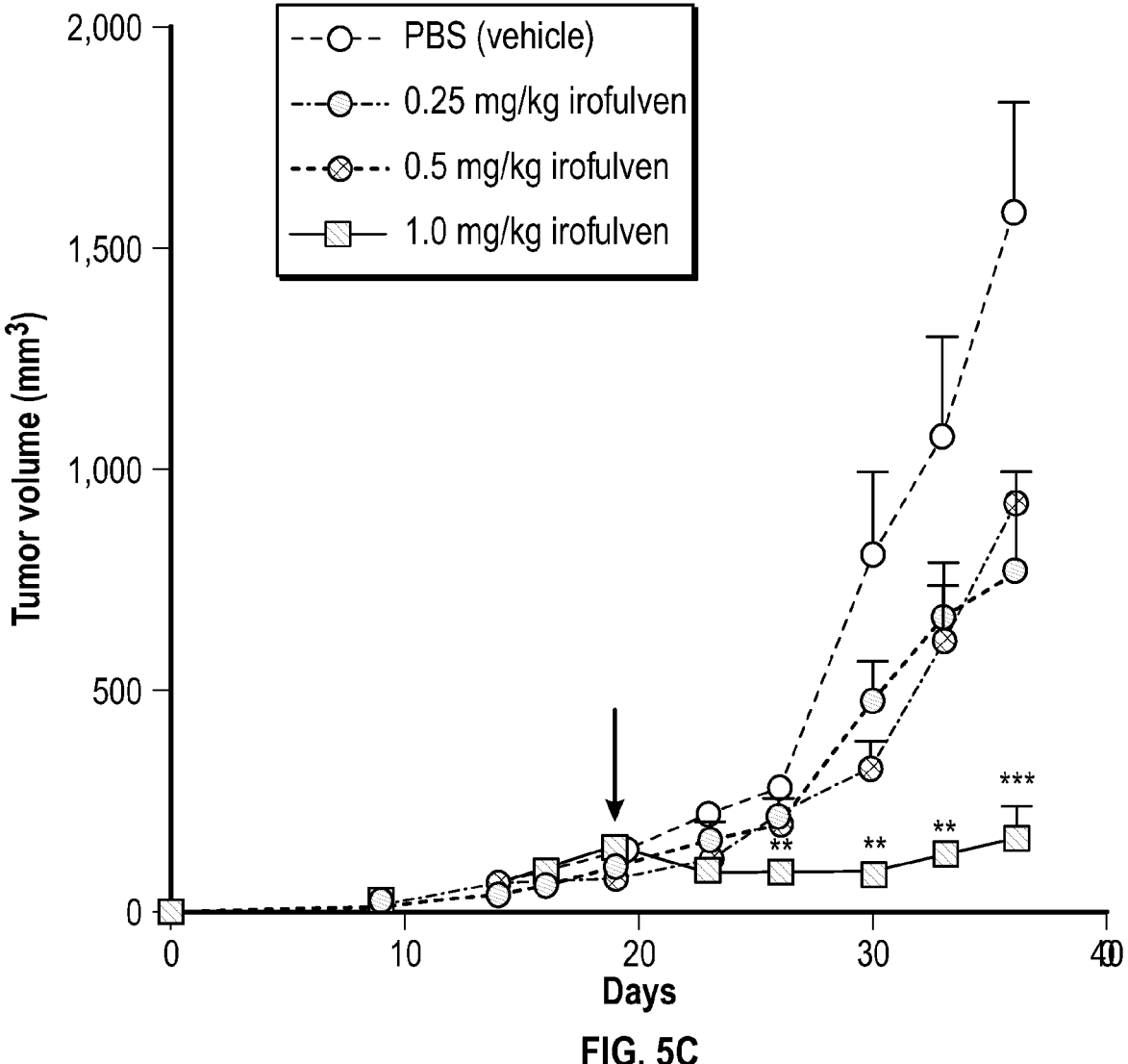
Figure 5D:
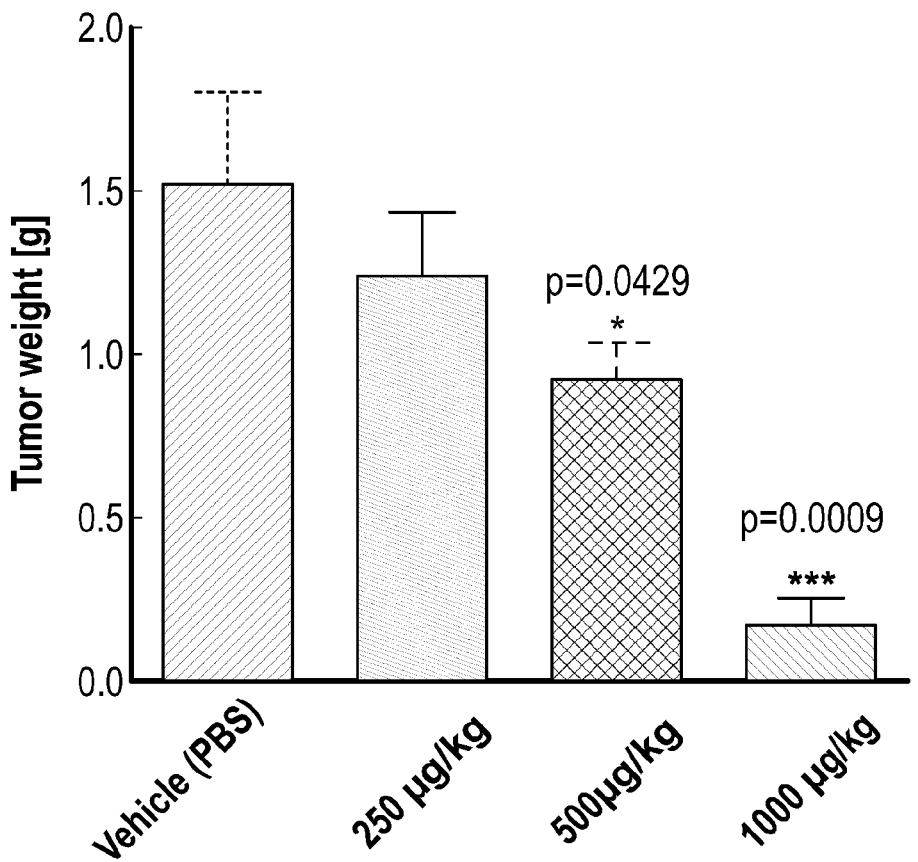
Figure 5D:
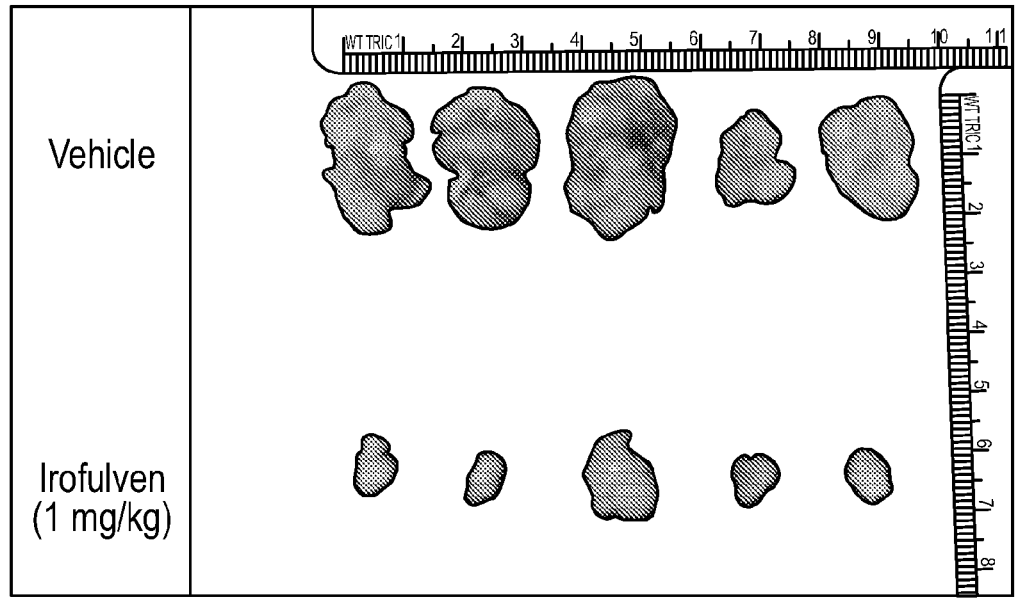

Finally, we wished to test if NER deficiency was sufficient to drive bladder tumor sensitivity to irofulven in vivo. We established NER-deficient KE1 xenografts and treated mice with increasing doses of irofulven twice weekly for a total of five doses. We observed a strong irofulven dose response with near complete tumor regression observed at an irofulven dose of 1 mg/kg (FIG. 5C; Example 2 and Example 4). Conversely, there was no response of the NER-proficient KU19-19 xenografts to 1 mg/kg irofulven.

Figure 6A:
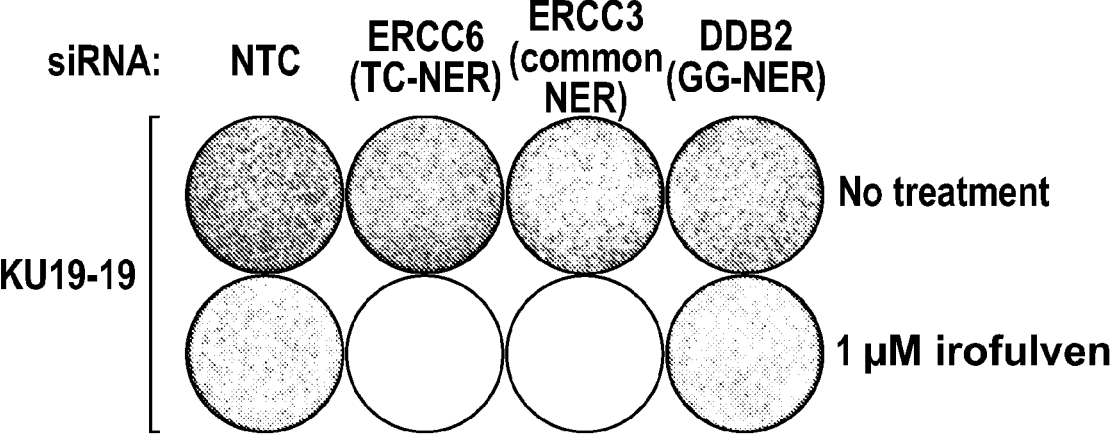
FIGS. 6A-6E demonstrate that irofulven sensitivity is conferred by TC-NER or common NER gene defects and persists in cisplatin-resistant models.
Figure 6A:
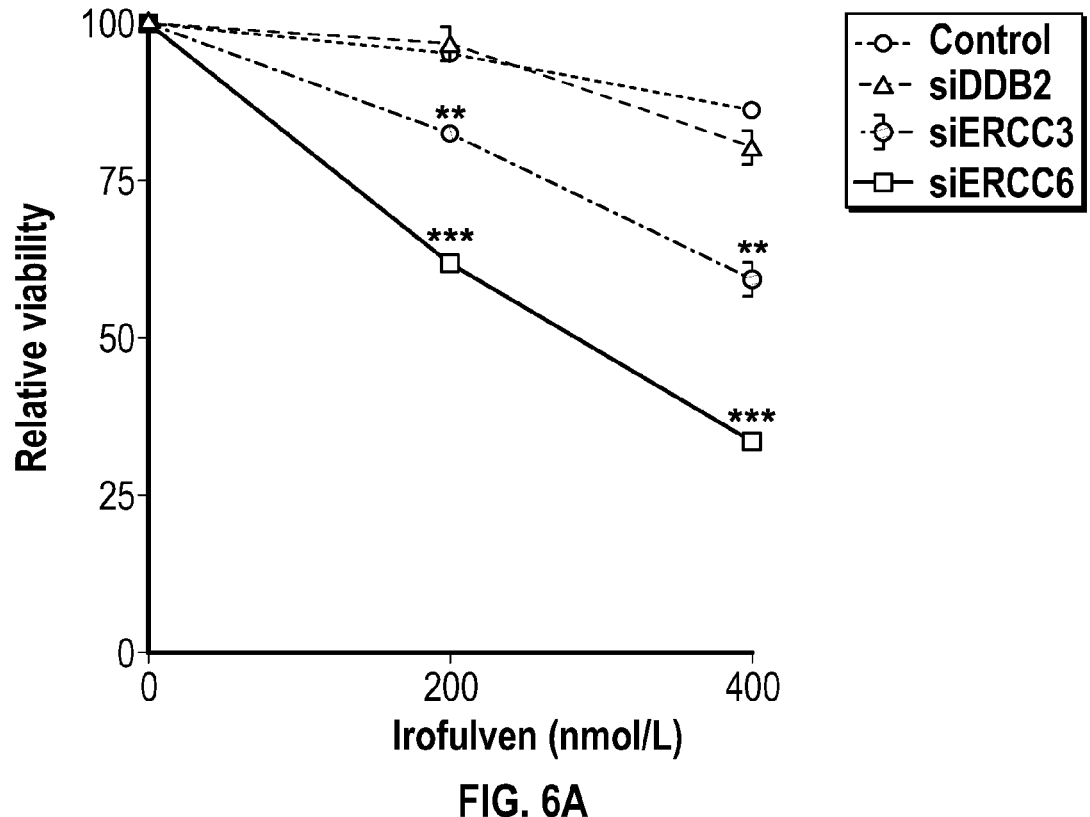

Irofulven Specifically Targets Cancer Cells with TC-NER or Common NER Pathway Defects To further investigate the specificity of the relationship between NER deficiency and irofulven sensitivity, we used siRNA to deplete genes in the TC-NER, GG-NER, or common NER pathways. Whereas depletion of the TC-NER gene ERCC6 or the common NER gene ERCC3 was sufficient to increase irofulven sensitivity in KU19-19 cells, depletion of the GG-NER gene DDB2 had minimal impact on irofulven sensitivity (FIG. 6A). These results are consistent with irofulven creating DNA lesions that are only recognized by the TC-NER pathway.

Figure 6B:
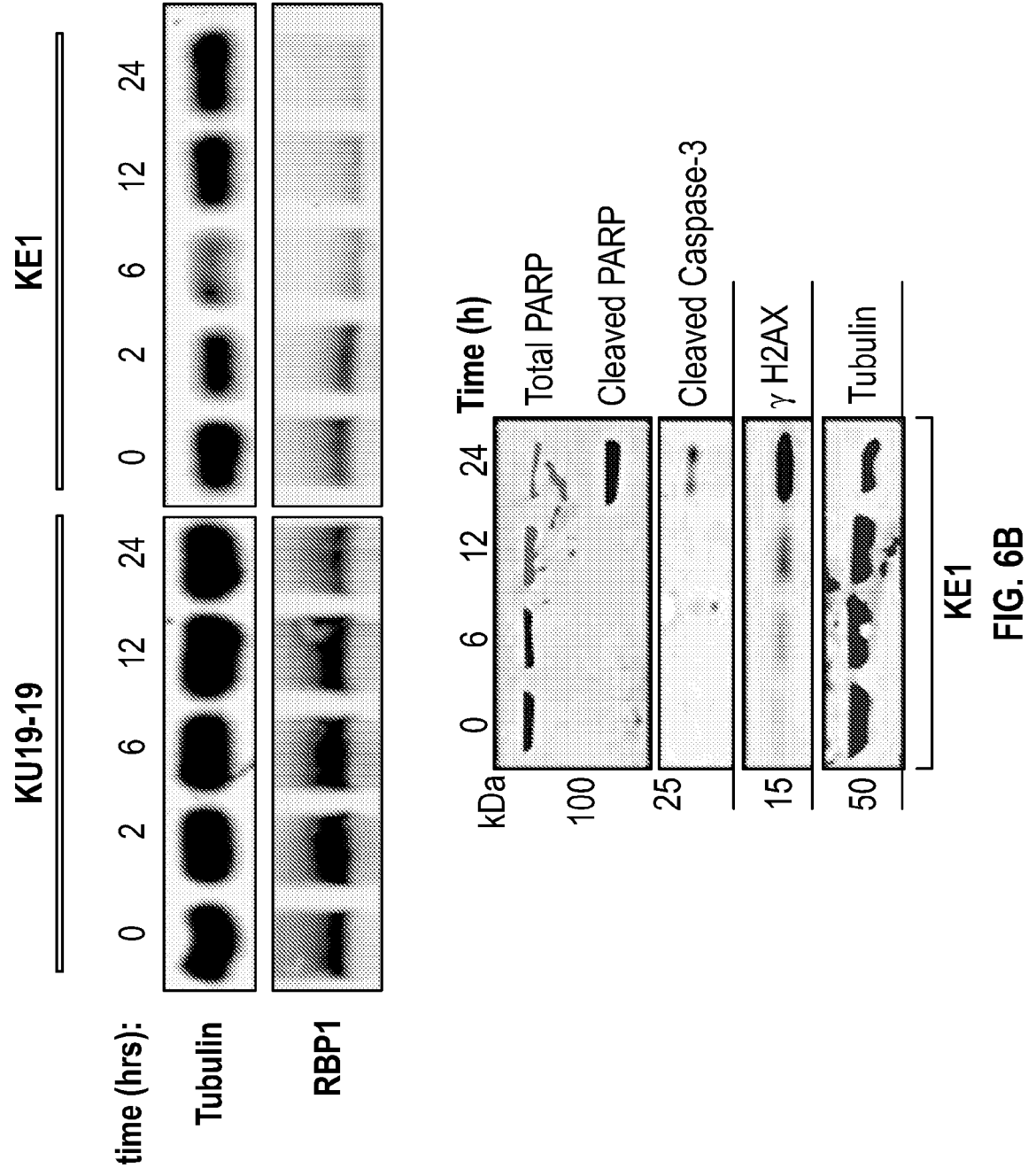

The TC-NER pathway is normally activated by RNA polymerase stalling at DNA lesions. However, in cells with loss or dysfunction of a TC-NER or common NER gene, stalled RNA polymerase can undergo ubiquitination and proteasomal degradation to prevent toxic accumulation of stalled polymerase complexes (39). Following irofulven treatment, we observed a time-dependent loss of RNA polymerase in NER-deficient KE1 cells but not in NER-proficient KU19-19 cells, consistent with an inability of KE1 cells to repair irofulven-mediated DNA damage via TC-NER (FIG. 6B, top). We also observed accumulation of the DNA damage marker phospho-H2AX ($\gamma$H2AX) as well cleaved PARP and cleaved caspase-3 in irofulven-treated NER-deficient cells, consistent with apoptotic cell death (FIG. 6B, bottom).

Figures 6C, 6D:
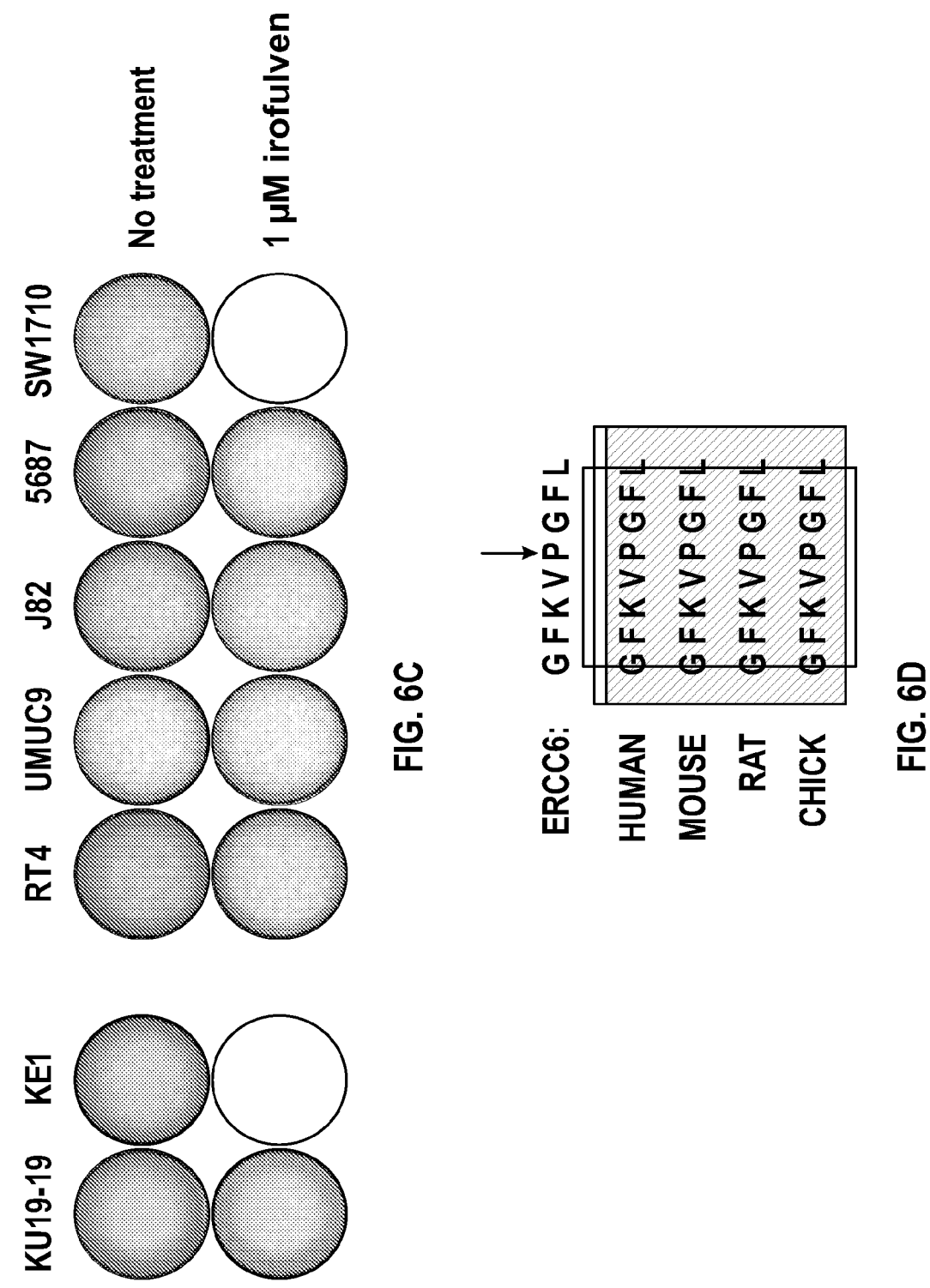
Figure 6E:
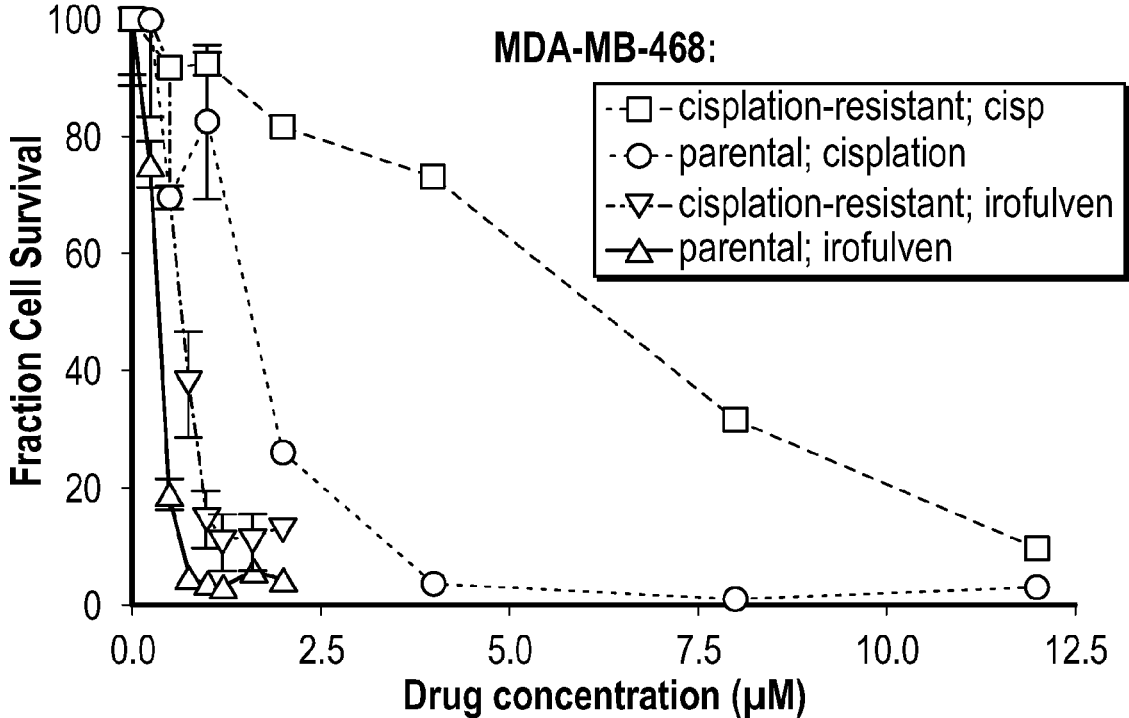
Figure 6E:
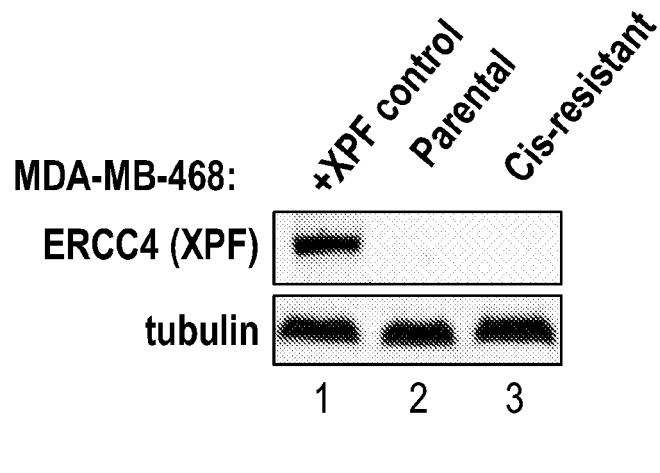
Figure 7A:
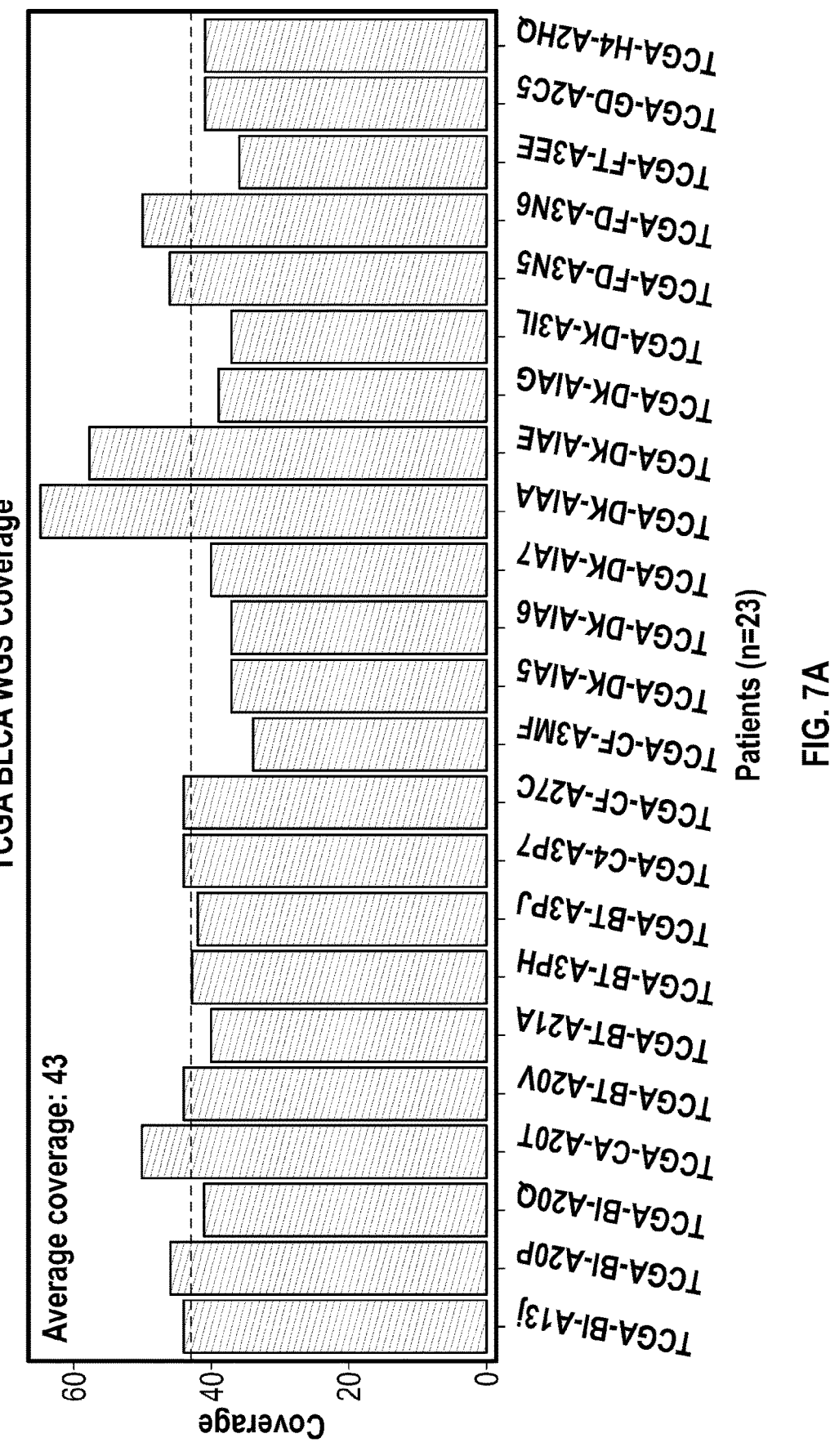
FIGS. 7A-7B show the average coverage of the analyzed samples in the TCGA BLCA WGS (FIG. 7A) and TCGA BLCA WES (FIG. 7B) cohorts.
Figure 7B:
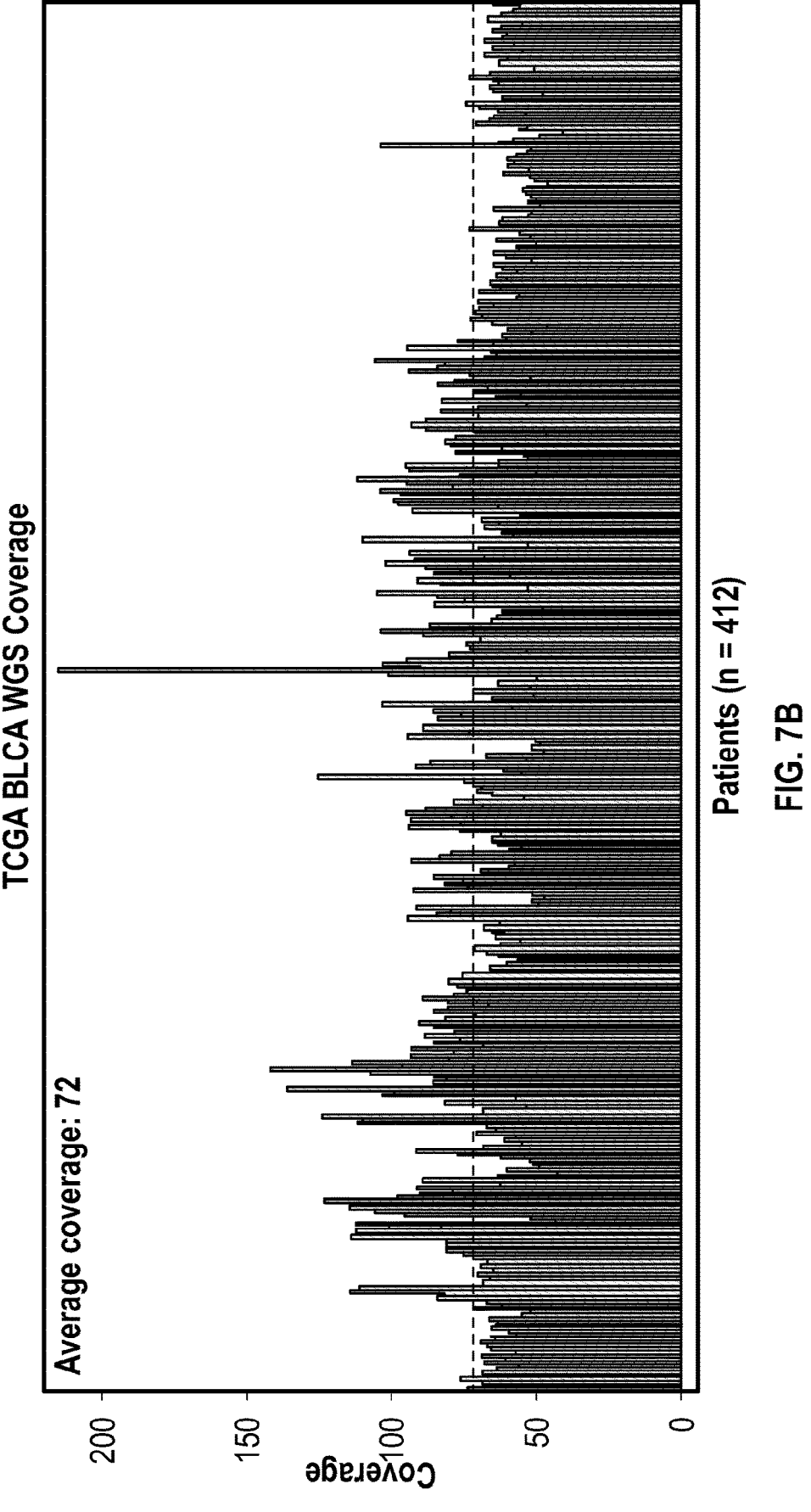

Most lines showed minimal sensitivity to irofulven, suggesting that the TC-NER and common NER pathways are intact in most bladder cancer cell lines. However, there was one clear exception: the bladder cancer cell line SW1710 demonstrated much higher sensitivity to irofulven. We examined mutational data from SW1710 and identified a P500R missense mutation within the conserved ATPase domain of the TC-NER gene ERCC6 that may confer TC-NER deficiency and irofulven sensitivity (FIG. 6C).

Cisplatin Resistance does not Confer Cross-Resistance to Irofulven

Platinum-based chemotherapy is a first-line treatment for numerous solid malignancies including bladder cancer, but platinum resistance frequently occurs and represents a challenging clinical problem. Although a variety of platinum resistance mechanisms have been characterized, restoration or upregulation of DNA repair is a common mechanism of resistance, particularly in HR-deficient breast and ovarian tumors[33]. Mechanisms of platinum resistance in NER deficient tumors have not been characterized, and we wished to determine if acquired resistance to cisplatin would confer cross-resistance to irofulven through restoration of NER. To test this, we derived cisplatin resistance in the NER-deficient MDA-MB-468 cell line by gradual exposure to escalating doses of cisplatin (Methods). Although the cisplatin IC50 was ~3.5-fold higher in the cisplatin resistant cell line, the cell line remained highly sensitive to irofulven (FIG. 6D). Immunoblotting showed lack of ERCC4 re-expression in the cisplatin-resistant cell line, suggesting that cisplatin resistance is driven by a mechanism other than restoration of NER. This result suggests that irofulven may still demonstrate useful clinical activity in NER-deficient tumors that have become resistant to platinum-based therapy.

Discussion of Results

Tumor DNA repair deficiency is of particular interest in clinical oncology because it can potentially be targeted using a synthetic lethal based strategy. However, the success of the synthetic lethal approach is dependent on accurate identification of the relevant DNA repair pathway deficiency from clinical tumor specimens as well as on the availability of a therapeutic agent that is specifically active in DNA repair deficient cells. Here, we describe a synthetic lethal approach that leverages clinical sequencing data to identify tumor NER deficiency as a marker of sensitivity to irofulven, a previously failed anti-cancer drug that specifically targets NER-deficient tumors.

Although DNA sequencing can identify loss or mutation of key DNA repair genes, relying exclusively on this approach to identify tumor DNA repair deficiency has several shortcomings including (1) uncertainty regarding the biological impact of novel mutations (i.e., variants of unknown significance), (2) the potential for secondary genetic events to modulate the effect of an observed mutation (for example, REV7 loss offsetting the impact of BRCA1 loss[34]), and (3) loss of pathway activity via an epigenetic mechanism or through alteration of a gene not previously implicated in the pathway. Mutational signature based approaches have the potential to overcome many of these challenges because they detect the genomic consequences of DNA repair pathway deficiency rather than the underlying cause. Furthermore, integrative analyses of multiple types of mutation events (SNVs, indels, rearrangements) may increase the ability of mutational signatures to identify clinically relevant DNA repair deficiency, as has been demonstrated for detection of HR deficiency in breast tumors[35]. Here, we develop and validate NERDetect, a composite mutational signature of NER deficiency in bladder cancer. In multiple independent cohorts, NERDetect scores were strongly associated with ERCC2 mutation status, and importantly, were also associated with cisplatin response independent of ERCC2 status. These findings suggest that the NERDetect score is a reliable predictor of NER function in clinical tumor specimens and that tumor NER capacity is a major determinant of clinical response to cisplatin-based chemotherapy.

The mutation events that comprise the NERDetect signature reflect the net result of DNA damage and repair processes in NER deficient tumors. Deletions >5 bp that lack flanking microhomology (the ID8 signature) are the strongest contributor to the NERDetect composite signature and are thus likely to be a direct consequence of NER's absence. Failure of the NER pathway to resolve a lesion may result in DNA breakage or replication fork collapse, and the resulting damage may be resolved through error-prone end joining with loss of >5 nucleotides at the site of initial DNA damage.

The COSMIC 5 SNV signature was also associated with NER loss. Studies across tumor types have shown that activity of COSMIC signature 5 increases with patient age[36], consistent with an endogenous source of DNA damage. NER typically operates in an error-free manner, and if the COSMIC 5 signature arises when NER fails to faithfully repair endogenous damage, then loss of NER would result in an increase in the activity of the signature.

Cisplatin-based chemotherapy is a front-line treatment option for advanced bladder cancer; however, only a subset of patients respond. Mutations in ERCC2 or other related DNA repair genes are present in ~20% of patients and are associated with improved cisplatin response. Although response rates are high in this subset of DNA repair deficient cases, patients without an obvious DNA repair gene alteration can also respond to cisplatin. However, until now, reliable predictive biomarkers did not exist to identify these patients. Although the NERDetect tool was trained on ERCC2 mutant bladder cancers, NERDetect scores were correlated with platinum response even among patients who lacked an ERCC2 mutation. This functional data demonstrates that loss of other NER genes can also induce the NERDetect composite mutational signature, and several of the WT ERCC2 cisplatin responders with a high NERDetect score harbored a predicted deleterious mutation in another NER gene such as ERCC4 or ERCC5 (Example 2). Together, these data demonstrate that NERDetect can be used to predict cisplatin response in patients who lack an ERCC2 mutation or other obvious DNA gene alteration. We identified an optimal threshold NERDetect score of ≥0.75 for bladder tumors sequenced from fresh frozen tissue, which is the same threshold used for the HRDetect tool[13]. Future efforts should focus on further validation of the NERDetect tool in a prospectively collected bladder cancer cohort.

Despite the proven efficacy of cisplatin-based therapy, 30-50% of bladder cancer patients are unable to tolerate cisplatin due to renal dysfunction or other medical comorbidities[41]. Although the role of immunotherapy in bladder cancer is expanding, optimal treatment of cisplatin-ineligible advanced bladder cancer patients remains unclear. For cisplatin-ineligible patients with an ERCC2 mutation and/or high NERDetect score, irofulven may provide an alternative approach to target tumor NER deficiency. We find that NER-deficient tumor cells are profoundly sensitive to irofulven in vitro and in vivo, whereas irofulven has minimal effect on viability of NER-proficient cells. Importantly, acquired cisplatin resistance in an NER-deficient tumor model confers minimal cross-resistance to irofulven, suggesting that irofulven may be a rationale treatment for patients with an ERCC2 mutation and/or high NERDetect score who progress on platinum-based chemotherapy.

Although ERCC2 mutations in bladder cancer are the best characterized example of clinically relevant tumor NER deficiency to date, several other tumor types may also NER-deficient subsets. For example, approximately 4% of high-grade epithelial ovarian tumors harbor a predicted deleterious alteration in an NER gene without a co-occurring BRCA1/2 alteration, and this subset of tumors has improved survival following platinum-based chemotherapy[42]. Similarly, up to 5% of advanced prostate tumors have deep deletion of an NER gene, which may impact sensitivity to carboplatin-based regimens.

Example 2: a Composite Mutational Signature of Nucleotide Excision Repair Deficiency Analysis Example 2 provides the following: (1) analyzed cohorts, (2) sequence alignments, (3) coverage, (4) mutation and copy number calling, (5) structural variant calling, (6) statistical analysis, (7) survival analysis, (8) cell lines, (9) xenograft studies, and (10) additional figures.

1. Analyzed Cohorts

In this study altogether 632 whole genome (WGS) and whole exome sequenced (WES) samples were analyzed from four urothelial bladder tumor cohorts (Table 2).

TCGA BLCA WGS

The WGS normal and tumor bam files were downloaded from the ICGC data portal available on the world wide web at https<dcc.icgc.org>.

TCGA BLCA WES

The WES normal and tumor bam files, as well as the vcf files generated by MuTect2 were downloaded from the TCGA data portal (available on the world wide web at https<portal.gdc.cancer.gov>).

DFCI/MSKCC WES

The normal and tumor bam files were downloaded from The database of Genotypes and Phenotypes (dbGaP) upon request (available on the world wide web at https<www.ncbi.nlm.nih.gov/gap/>) using the phs000771 accession code.

BGI WES

The normal and tumor fastq files were downloaded from the Sequence Read Archive (SRA) database (available on the world wide web at https<www.ncbi.nlm.nih.gov/sra>) using the SRA063495 accession code. From the 99 WES samples 98 were successfully analyzed, because one patient's ("B89-16") normal WES fastq files were missing from the database.

Philadelphia WES

The normal and tumor barn files were downloaded from The database of Genotypes and Phenotypes (dbGaP) upon request (available on the world wide web at https<www.ncbi.nlm.nih.gov/gap/>). The tumor samples in this cohort are derived from formalin-fixed paraffin embedded (FFPE) tissues.

2. Sequence Alignment

The alignment process of the fastq files from the BGI cohort consisted of three major steps.

Quality control checks with FastQC at the following website available on the world wide web at <bioinformatics.babraham.ac.uk/projects/fastqc> and quality trimming and adapter clipping with Trimmomatic [45].

Alignment of the reads to the GRCh37 human reference genome using the Burrows-Wheeler Alignment Tool (BWA, version 0.7.6a-r433) with the BWA-MEM algorithm.

In the final post-processing step the resulting bam files were sorted, indexed and duplicated reads were removed from them with the sambamba tool [46]. The aligned reads were realigned near indels and base quality scores were recalibrated using the GATK IndelRealigner and BQSR [39], respectively.

3. Coverage

In order to determine the average coverage of the WGS and WES bam files in each cohort samtools [47] was used. The average coverage (Davg) in a given cohort was calculated as follows $$D_{avg} = \frac{1}{N} \sum_{i=1}^{N} \frac{1}{M} \sum_{j=1}^{M} d_{ij}, \tag{3.1}$$

where $d_{ij}$ is the depth at the jth position within an exonic region of the genome of the ith sample, M is the number of exonic positions examined in the genome, and N is the number of samples in a given cohort. The average coverage of the analyzed WGS and WES samples from the TCGA BLCA cohort and the WES samples from the BGI, DFCI/MSKCC and Philadelphia cohorts are shown in FIG. 7 and FIG. 8, respectively.

4. Mutation and Copy Number Calling 4.1 Genotyping

Genotypes were determined according to the following scheme:
  germline variants were called via GATK [39](version 3.8) HaplotypeCaller in key NER-related genes in WES and WGS samples,
  somatic point mutations and indels were called with GATK (version 3.8) MuTect2 in WGS samples; whole exome vcf files generated by MuTect2 were downloaded from the TCGA data portal.

The high fidelity of the reported germline and somatic variants was ensured by the application of additional hard filters (Tables 3 and 4) on top of the tools' default ones (FILTER=="PASS").

The pathogenicity of the variants was assessed by using Intervar [41](version 2.0.1) which classifies variants into five categories: "Benign", "Likely Benign", "Uncertain significance", "Likely Pathogenic" and "Pathogenic". Mutations in exonic regions that were not synonymous SNVs and classified as "Pathogenic" or "Likely Pathogenic" were considered as deleterious. Variants with "Unknown Significance" were collected separately, but they did not affect the genotyping scheme. ERCC2 mutations were further manually curated based on previous studies [5, 28, 29].

In the Philadelphia FFPE cohort somatic SNPs were identified by MuTect [48], with computational filtering of artifacts introduced by DNA oxidation during sequencing or FFPE-based DNA extraction using a filter-based method [49]. Missense mutations in ERCC2 gene were considered as deleterious.

In order to confirm that the RT4 and KU19-19 cell lines do not have a known NER pathway alteration, a csv file containing annotated somatic mutations from several cell lines was downloaded from the depmap portal (available on the world wide web at https<depmap.org/portal/download/>).

4.2 Mutations in NER-Related Genes

Figure 9:
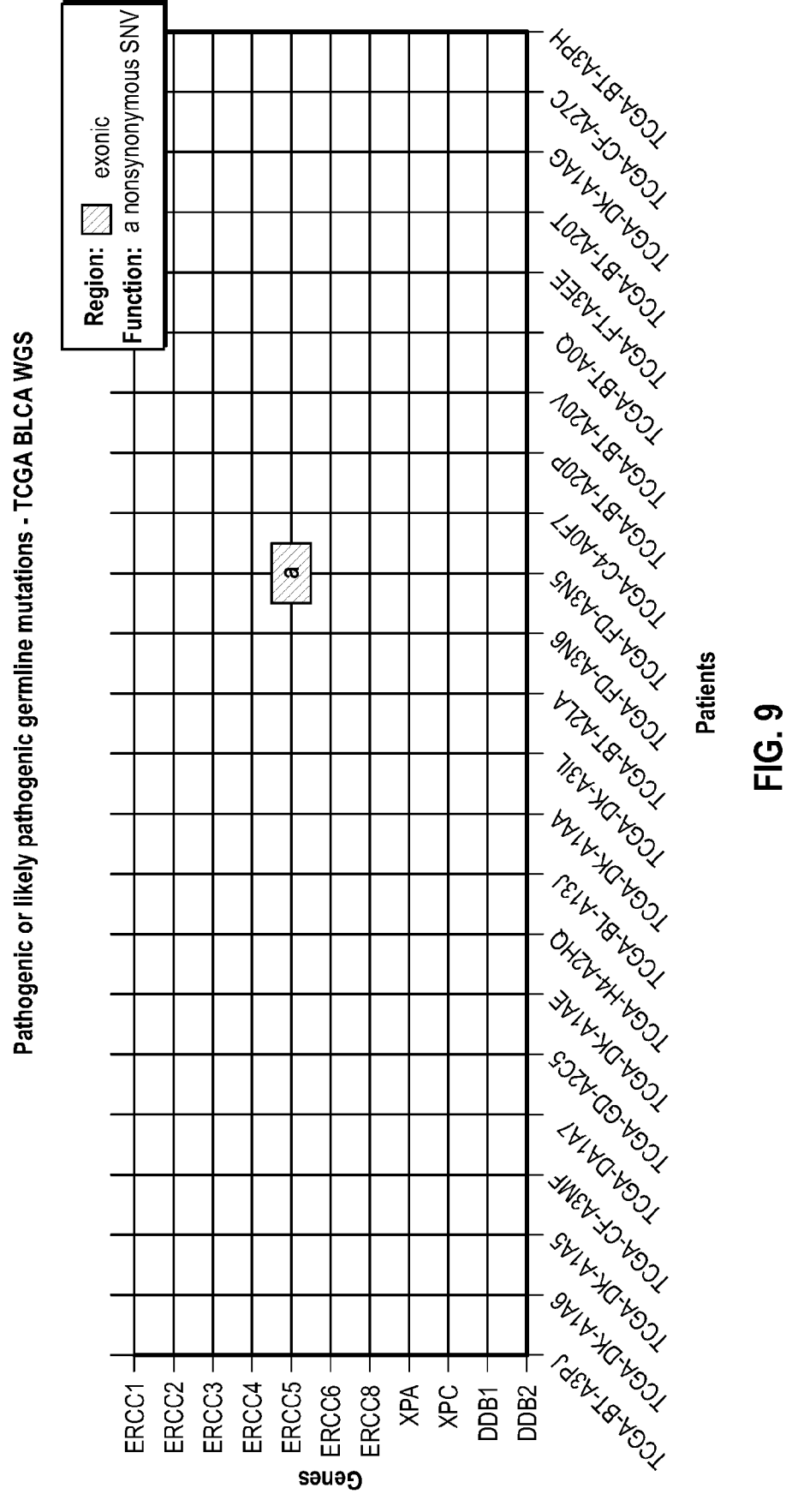
FIG. 9 shows pathogenic or likely pathogenic germline and somatic mutations in the TCGA WGS cohort.
Figure 9:
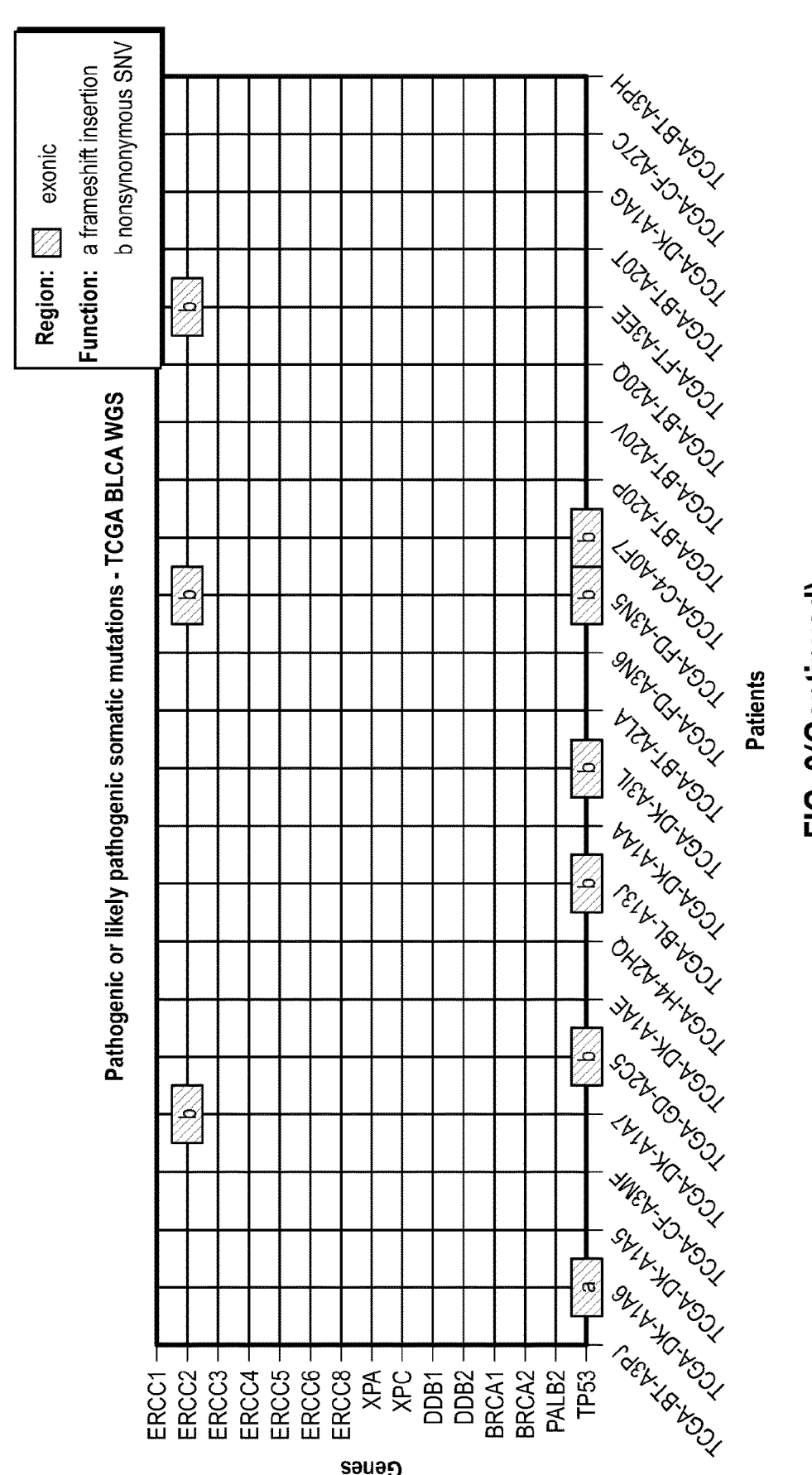
Figure 10:
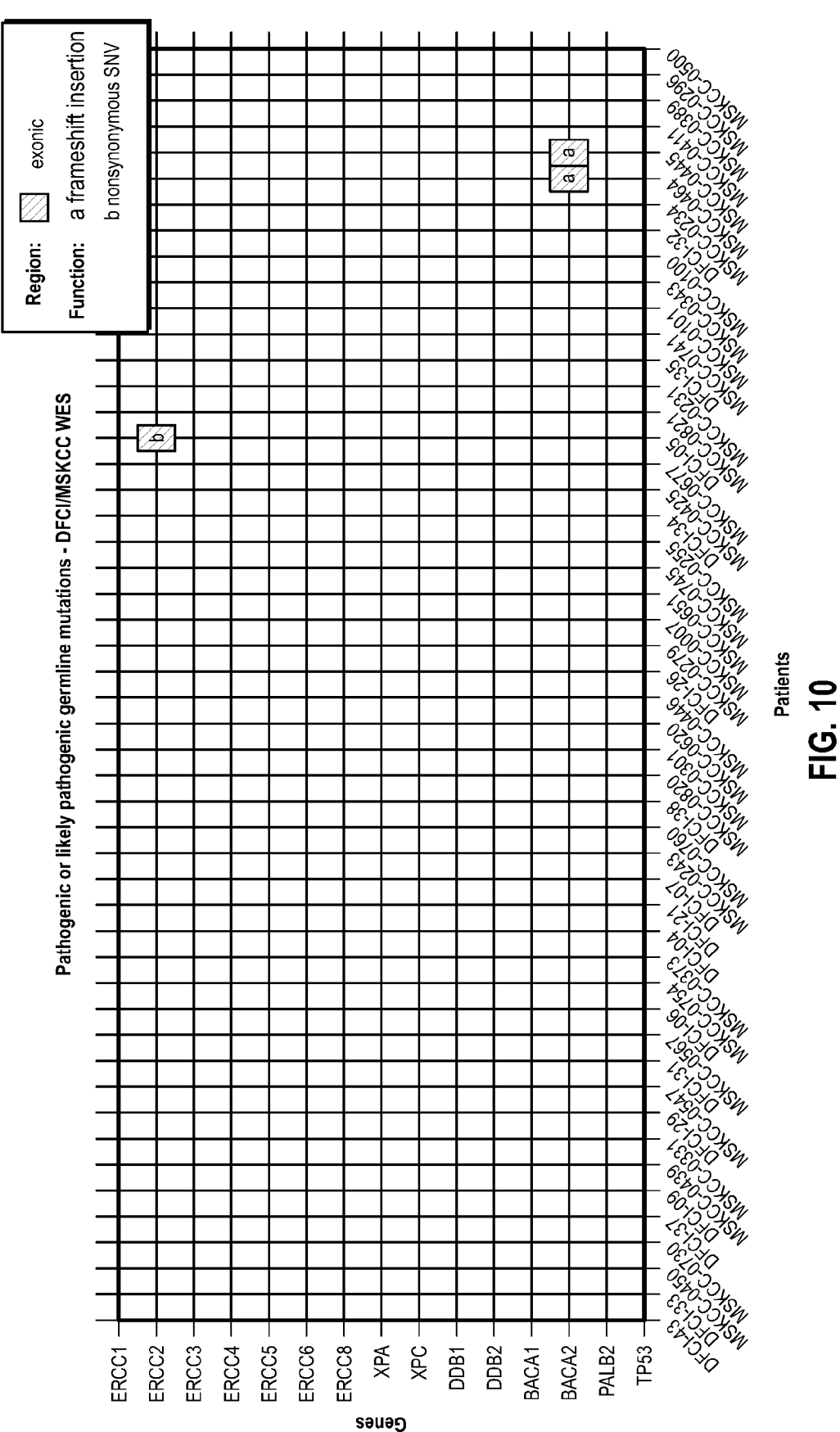
FIG. 10 shows pathogenic or likely pathogenic germline and somatic mutations in the DFCI/MSKCC WES cohort.
Figure 10:
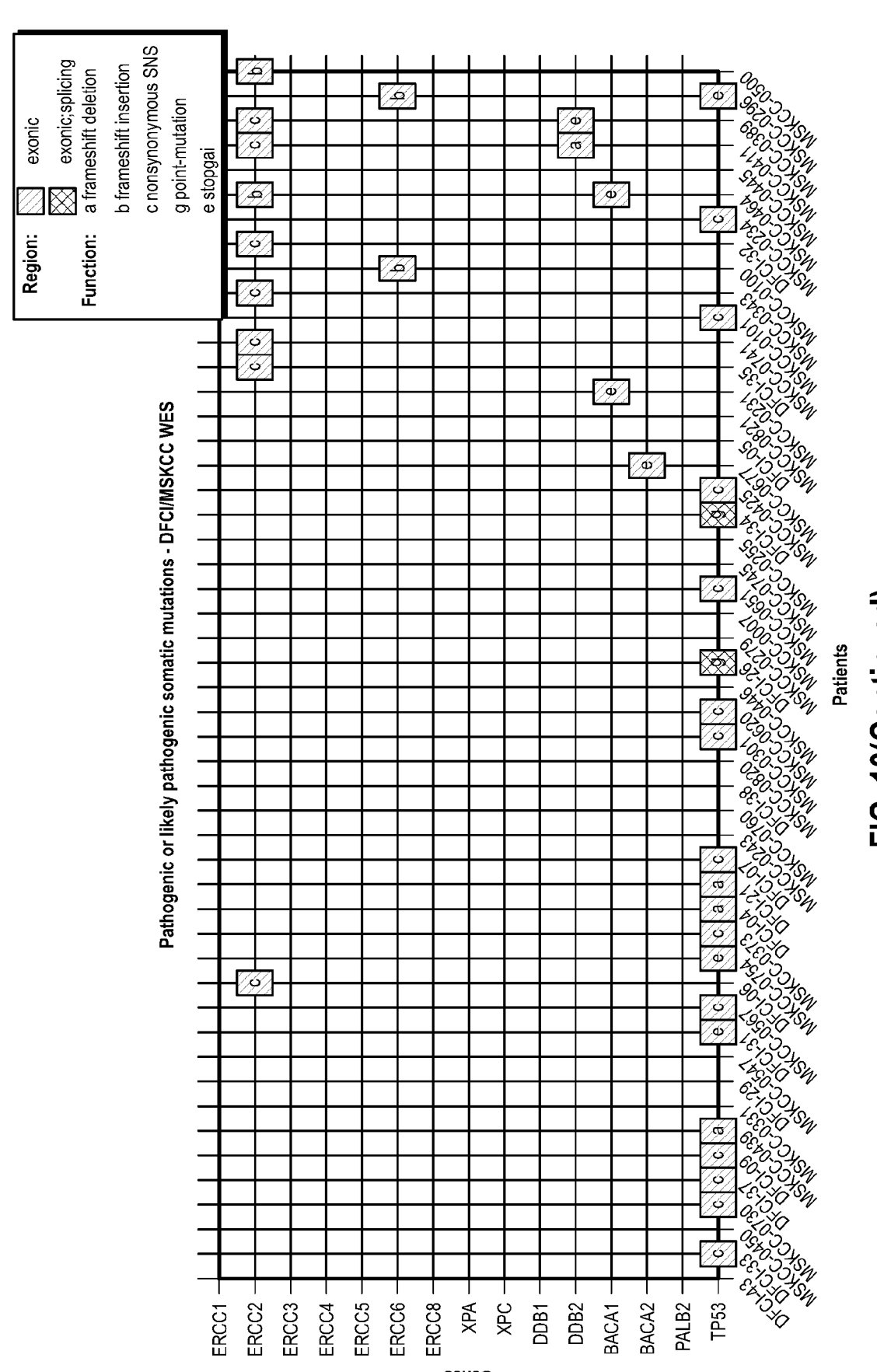
Figure 11:
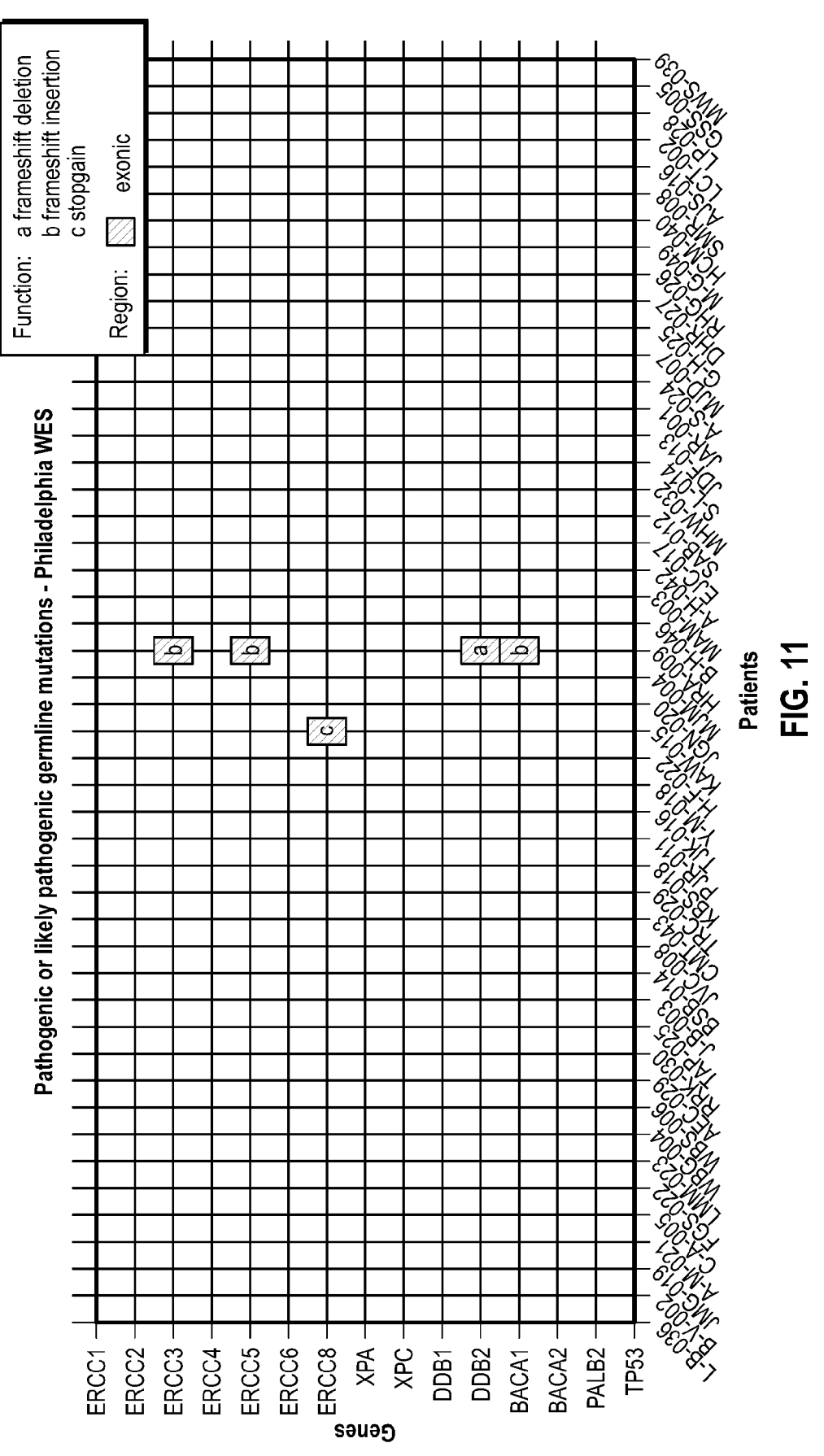
FIG. 11 shows pathogenic or likely pathogenic germline and somatic mutations in the Philadelphia WES cohort.
Figure 11:
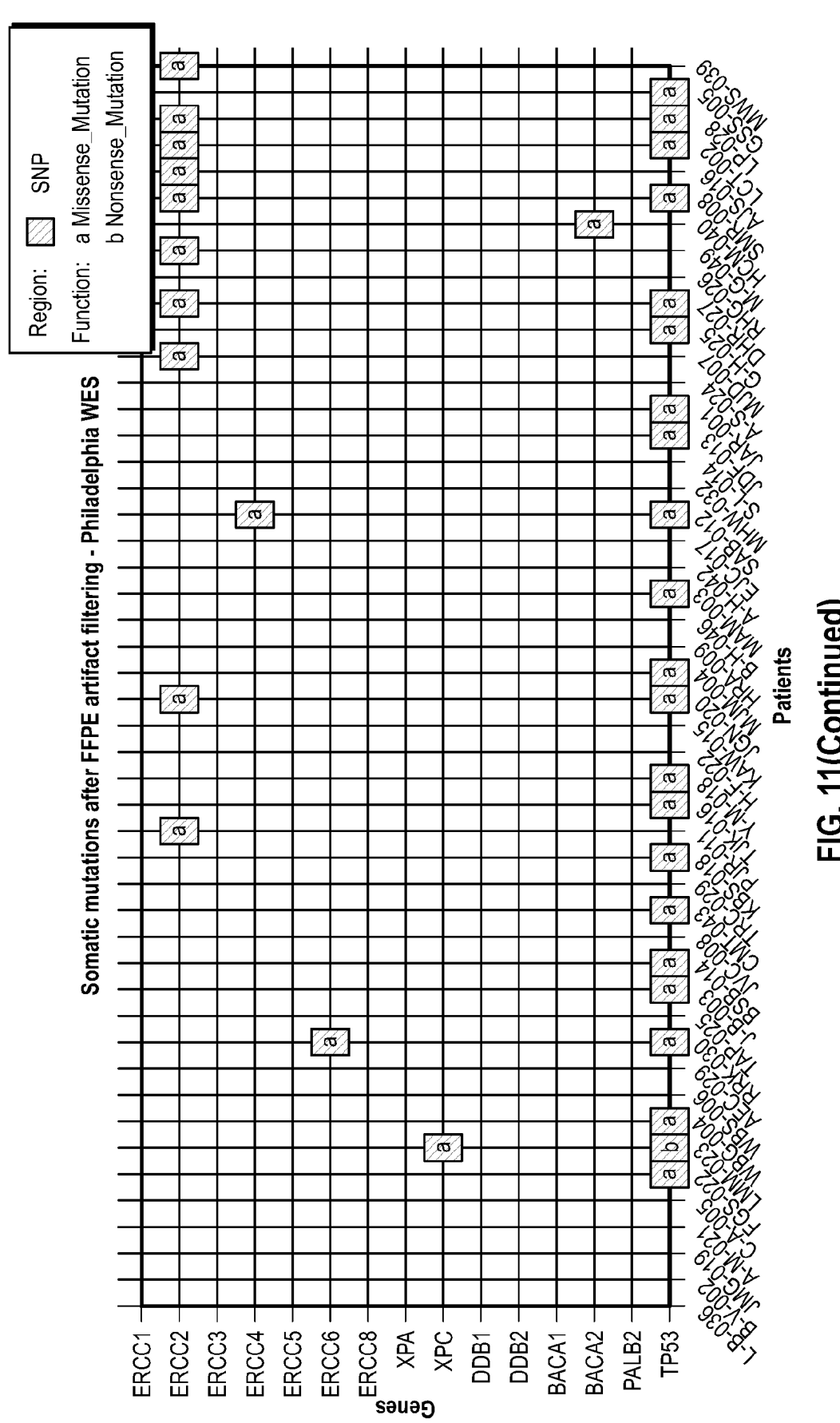
Figure 12:
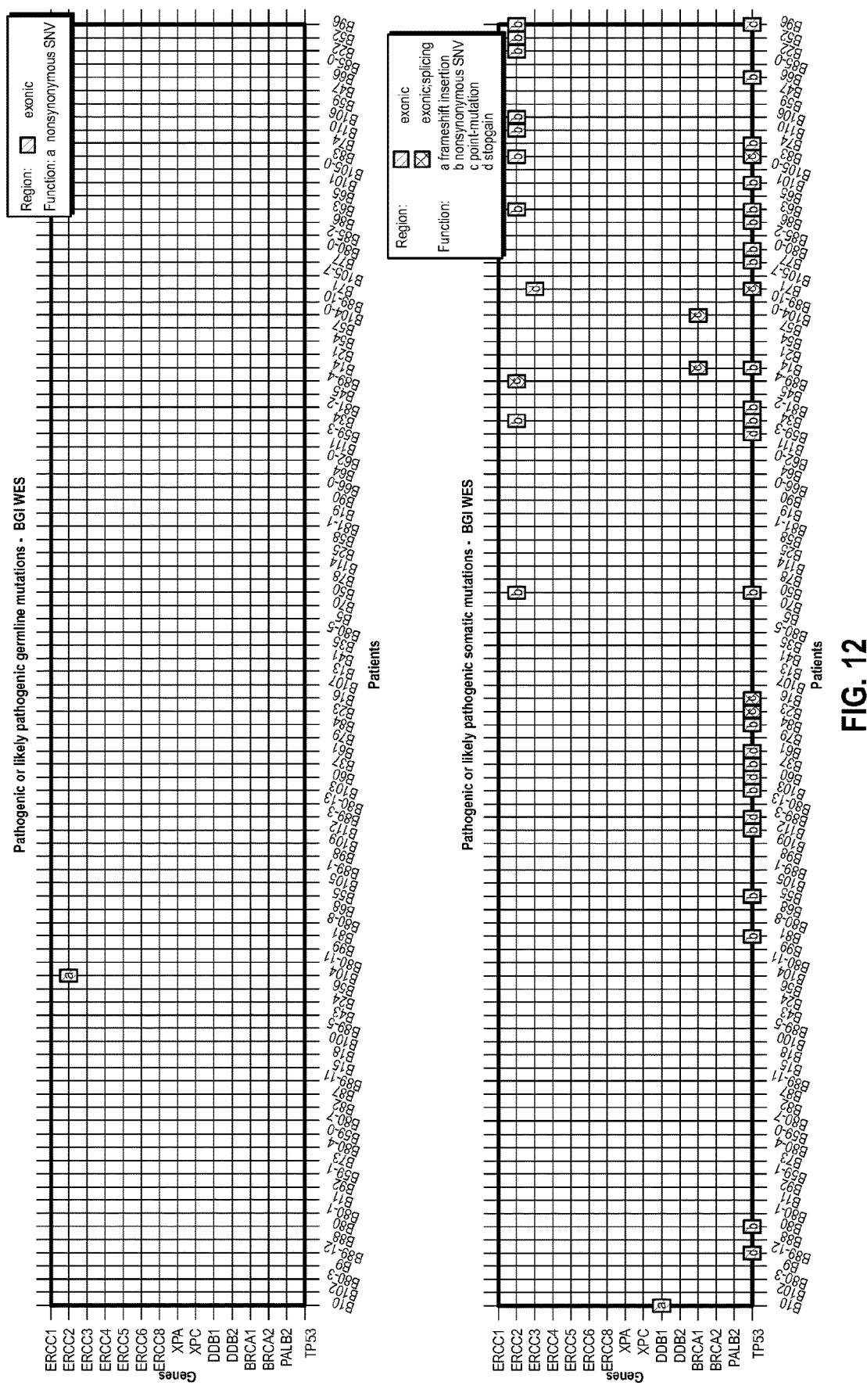
FIG. 12 shows pathogenic or likely pathogenic germline and somatic mutations in the BGI WES cohort.
Figure 13:
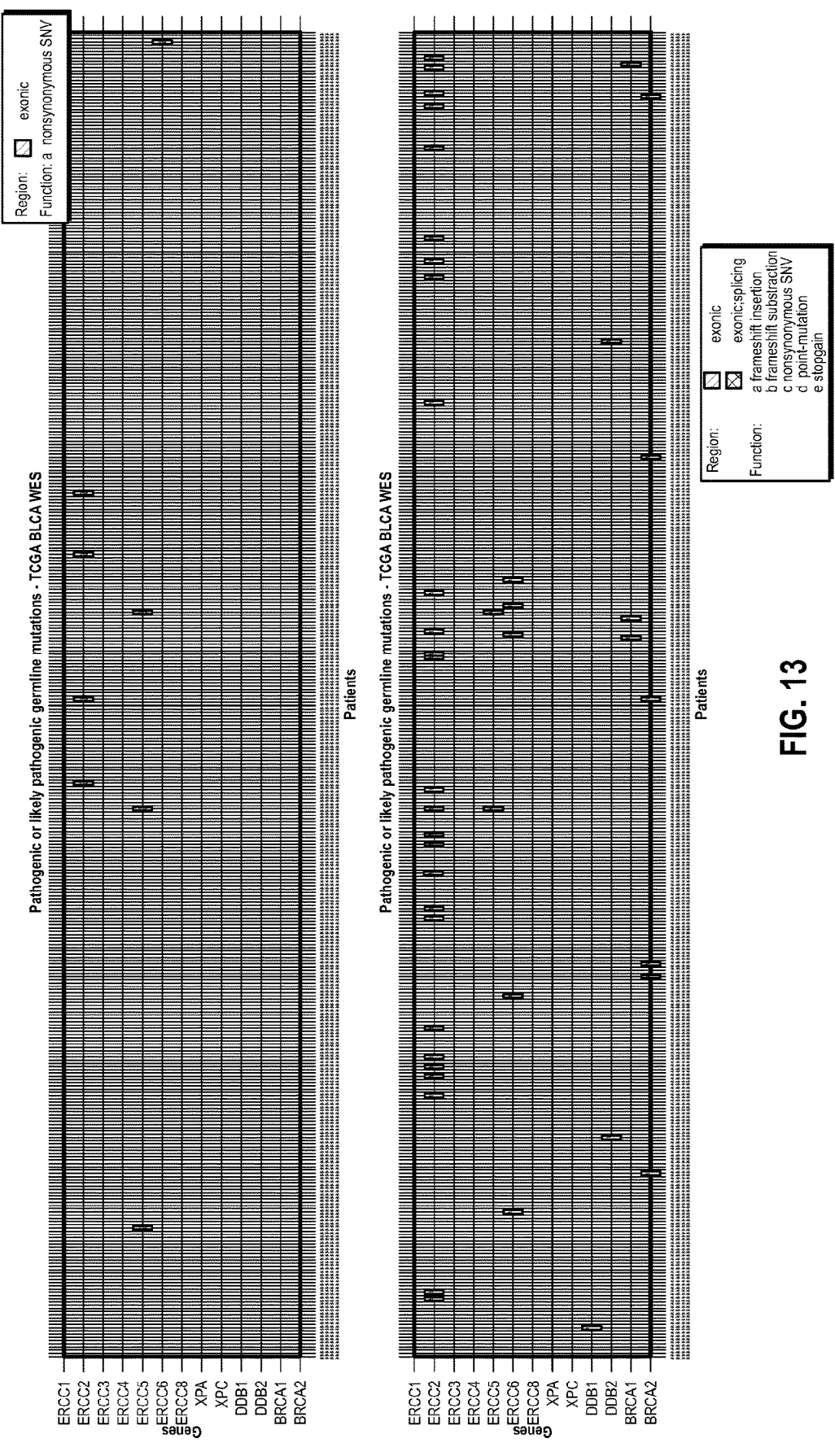
FIG. 13 shows pathogenic or likely pathogenic germline and somatic variants in the TCGA WES cohort.
Figure 14:
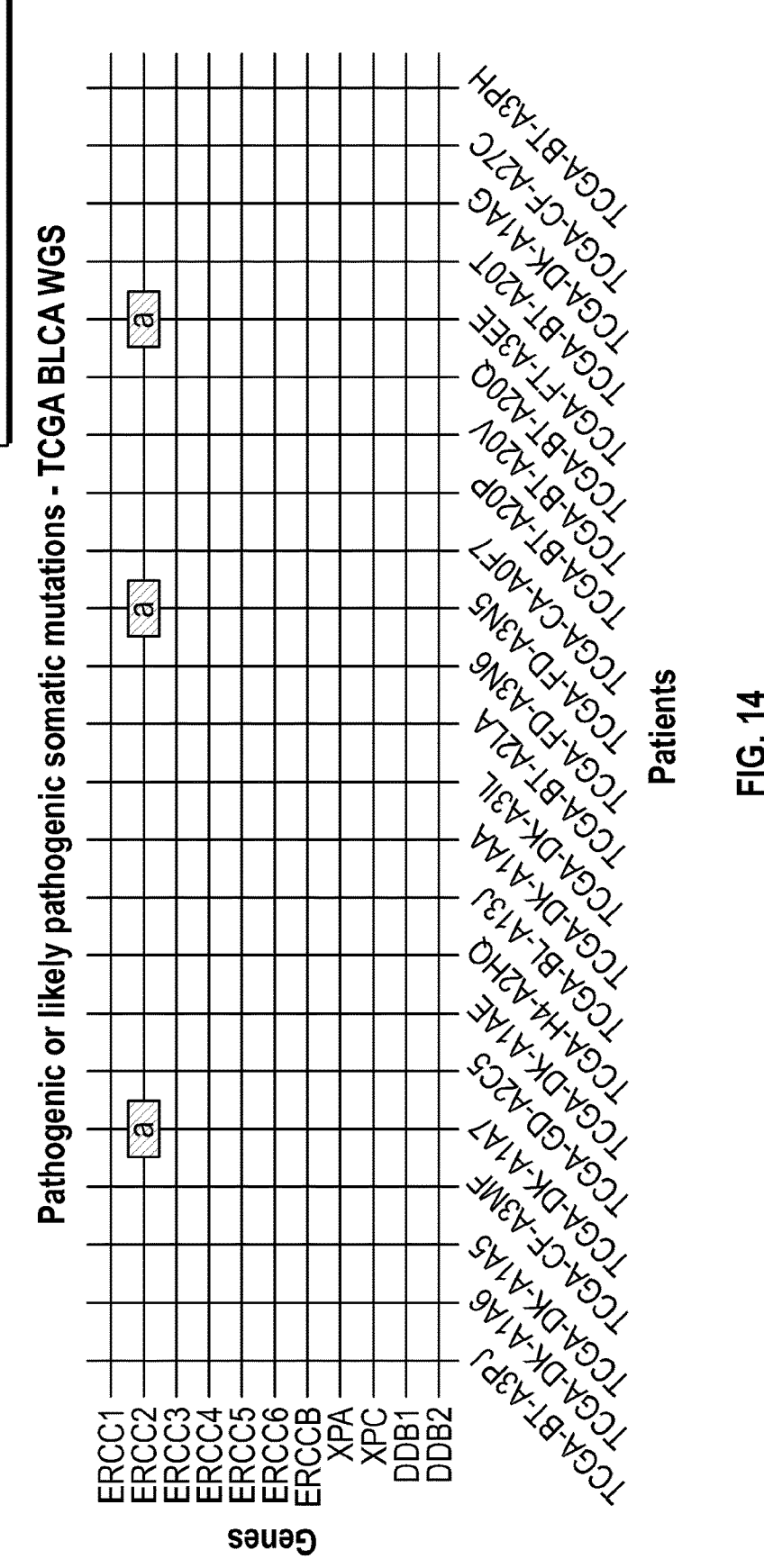
FIG. 14 shows pathogenic or likely pathogenic and UNS somatic variants in the TCGA WGS cohort.
Figure 14:
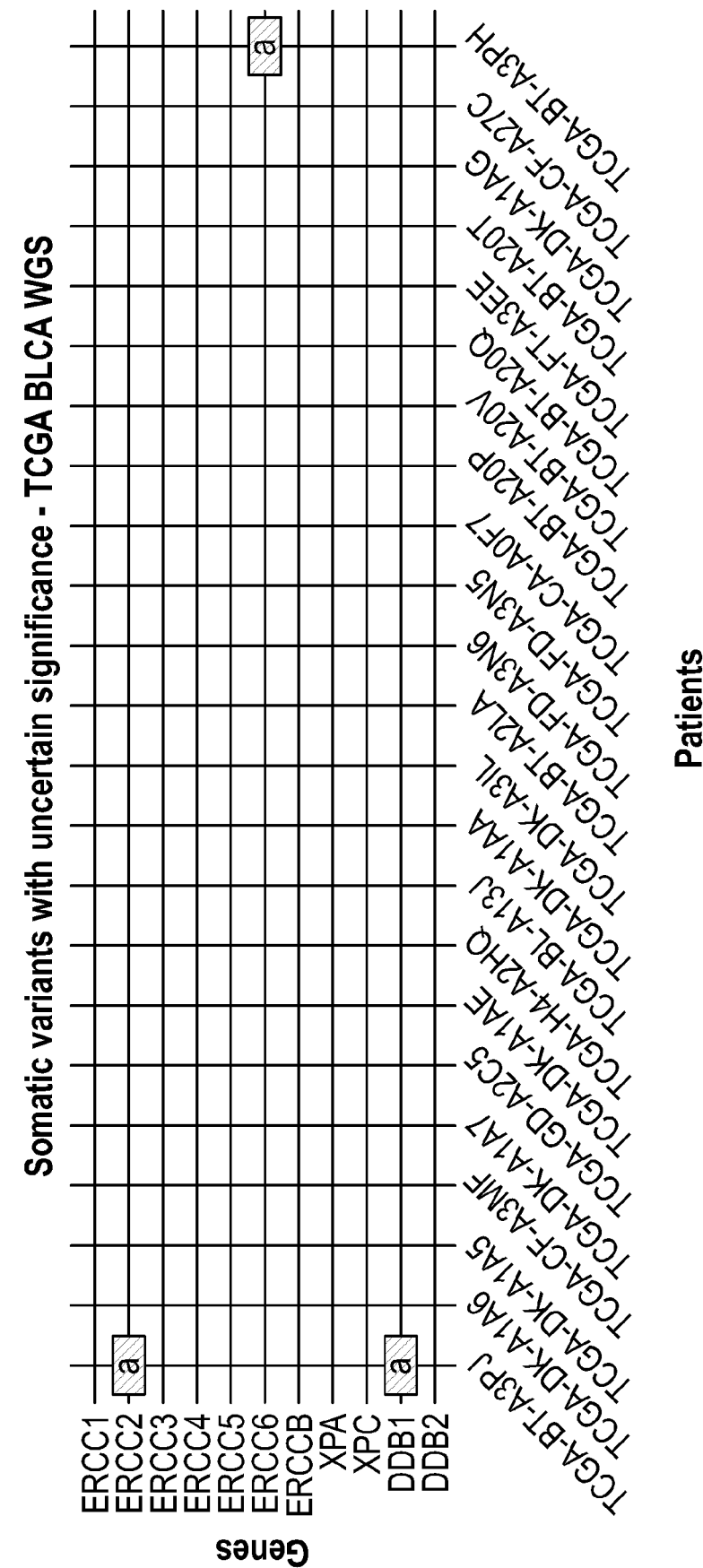
Figure 15:
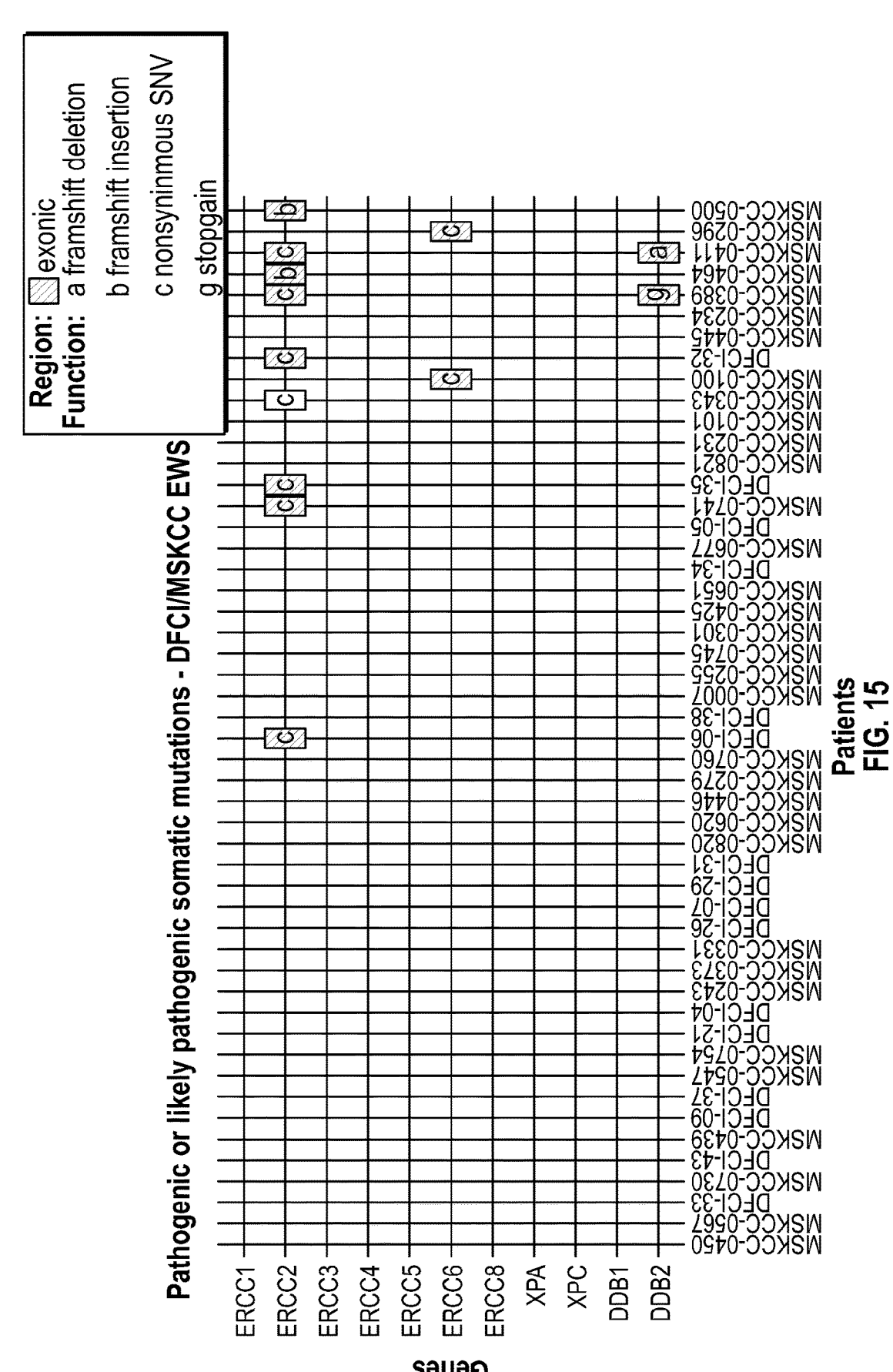
FIG. 15 shows pathogenic or likely pathogenic and UNS somatic variants in the DFCI/MSKCC WES cohort.
Figure 16:
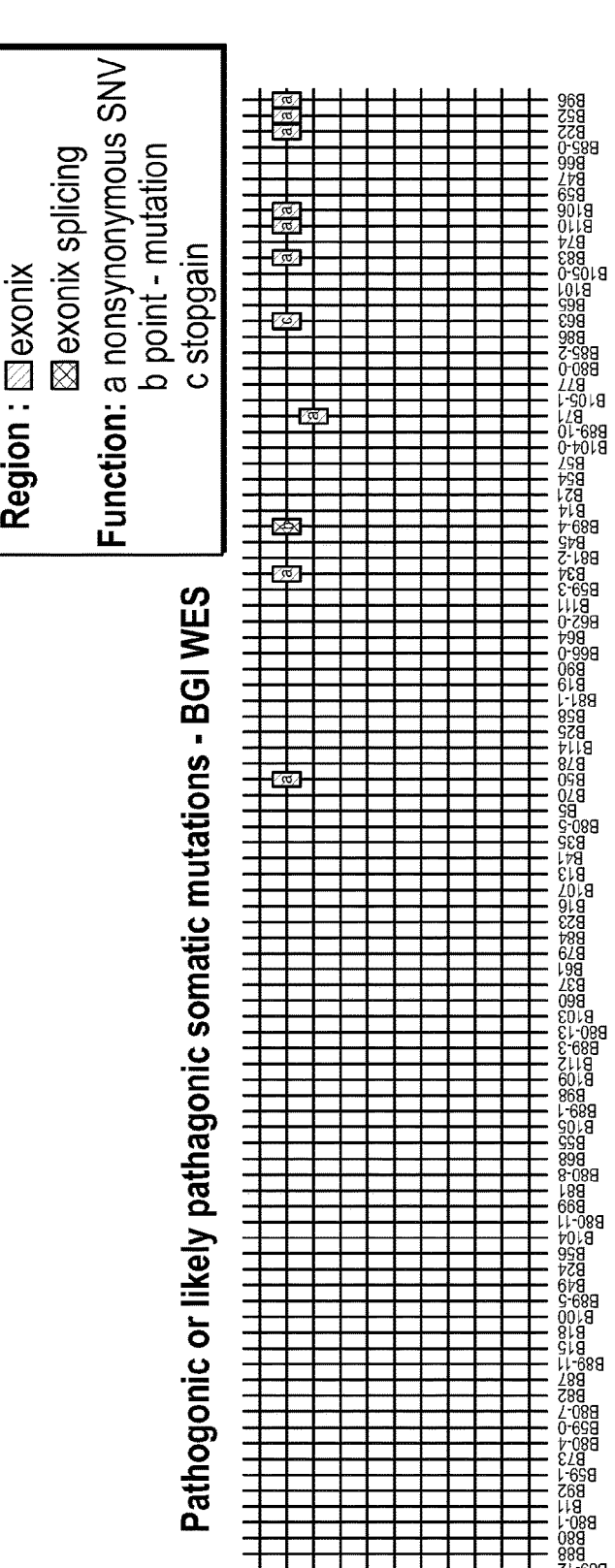
FIG. 16 shows pathogenic or likely pathogenic and UNS somatic variants in the BGI WES cohort.
Figure 16:
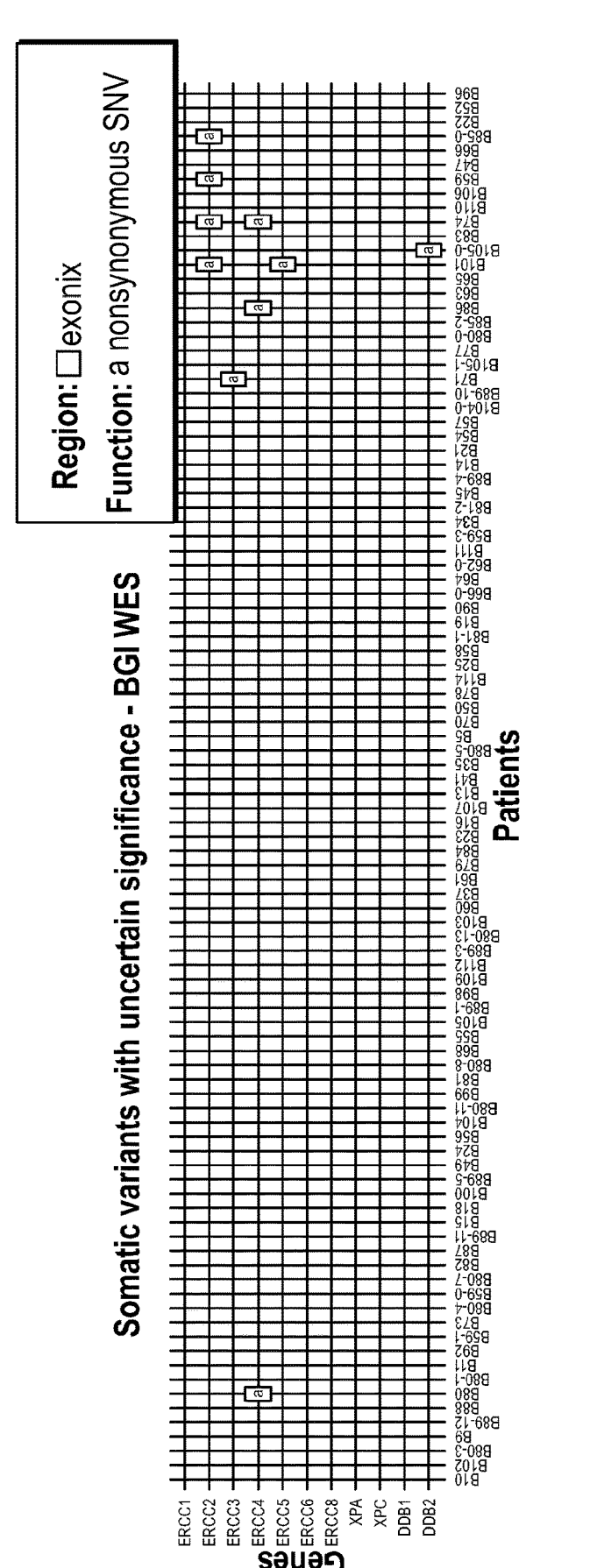
Figure 17:
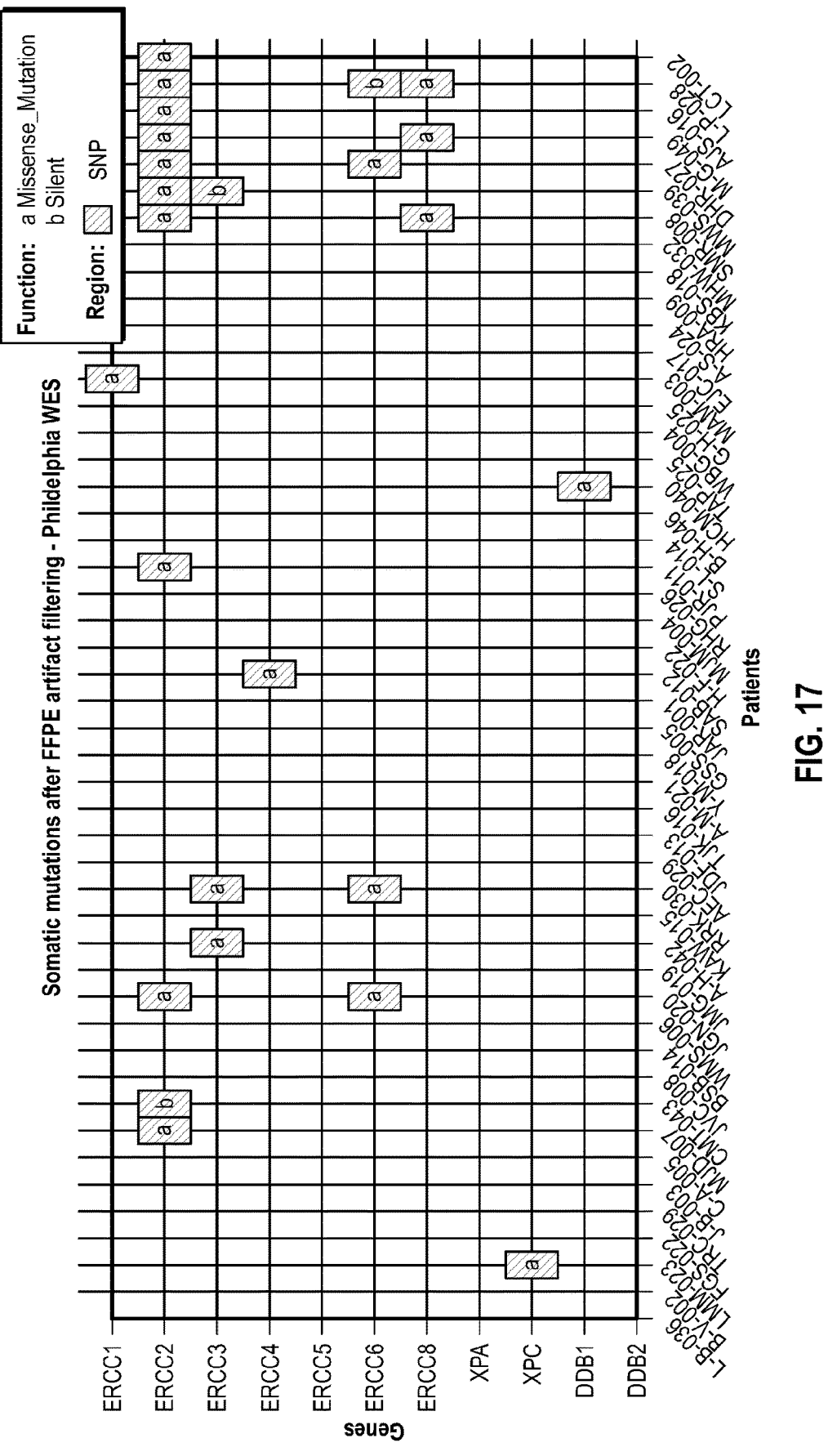
FIG. 17 shows somatic mutations in NER genes in the Philadelphia WES cohort after FFPE artifact filtering.

Germline and somatic mutations found in key NER-related genes in the TCGA WGS samples are summarized in FIG. 9 and FIG. 14; DFCI/MSKCC WES cohort are summarized in FIG. 10 and FIG. 15; Philadelphia WES cohort after FFPE artifact filtering are summarized in FIG. 11 and FIG. 17; BGI WES cohort are summarized in FIG. 12 and FIG. 16; TCGA WES samples are summarized in FIG. 13.

Figure 18:
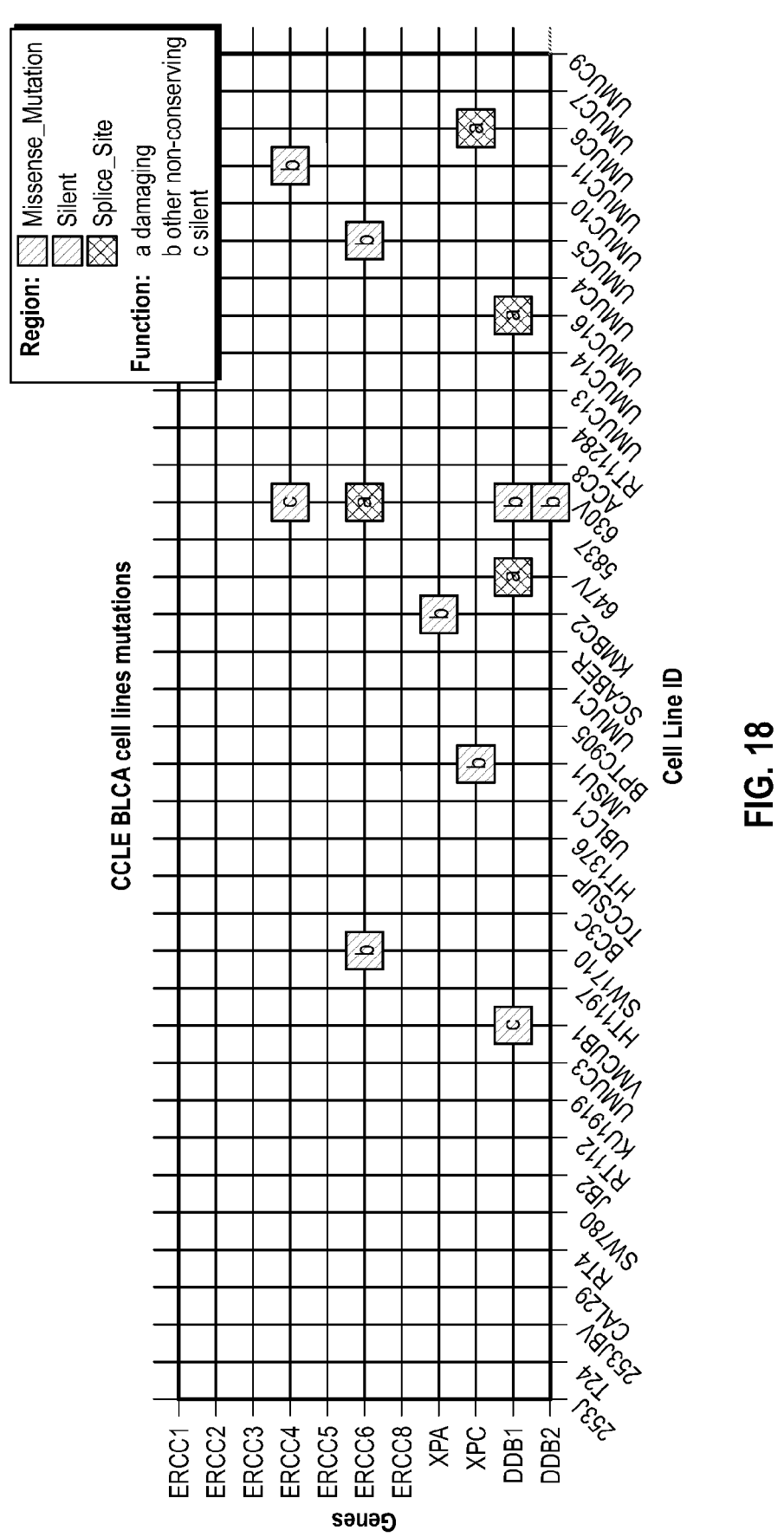
FIG. 18 shows somatic mutations in NER genes in the RT4 and KU19-19 cell lines according to the CCLE database.

Somatic mutations found in key NER genes in the RT4 and KU19-19 cell lines according to the CCLE database are summarized in FIG. 18.

4.3 Loss of Heterozygosity

In order to estimate tumor cellularity and ploidy and to infer allele-specific copy number profiles sequenza was used. The fitted models were in the ploidy range of [1, 5] and cellularity range of [0, 1]. When the predictions of a fitted model significantly differed from the expected ploidy-cellularity values, an alternative solution was selected manually. If the copy-numbers of either the A or B alleles dropped to zero within the coordinates of a gene, then an LOH event was registered. The summary of estimated LOH events in the TCGA WGS cohort is shown in FIG. 19A;
  DFCI/MSKCC and Philadelphia WES cohorts are shown in FIG. 19B-19C;
  BGI WES cohort is shown on the upper panel of FIG. 20;
  TCGA WES cohort is presented on the lower panel of FIG. 20.

4.4 Final Genotypes

Genotyping is based on the presence of a pathogenic or likely pathogenic germline/somatic mutation and whether a loss of heterozygosity event occurred in a given NER-related gene.
  Wild type: no pathogenic or likely pathogenic germline or somatic mutation(s);
  Wild type with LOH: no pathogenic or likely pathogenic germline or somatic mutation(s), but an LOH event occurred;
  Heterozygote mutant: at least a pathogenic or likely pathogenic germline or a somatic mutation is present, but no LOH;
  Heterozygote mutant with LOH: a pathogenic or likely pathogenic germline or somatic mutation is present and an LOH event occurred.

4.5 Somatic Single Base Substitution Signatures—Mutational Signature Extraction

Somatic single base substitution signatures were extracted with the help of the deconstructSigs R package which determines the linear combination of pre-defined signatures [12] that most accurately reconstructs the mutational profile of a single tumor sample.

The selected signatures, the linear combination of which could lead to the final mutational catalog, were confined to those, that were reported to be present in bladder carcinoma according to the Catalogue of Somatic Mutations in Cancer (COSMIC v2) (available on the world wide web at https<cancer.sanger.ac.uk/cosmic/signatures_v2>, BLCA: Signature 1, 2, 5, 10, 13). Signature 3 and Signature 8 were also extracted, since Signature 3 is associated with failure of DNA double-strand break repair by homologous recombination [16] and characterized by a broad spectrum of base changes. Signature 4 is associated with exposure to tobacco carcinogens [50] and it is well known that smoking is a strong risk factor for bladder cancer [51]. Elevated levels of Signature 8 mutations were observed in adult stem cells (ASCs) from NER-deficient Ercc1-/Δ mice and in a GG-NER-deficient human organoid culture [30].

After the evaluation of their signature compositions, the mutational catalogs of the samples were reconstructed, and the cosines of the angles between the 96-dimensional original and reconstructed vectors were calculated (cosine similarity). In the BGI WES cohort, Signature 22 was also extracted, since the addition of it to the initial set of signatures improved the cosine similarity between the original and the reconstructed vectors. Signature 22 has been linked to exposure to aristolochic acid, an ingredient in some food supplements that are most commonly used in Asian countries [52]. However, in this cohort the mean similarity was somewhat lower than in the other WES cohorts (Table 5) probably due to the lower sequencing coverage (FIG. 8). In the other cohorts, cosine similarities were high, mean cosine similarity ≥0.92 (Table 5), between the original and the reconstructed mutational profiles.

TABLE 5

Mean cosine similarity between original and reconstructed mutational catalogs in the analyzed cohorts.

| Cohort | Mean cosine similarity |
|---|---|
| TCGA WGS | 0.99 |
| TCGA WES | 0.93 |
| DFCI/MSKCC | 0.92 |
| BGI WES | 0.85 |
| Philadelphia WES | 0.94 |

| Cell Lines | Mean cosine similarity |
|---|---|
| BLCA WGS | 0.91 |

The SBS signature composition of samples in the TCGA WGS cohort clearly shows that ERCC2 somatic mutants (TCGA-FT-A3EE, TCGA-DK-A1A7, and TCGA-FD-A3N5, denoted in FIG. 21A) have elevated Signature 5 contributions (FIG. 23A-23F, FIG. 45). A similar pattern also present in the WES samples in all of the analyzed cohorts (FIGS. 25, 27, 29).

4.6 Indel Signatures

SBS/index.tt, small insertion and deletion (ID) signatures (17 COSMIC v3) [1] were also extracted as described in the previous section. The previously identified matrix of SBS signatures was downloaded using the link below.

Signatures extracted from counts of mutations observed in exomes:

Similarly, to single base substitution signatures, small insertion and deletion (ID) signatures (17) were characterized by Alexandrov et al. [25] using methods based on non-negative matrix factorization (NMF). The identified matrices of indel signatures (P) were downloaded from the following links:

separate extraction of ID signatures from all PCAWG whole genome samples together: available on the world wide web at https<www.synapse.org/#!Synapse: syn18497696>;

separate extraction of ID signatures from all TCGA whole exome samples together: available on the world wide web at https<www.synapse.org/#!Synapse: syn12025148>.

Insertions and deletions in each sample were classified into an 83-dimensional indel catalog (M) with the help of the ICAMS R package [43]. The M and the P matrices were used in a non-negative least-squares problem to estimate the matrix of exposures to mutational processes (E).

$$\min_{E_i} \|PE_i - M_i\|^2 \text{ subject to } E_i \geq 0 \text{ for } i = 1, \ldots, N \qquad (4.1)$$

where i is a given sample.

Figure 26A:
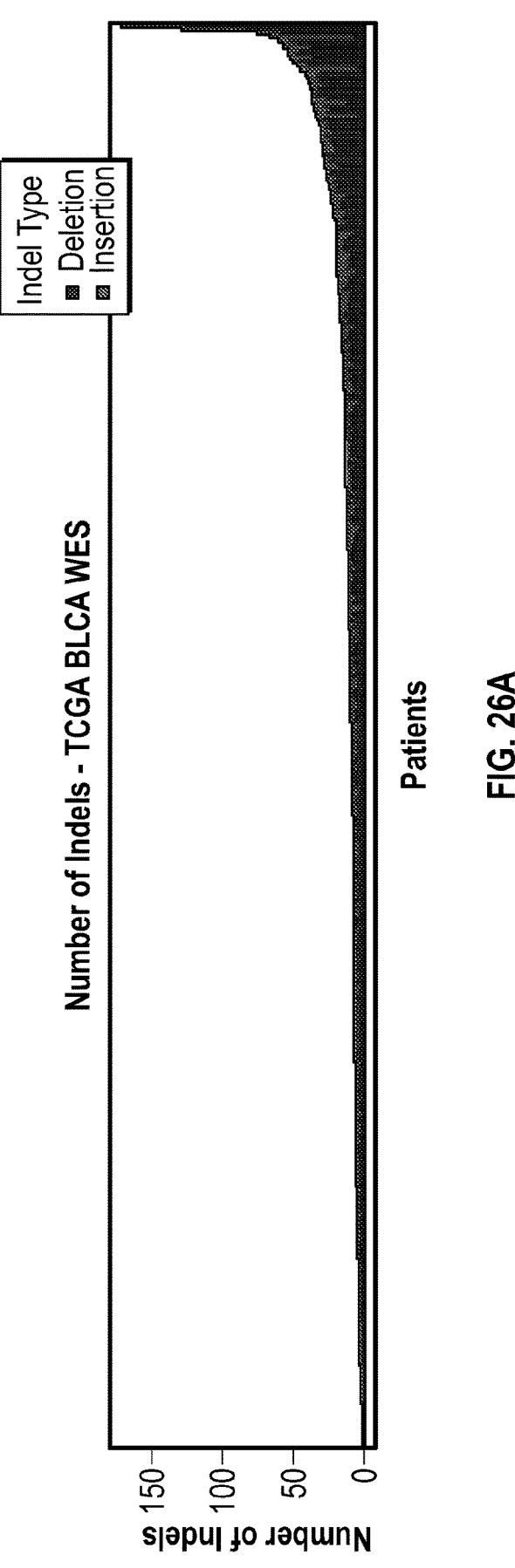
FIG. 26A shows the number of indels and the extracted indel signatures in the TCGA BLCA WES cohort.
Figure 26B:
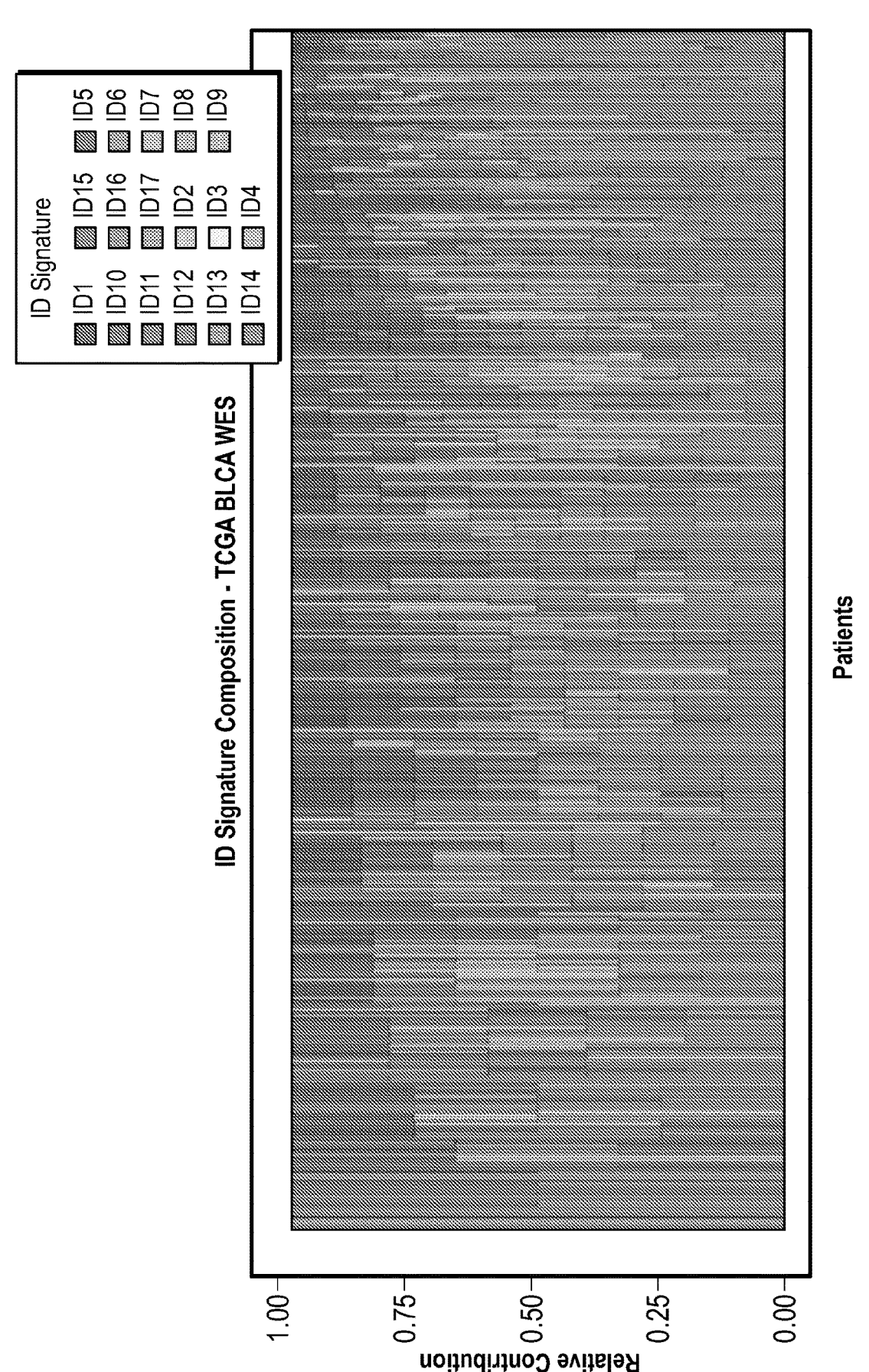
FIG. 26B demonstrates TCGA BLCA WES: ID signature composition of samples.
Figure 27A:
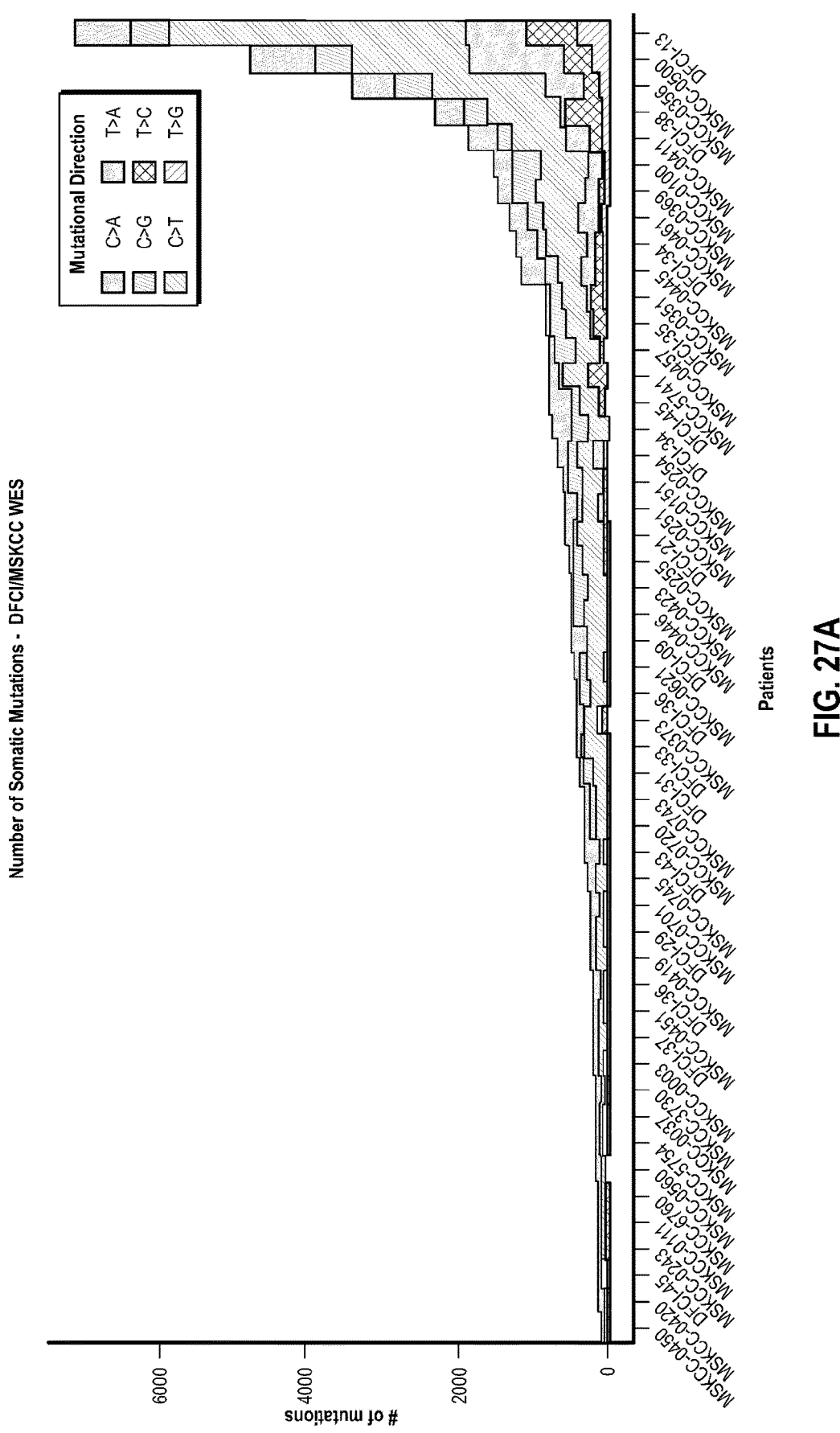
FIGS. 27A-27B show the number of single base substitutions in the DFCI/MSKCC (FIG. 27A, top) and Philadelphia WES cohorts (FIG. 27B, top). The extracted single base substitution signature composition of samples in the DFCI/MSKCC (FIG. 27A, bottom) and Philadelphia WES cohorts (FIG. 27B, bottom) are shown.
Figure 27B:
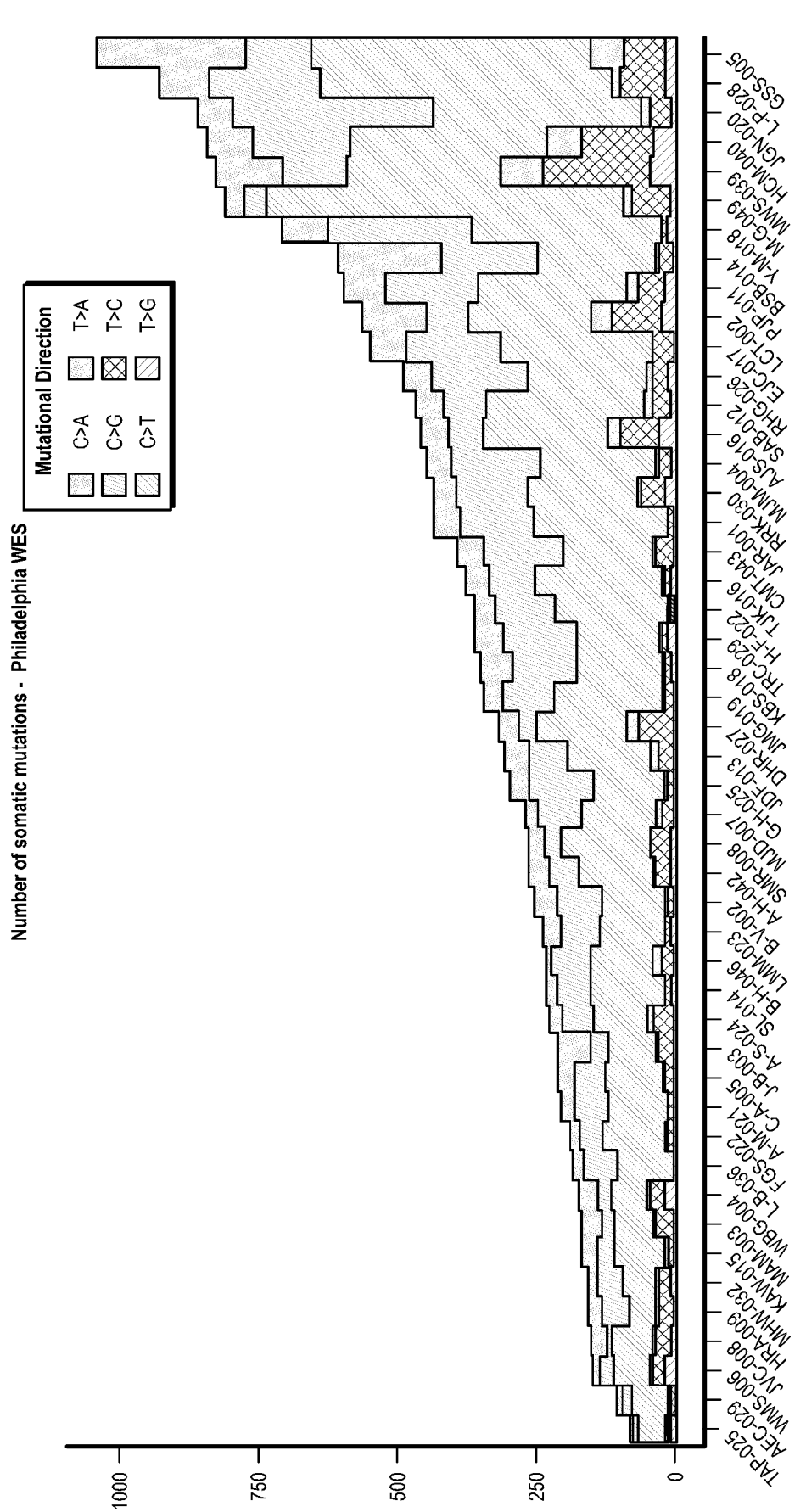
Figure 27C:
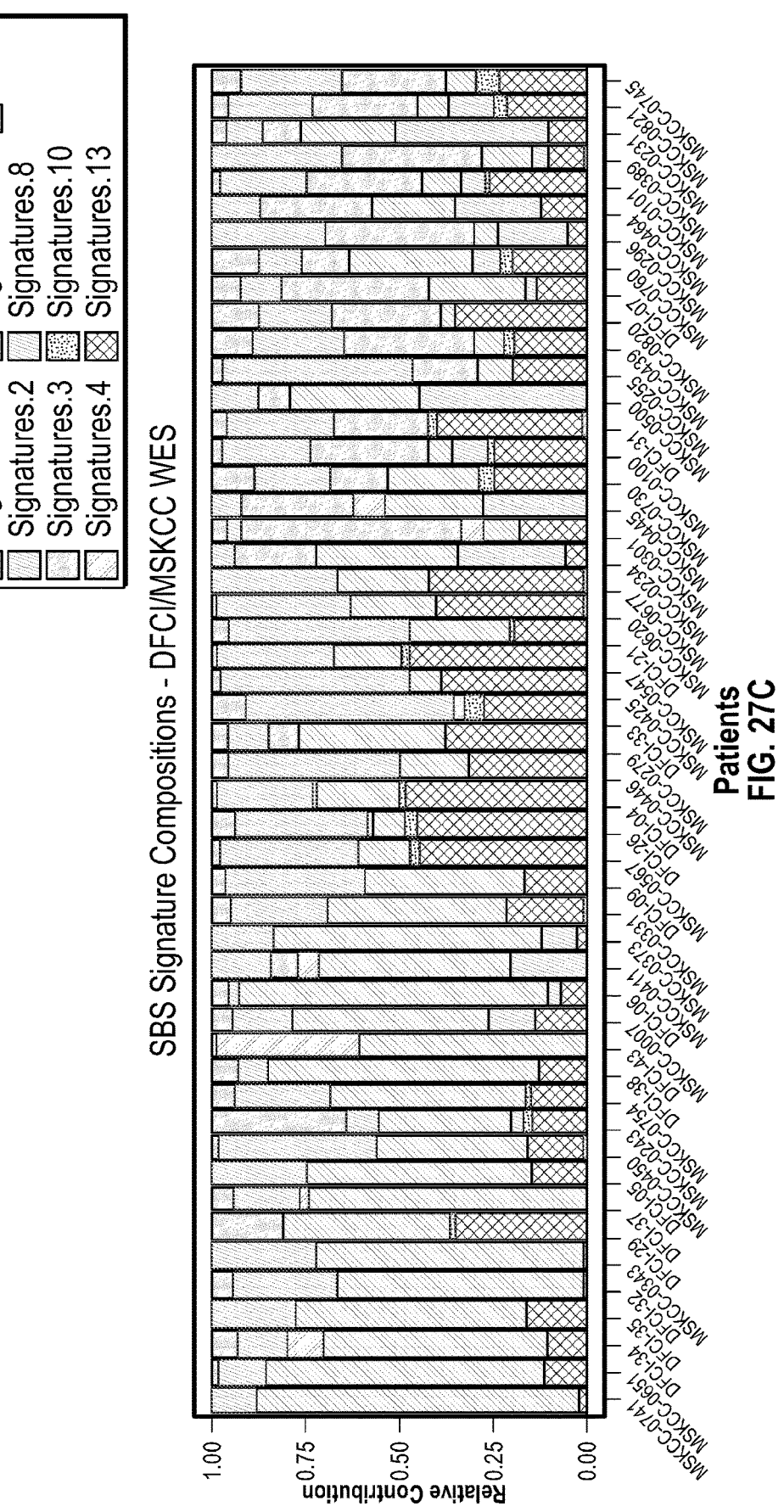
FIGS. 27C-27E show SBS (FIG. 27C), DBS (FIG. 27D) and ID (FIG. 27E) signature composition of samples in the DFCI/MSKCC cohort.
Figure 27D:
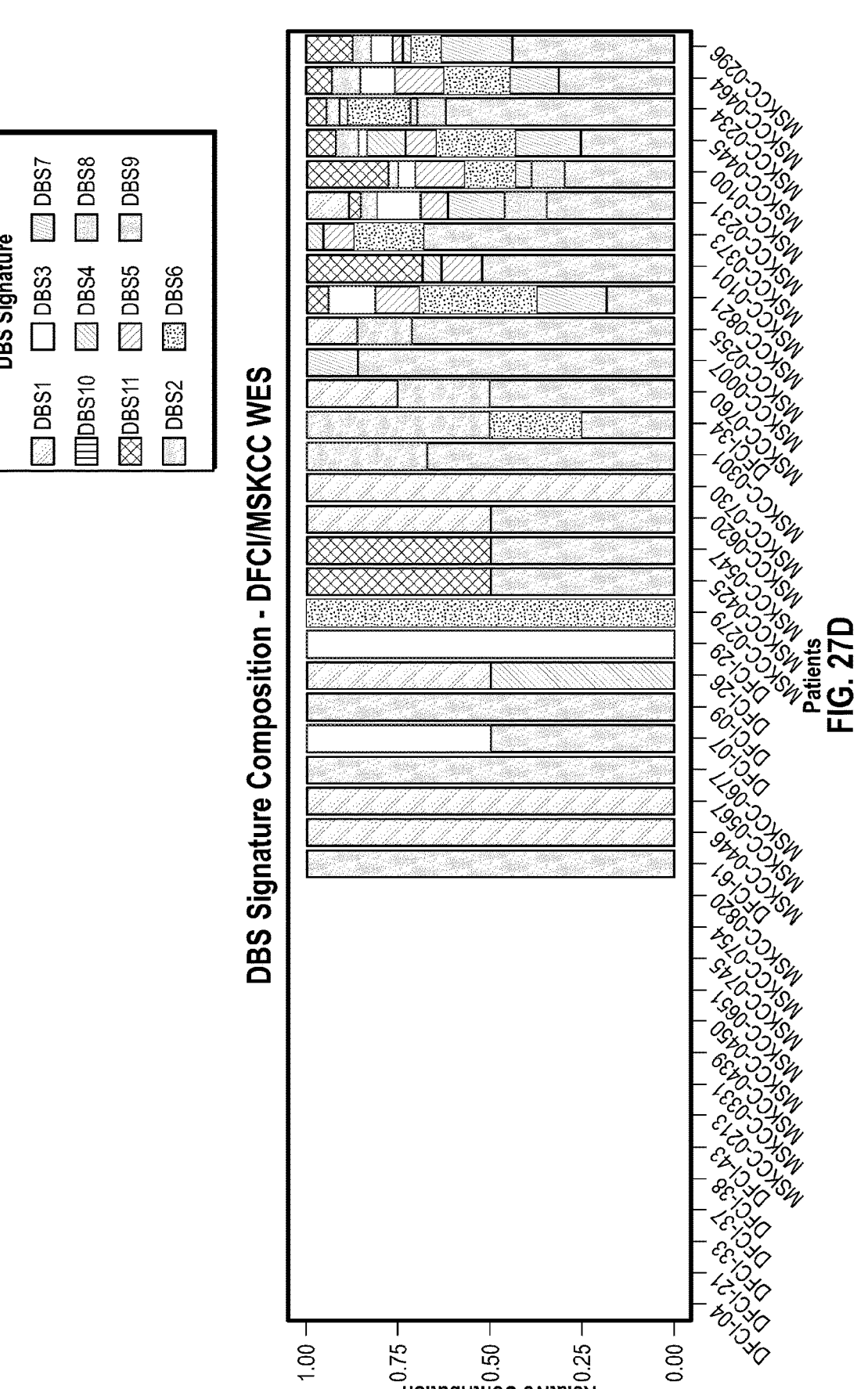
Figure 27E:
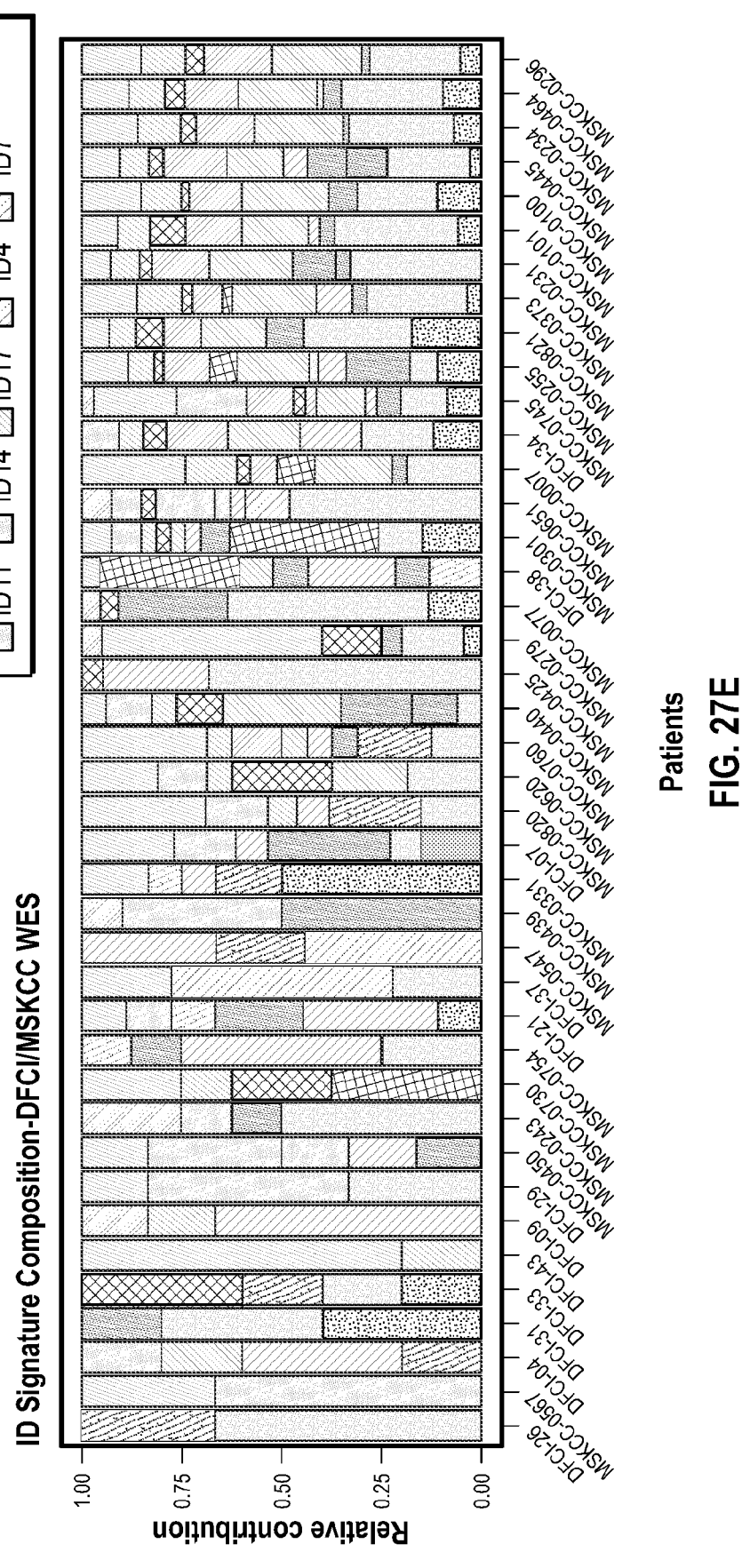
Figure 27F:
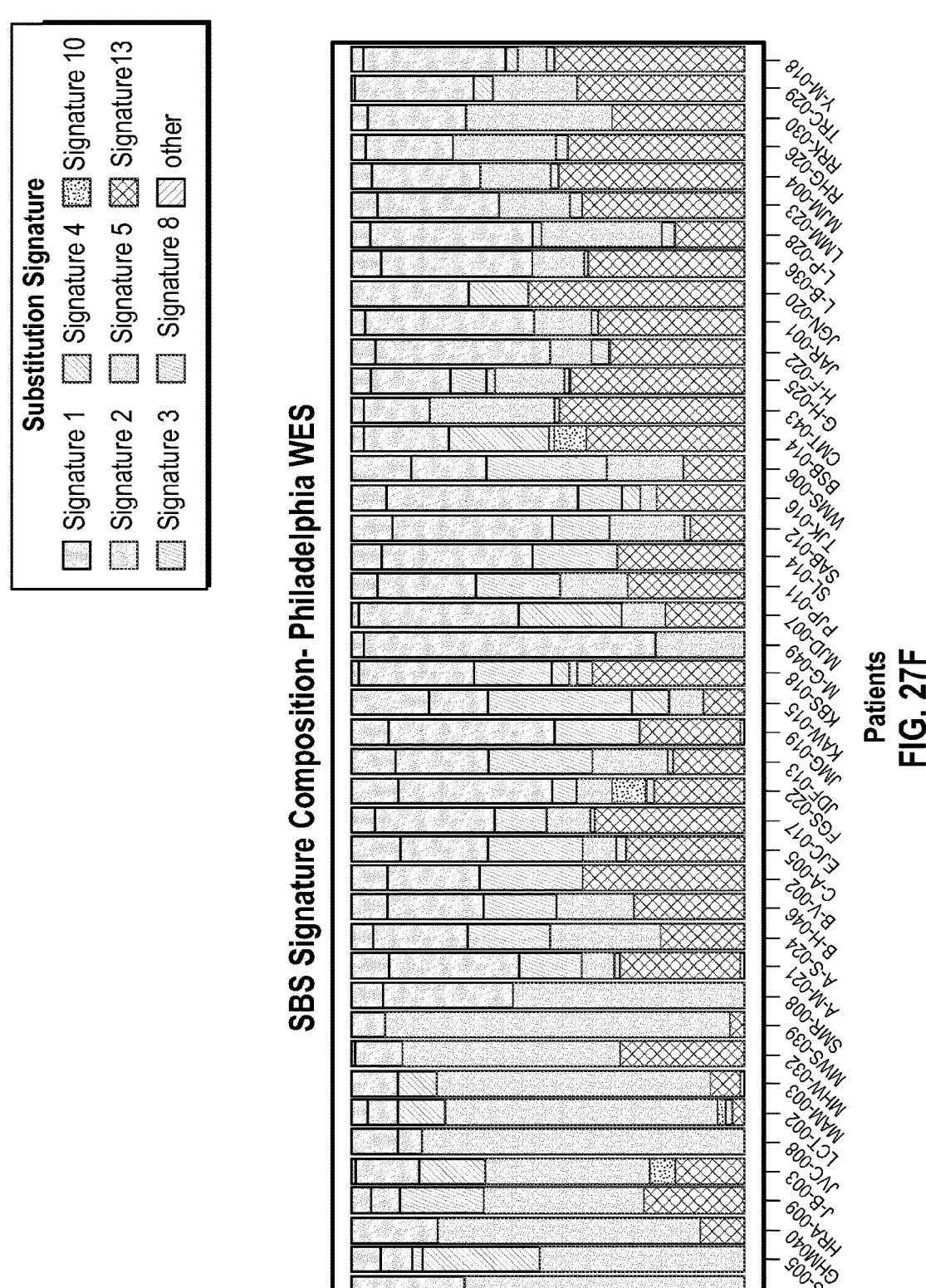
FIGS. 27F-27H show SBS (FIG. 27F), DBS (FIG. 27G) and ID (FIG. 27H) signature composition of samples in the Philadelphia cohort.
Figure 27G:
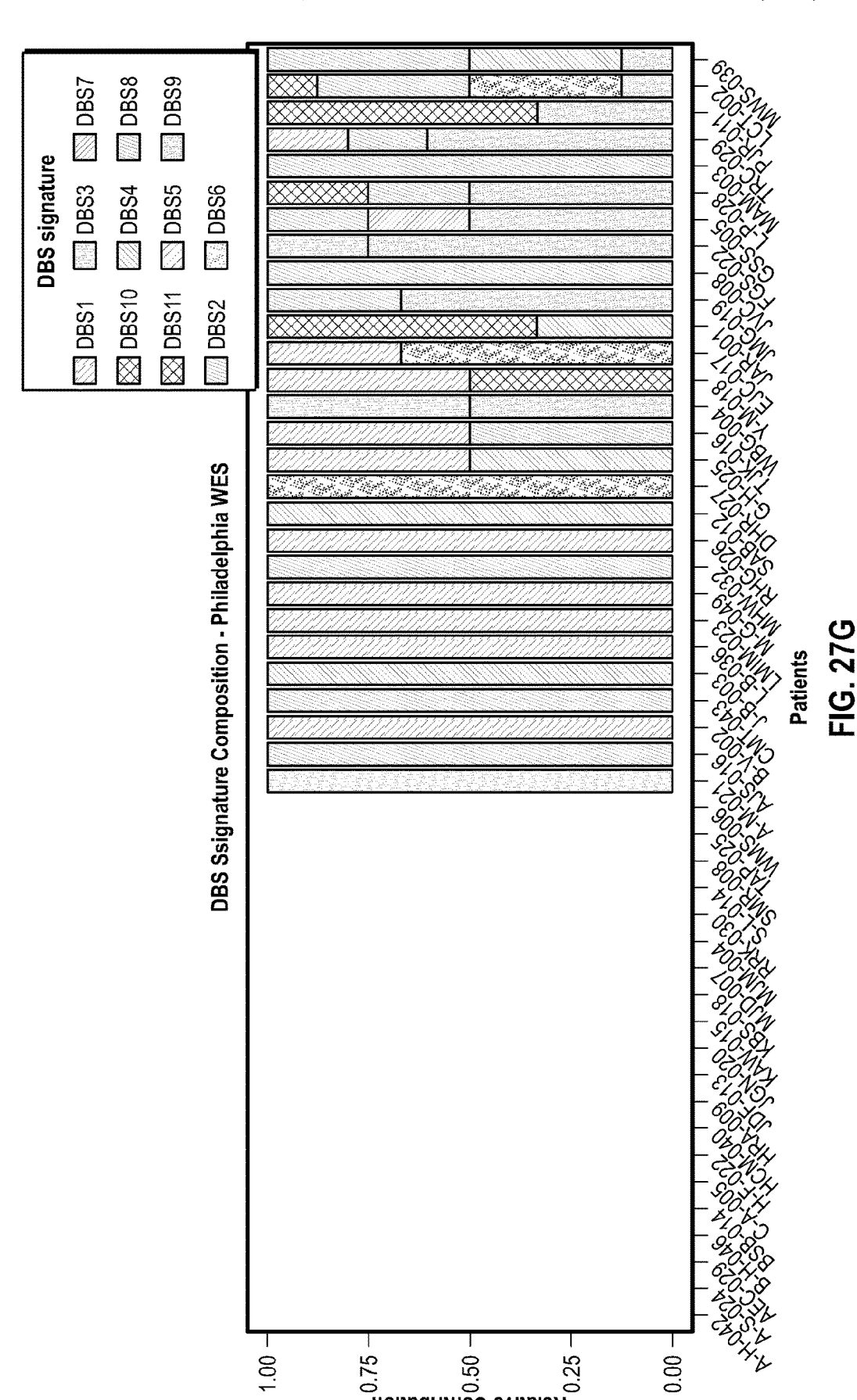
Figure 27H:
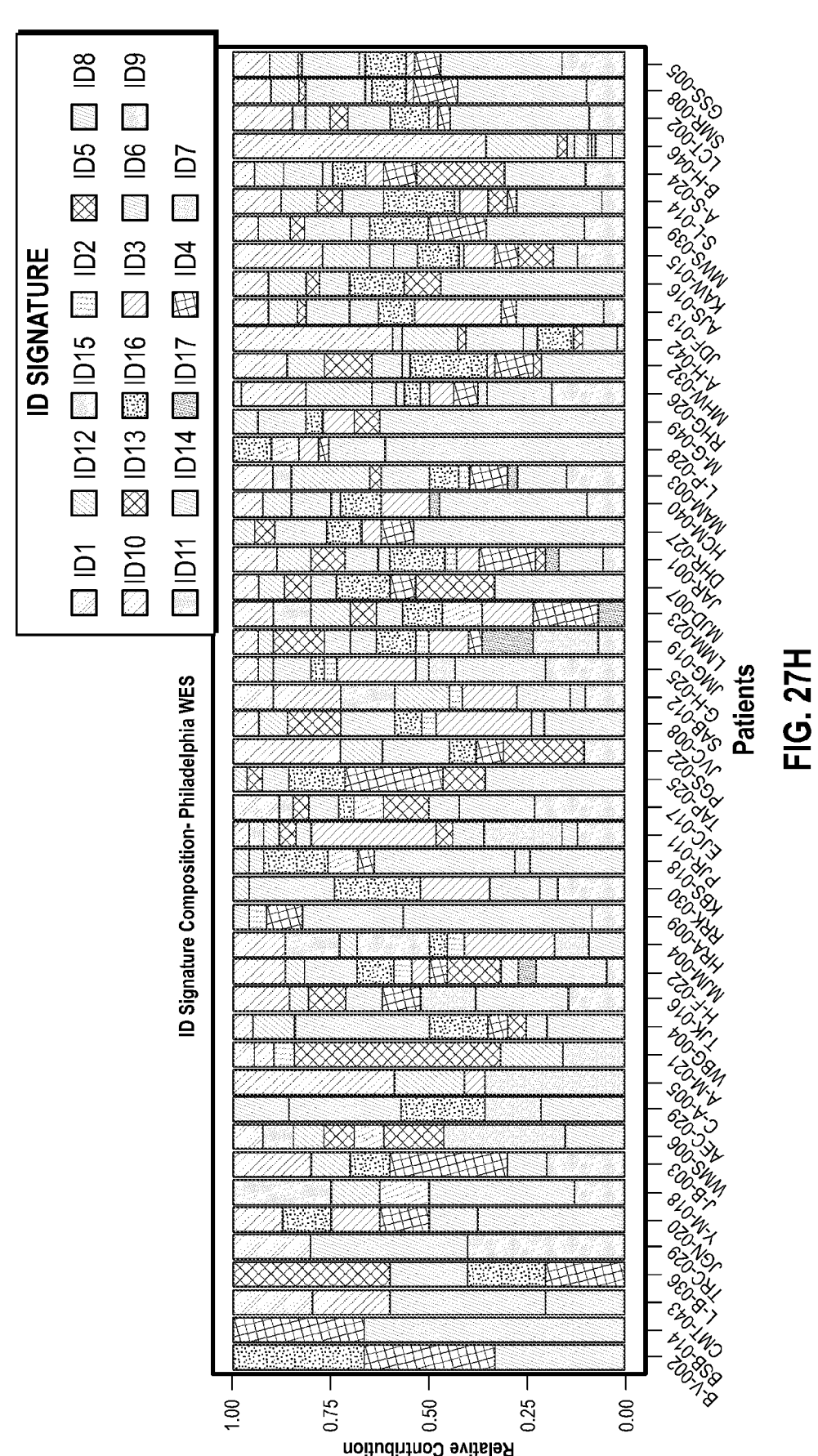
Figure 28A:
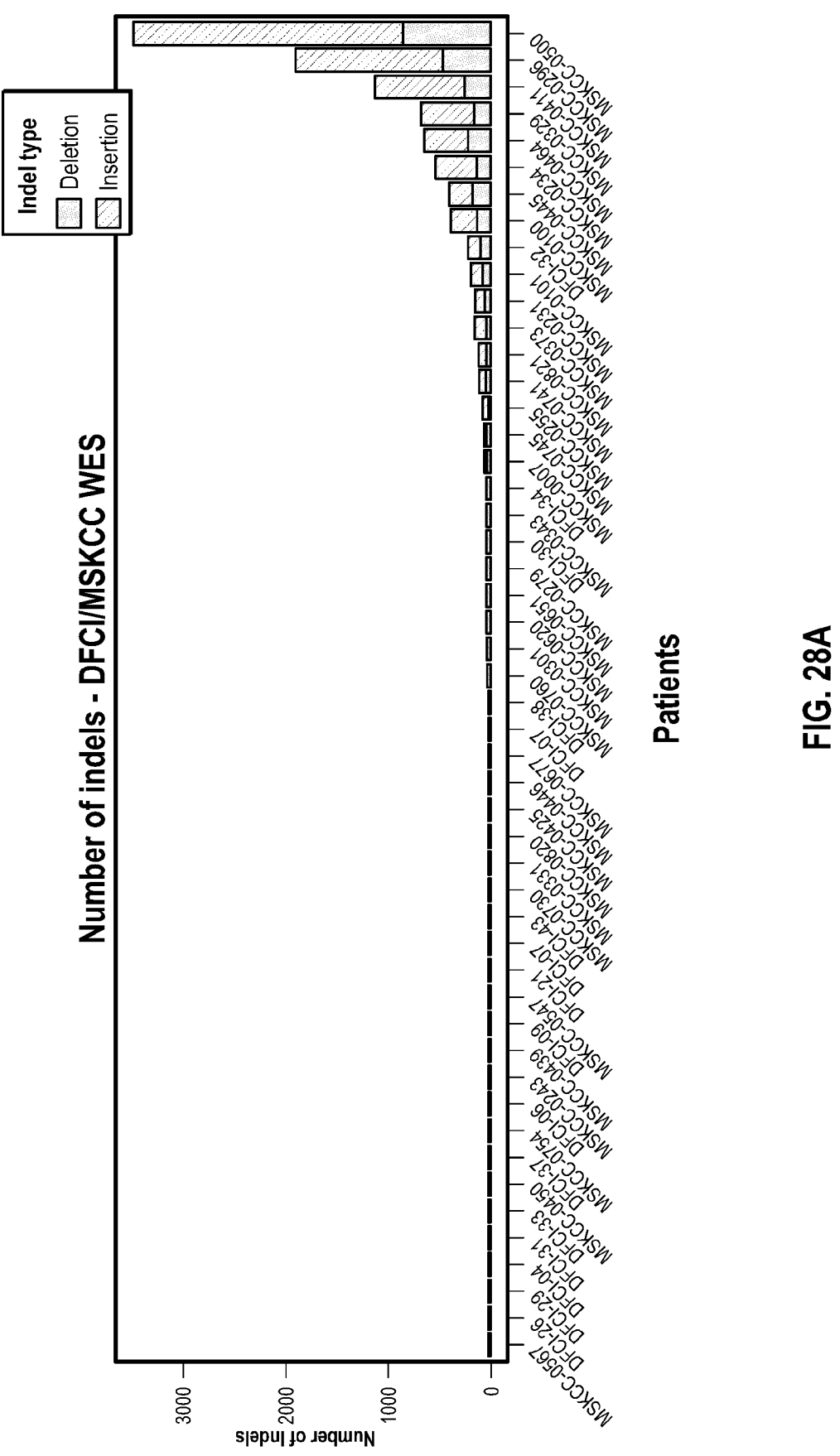
FIG. 28A-28B shows the number of indels in the DFCI/MSKCC (FIG. 28A, top) and Philadelphia WES cohorts (FIG. 28B, top). The extracted indel signature composition of samples in the DFCI/MSKCC (FIG. 28A, bottom) and Philadelphia WES cohorts (FIG. 28, bottom) are shown.
Figure 28B:
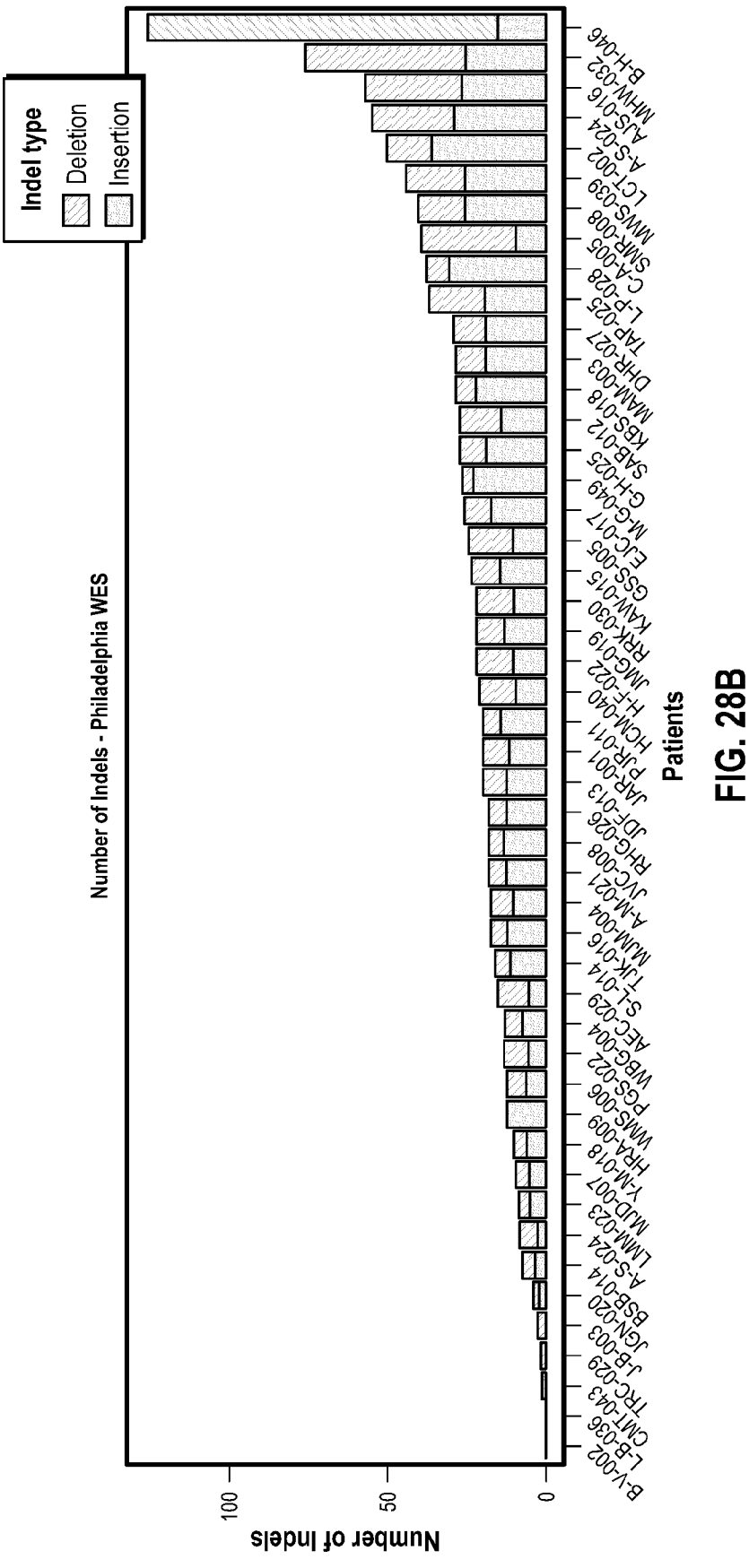
Figure 29A:
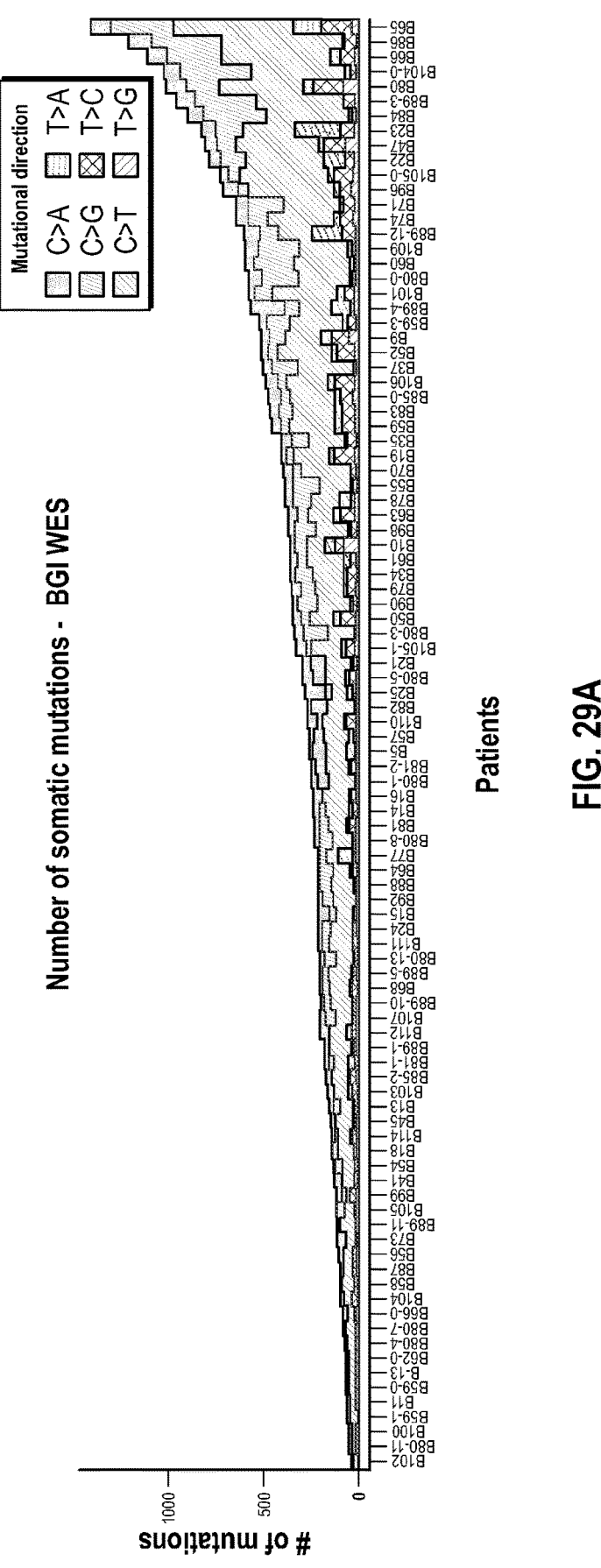
FIG. 29A shows the number of single base substitutions in the BGI WES cohort (top panel). Bottom panel: The extracted single base substitution signature composition of samples in the BGI WES cohort.
Figure 29B:
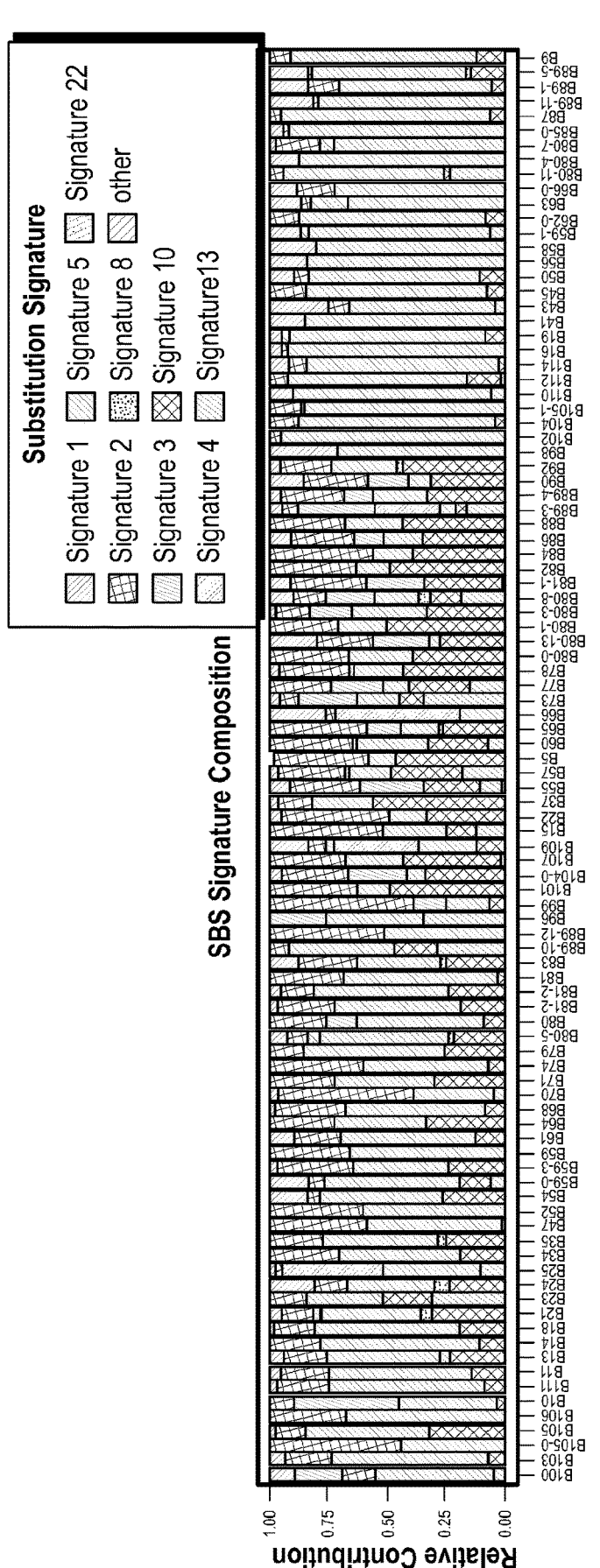
FIGS. 29B-29D show SBS (FIG. 29B), DBS (FIG. 29C) and ID (FIG. 29D) signature composition of samples in the BGI cohort.
Figure 29C:
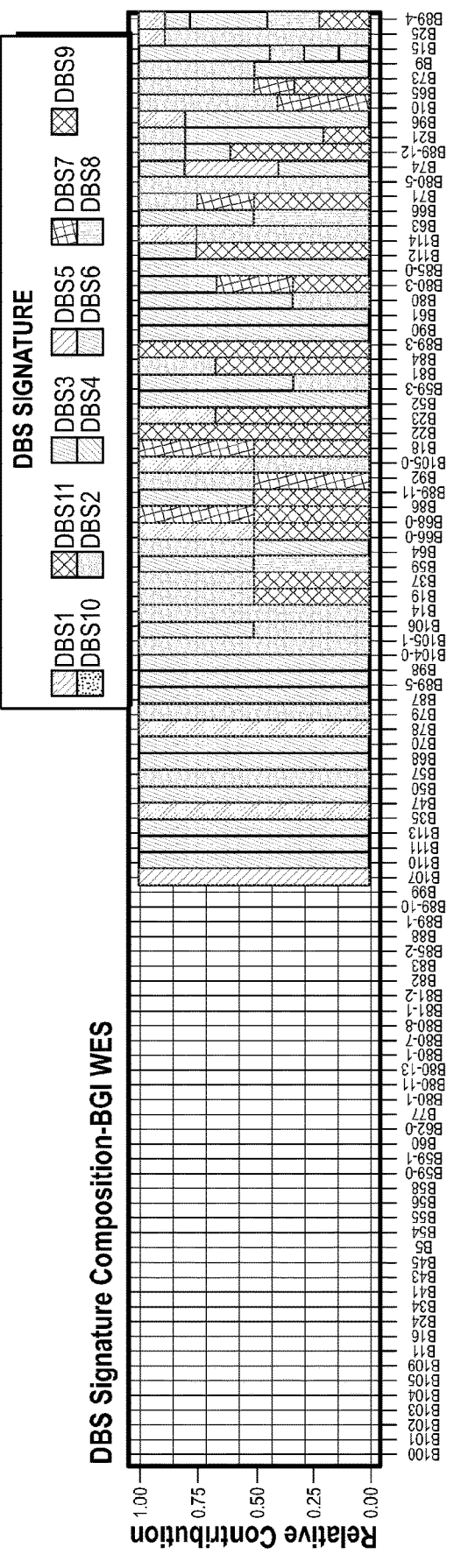
Figure 29D:
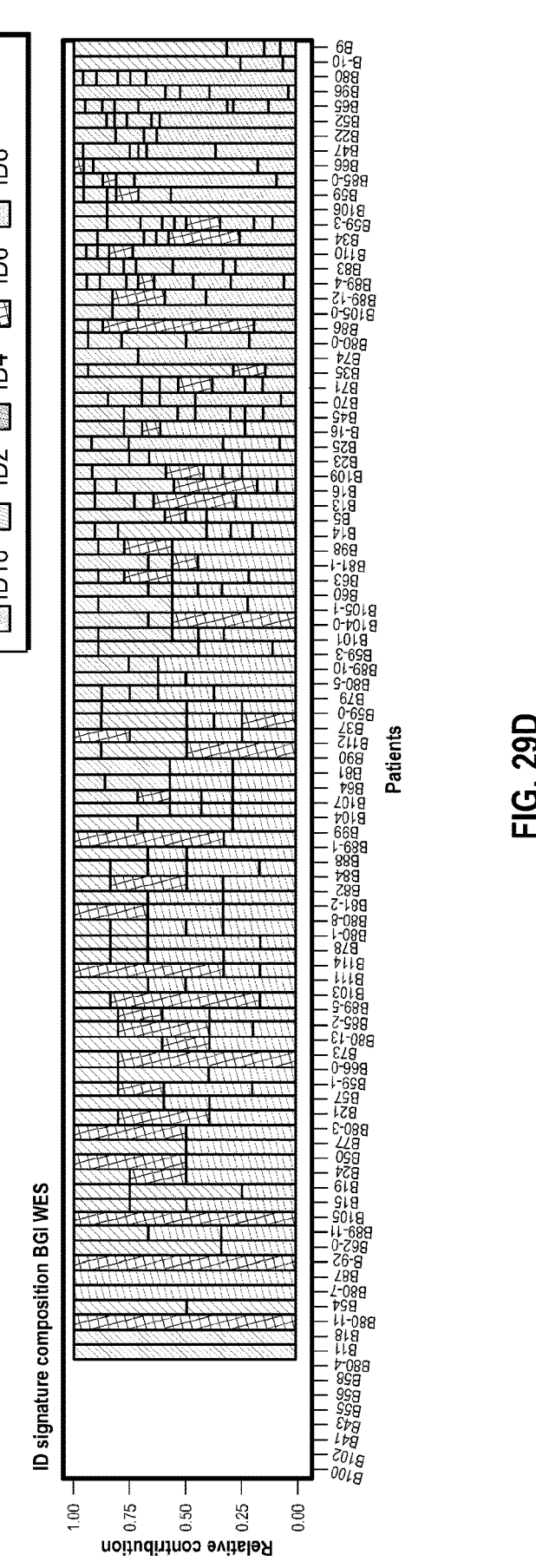
Figure 30:
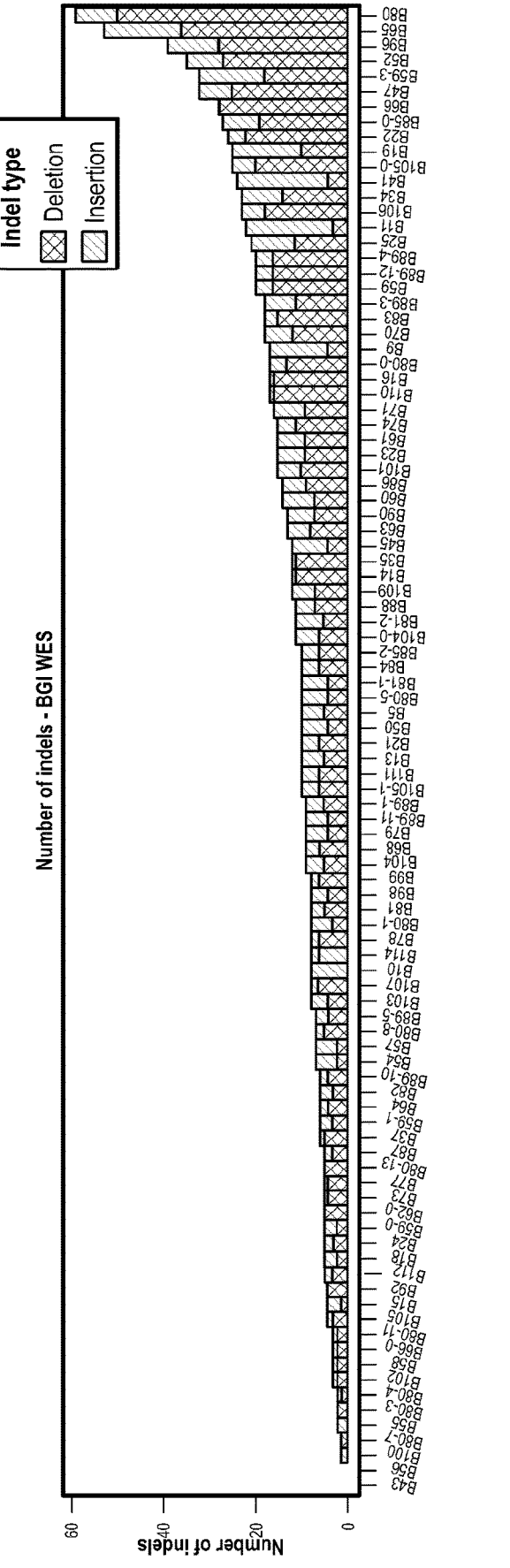
FIG. 30 shows the number of indels in the BGI WES cohort (top panel). Bottom panel: The extracted indel signature composition of samples the BGI WES cohort.

The ID signature composition of samples in the TCGA WGS cohort clearly demonstrates that ERCC2 somatic mutants (TCGA-FT-A3EE, TCGA-DK-A1A7, and TCGA-FD-A3N5, denoted in FIG. 21) have elevated ID8 contributions (FIG. 23A-23F). A similar pattern is also present in the WES samples in all of the analyzed cohorts (FIGS. 26, 28, 30).

One sample from the DFCI/MSKCC cohort (DFCI-43) had an extremely low cosine similarity, probably due to the low number of mutations after filtering, thus the results regarding this sample should not be considered reliable. The most recent version of single base substitution signatures are available on the world wide web at https://<cancer.sanger-.ac.uk/cosmic/signatures/>. The most recent version of single base substitution signatures SBS/index.tt, COSMIC v3 [1] was also extracted as described in the previous section. The previously identified matrix of SBS signatures were downloaded using the link below.

Signatures extracted from counts of mutations observed in exomes:

available on the world wide web at https://<synapse-.org/#!Synapse:syn12026190>.

Cosine similarity of the SBS signature profiles (COSMIC v2 and COSMIC v3) of each sample were calculated and presented in FIGS. 42 and 43. The average cosine similarity between the extracted COSMIC v2 and COSMIC v3 signatures in each cohort was above 0.9.

4.7 Transcription Strand Asymmetry

Transcription strand bias analysis was carried out using the MutationalPatterns R package, which allows for the easy characterization and visualization of mutational patterns [26]. The transcriptional strand of the mutations within gene bodies can be determined using DNA transcription as the reference frame [27]. Base substitutions located on the same strand as the gene definition are defined as "untranscribed" and on the opposite strand as "transcribed". The ratio of the number of base substitutions on the transcribed and the untranscribed strand is used as the measure of strand asymmetry.

5. Structural Variant Calling

Structural variants (SVs) were called using BRASS (version 6.0.0). In the analysis only those variants were considered, that were supported by at least 6 read-pairs that were successfully de novo assembled by velvet [53].

5.1 Rearrangement Signatures

The resulting structural variants in each sample were mapped to the 32-dimensional rearrangement signature catalog described in breast cancer (M) [44]. The previously identified matrix of rearrangement signatures (P) was downloaded from the following link: static-content.springer.com/esm/art %3A10.1038%2Fnature17676/MediaObjects/41586_2016_BFnature17676_MOESM47_ESM.zip Similar to the ID signature extraction, the M and the P matrices were used in a non-negative least-squares problem to estimate the matrix of exposures to mutational processes (E) (Suppl. Eq. 4.1).

Structural variants and rearrangement signatures were only determined in the TCGA WGS cohort and no characteristics of ERCC2 mutant samples have been observed. The summary of structural variants and rearrangement signature compositions are displayed in FIG. 24 and FIG. 45.

6. Statistical Analysis

The inventors first noticed signs of a characteristic mutational pattern related to ERCC2 somatic mutation during the analysis of the TCGA BLCA WGS cohort. Since the number of samples in this cohort is only 23 from which only three patients have a pathogenic or likely pathogenic ERCC2 somatic mutation (FIG. 14), we moved on to analyze the TCGA BLCA WES samples (n=412). In line with the observations from the WGS samples, a similar pattern seemed to emerge from the WES analysis. Therefore, we set out to build a statistical model for detecting genomic features associated with deficiency in ERCC2 and the NER pathway. The classification model was trained on the TCGA BLCA WES data. The information gained from the extraction of signatures of single base substitutions, signatures of indels and transcriptional strand bias were utilized to build a logistic regression model.

From the 412 TCGA BLCA WES samples 31 were excluded from the training-test (data not shown) set according to the following criteria:

containing fewer than 50 somatic mutations after filtering;

MSI samples identified by Bonneville et al. [54]; and potential BRCA1- or BRCA2-deficient samples (FIG. 13).

From the 27 pathogenic or likely pathogenic ERCC2 somatic mutants, 25 were considered as NER-deficient (Table 3). These 25 samples composed the first class with label "1" and the rest of the samples formed the second class with label "0". Examining the distribution of Signature 5 mutations, ID8 mutations and the number of deletions of ERCC2 mutant samples, two samples (TCGA-XF-A9SJ and TCGA-ZF-A9RG) were considered as outliers, since they were further from the mean than two times the standard deviation.

6.1 Data Transformation

In order to reduce right skewness of the data and to ensure that the distributions of the features more resemble to Gaussian curves, the input variables (x_i) were log-transformed, according to the following formula:

$$x_i' = \ln(x_i + 1)$$

The constant shift was added to keep the xi=0 values away from $-\infty$.

The log-transformed data were standardized (each feature had a mean of 0 and a standard deviation of 1) to make the variables comparable to one another.

$$x_i'' = \frac{x_i' - \mathbb{E}[x_i']}{\sigma(x_i')} \tag{6.2}$$

6.2 Principal Component Analysis

Figure 31A:
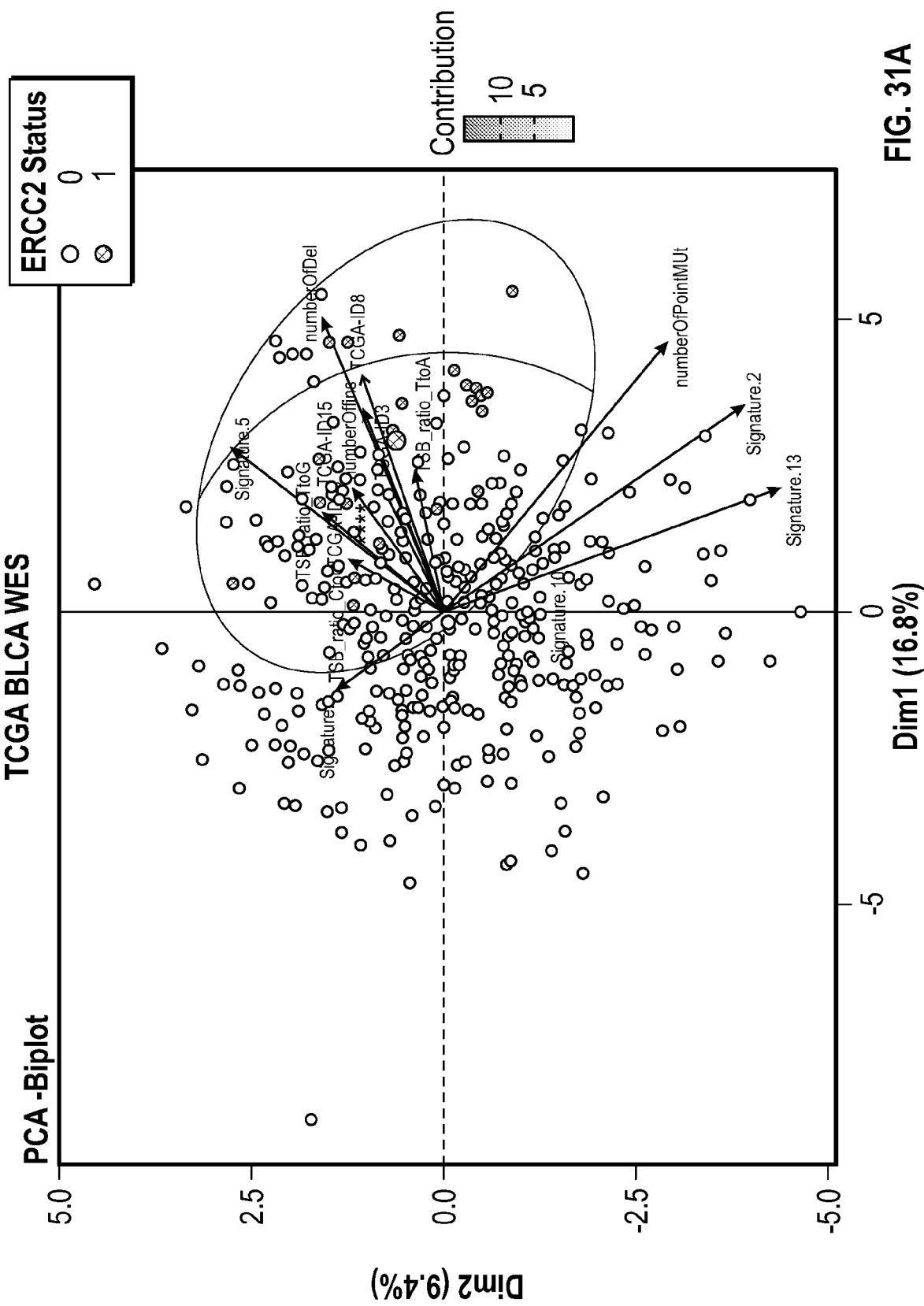
FIG. 31A shows PCA biplot—combines the PC scores of the observations and the loading vectors of the variables on the same plot.

To find a lower-dimensional representation of the data, a principal component analysis (PCA) was carried out with the factoextra R package. The correlation between a component and a variable estimates the information they share. Variables that correlate with PC1 and PC2 are the most important in explaining the variance in the data set (FIG. 31A). Variables that do not correlate with any PC or correlate with the last dimensions, are variables with low contribution and might be removed to simplify the overall analysis.

Figure 31B:
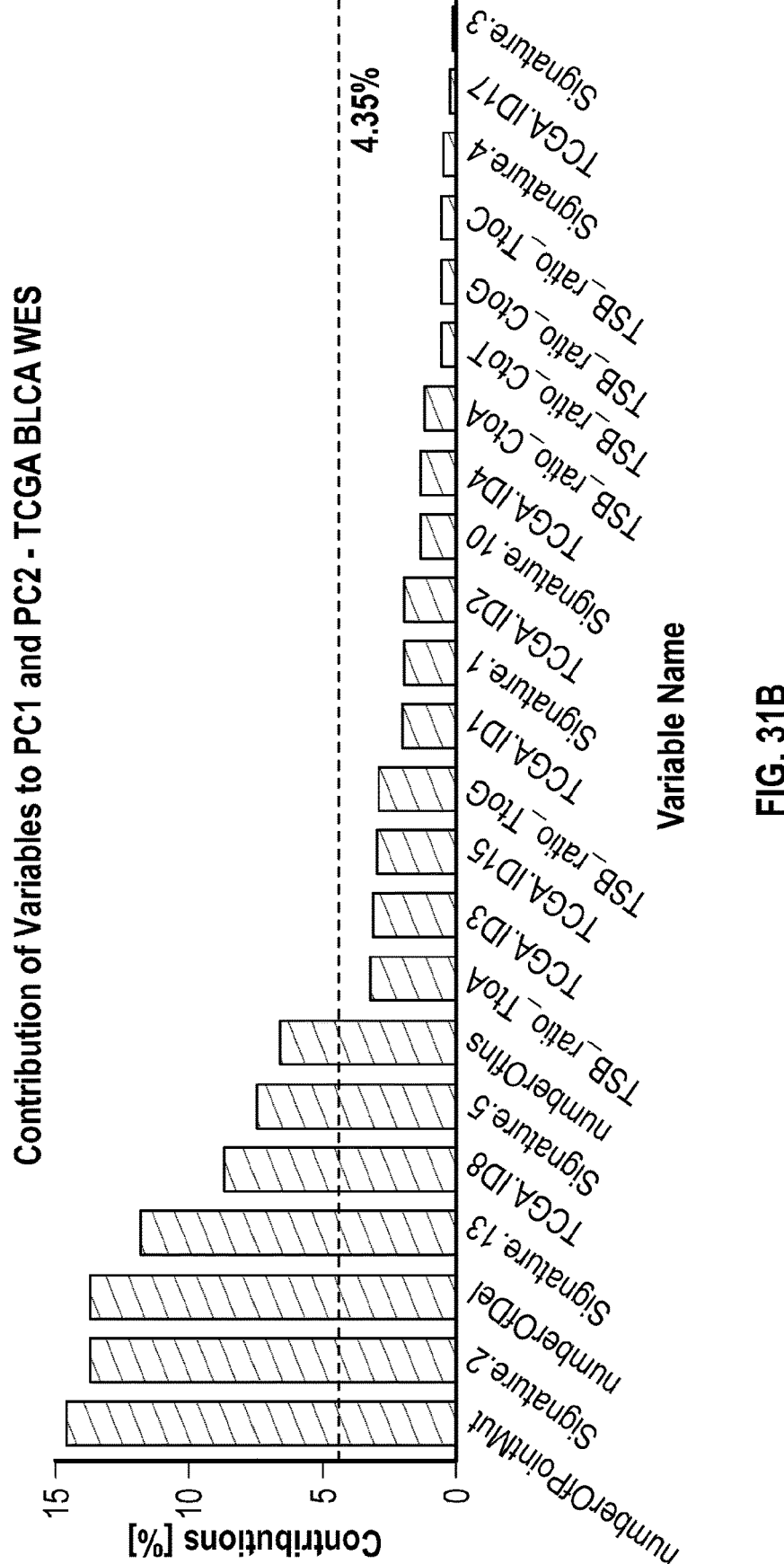
FIG. 31B shows the variables that contribute the most to the first two principal components and explain most of the variance in the data.

If the contribution of the variables were uniform, the expected value in percentage would be ⅟₂₃·100=4.35%, as it is indicated in FIG. 31B with the red dashed line. For the first two PCs, a variable with a contribution larger than this cutoff was considered as important.

Although variables describing transcriptional strand bias are below the threshold they were added to the list of pre-selected features, since it is well known that the decrease of transcriptional strand asymmetry potentially reveals a deficiency in TC-NER [27].

6.3 Train and Test Sets

The size of the final data set used in the model-building process is shown in Table 6. The data set was randomly split into train (67%) and test (33%) sets.

TABLE 6

The number of samples in both classes in the training-test set before and after oversampling.

| Status | Train | Test | Total | TrainSMOTE |
|---|---|---|---|---|
| NER proficient | 236 | 120 | 356 | 229 |
| NER deficient | 19 | 6 | 25 | 228 |
| Total | 255 | 126 | 381 | 457 |

The resulting sets were highly imbalanced, only 6.6% of the samples in the training-test set were categorized as NER-deficient. In order to overcome this problem a well-known oversampling technique, SMOTE (Synthetic Minority Oversampling Technique), implemented in the DMwR R package was used. In SMOTE, the minority class is oversampled by taking each minority class sample and introducing synthetic examples along the line segments joining any or all of the k minority class nearest neighbors. This approach effectively forces the decision region of the minority class to become more general. After oversampling the minority class in the training data set, the number of the positive and negative labels were almost equivalent (Table 7).

6.4 Signature S as a Single Predictor

A strong association between somatic ERCC2 mutations and activity of a mutational signature characterized by a broad spectrum of base substitutions, Signature 5* (closely resembles COSMIC Signature 5–cosine similarity 0.90), has been found by Kim et al. [13]. We investigated whether Signature 5 alone is a good predictor of ERCC2 mutational status and potential NER deficiency using the glm( ) function from the stats R package. The weights of the model are presented in Table 7. The standard error of the coefficients was calculated by using a bootstrapping approach.

TABLE 7

Weights of the Signature 5 model.

| Model parameter | Weights |
|---|---|
| Intercept | −2.594 ± 0.009 |
| Signature.5 | 3.88 ± 0.01 |

Figure 32:
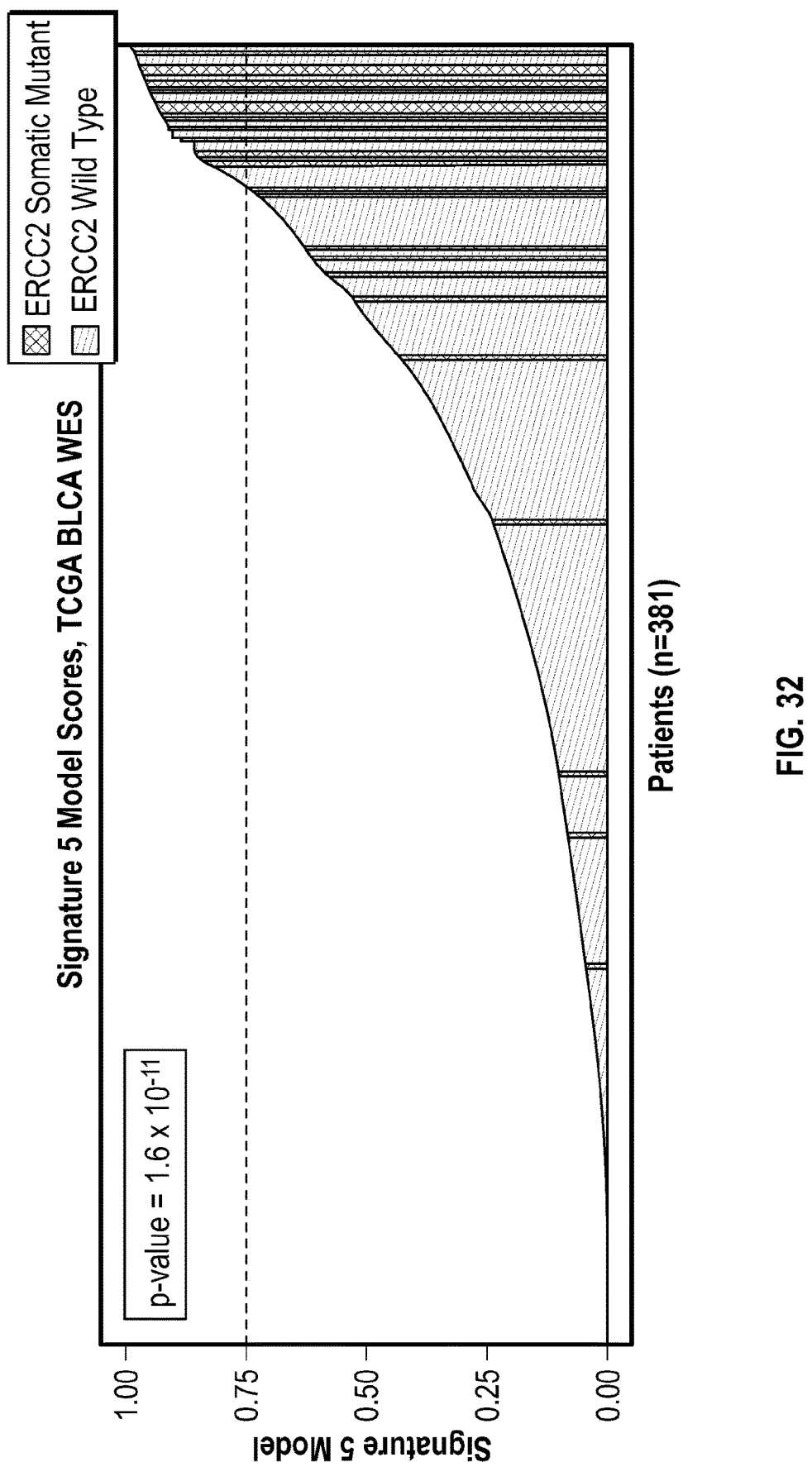
FIG. 32 shows COSMIC Signature 5 model scores in the train-test set.

ERCC2 somatic mutants were highly enriched among patients with high Signature 5 model score (FIG. 32) which is in agreement with the previous observation [13]. The p-value was calculated by the Fisher's exact test.

6.5 NERDetect

A lasso logistic regression [55] model was used to identify the final set of the genomic features from the pre-selected feature list that could distinguish between the two categories of patient samples: those affected and not affected by NER deficiency.

Inputs of the algorithm were as follows:

the number of mutations associated with signatures of single base substitutions: signature 2, 5, 13;

the number of mutations associated with a signature of insertions and deletions: ID8 signature; the number of deletions (1-50 bp); the number of insertions (1-50 bp); the number of point mutations; and the ratio of the number of a certain type of base substitution on the transcribed and untranscribed strand: transcription strand bias C>A, C>G, C>T, T>A, T>C, T>G.

A computer implementation of this model is available in the glmnet R package. Optimal coefficients are obtained by minimizing the objective function $$\min_{\beta \in \mathbb{R}^p} \frac{1}{N} \|y - X\beta\|_2^2 + \lambda \|\beta\|_1$$

where y is the response variable, X is the matrix of features, $\beta$ is the vector of weights, $\lambda$ is the regularization parameter and N is the number of samples. The 11 norm of the coefficient vector, $1\beta\mathfrak{l}\_1$, is added to the loss function as a penalty term. As a consequence of this constraint, the lasso restricts the coefficients of the model by pulling them toward zero; some of the variables become exactly zero. The regularization parameter, $\lambda$, was chosen by a k-fold (default k=10) cross validation with the cv. glmnet( ) function. In order to reduce stochasticity caused by the random selection of the folds, the cross validation procedure was performed 1000 times, the average of the $\lambda$s was taken and the standard error was estimated.

All $\beta$ weights were constrained to be positive because they supposedly reflect the biological presence of mutational processes that are, in this case, associated with NER deficiency. The weights of the final model are shown in Table 8. The standard error of the coefficients was calculated with a bootstrapping method.

Multiple logistic regression models with different regularization were trained and tested with bootstrapping. In the selection of the final logistic regression model we followed the principle of Occam's razor, i.e. the model that resulted in the range of the lowest cross-validation errors and was the simplest in complexity was preferred. The model with the lasso regularization ($\alpha$=1) and the $\lambda$=0.02906±0.00014 regularization parameter met this criteria (FIG. 1E).

6.6 Optimal Cutoff

The optimal cut-off value was defined by using the cutpointr R package in the TCGA BLCA WES training-test set. The minimization of misclassification cost of ERCC2 mutation status after a loess smoothing [56] with equal weights of FP and FN errors yielded the 0.75 optimal cutoff (FIG. 33).

6.7 Model Performance and Validation

The composite NERDetect signature scores of the samples in the whole training-test set are shown in FIG. 1F demonstrating that high NERDetect scores (≥0.75) were strongly associated with ERCC2 mutation status (p<2.2·10-16). To validate the ability of the NERDetect classifier to discriminate between ERCC2 mutant and WT bladder tumors, three additional independent bladder cancer cohorts [5, 28, 29] were analyzed. In each validation cohort, ERCC2 mutant cases were significantly associated with a NERDetect score≥0.75 (p=1.8·10-4 in the DFCI/MSKCC cohort, p=2.5·10-6 in the BGI cohort, and p=1.6·10-6 in the Philadelphia cohort, FIG. 2A-2C). P-values were calculated by the Fisher's exact test.

Figure 34A:
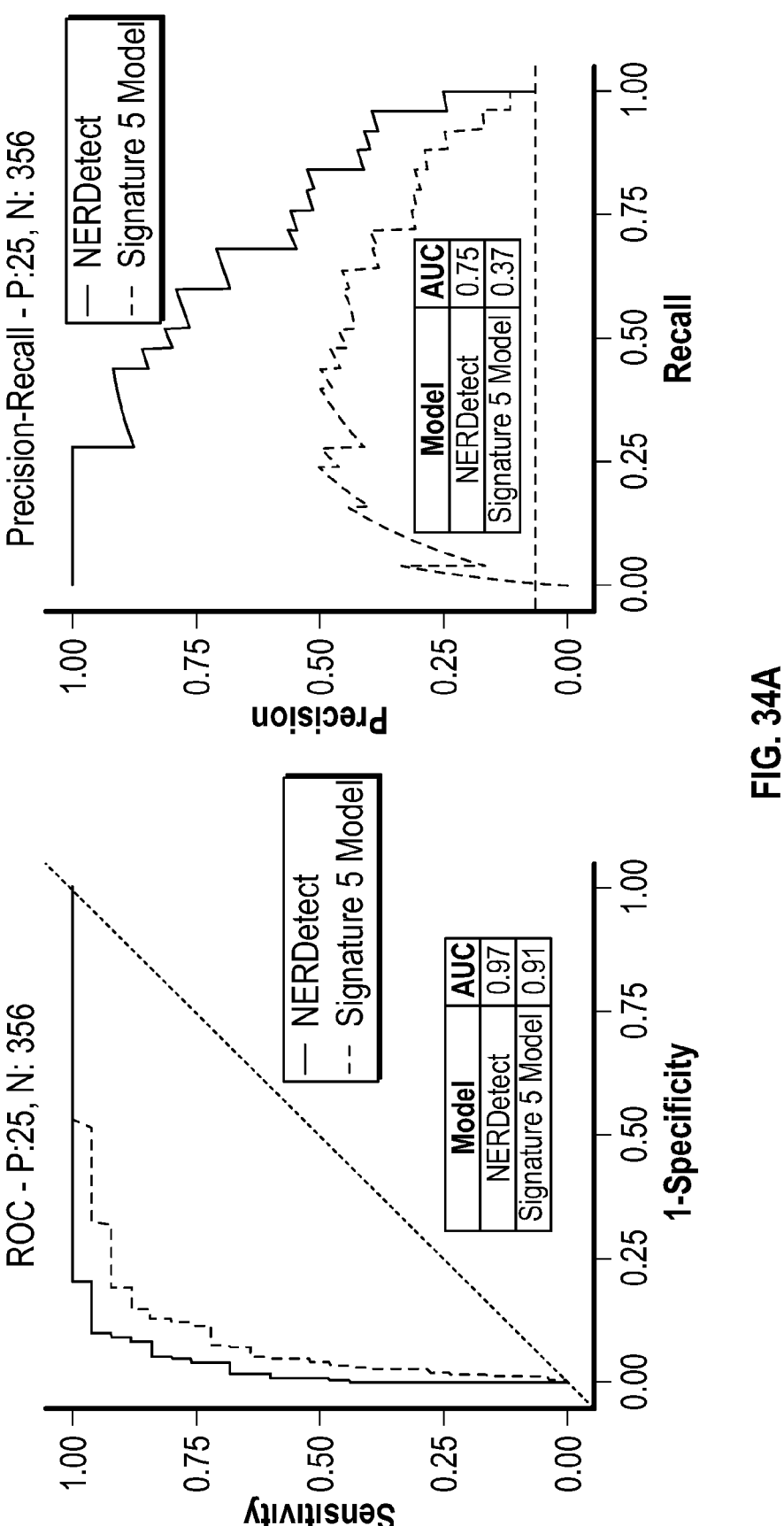
FIG. 34A shows performance of NERDetect and COSMIC Signature 5 alone in the training-test set. Performance of NERDetect in the DFCI/MSKCC (FIG. 34B), BGI (FIG. 34C) and Philadelphia (FIG. 34D) validation cohorts.
Figures 34B, 34C, 34D:
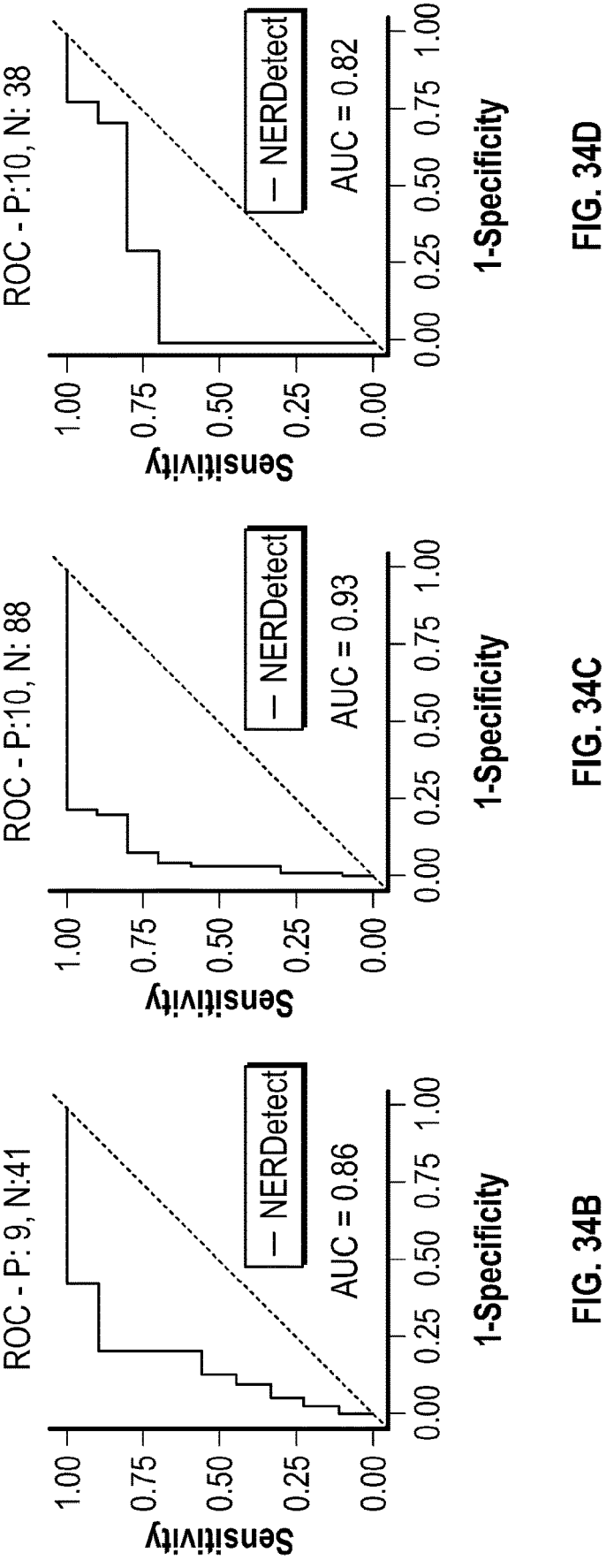

To measure the performance of the classifier on the training-test set and the validation sets, ROC and precisionrecall curves with the AUC values were plotted (FIG. 34). As it is demonstrated in FIG. 34A, the composite NERDetect signature more accurately identified ERCC2 mutant cases than was previously possible using COSMIC Signature 5 alone: the NERDetect signature AUCROC and AUCPRC were 0.97 and 0.75, respectively, compared to 0.91 and 0.37 with the COSMIC Signature 5.

TABLE 8

The distribution of the weights of the variables from bootstrapping is shown on the figure. The midline represents the median, the two edges of the box represent the lower and upper interquartile range (IQR), the upper whisker = min(max(x), Q3 + 1.5 × IQR) and the lower whisker = min(max(x), Q1 − 1.5 × IQR). The red dots indicate the final weights used in the NERDetect model. The mean and standard error of the coefficients are summarized in the table.

| Model parameter | Boot Coef | Final Coef |
|---|---|---|
| Intercept | −2.43 ± 0.01 | −2.384 |
| Signature.2 | 0.0015 ± 0.0005 | 0 |
| Signature.5 | 0.530 ± 0.006 | 0.5377 |
| Signature.13 | 0.0002 ± 0.0002 | 0 |
| TCGA.ID8 | 1.852 ± 0.009 | 1.816 |
| TSB_ratio_CtoA | 0.0002 ± 0.0002 | 0 |
| TSB_ratio_CtoG | 0.00008 ± 0.00007 | 0 |
| TSB_ratio_CtoT | 0 | 0 |
| TSB_ratio_TtoA | 0.193 ± 0.005 | 0.1911 |
| TSB_ratio_TtoC | 0 | 0 |
| TSB_ratio_TtoG | 0.0015 ± 0.0006 | 0 |
| numberOfDel | 0.28 ± 0.008 | 0.254 |
| numberOfIns | 0.0021 ± 0.0005 | 0 |
| numberOfPointMut | 0.00006 ± 0.00005 | 0 |

Figure 3C:
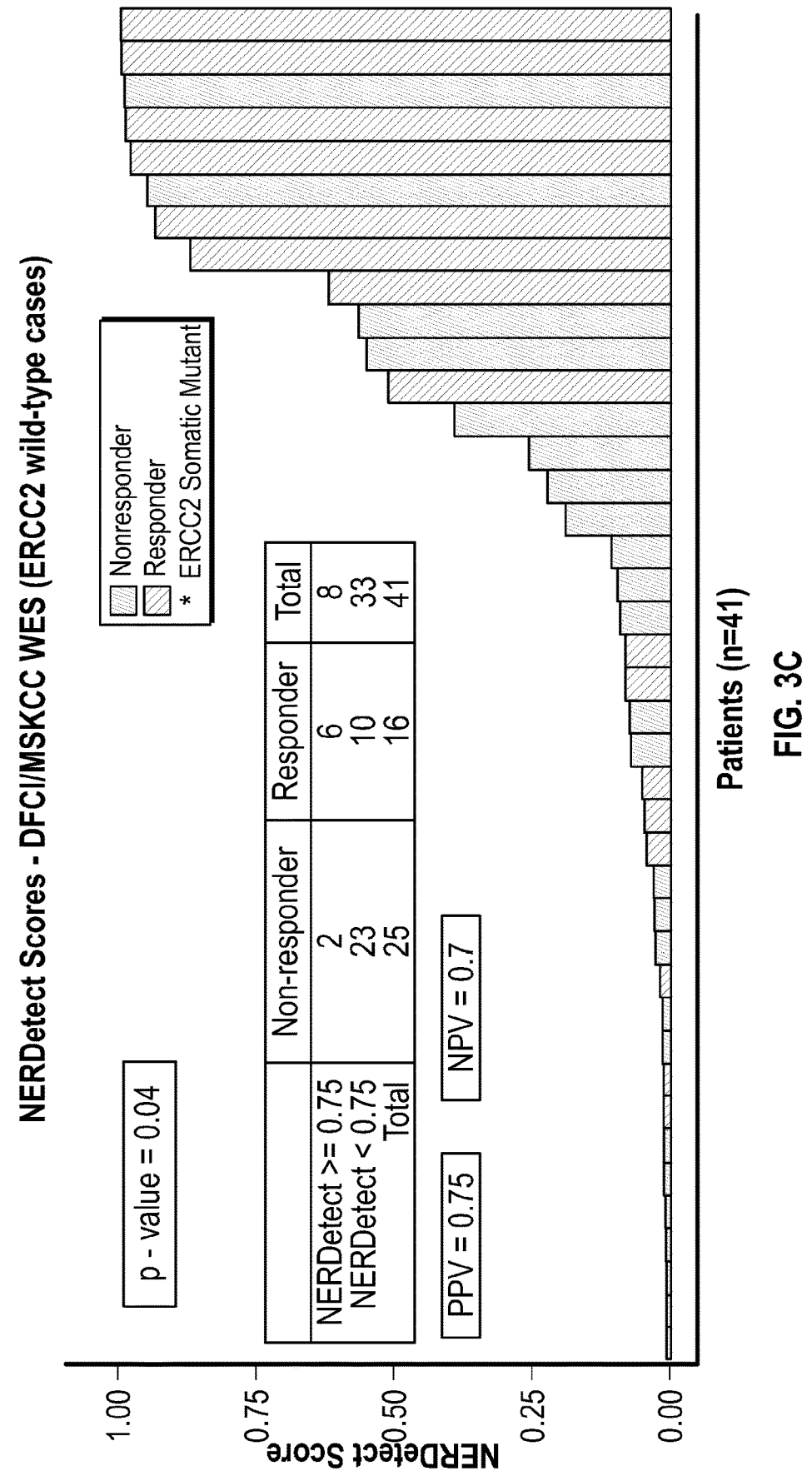
Figure 3D:
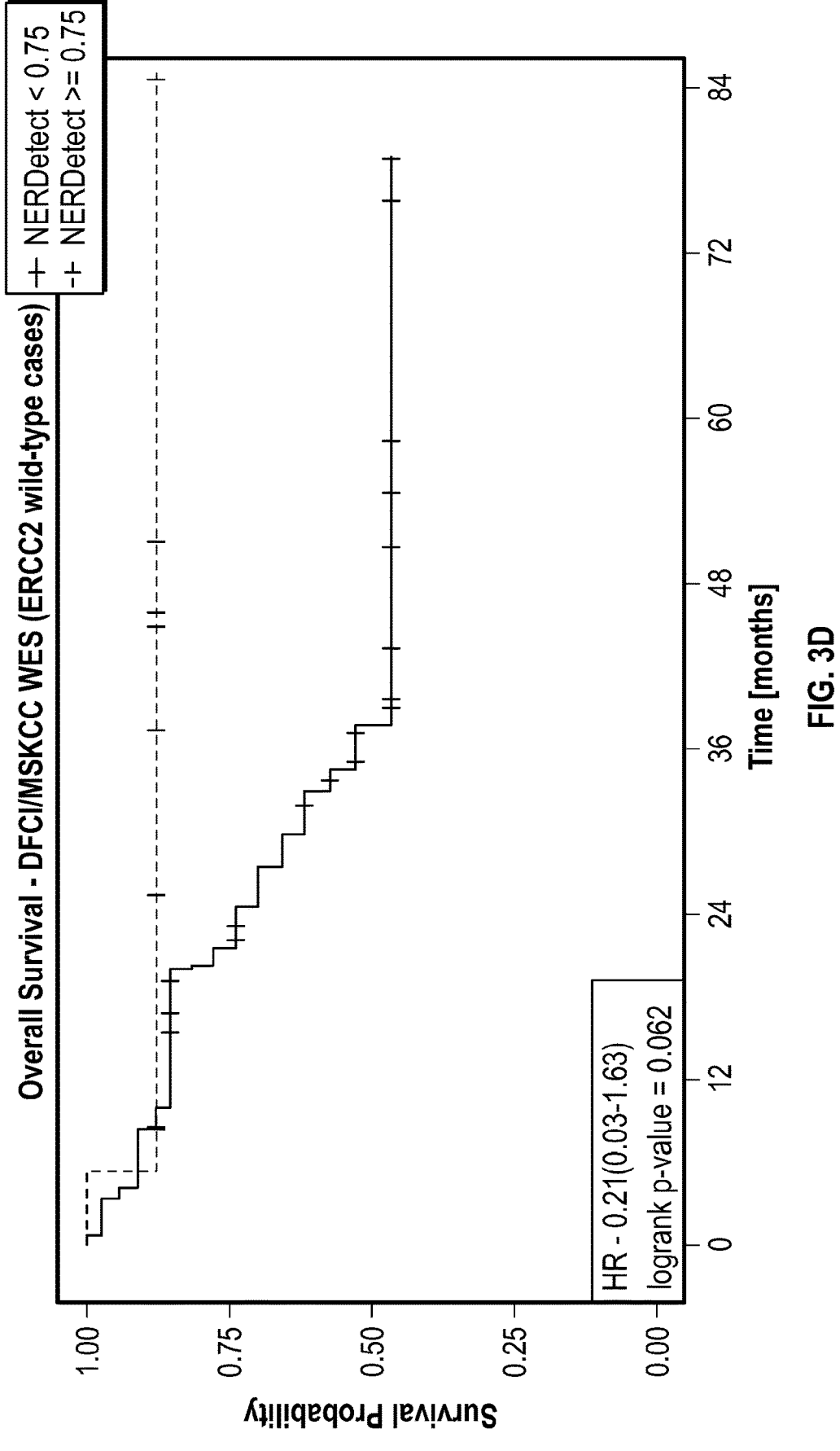
Figure 35:
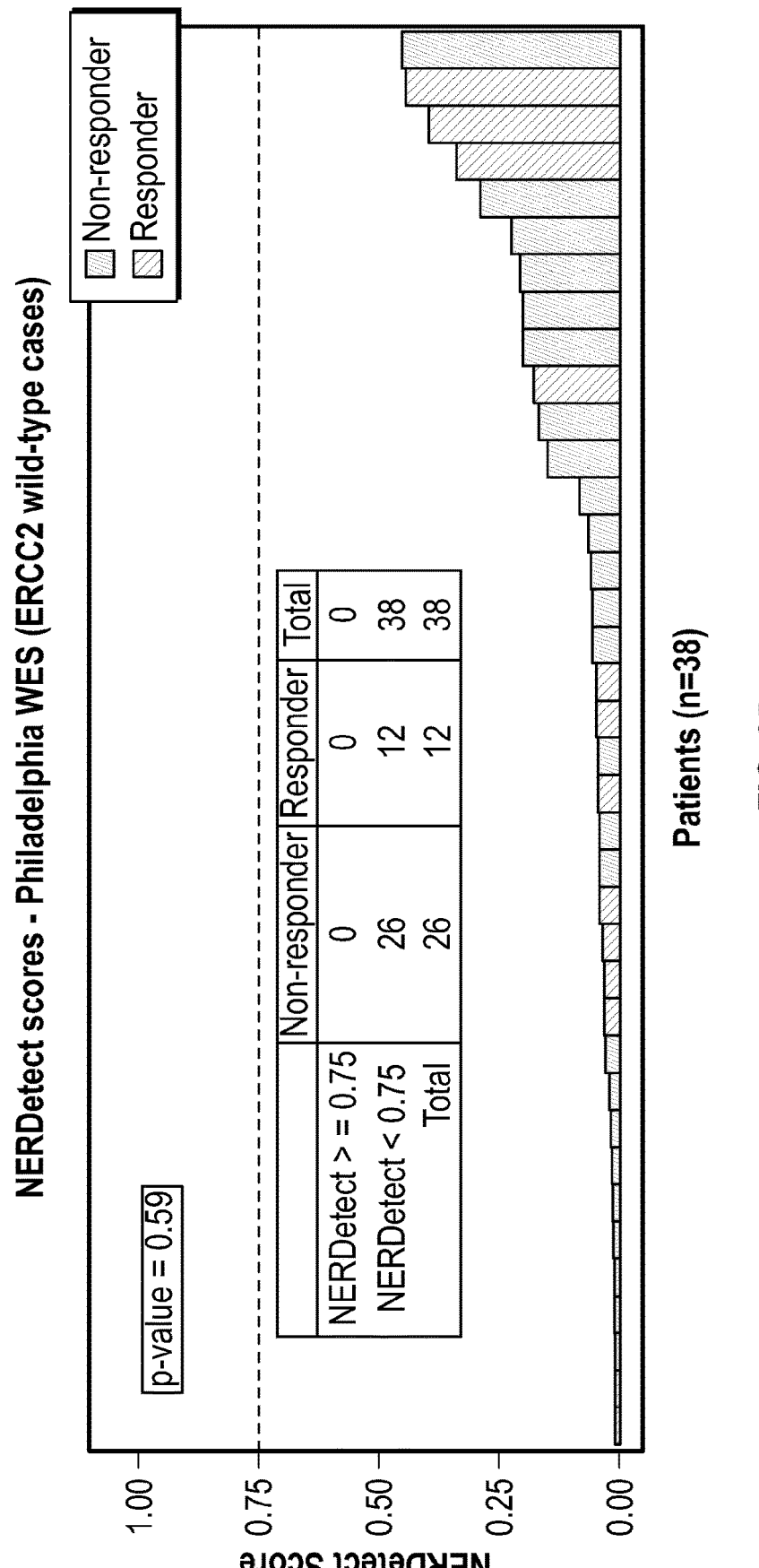
FIG. 35 shows NERDetect scores of ERCC2 WT cases in the FFPE-derived Philadelphia WES cohort.

In addition, NERDetect scores≥0.75 were strongly associated with cisplatin response in both the DFCI/M-SKCC and Philadelphia cohorts (p=5.8·10-4 and p=0.016, FIG. 3A-3B). Importantly, there was a significant enrichment of cisplatin responders among the ERCC2 wild-type cases with high NERDetect scores in the DF-CI/MSKCC cohort (p=0.04, FIG. 3C). In the FFPE-derived Philadelphia cohort, NERDetect scores were lower than in the other cohorts (which were derived from fresh frozen tissue), and there were no WT ERCC2 cases with NERDetect score≥0.75 (FIG. 35).

7. Survival Analysis

Figures 36A, 36B:
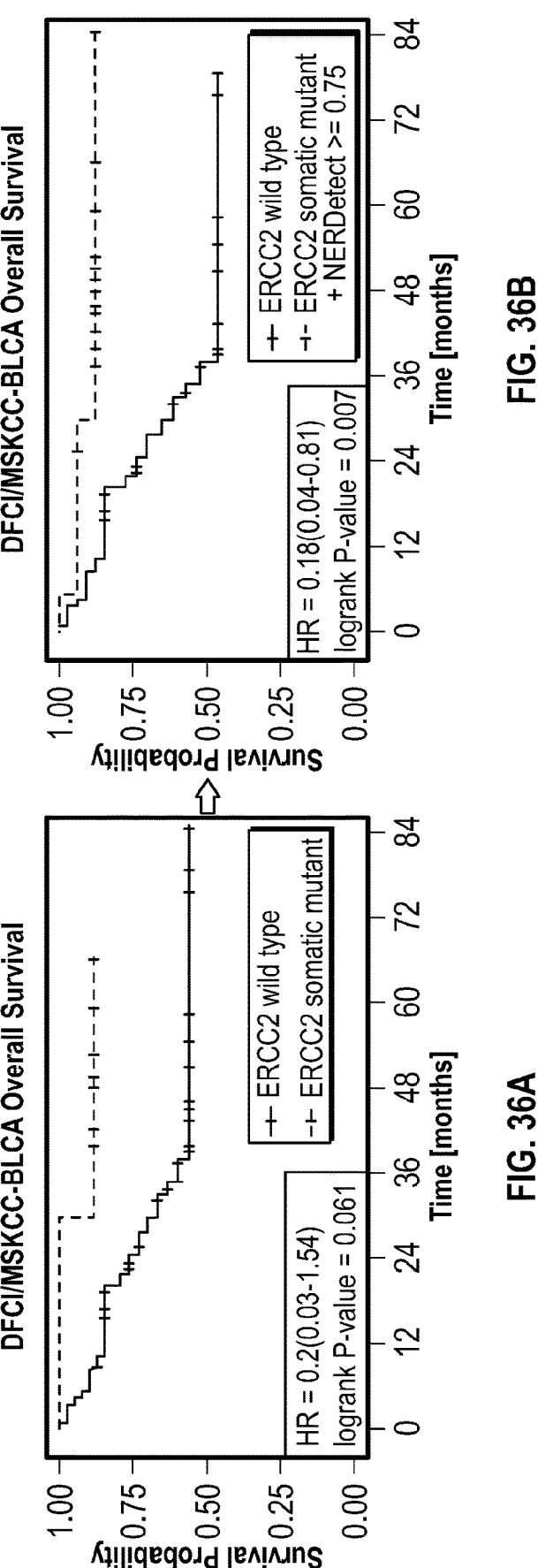
FIGS. 36A-36C show the DFCI/MSKCC cohort.
Figure 36C:
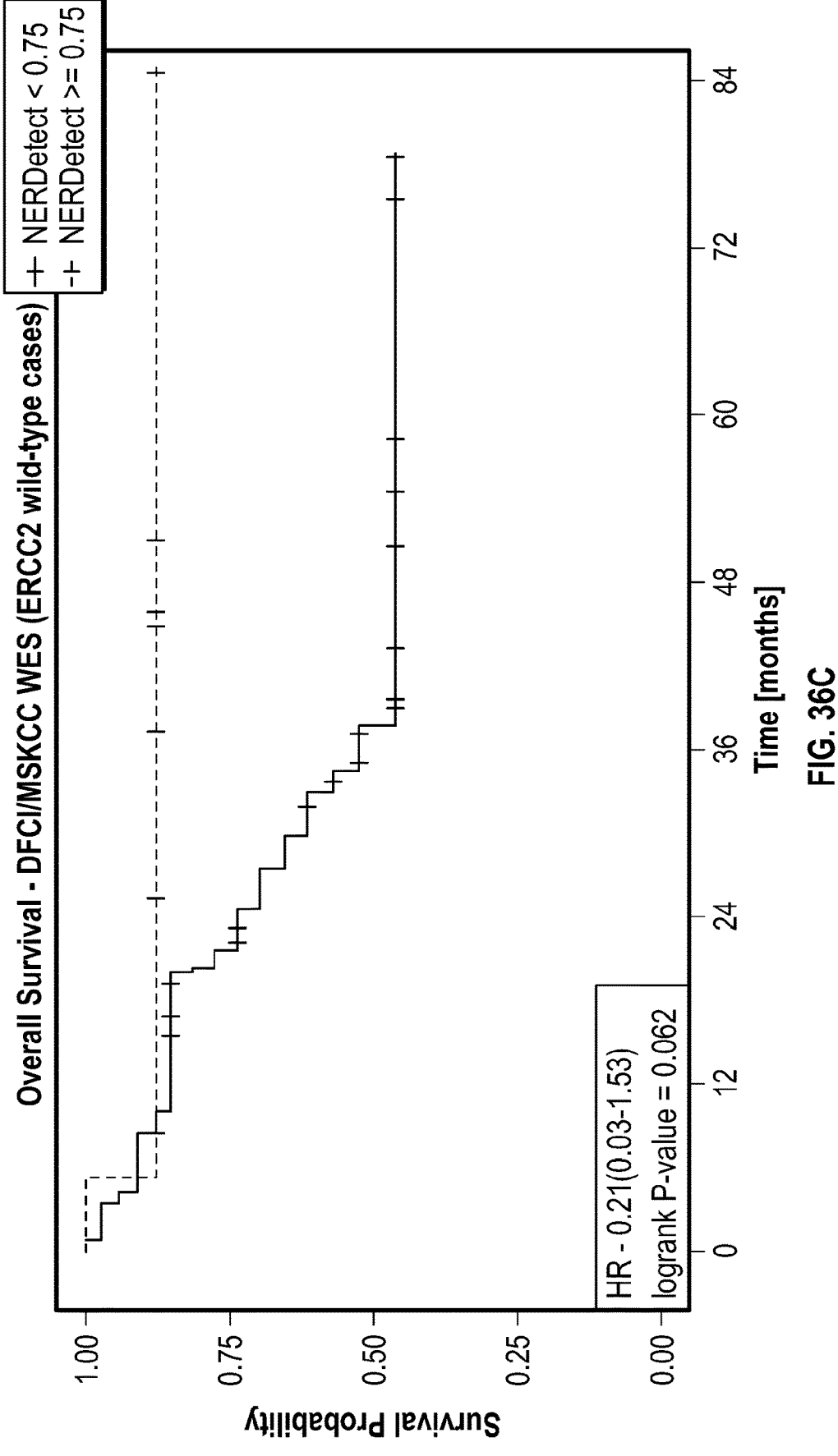
Figures 37A, 37B:
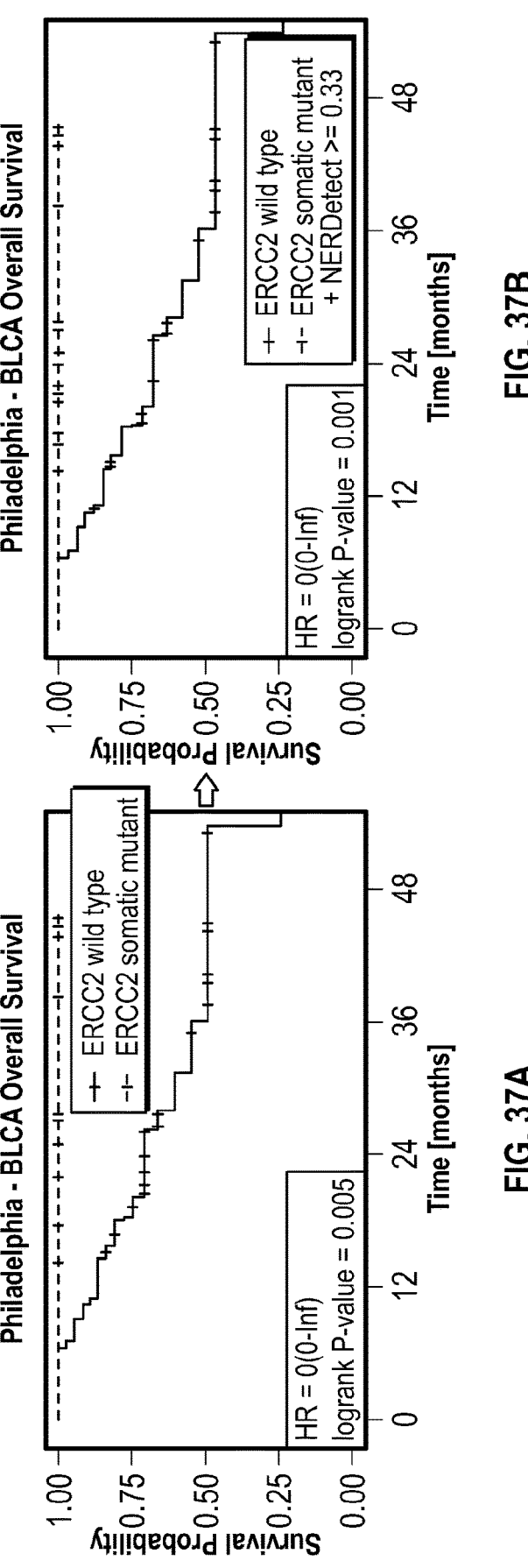
FIGS. 37A-37C show the Philadelphia cohort.
Figure 37C:
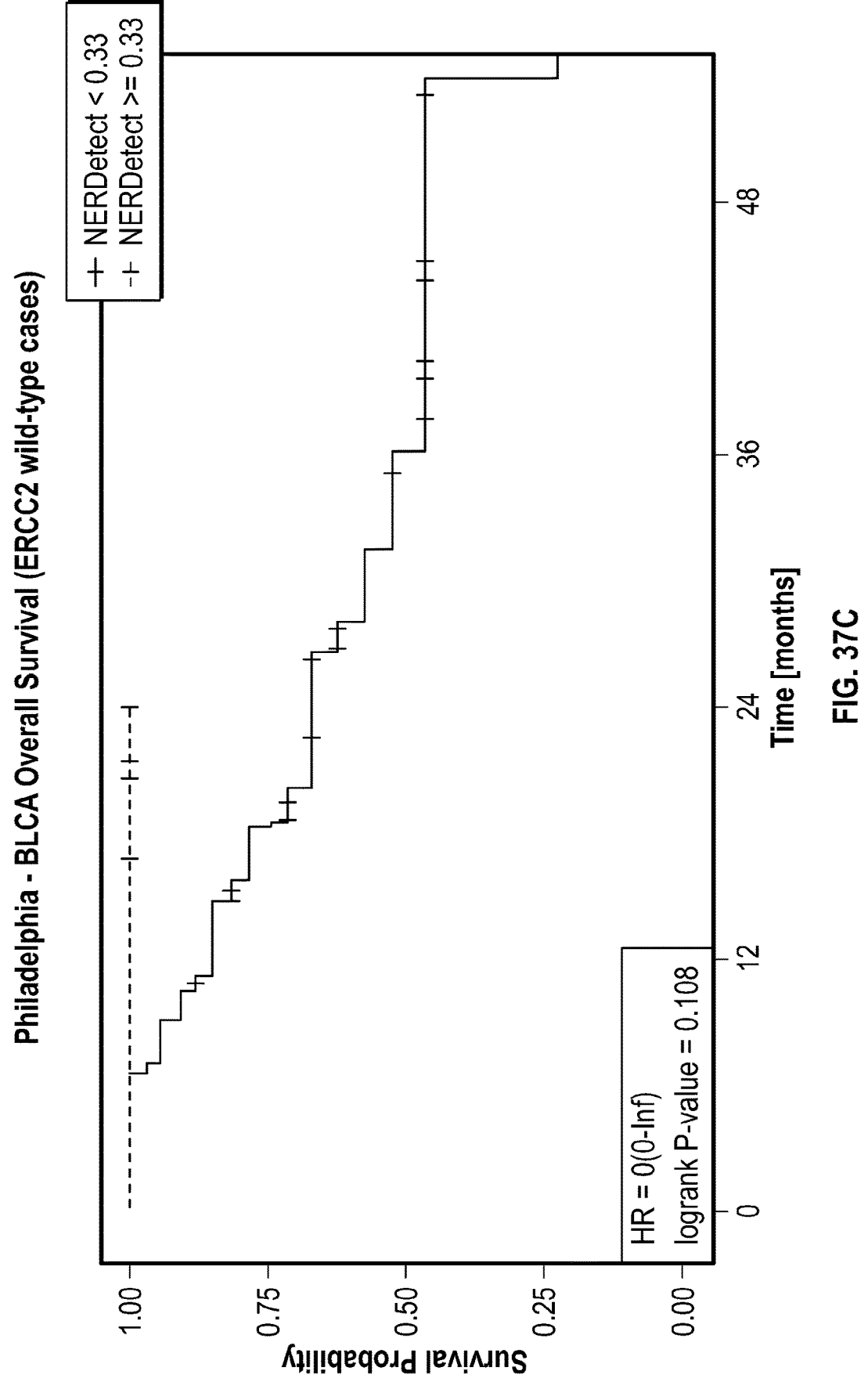
Figure 38:
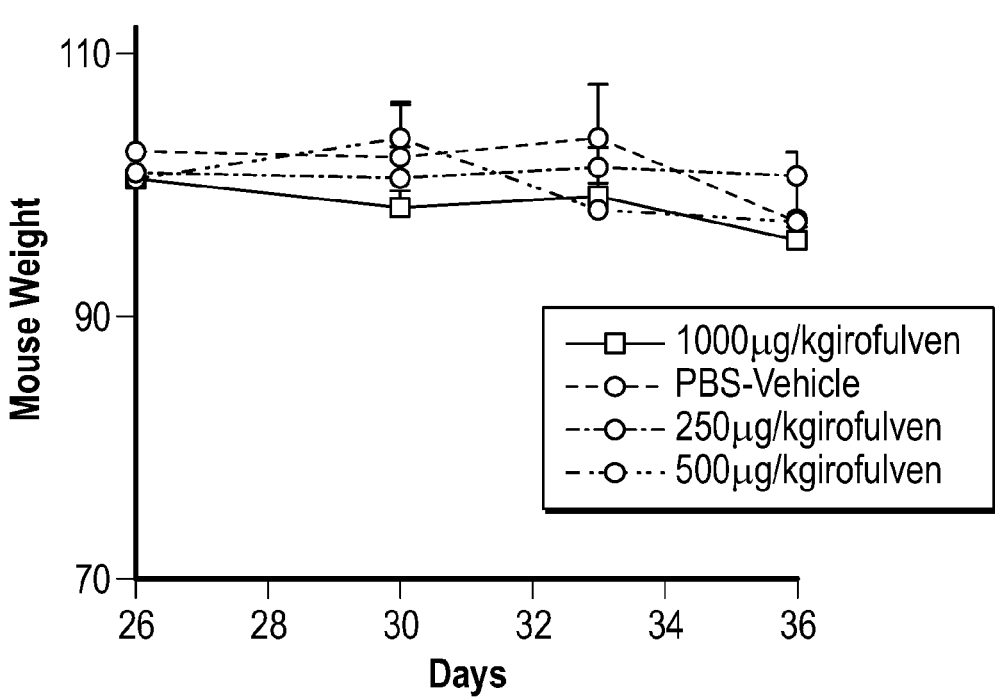
FIG. 38 shows the NER-deficient KE1 xenografts showed a strong irofulven dose response with near complete tumor regression observed at an irofulven dose of 1 mg/kg.
Figure 38:
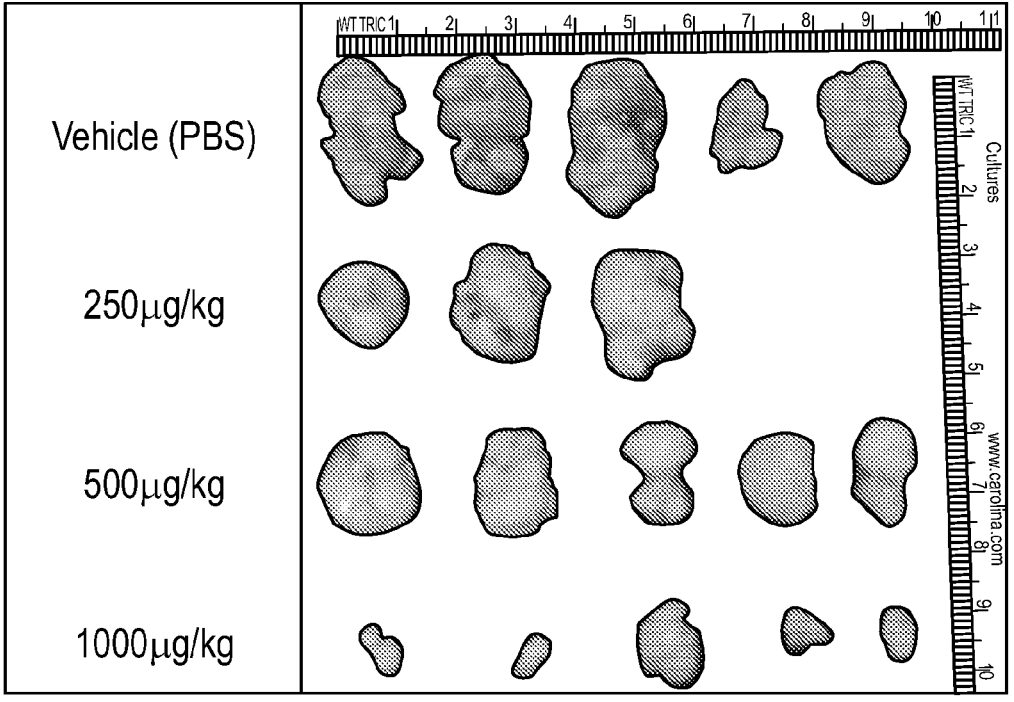
Figure 39:
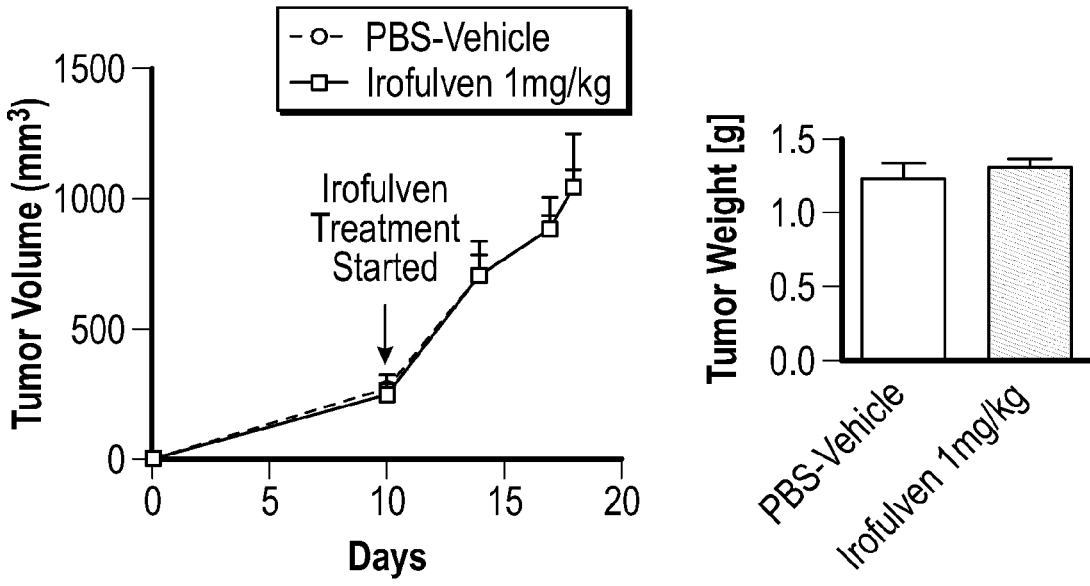
FIG. 39 shows the NER-proficient KU19-19 xenografts did not show response to irofulven treatment at 1 mg/kg dose.
Figure 39:
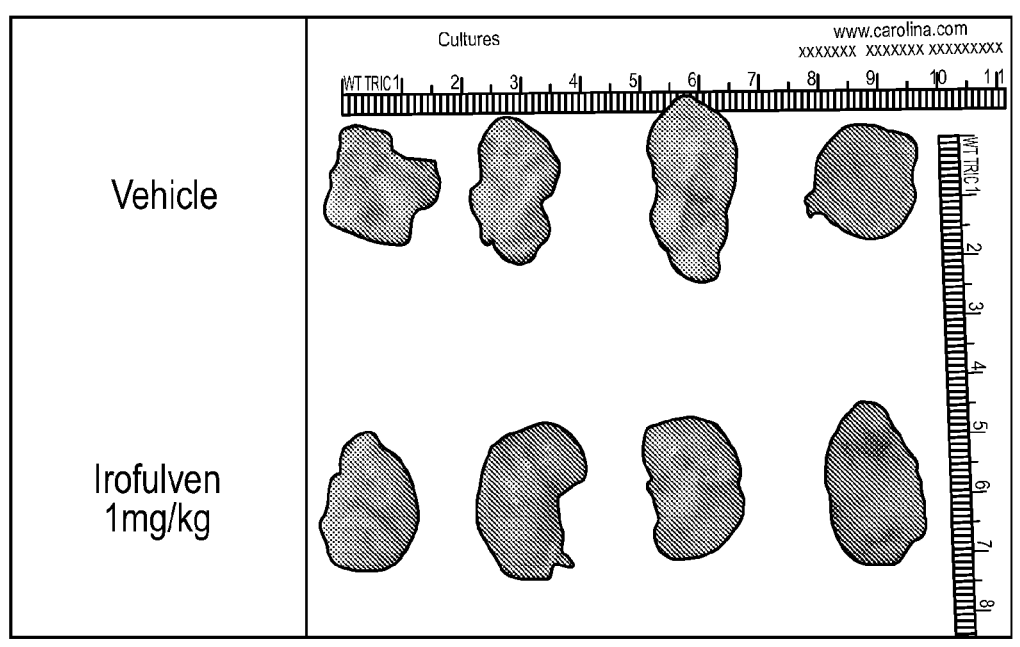
Figure 40A:
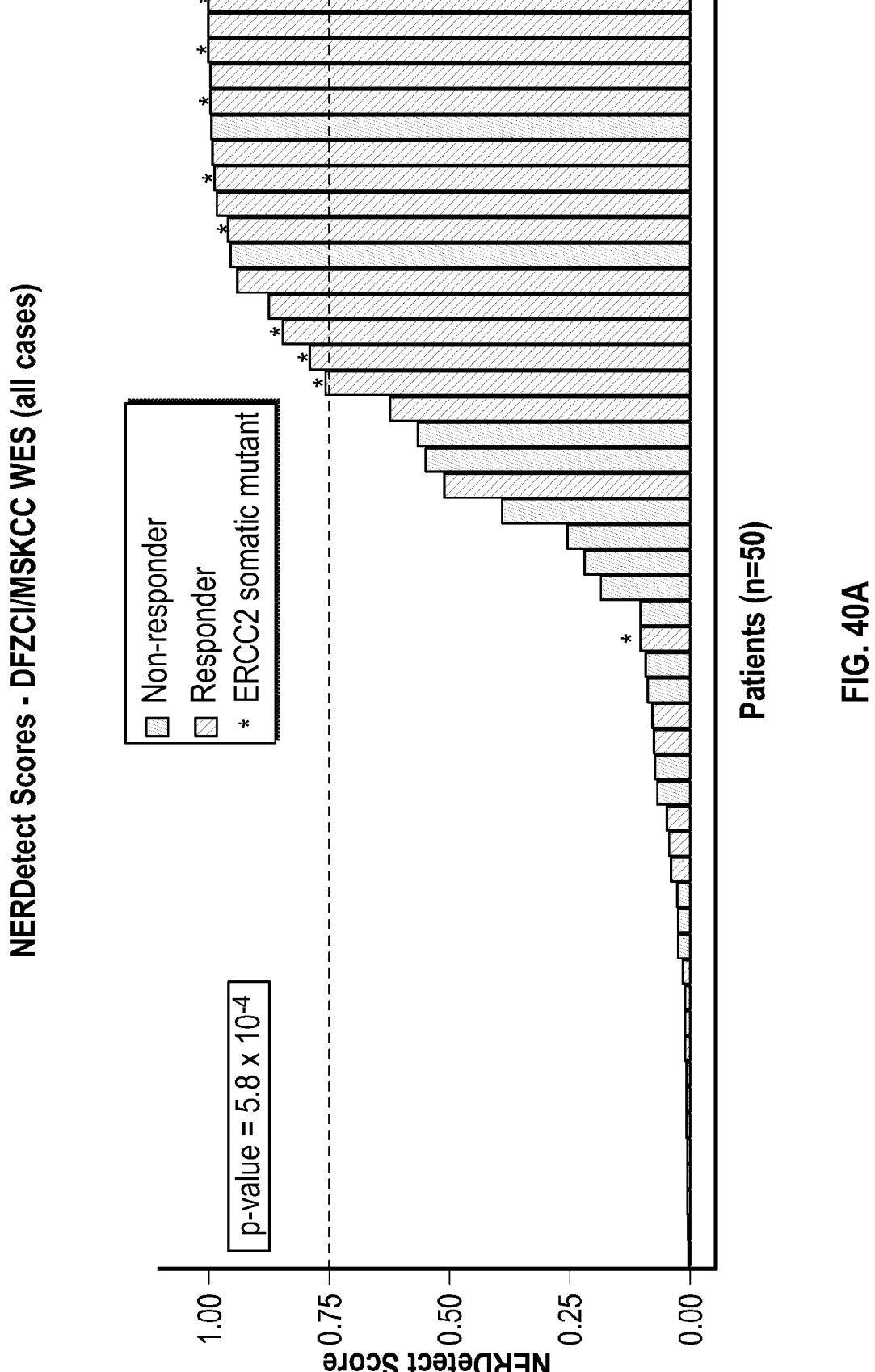
FIGS. 40A-40B show the composite NERDetect signature scores combined with the genotypes of samples in the DFCI-MSKCC (FIG. 40A) and Philadelphia (FIG. 40B) cohorts. Two WT ERCC2 cisplatin responders with a high NERDetect score harbored a predicted deleterious mutation in another NER gene, ERCC6.
Figure 40B:
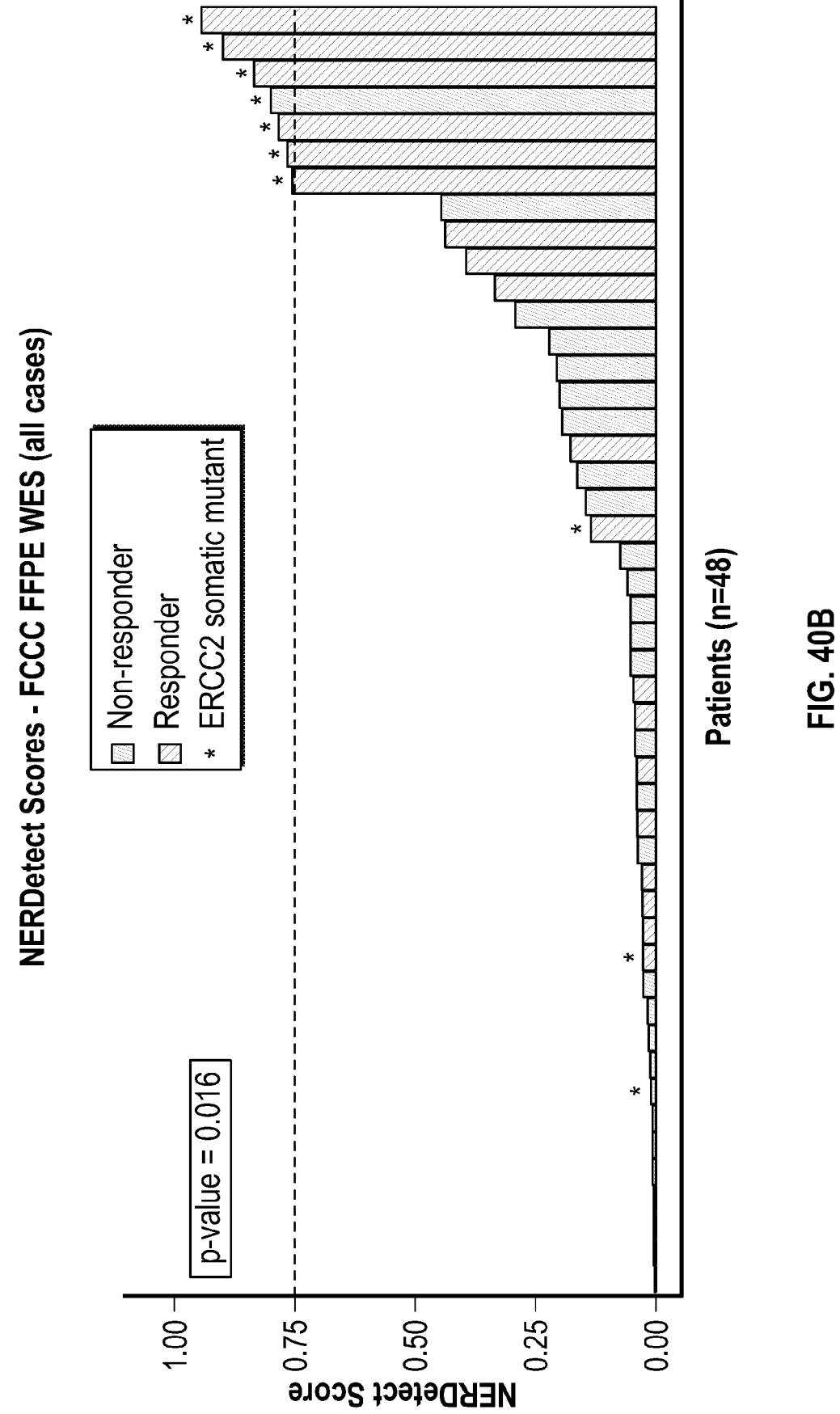
Figure 40C:
FIGS. 40C-40D show the composite ERCC2mut signature scores combined with the genotypes of samples in the DFCI-MSKCC (FIG. 40C) and Philadelphia (FIG. 40D) cohorts. Two WT ERCC2 cisplatin responders with a high ERCC2mut score harbored a predicted deleterious mutation in another NER gene, ERCC6.
Figure 40D:
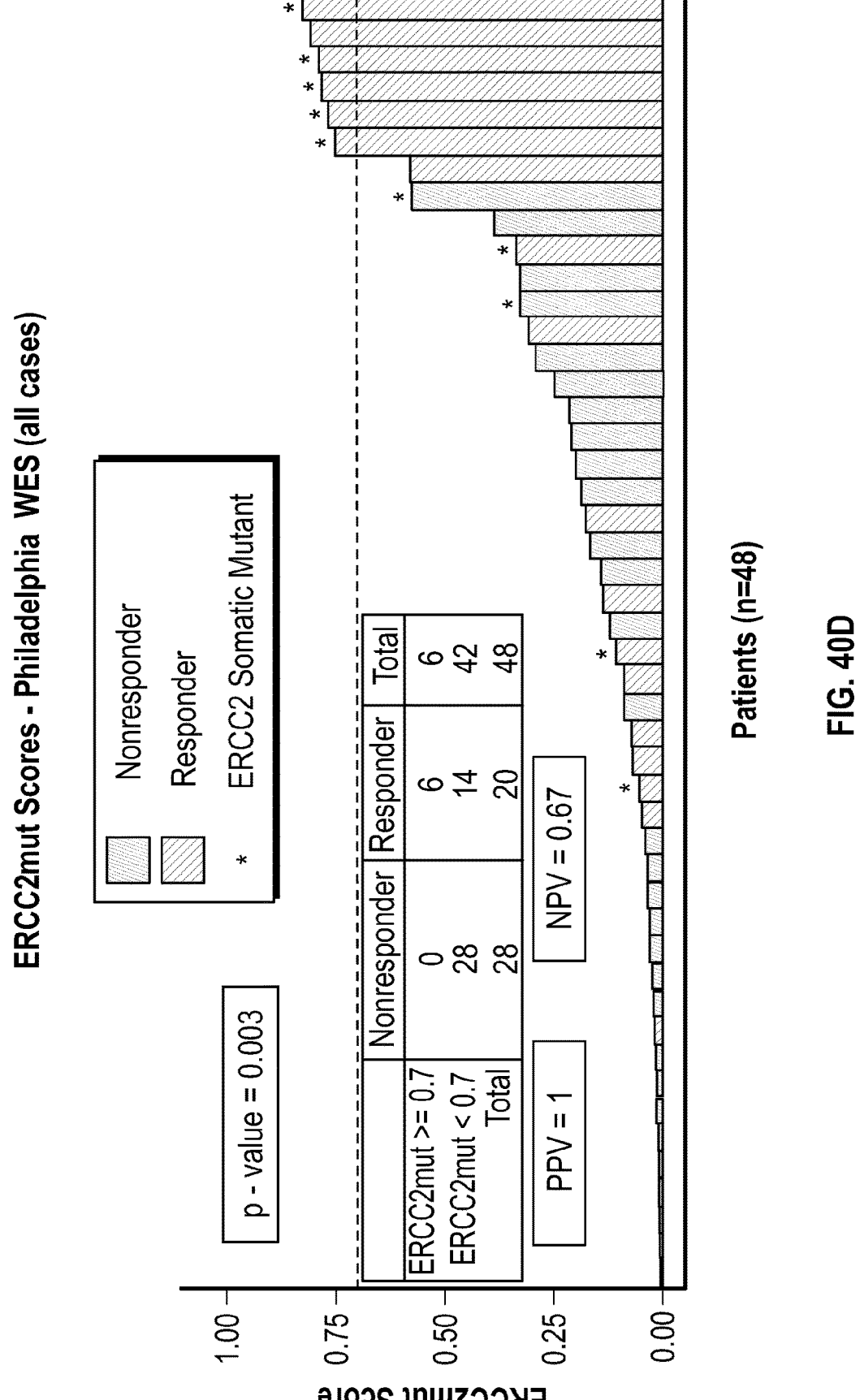

Survival analysis was carried out using the survival and survminer R packages. The estimated Kaplan-Meier curves of patients who received neoadjuvant cisplatin-based chemotherapy are shown in FIG. 36 for the DFCI/MSKCC cohort and FIG. 37 for the Philadelphia cohort. P-values are calculated using the log-rank test. Individuals harboring ERCC2 somatic mutations have a significantly better survival than the ERCC2 wild-type cases (FIGS. 36A and 37A) as it was previously shown by Liu et al. [28]. Adding patients with NERDetect score≥20.75 (≥0.33 in the FFPE derived Philadelphia cohort) to ERCC2 mutant cases further improves the difference in overall survival (FIGS. 36B and 37B). ERCC2 wild-type patients with high NERDetect score (≥0.75 or ≥0.33 in the FFPE derived Philadelphia cohort) demonstrated strong trend towards improved survival in both the DFCI/MSKCC and Philadelphia cohorts (FIGS. 36C and 37C).

8. Cell Lines

8.1 Cell Lines and Reagents

The TK6 human lymphoblastoma cell line, and an isogenic XPA−/− knockout modification were used for assaying spontaneous mutagenesis [31]. After the isolation of an ancestral clone, cells were cultured for 60 days, at which point descendent clones were isolated. Genomic DNA from the ancestral and descendent clones was isolated as soon as a sufficient number of cells was available. Whole genome sequencing (WGS) to an average depth of 30 was performed on Illumina HiSeq X instruments by Novogene, China.

Bladder cancer cell lines were purchased from ATCC. The KE1 bladder cancer cell line is a derivative of KU19-19 in which an ERCC2 mutation has been introduced by CRISPR/Cas9 gene editing [6]. The MDA-MB-468 breast cancer cell line and its ERCC4-complemented derivative have been previously described [32]. Small interfering RNAs (siRNAs) targeting specific NER genes as well as a non-targeting siRNA (siNTC) were purchased from Integrated DNA Technologies Inc. (Coralville, IA, USA; see below for sequences). Cells were seeded in 6-well plates and grown to 50% confluency. A transfection mixture containing siRNA diluted to a final concentration of 30 nM in Opti-MEM media containing Lipofectamine 3000™ (Life Technologies; Carlsbad, CA) was then added to cells. After 48 hours, cells were trypsinized and re-aliquoted to separate wells and transfected with 15 nM siRNA for 24 hours immediately prior to viability assays performed as described below.

TABLE 9

Sequences for siRNA duplexes.

| Gene | IDT Catalogue No. | Sequence |
|---|---|---|
| DDB2 | hs.Ri.DDB2.13.1-SEQ 1 | AGGUUAUCUUGGAACUAAAUG ACTT (SEQ ID NO: 1) |
| | hs.Ri.DDB2.13.1-SEQ 2 | AAGUCAUUUAGUUCCAAGAUA ACCUUG (SEQ ID NO: 2) |
| ERCC3 | hs.Ri.ERCC3.13.1-SEQ 1 | CUGUCAACCCUGAUAUCAACA UUGA (SEQ ID NO: 3) |
| | hs.Ri.ERCC3.13.1-SEQ 2 | UCAAUGUUGAUAUCAGGGUUG ACAGAA (SEQ ID NO: 4) |
| ERCC6 | hs.Ri.ERCC6.13.1-SEQ 1 | CAAGCCAGAAUACUGCUAAAC AACA (SEQ ID NO: 5 |
| | hs.Ri.ERCC6.13.1-SEQ 2 | UGUUGUUUAGCAGUAUUCUGG CUUGAGA (SEQ ID NO: 6) |

8.2 Cell Line Mutational Signatures

KU19-19 and KE1 cell populations were single cell sorted, and individual cells were expanded and then split into multiple populations of at least 1·106 cells. Each population of KU19-19 or KE1 cells was propagated in culture for 30 days while maintaining the population above 1·106 cells at all times. After 30 days, each population was single cell sorted and individual clones were grown to ~1·106 cells. Cells were frozen, lysed, and genomic DNA was isolated. Whole genome sequencing (WGS) was performed at the Broad Institute to an average depth of 30×. Somatic mutations were called using IsoMut [31], which accurately identifies experimentally induced mutations in multiple isogenic samples. Single base substitution signatures and indel signatures were extracted as described above. The NERDetect signature scores of the cell line samples are presented in FIG. 4B. The p-value was calculated by the Wilcoxon rank-sum test.

8.3 In Vitro Drug Sensitivity Assays

Cells were seeded in either 96-well (5,000 cells/well) or 24-well (20,000 cells/well) plates. The following day, irofulven and cisplatin stock solutions were serially diluted in media and added to cells. After 48 to 72 hours, media was removed and CellTiter-Glo® reagent (Promega; Madison, WI) was added. Plates were scanned using a luminescence microplate reader (BioTek). Survival at each drug concentration was plotted as a percentage of survival in drug-free media with error bars representing the standard deviation of at least three experiments.

For crystal violet imaging experiments, cells were seeded in 6-well plates (100,000-200,000 cells/well) with 15 nM siRNA transfection mixture (as detailed above). At 24 hours, fresh media containing irofulven or PBS was added and the cells were incubated for an additional 72 hours. Cells were then fixed in formalin solution for 30 minutes and stained with crystal violet prepared in equal volumes of methanol and water. Excess crystal violet was removed by washing with PBS, and plates were then dried and imaged.

8.4 Immunoblotting

Cells were lysed with ice-cold RIPA buffer supplemented with protease and phosphatase inhibitors (Roche). Samples were then sonicated and protein concentrations were determined using the Bradford assay. Sample buffer (Bio-Rad) was added and samples were then denatured at 900-C for 10 mins. Samples were then loaded in NuPAGE™ protein gel (Thermo Fisher Scientific) and run at 90 V for 2-3 hours. The gels were then transferred to nitrocellulose membranes at 30 V overnight. Membranes were blocked for 30 mins in 5% milk in TBS buffer. Sections of the membrane corresponding to the appropriate molecular weights were stained overnight in primary antibodies: XPF (1:700, clone D3G8C rabbit mAB, Cell Signaling), β-tubulin (1:1000, mouse mAB, Santa Cruz Technologies), Rpb1 CTD (1:1000, clone 4H8 Mouse mAb, Cell Signaling) prepared in 1% milk in TBST. A Licor Odyssey Infrared Imaging System was used for signal detection using IRDYE-conjugated secondary antibodies (LICOR Biosciences).

9. Xenograft Studies

Six week old female athymic nude mice, NU/J (Stock No: 002019) were purchased from Jackson Laboratory (Bar Harbor, ME) and housed at the Dana-Farber Cancer Institute Animal Resources Facility. All animal experiments were performed in accordance with an IACUC-approved protocol. At 7-10 weeks of age, mice were anesthetized with isoflurane and subcutaneously injected on the left flank with 3 million KE1 or 1 million KU19-19 cells mixed 1:1 with Matrigel (BD Biosciences; Mississauga, ON) in PBS. Tumor size was measured with a digital caliper twice weekly and calculated using the formula:

$$(L \cdot W^2) \times \frac{1}{2}.$$

Drug treatments were administered when the average tumor volume reached a minimum of 100 mm³. Irofulven was prepared in PBS to a stock concentration of 200 µg/ml and was delivered intraperitoneally (IP) twice weekly at doses of 250 μg/kg, 500 μg/kg or 1 mg/kg for a total of 5 injections or until the tumor reached a pre-specified protocol endpoint. Control mice were injected with PBS alone. At the end of the experiment, mice were sacrificed and tumors were excised for tumor weight measurements and imaging.

Figures 54A, 54B:
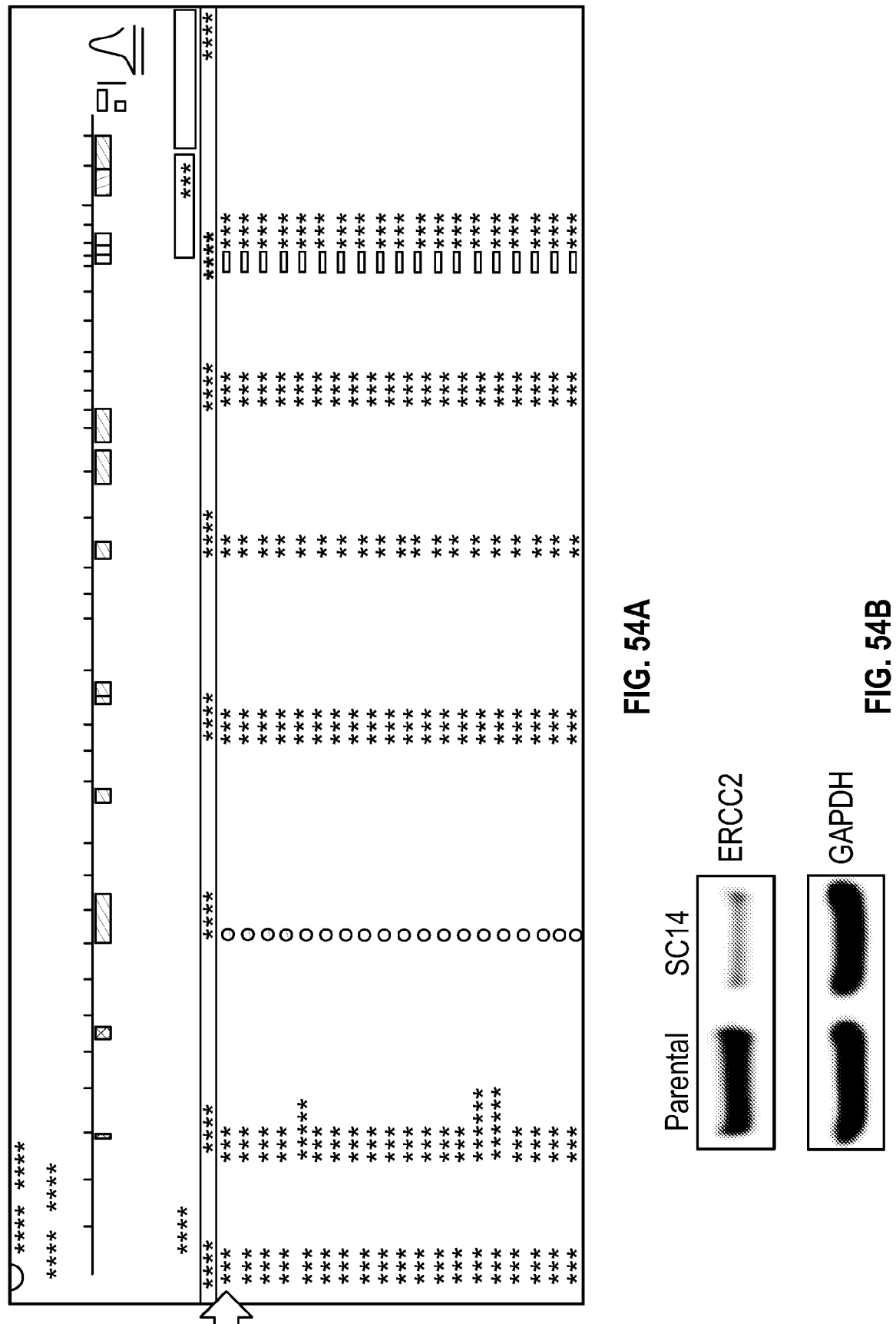
FIGS. 54A-54B show the presence of the ERCC2 P463L mutation in the derivative cell line (SC14) was confirmed by next-generation sequencing (FIG. 54A), and immunoblotting demonstrated the presence of a full-length ERCC2 gene product in the SC14 line (FIG. 54B).
Figure 55A:
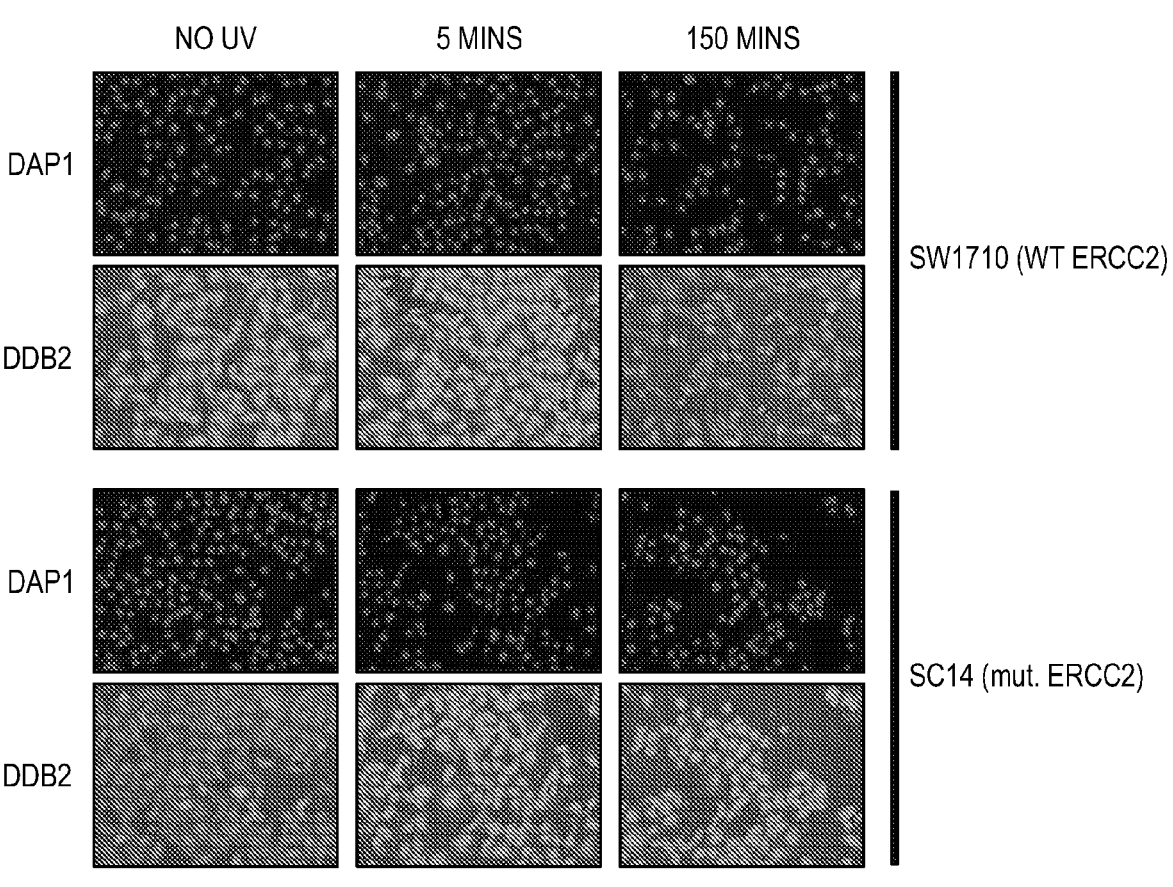
FIG. 55A shows the ERCC2-mutant SC14 line failed to resolve UV-induced DDB2 foci in an immunofluorescent NER reporter assay consistent with loss of NER capacity.
Figure 55B:
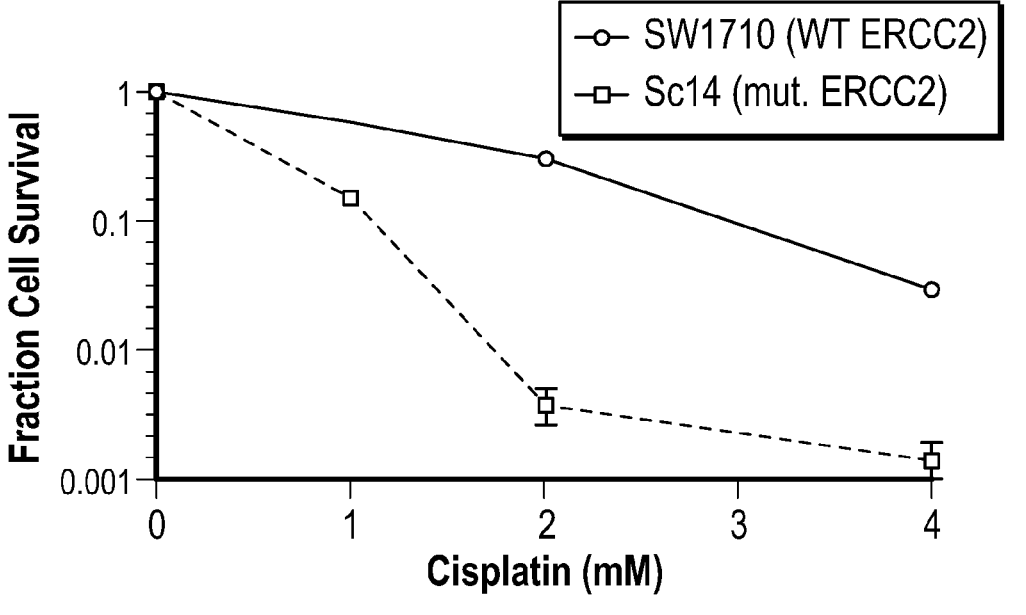
FIG. 55B shows the SC14 line displayed significantly increased sensitivity to cisplatin.
Figure 56:
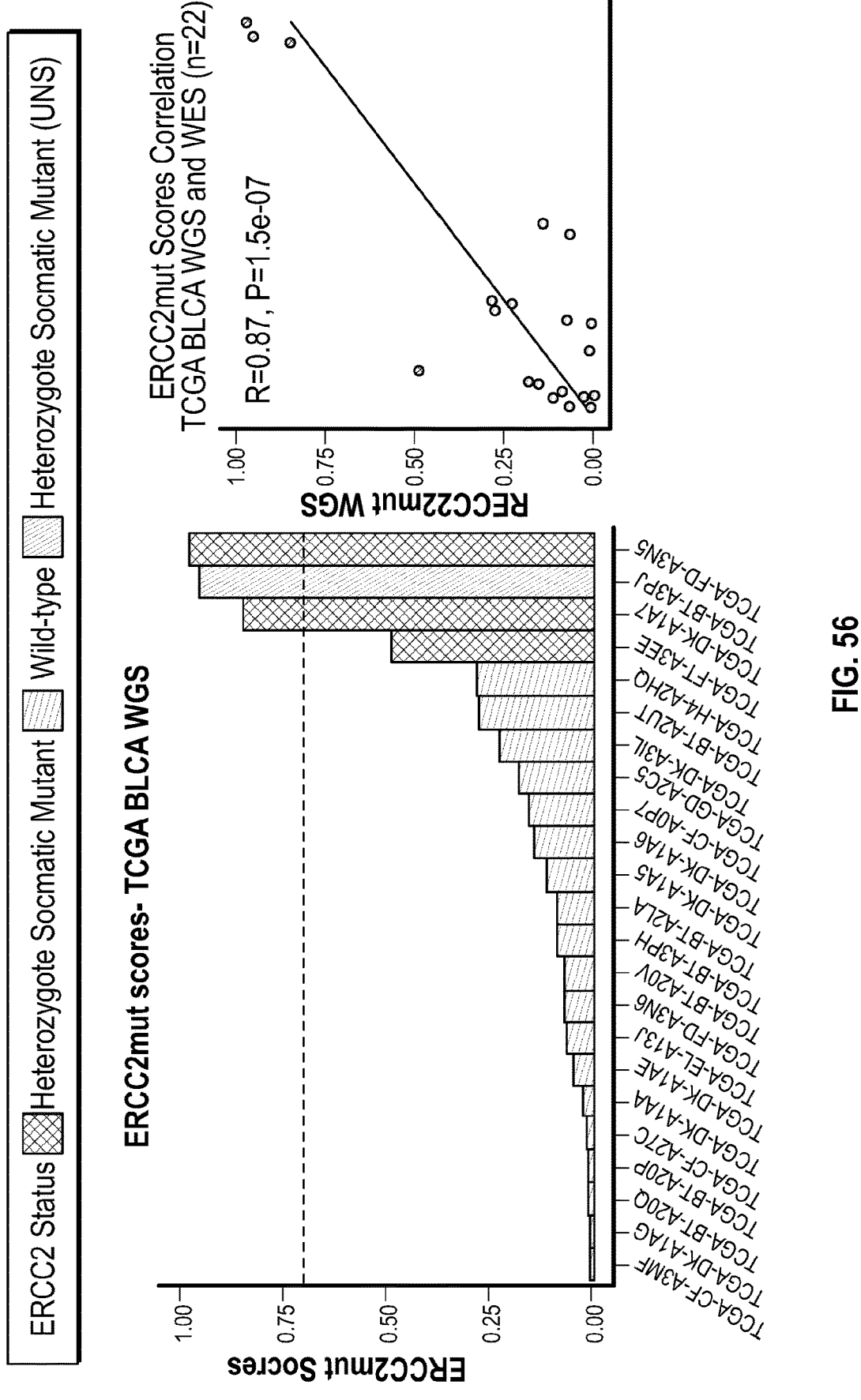
FIG. 56 shows the ERCC2mut classifier was applied to the subset of TCGA cases with WGS samples available (n=23) and there was a very strong correlation (0.87) between scores calculated using WGS and WES samples.

Example 3: CRISPR/Cas9 Techniques to Introduce a Clinically Observed ERCC2 Mutation To further investigate the relationship between ERCC2 mutations and irofulven sensitivity, the inventors used similar CRISPR/Cas9 techniques to introduce a clinically observed ERCC2 mutation (P463L) in SW1710, another bladder cancer cell with no baseline NER dysfunction. The presence of the ERCC2 P463L mutation in the derivative cell line (SC14) was confirmed by next-generation sequencing, and immunoblotting demonstrated the presence of a full-length ERCC2 gene product in the SC14 line (FIG. 54A-54B). The ERCC2-mutant SC14 line failed to resolve UV-induced DDB2 foci in an immunofluorescent NER reporter assay (6,38) (data not shown), consistent with loss of NER capacity. As was observed for the NER-deficient KE1 bladder cancer line, the SC14 line also displayed significantly increased sensitivity to irofulven (FIG. 5B, middle) as well as cisplatin (FIG. 55). Together, these data demonstrate that introduction of distinct, clinically relevant ERCC2 mutations in bladder cancer cell lines is sufficient to confer NER deficiency and drive marked sensitivity to irofulven.

Finally, the inventors determined if NER deficiency conferred by alterations in genes other than ERCC2 is also sufficient to drive irofulven sensitivity. It was discovered that the breast cancer cell line MDA-MB-468 is NER deficient due to epigenetic silencing of ERCC4 (XPF), and that NER activity and cisplatin sensitivity of the cell line could be rescued by re-expression of WT ERCC4 (35). The inventors tested irofulven sensitivity of the NER-deficient parental MDA-MB-468 line as well as its WT ERCC4-complemented counterpart and again observed dramatically higher irofulven sensitivity in the NER-deficient compared to NER-proficient cell line (FIG. 5B, bottom), suggesting that NER loss mediated by dysfunction of an NER gene beyond ERCC2 can also drive irofulven sensitivity. See also, Example 7 for additional methods.

Example 4: ERCC2Mut Signature Scores are Associated with Cisplatin Response

Figure 43A:
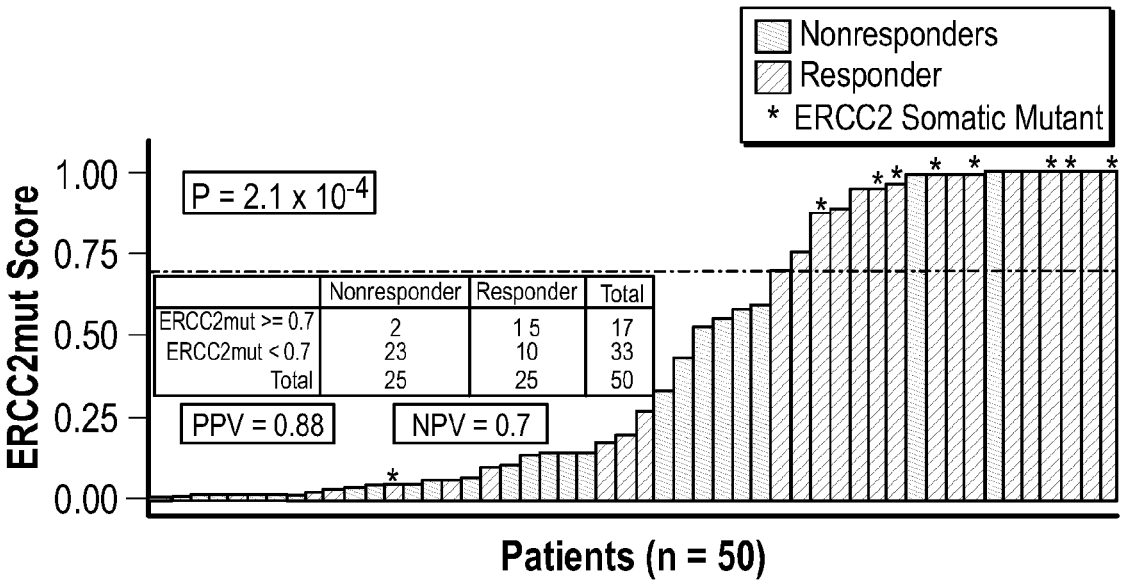
FIGS. 43A-43D show ERCC2mut signature scores are associated with cisplatin response, including among wild-type (WT) ERCC2 cases. Cisplatin responders are colored in gray and non-responders are in black.
Figure 43B:
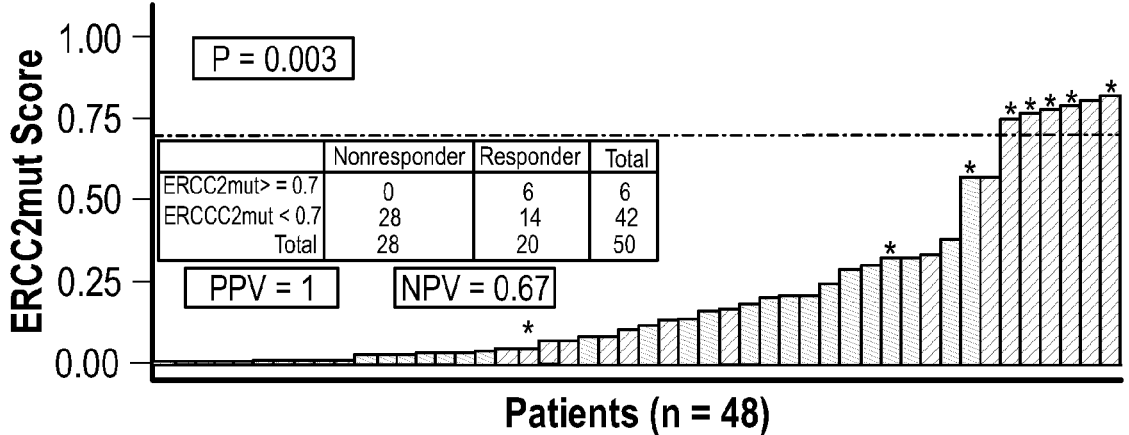
Figures 45A, 45B:
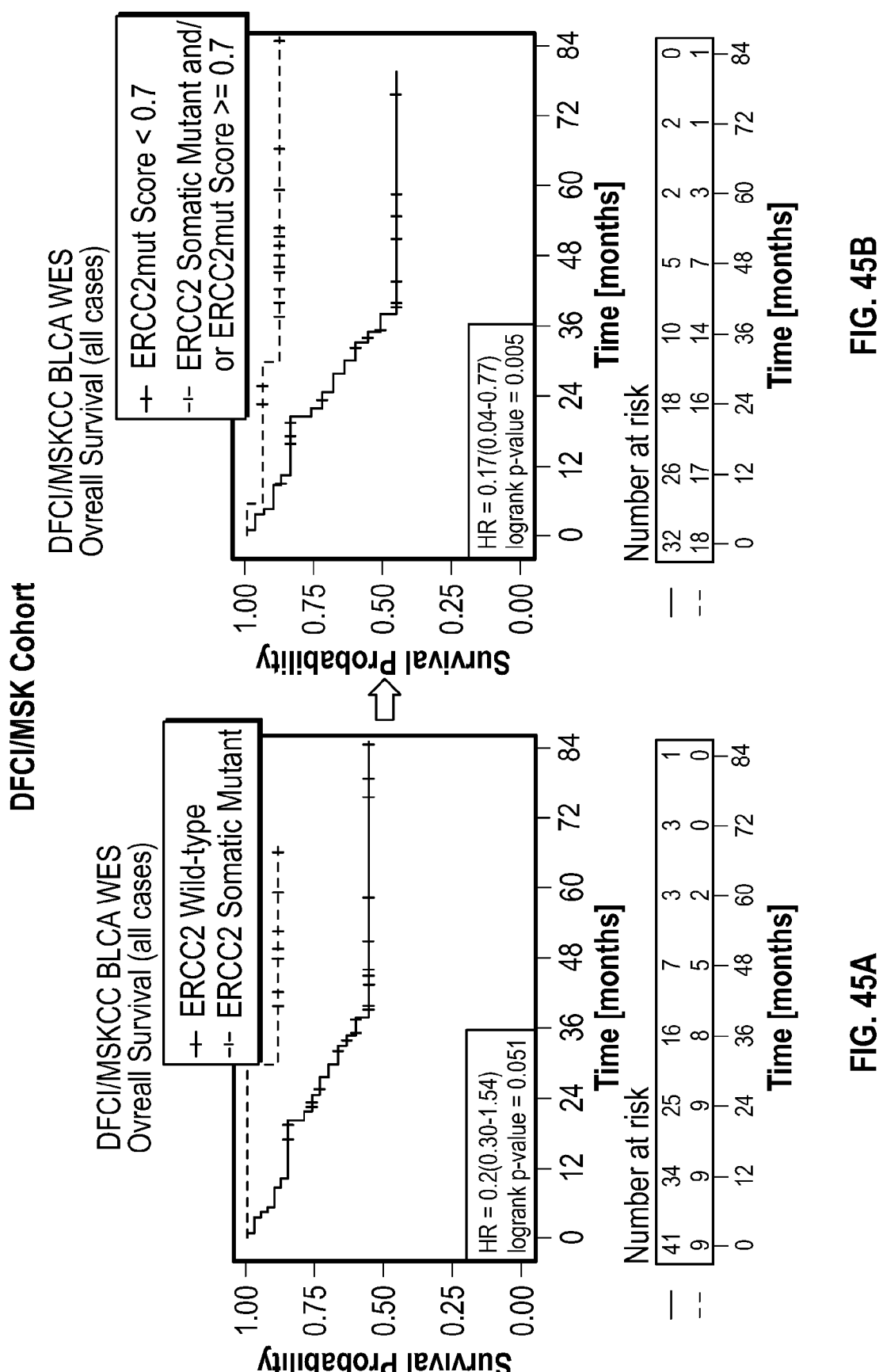
FIGS. 45A-45C show the overall survival of patients in the DFCI/MSKCC cohort.
Figure 45C:
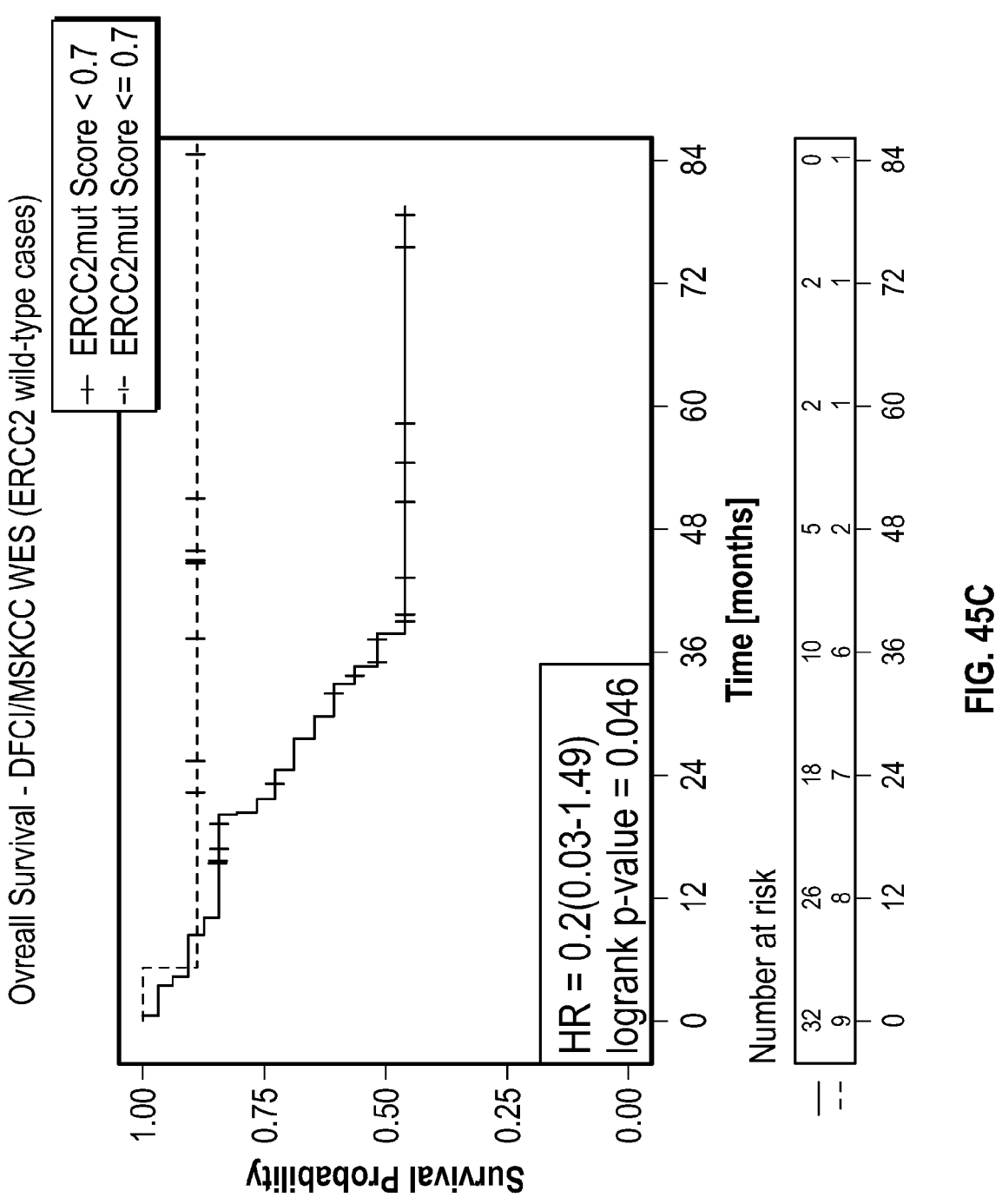
Figures 46A, 46B:
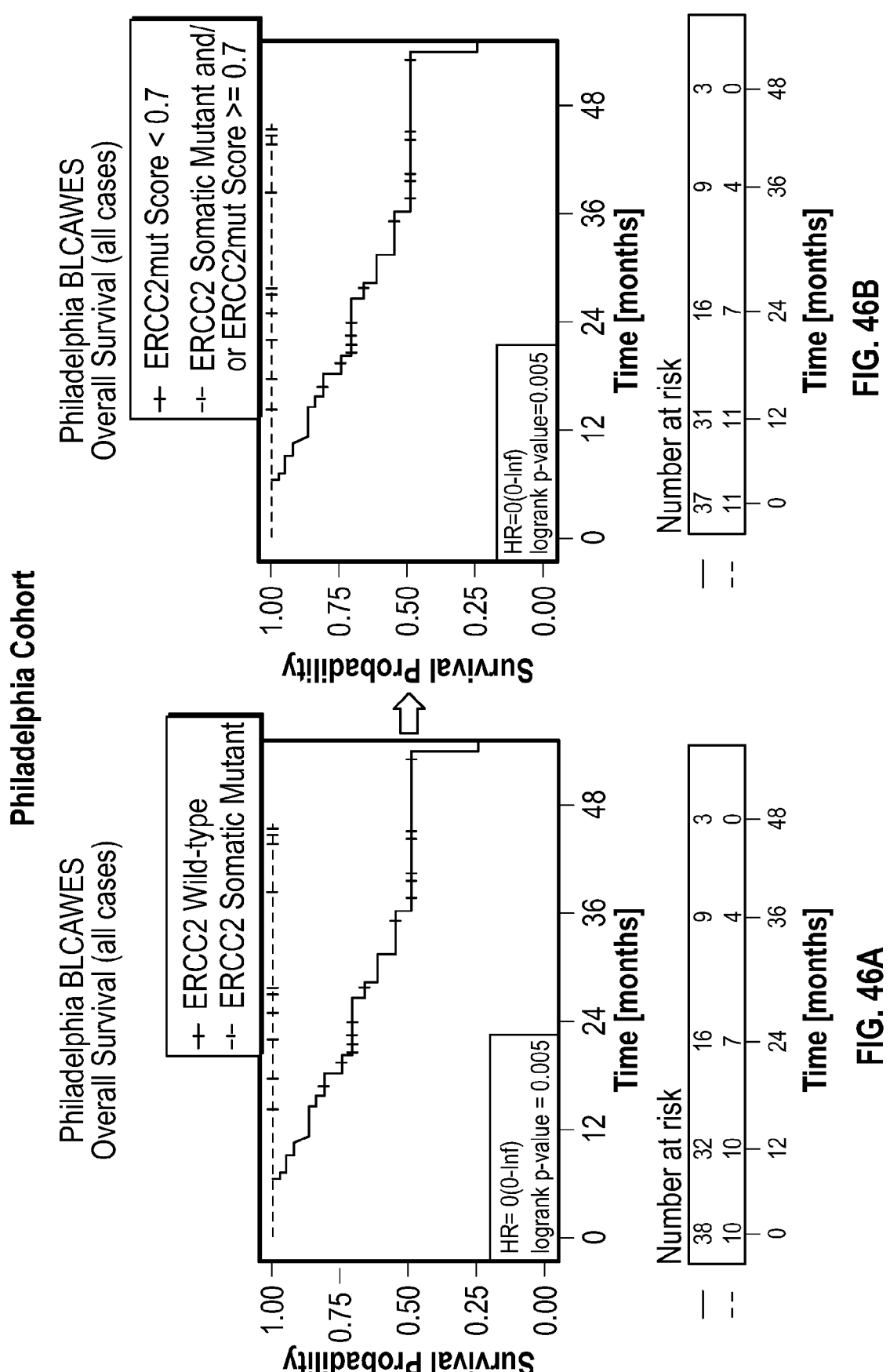
FIGS. 46A-46C show the overall survival of patients in the Philadelphia cohort.
Figure 46C:
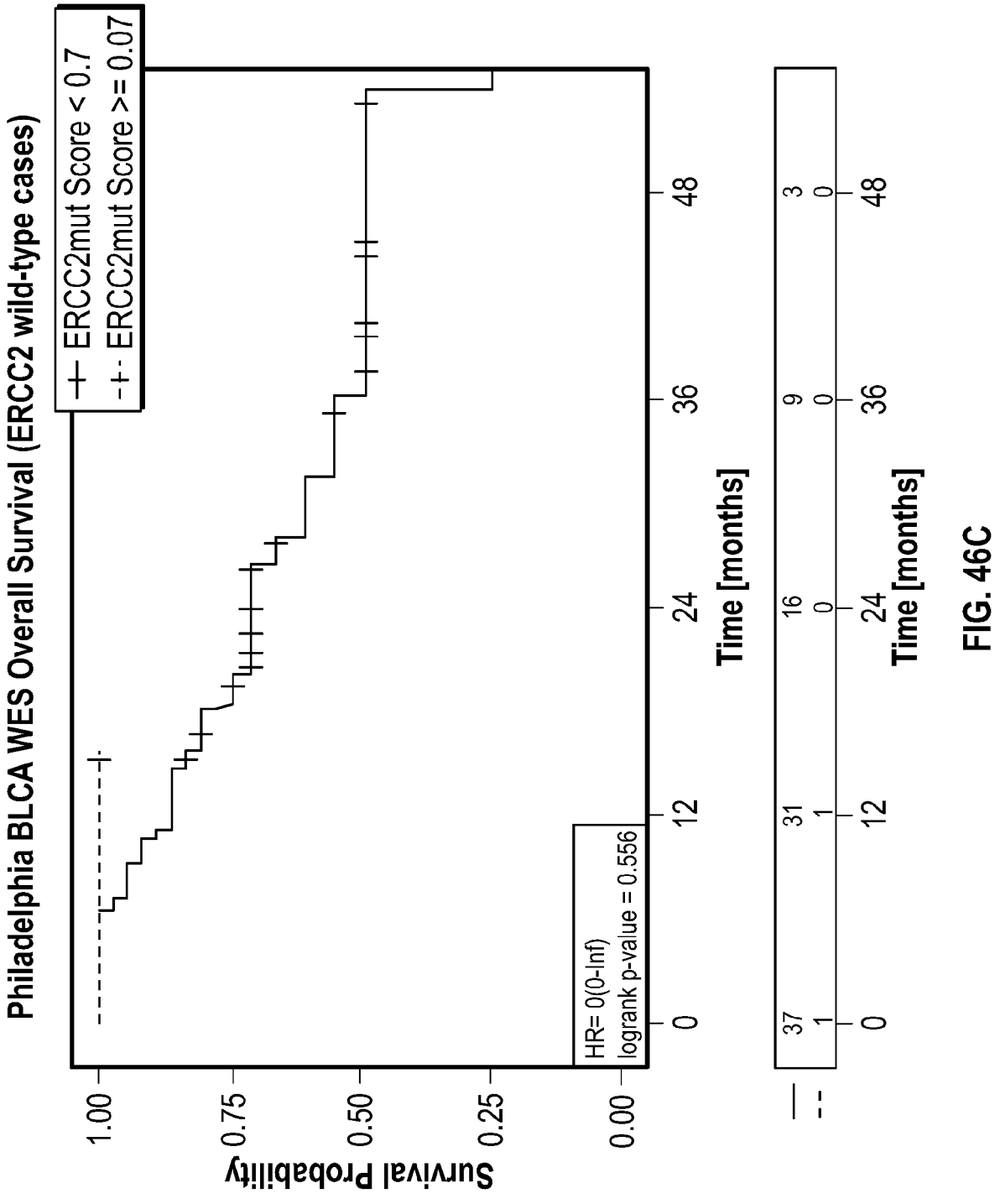

Patients in the DFCI/MSK and Philadelphia cohorts were treated with cisplatin-based chemotherapy followed by radical cystectomy, and cisplatin responders were defined as patients with no residual invasive disease on pathologic examination of the cystectomy specimen. We found that the ERCC2mut signature scores were strongly associated with cisplatin response in both the DFCI/MSK and Philadelphia cohorts (p=2.1×10⁻⁴ and p=0.003, respectively; Fisher's exact test; FIGS. 43A-43B). For example, in the DFCI/MSKCC cohort, 15 of 17 cases (88%) with an ERCC2mut signature score≥0.70 had a complete response versus only 10 of 33 (30%) cases with a score<0.70 (FIG. 43A). In the Philadelphia cohort, all six cases (100%) with an ERCC2mut signature score≥0.70 had a complete response versus only 14 of 42 (33%) cases with score<0.70 (FIG. 43B). In both cohorts, overall survival was significantly longer in patients with a score≥0.70 (FIGS. 45-46).

Figure 43C:
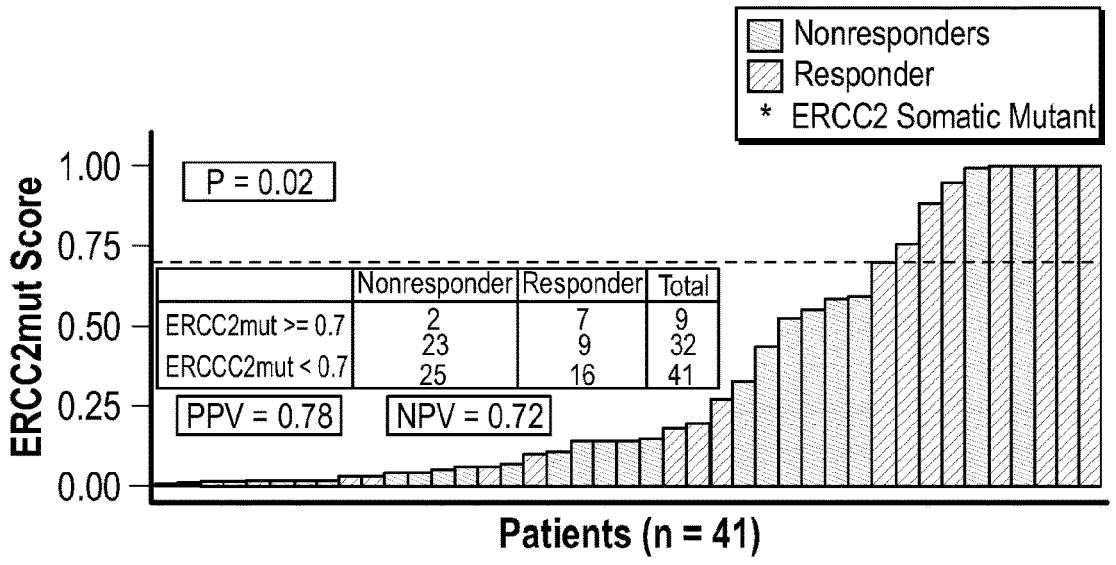
Figure 43D:
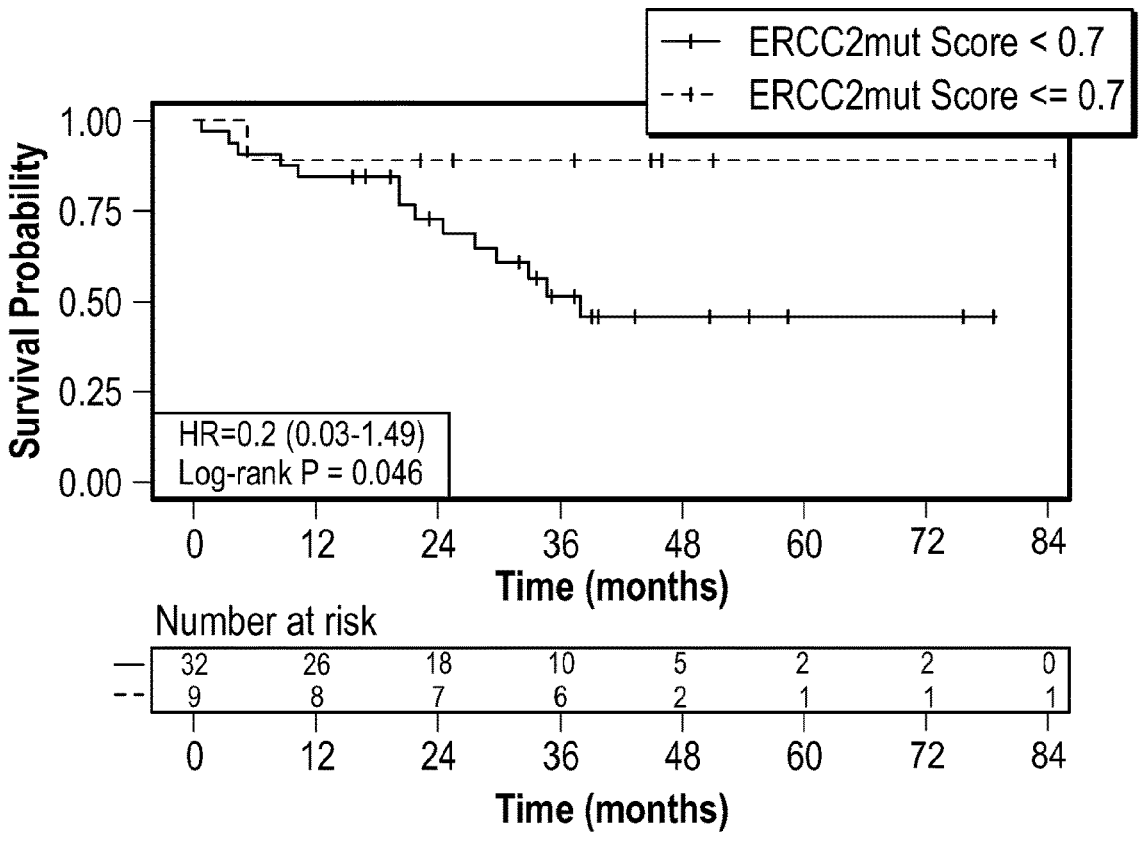
Figure 47:
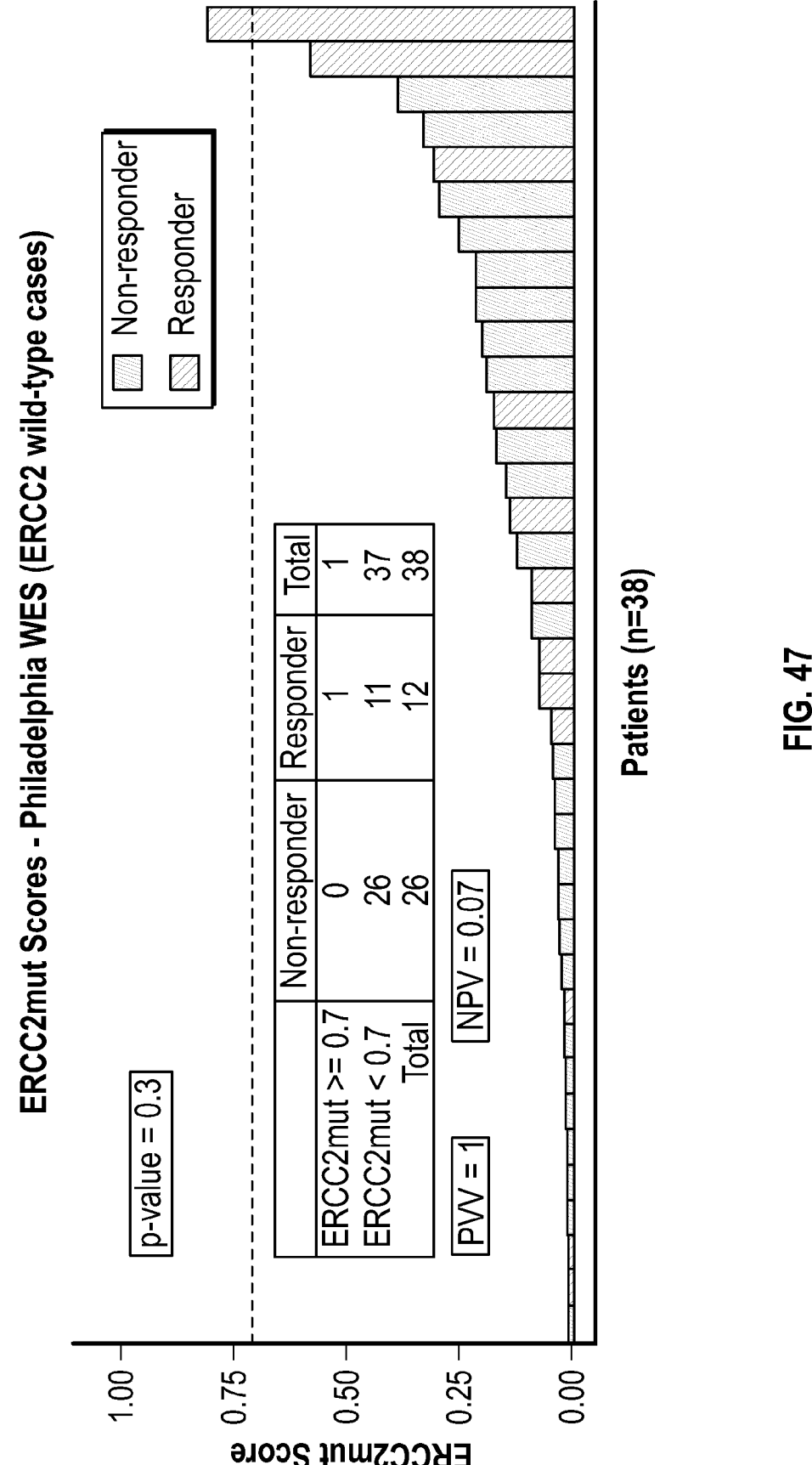
FIG. 47 demonstrates the ERCC2mut scores of WT ERCC2 cases in the FFPE-derived Philadelphia WES cohort.

Next the analysis was restricted to patients without an ERCC2 mutation since this is the subset of patients for whom cisplatin response is currently most difficult to predict. Among the 41 WT ERCC2 cases in the DFCI/MSK cohort, only 16 (39%) were cisplatin responders (FIG. 43C). However, there was a significant enrichment of cisplatin responders among the cases with high ERCC2mut signature scores: seven of the nine (78%) WT ERCC2 patients with a score≥0.70 were responders versus only 9 of the 32 (28%) WT ERCC2 patients with an ERCC2mut score<0.70 (p=0.02). Therefore, WT ERCC2 cases with a high ERCC2mut signature score were nearly three times as likely to have complete response to cisplatin as WT ERCC2 patients with a low score. In addition, WT ERCC2 patients with ERCC2mut score≥0.70 had significantly better survival than WT ERCC2 patients with lower scores (p=0.046; FIG. 43D). ERCC2mut scores were lower in the FFPE-derived Philadelphia cohort than in the other cohorts (which were derived from fresh frozen tissue), and there was only one WT ERCC2 case with a score≥0.70 (FIG. 43B; FIG. 47). Together, these data demonstrate that the composite ERCC2mut signature is associated with cisplatin response, including in bladder tumors that lack an ERCC2 mutation. This result suggests that the ERCC2mut composite signature may reflect tumor NER deficiency conferred by mechanisms beyond ERCC2 mutation and may therefore provide additional predictive power to prioritize patients for NER-targeting agents such as cisplatin or irofulven.

Figure 44A:
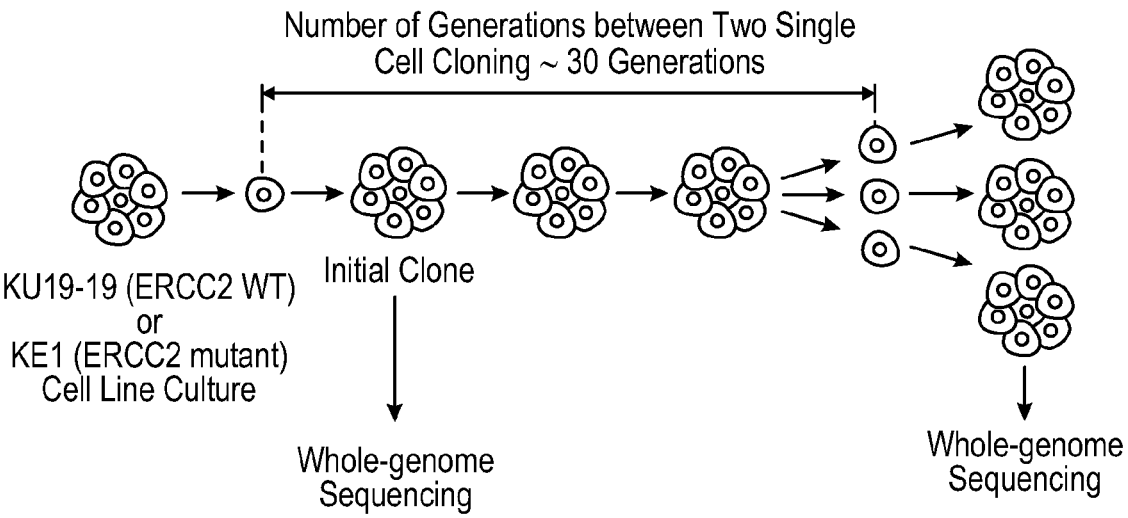
FIGS. 44A-44B show that NER deficiency drives the ERCC2mut composite mutational signature.
Figure 44B:
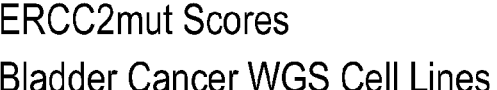
Figure 44B:
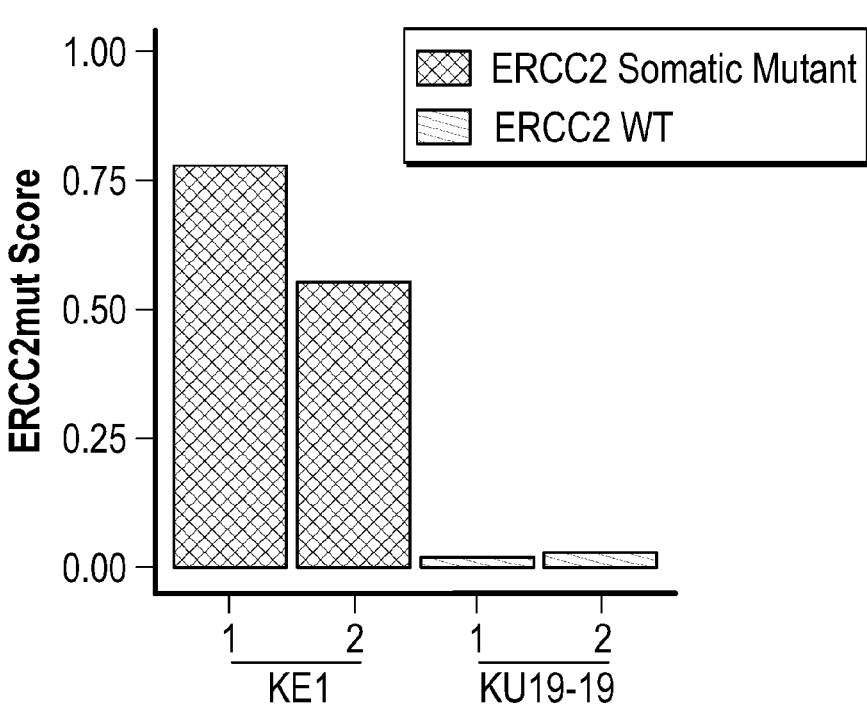
Figure 48:
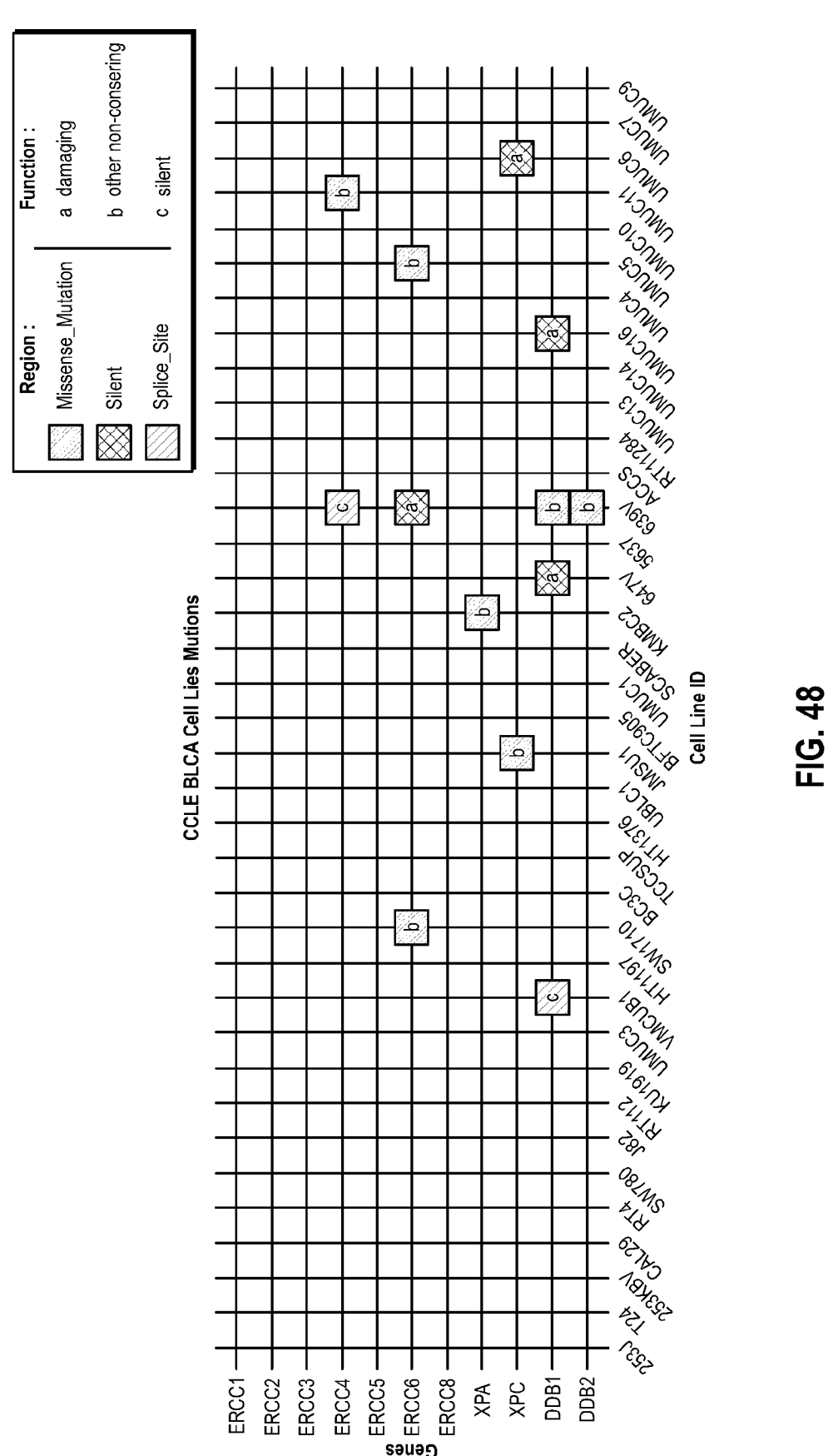
FIG. 48 shows somatic mutations in NER genes in the KU19-19 cell line according to the CCLE database.

Example 5: NER Deficiency Drives the ERCC2Mut Composite Mutational Signature To further investigate the relationship among NER pathway function, sensitivity to NER-directed therapy, and the ERCC2mut composite mutational signature, we tested if ERCC2 inactivation was sufficient to generate the composite mutational signature. KU19-19 is a bladder cancer cell line with no known NER pathway alterations (FIG. 48) while KE1 is an ERCC2-mutated derivative of KU19-19 that is NER deficient and displays increased sensitivity to cisplatin and irofulven (FIG. 5B) (6). For each cell line, separate clonal populations were propagated in parallel for 30 days and single cells were isolated, expanded to ~1×10⁶ cells, and harvested for genomic DNA isolation (FIG. 44A). Whole genome sequencing was performed from clonal 'parental' (P0) populations as well as from two independent 'post-propagation' clonal populations. Mutations were called as previously described (36) and ERCC2mut scores were determined for each sample (Example 2). Among the post-propagation populations, the NER deficient KE1 cell line clones had significantly higher composite mutational signature scores than NER proficient KU19-19 clones (FIG. 44B). These data demonstrate that NER deficiency created by loss of an NER gene is sufficient to induce the composite mutational signature and further supports a direct link among NER deficiency, the composite mutational signature, and sensitivity to cisplatin and irofulven.

Example 6: Mutational Signature Extraction

Somatic single base substitution signatures were extracted with the help of the deconstructSigs R package which determines the linear combination of pre-defined signatures [2] that most accurately reconstructs the mutational profile of a single tumor sample.

The selected signatures, the linear combination of which could lead to the final mutational catalog, were confined to those, that were reported to be present in bladder carcinoma according to the Catalogue of Somatic Mutations in Cancer (available on the world wide web at https://<cancer.sanger-.ac.uk/cosmic/signatures_v2.tt> (COSMIC v2), BLCA: Signature 1, 2, 5, 10, 13). In addition, Signature 3, Signature 4 and Signature 8 were also extracted. Signature 3 is associated with failure of DNA double-strand break repair by homologous recombination [11] and characterized by a broad spectrum of base changes. Signature 4 is associated with exposure to tobacco carcinogens [3] and it is well known that smoking is a strong risk factor for bladder cancer [14]. Elevated levels of Signature 8 mutations were observed in adult stem cells (ASCs) from NER-deficient Ercc1-/Δ mice and in a GG-NER-deficient human organoid culture [30].

Figure 8A:
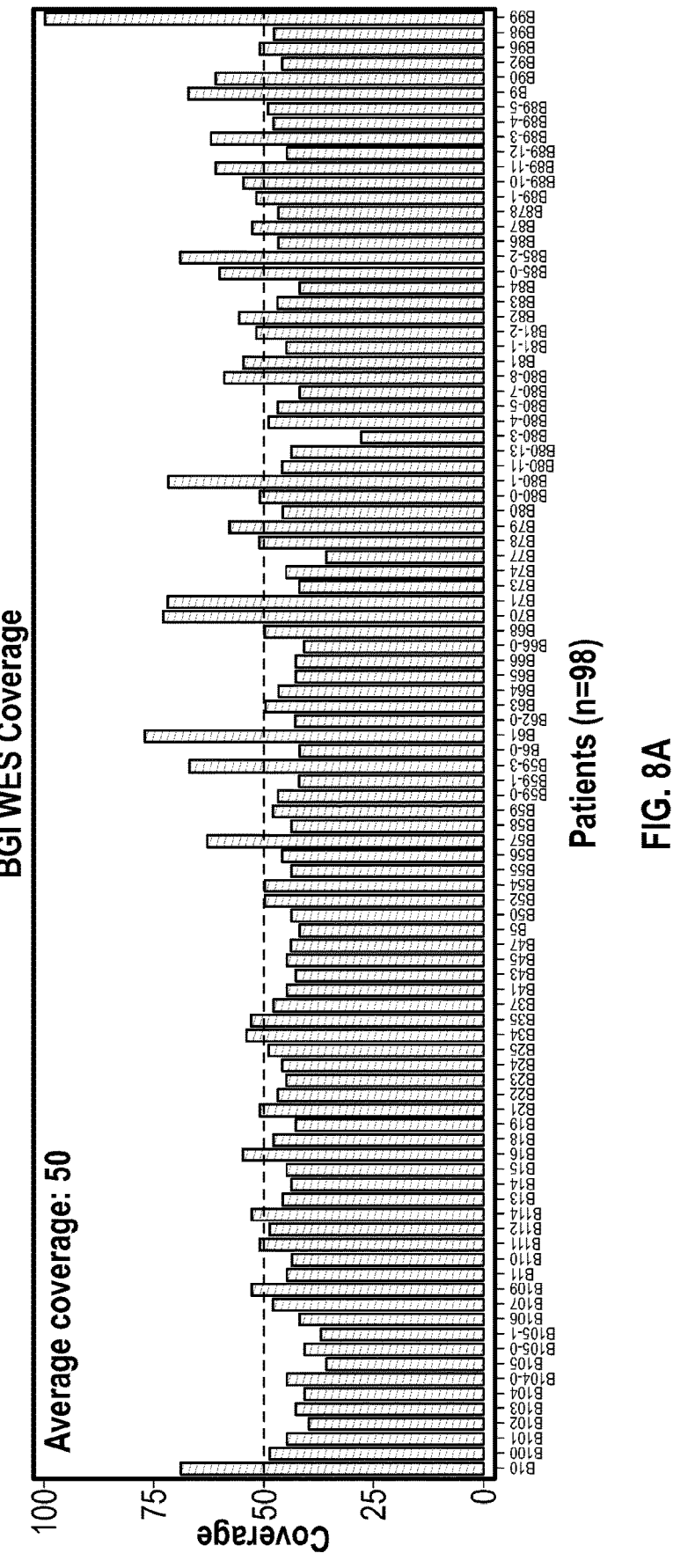
FIGS. 8A-8C show the average coverage of samples in the BGI (FIG. 8A), DFCI/MSKCC (FIG. 8B), and Philadelphia (FIG. 8C) WES cohorts.
Figure 8B:
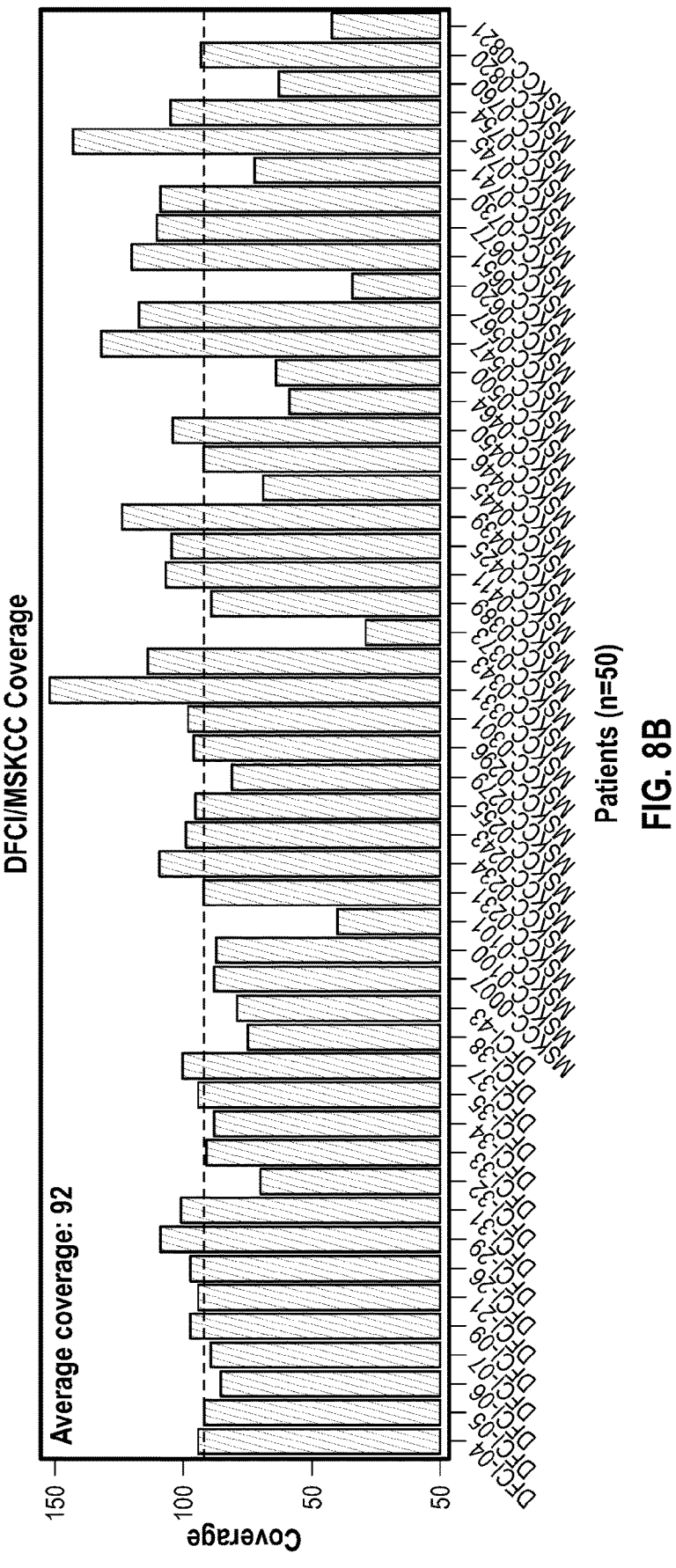
Figure 8C:
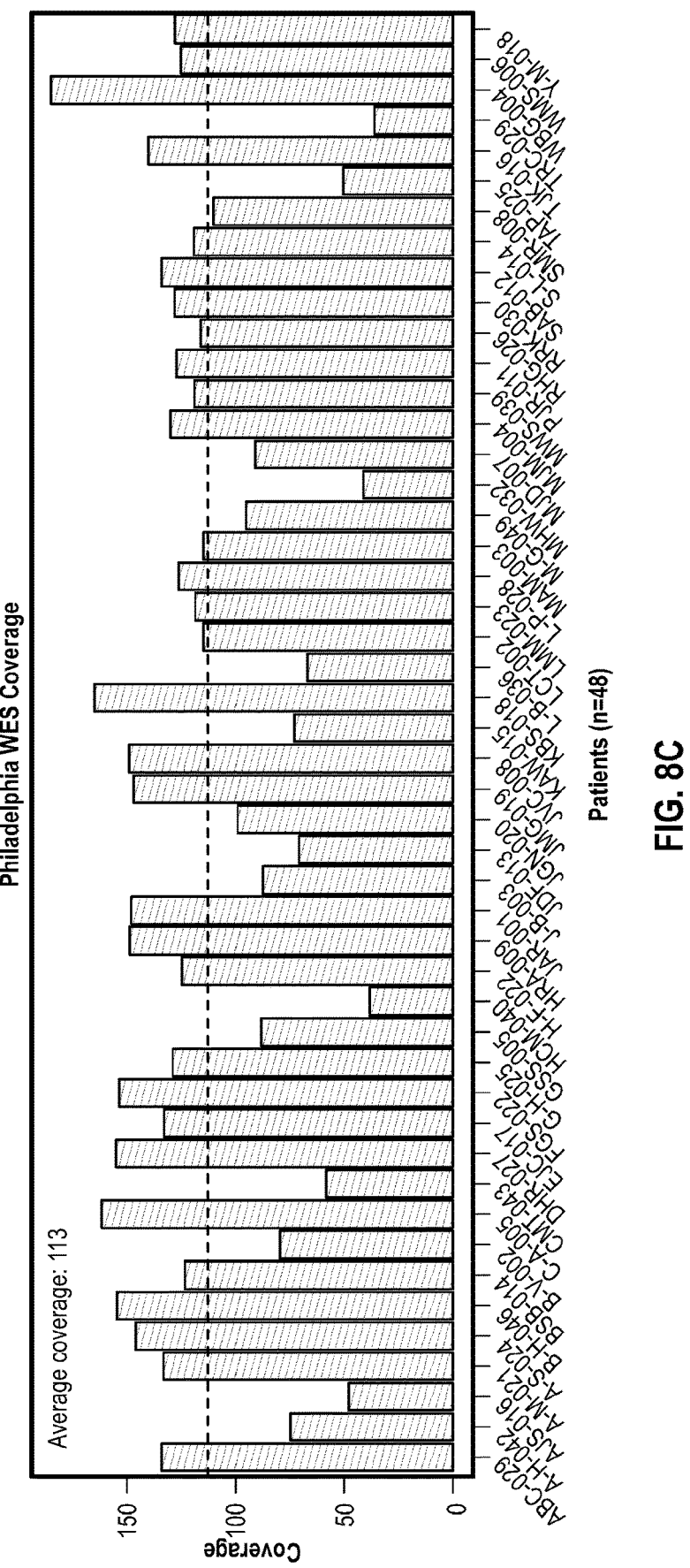

After the evaluation of their signature compositions, the mutational catalogs of the samples were reconstructed, and the cosines of the angles between the 96-dimensional original and reconstructed vectors were calculated (cosine similarity). In the BGI WES cohort, Signature 22 was also extracted, since the addition of it to the initial set of signatures improved the cosine similarity between the original and the reconstructed vectors. Signature 22 has been linked to exposure to aristolochic acid, an ingredient in some food supplements that are most commonly used in Asian countries [23]. However, in this cohort the mean similarity was somewhat lower than in the other WES cohorts (Table 5) probably due to the lower sequencing coverage (FIGS. 8A-8C). In the other cohorts, cosine similarities were high, mean cosine similarity ≥0.92 (Table 5), between the original and the reconstructed mutational profiles.

SBS Signatures COSMIC v3

The most recent version of single base substitution signatures (available on the world wide web at https://<cancer.sanger.ac.uk/cosmic/signatures/SBS/index.tt>, COSMIC v3) [1] was also extracted as described in the previous section. The previously identified matrix of SBS signatures was downloaded using the link below.

Signatures Extracted from Counts of Mutations Observed in Exomes:

On the world wide web at https://<synapse.org/#!Synapse:syn12026190>.

Figure 52:
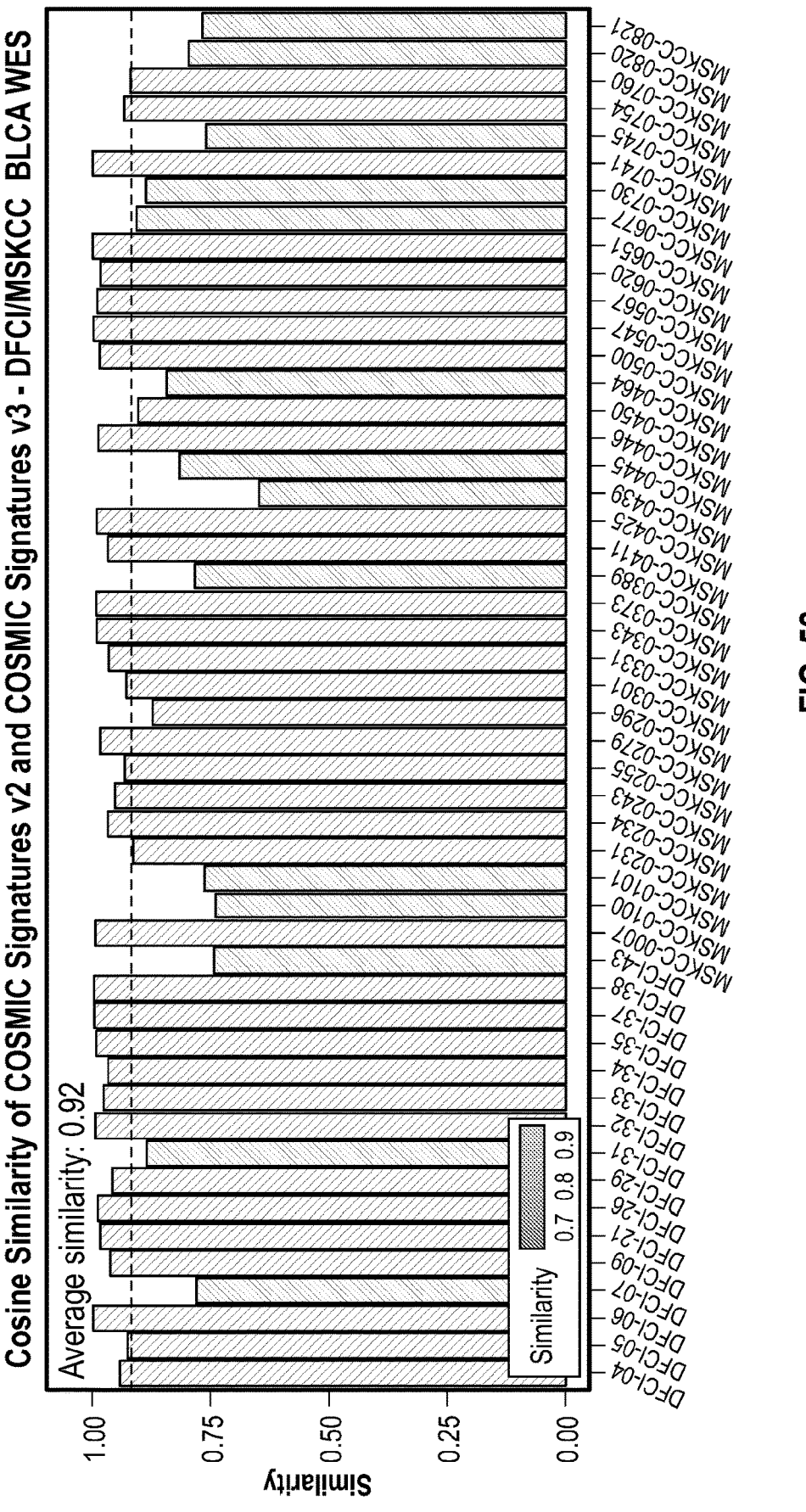
FIG. 52 demonstrates cosine similarity of SBS signature profiles of samples in the DFCI/MSKCC cohort (upper panel) and in the Philadelphia cohort (bottom panel).
Figure 52:
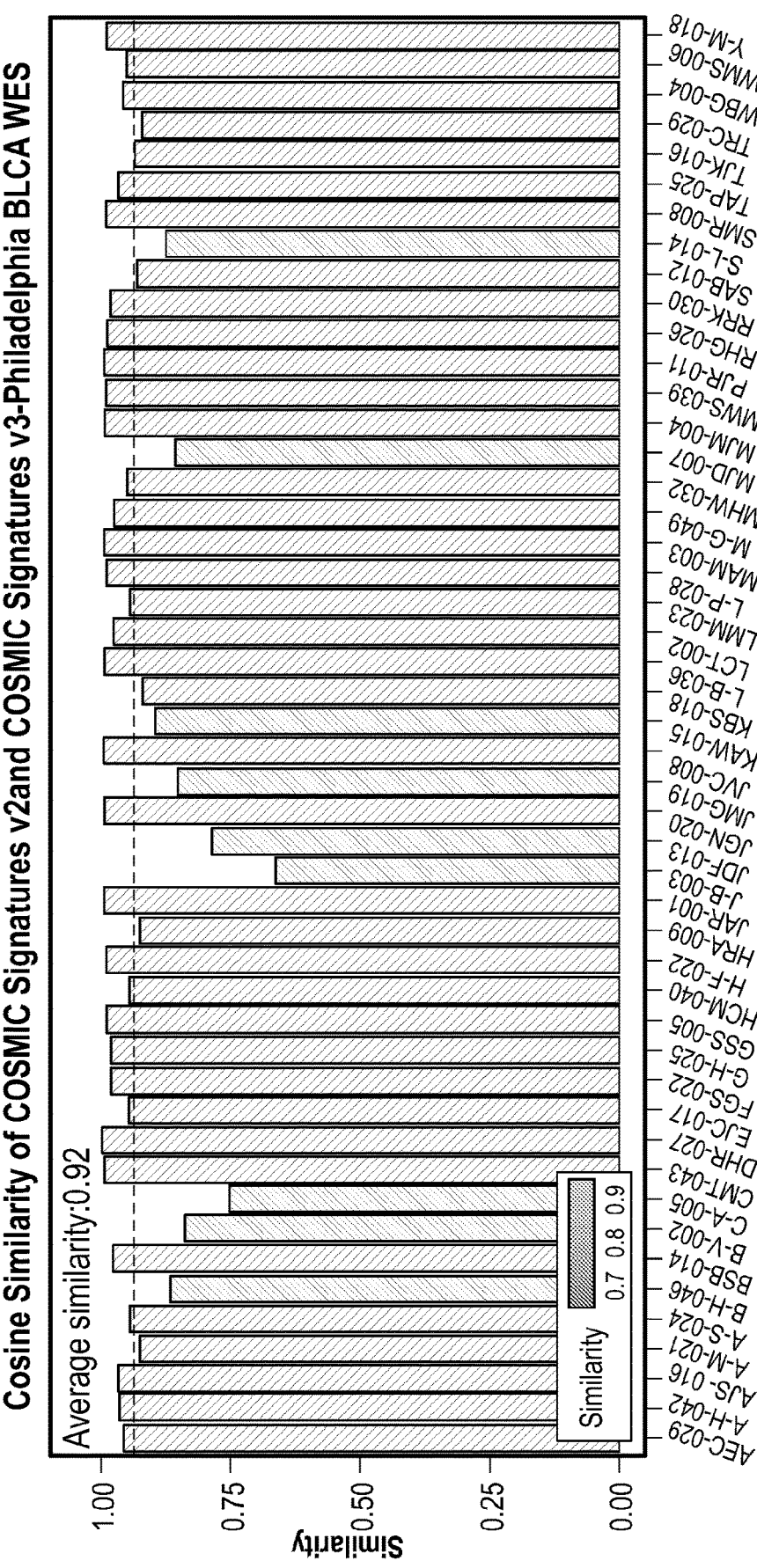
Figure 53:
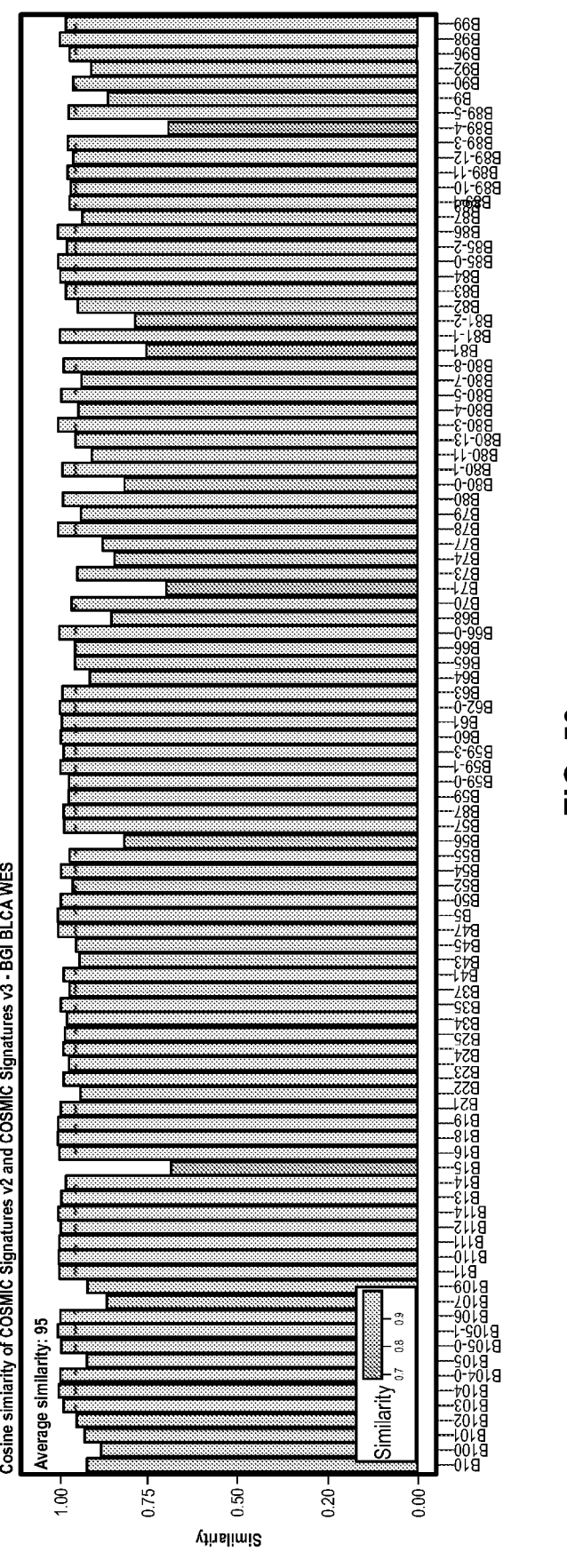
FIG. 53 shows cosine similarity of SBS signature profiles of samples in the BGI cohort (upper panel) and in the TCGA cohort (bottom panel).

Cosine similarity of the SBS signature profiles (COSMIC v2 and COSMIC v3) of each sample was calculated and presented in FIGS. 52-53. The average cosine similarity between the extracted COSMIC v2 and COSMIC v3 signatures in each cohort was above 0.9.

Doublet Base Substitution (DBS) Signatures

Doublet base substitution (DBS) signatures (11) were characterized by Alexandrov et al. [251] using methods based on non-negative matrix factorization (NMF). The identified matrices matrix of indelDBS signatures (P) were downloaded using the following link below.

Separate extraction of DBS signatures from all PCAWG whole genome samples together: available on the world wide web at https://<synapse.org/#!Synapse:syn18497696>;

Separate extraction of ID signatures from all TCGA whole exome samples together: available on the world wide web at https://<synapse.org/#!Synapse:syn12025148>.

Doublet base substitutions in each sample were classified into a 78-dimensional indel DBS catalog (M) with the help of the ICAMS R package [7]. The M and the P matrices were used in a non-negative least-squares problem to estimate the matrix of exposures to mutational processes (E).

$$\min_{E_i} \|PE_i - M_i\|^2, \quad \text{subject to } E_i \geq 0, \quad \text{for all } i = 1, \ldots, N$$

where i is a given sample.

Indel (ID) Signatures

Similar to doublet base substitution signatures, small insertion and deletion (ID) signatures (17) were also characterized [1] and the identified matrix of ID signatures (P) was published.

Separate extraction of ID signatures from all PCAWG whole genome samples together available on the world wide web at synapse.org/#!Synapse:syn12025148;

Insertions and deletions in each sample were classified into an 83-dimensional indel catalog (M) with the help of the ICAMS R package [7]. The M and the P matrices were used in a non-negative least-squares problem to estimate the matrix of exposures to mutational processes (E) (Example 5 equation).

Transcription Strand Asymmetry

Transcription strand bias analysis was carried out using the MutationalPatterns R package, which allows for the easy characterization and visualization of mutational patterns [4]. The transcriptional strand of the mutations within gene bodies can be determined using DNA transcription as the reference frame [16]. Base substitutions located on the same strand as the gene definition are defined as "untranscribed" and on the opposite strand as "transcribed". The ratio of the number of base substitutions on the transcribed and the untranscribed strand was used as the measure of strand asymmetry.

Example 7: CRISPR/Cas9-Mediated Knock-In of ERCC2 P463L Mutation

CRISPR/Cas9 gene editing was used to introduce an inactivating mutation at the endogenous ERCC2 locus (Example 3).

The inventors used a knock-in strategy that involved introduction of a double strand break induced by Cas9/sgRNA in the 3' proximal region of the P463 coding sequence of exon 15 of ERCC2, and a donor template consisting of the L463 mutation flanked by sequences homologous to the ERCC2 genomic sequence, as well as a GFP fluorescent reporter cassette used as template incorporation marker. The crispr.mit.edu website was used to design sgRNA targeting P463 codon harboring exon 15 of ERCC2, and the oligos were subcloned into LentiCRISPRv2 (Addgene®). The donor carrier plasmid, BSSK-S1, was generated from Bluescript (+) vector (Addgene®) by removing the Bam H1 site using Not I/Sma I double digestion, Mung Bean Nuclease blunt-ending, followed by re-ligation. The homology P463L repair template was first PCR amplified from human genomic DNA using KAPA HiFi polymerase (KAPA Biosystems®), with 1148-bp and 1103-bp homologous arms on the left and right sides of the exon 15. The P463L mutation (CCG CTG) and sgRNA-specific PAM alterations were introduced by site-directed mutagenesis using KAPA HiFi polymerase, and the whole sequence was then subcloned into the EcoR I site of BSSK-S1 to generate the donor template plasmid. To facilitate easier identification of P463L knock in clones, a loxP flanked GFP reporter cassette was inserted into the 5' region of the P463 codon using a Bam H1 restriction site, to serve as template incorporation marker. This GFP cassette was PCR amplified from the CDH-CMV-MCS-EF1α-copGFP vector (SBI System Biosciences).

SW1710 cells were electroporated with both LentiCRIS-PRv2 Cas9/sgRNA and P463L donor template plasmids, using Nucleofector II electroporator (Amaxa Biosystems) and Basic Nucleofector Kit for epithelial cells (Cat #VPI-1005, Lonza), according to manufacturers' instructions. Following a 2-day recovery, transfected cell pools were FACS sorted into GFP+ single clones which were subsequently expanded, screened by locus PCR and Sanger sequencing, then validated by RT-PCR and targeted next generation sequencing using the MSK-MPACT assay. The sequences of sgRNA and PCR primers are listed in Table 10.

TABLE 10

The sequences of sgRNA and PCR primers.

| Name | Sequence |
|------|----------|
| P463L targeting sgRNA | GGCAACCTTCACCATGACGC (SEQ ID NO: 7) |
| P463L template amplif-F | GTGACATGGCTGGACTCAGG (SEQ ID NO: 8) |
| P463L template amplif-R | ATCCCGAAGAACACCCCTC (SEQ ID NO: 9) |
| P463L mutagenesis-forward | ACAGACACTGTCCCTGCTGGACATCTACCC (SEQ ID NO: 10) |
| P463L mutagenesis-reverse | GGGTAGATGTCCAGCAGGGACAGTGTCTGT (SEQ ID NO: 11) |
| PAM mutagenesis-forward | TTCACCATGACGCTAGCACGGGTCTGCCTC (SEQ ID NO: 12) |
| PAM mutagenesis-reverse | GAGGCAGACCCGTGCTAGCGTCATGGTGAA (SEQ ID NO: 13) |
| loxP-GFP-loxP-F | TAGGATCCTGGCCAGCCGGCATAACTTCGT ATAATGTATGCTATACGAAGTTATGGATCT GCGATCGCTCCGG (SEQ ID NO: 14) |
| loxP-GFP-loxP-R | TAGGATCCTGGCCAGCCGGCATAACTTCGT ATAGCATACATTATACGAAGTTATAGGCGG GGAGGCGGCCCAAAGG (SEQ ID NO: 15) |
| P463L CRISPR-seq-F1 | AGTCCTGCTGAGATCCCTCC (SEQ ID NO: 16) |
| P463L CRISPR-seq-R1 | AAGGAAGGAGGGCGGCCCCTT (SEQ ID NO: 17) |
| P463L RT-F1 | AGCGTTTCCAGTCTGTCATCA (SEQ ID NO: 18) |
| P463L RT-R1 | GCAATATCCTCCCGGGTCTC (SEQ ID NO: 19) |

Example 8: Statistical Analysis

The TCGA database only contains 23 WGS cases; therefore, we used mutational features extracted from 412 WES samples to train a logistic regression based classifier of ERCC2 mutation status.

From the 412 TCGA BLCA WES samples 17 were excluded from the training (Table 1) set according to the following criteria:

containing fewer than 50 somatic mutations after filtering;

MSI samples identified by Bonneville et al. [6].

The training set consisted of 28 ERCC2 somatic mutant and 367 wild-type samples.

Data Transformation

In order to reduce right skewness of the data and to ensure that the distributions of the features more resemble to Gaussian curves, the input variables $(x_i)$ were log-transformed, according to the following formula:

$$x_i' = \ln(x_i + 1) \tag{9.1}$$

The constant shift was added to keep the $x_i=0$ values away from $-\infty$.

The log-transformed data were standardized (each feature had a mean of 0 and a standard deviation of 1) to make the variables comparable to one another.

$$x_i'' = \frac{x_i' - \mathbb{E}[x_i']}{\sigma[x_i']} \tag{9.2}$$

Training Set

The training set was highly imbalanced, only 7.1% of the samples were categorized as ERCC2 mutants. In order to overcome this problem a well-known oversampling technique, SMOTE (Synthetic Minority Oversampling Technique) [8], implemented in the DMwR R package, was used. In SMOTE, the minority class is oversampled by taking each minority class sample and introducing synthetic examples along the line segments joining any or all of the k minority class nearest neighbors. This approach effectively forces the decision region of the minority class to become more general. The size of the final data set used in the model-building process was shown in Table 11.

TABLE 11

The number of samples in both classes in the training set before and after oversampling.

| Status | Train | Train$_{SMOTE}$ |
|--------|-------|-----------------|
| ERCC2 mutant | 28 | 280 |
| ERCC2 wild-type | 367 | 365 |
| Total | 395 | 645 |

ERCC2mut Classifier

A lasso logistic regression model was used to identify the mutational features that could distinguish between the two categories of patient samples. Inputs of the algorithm were as follows SBS signatures (COSMIC v2),
DBS signatures,
ID signatures,
the ratio of the number of a certain types of base substitutions on the transcribed and untranscribed strand: transcription strand bias C>A, C>G, C>T, T>A, T>C, T>G.

A computer implementation of this model is available in the glmnet R package. Optimal coefficients were obtained by minimizing the objective function $$\min_{\beta \in \mathbb{R}^p} \frac{1}{N} \|y - X\beta\|_2^2 + \lambda \|\beta\|_1$$

where y is the response variable, X is the matrix of features, $\beta$ is the vector of weights, $\lambda$ is the regularization parameter and N is the number of samples. The 11 norm of the coefficient vector, $\|\beta\|_1$, is added to the loss function as a penalty term. As a consequence of this constraint, the lasso restricts the coefficients of the model by pulling them toward zero; some of the variables become exactly zero. The inventors constrained all $\beta$ weights to be positive because they supposedly reflect the biological presence of mutational processes that are, in this case, associated with ERCC2 mutation status. The regularization parameter, $\lambda$, was chosen by a k-fold (default k=10) cross validation with the cv.glmnet( ) function.

Figure 41:
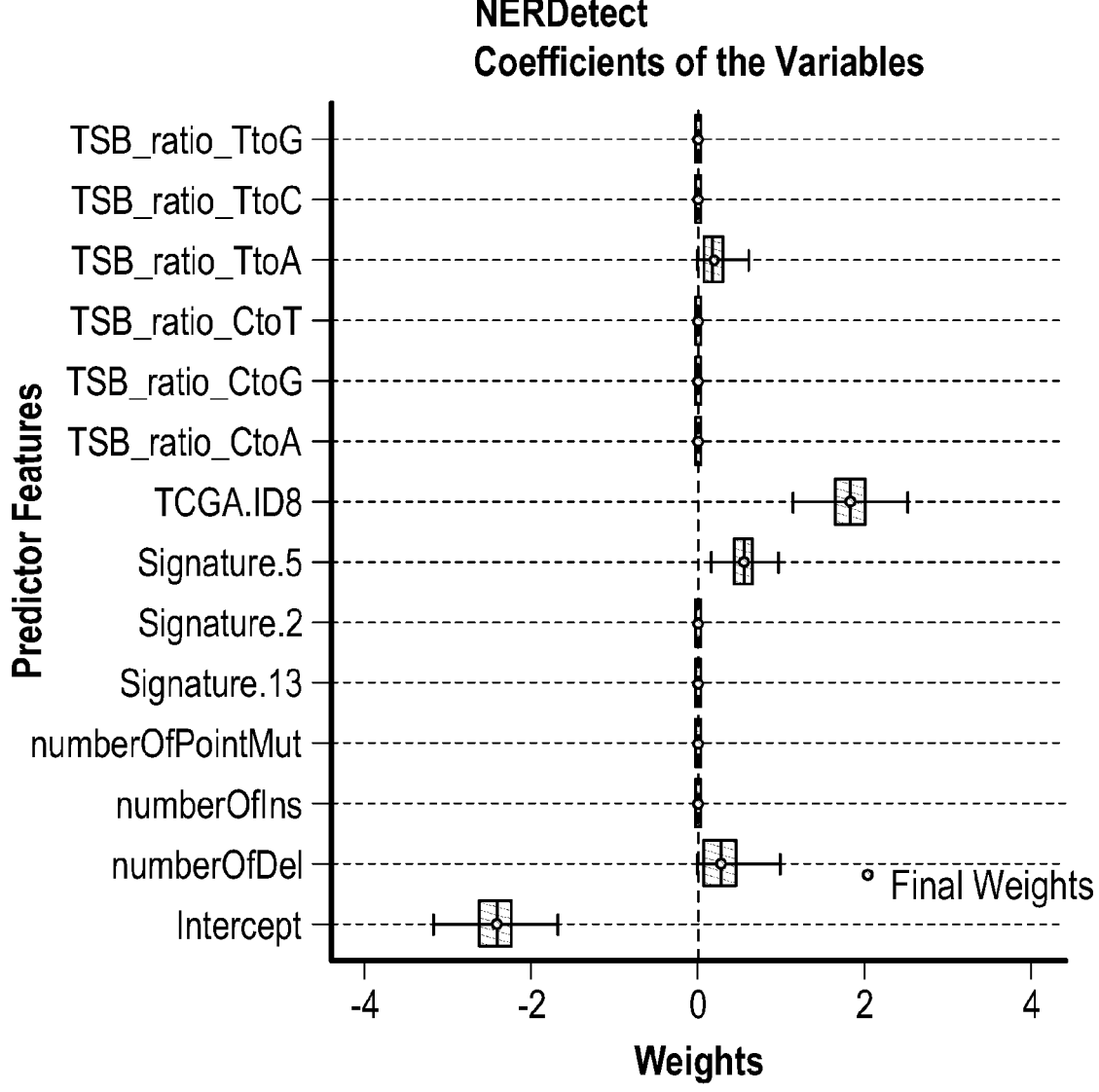
FIG. 41 shows the distribution of the weights of the variables from bootstrapping. The midline represents the median, the two edges of the box represent the lower and upper interquartile range (Q3+1.5·IQR) and the lower whisker=max(min(x), Q1-1.5·IQR). The dots indicate the final weights used in the NERDetect model. The mean and standard error of the coefficients are summarized in the table.

A repeated k-fold cross-validation strategy was used to assess the robustness and generalizability of the learned weights using the caretR package. The training data set was split into k=10 folds each containing N/$\kappa$ observations. Each fold was held out and treated as a test set exactly once while the remaining K−1 folds were used for model parameter selection. In order to reduce stochasticity caused by the random selection of the folds, the cross-validation procedure was repeated 10 times. The optimal model was selected to be the candidate model with the largest accuracy and cross-validation error within one standard error of the minimal cross-validation error. Using these selected tuning parameters, the final model was then refit to the original training set and the coefficients of the genomic features were identified for a $\lambda$ value of 0.0172 ($\lambda_{mean}$=0.0183; $\lambda_{sd}$=0.0030). Finally, the stability of each coefficient was assessed using a bootstrapping method. We chose 2 of the samples from the training set randomly without repeat, the previously described training process was repeated 1000 times, the resulting distributions of the weights of the variables were stored and the standard errors of the coefficients were calculated (FIG. 41 and Table 12).

TABLE 12

The distributions of the weights of the
variables from bootstrapping.

| Model parameter | Boot Coef | Final Coef |
|---|---|---|
| ID8 | 1.4307 ± 0.0056 | 1.463 |
| Signature.2 | 0.5222 ± 0.0056 | 0.6159 |
| Signature.5 | 0.4412 ± 0.0042 | 0.4817 |
| ID10 | 0.4438 ± 0.0026 | 0.4609 |
| TSB_ratio_TtoA | 0.3208 ± 0.0030 | 0.3798 |
| TSB_ratio_CtoG | 0.2117 ± 0.0034 | 0.2855 |
| DBS4 | 0.1982 ± 0.0022 | 0.2381 |
| ID2 | 0.1240 ± 0.0025 | 0.1688 |
| TSB_ratio_TtoG | 0.1019 ± 0.0032 | 0.1272 |
| Intercept | −2.0578 ± 0.0089 | −2.208 |

On the boxplot the midline represents the median, the two edges of the box represent the lower and upper interquartile range (IQR), the upper whisker=min(max(x), Q3+1.5×IQR) and the lower whisker=max(min(x), Q1−1.5×IQR). The red dots indicate the final weights used in the ERCC2mut model. The means and standard errors of the non-zero coefficients are summarized in the table.

The same process described here was repeated using the most recent version of the COSMIC v3 mutational signatures to build a second model (ERCC2mut COSMIC v3). The final weights of the ERCC2mut COSMIC v3 model and additional information are described in Table 13.

TABLE 13

The distributions of the weights of the
variables from bootstrapping.

| Model parameter | Final Model Coefficients |
|---|---|
| Intercept | −2.528 |
| SBS2 | 0.5 |
| SBS5 | 0.2796 |
| DBS4 | 0.4731 |
| DBS7 | 0.08877 |
| ID8 | 1.831 |
| ID10 | 0.1669 |
| TSB_ratio_CtoG | 0.06575 |
| TSB_ratio_TtoG | 0.2633 |

Model Validation

Figure 42A:
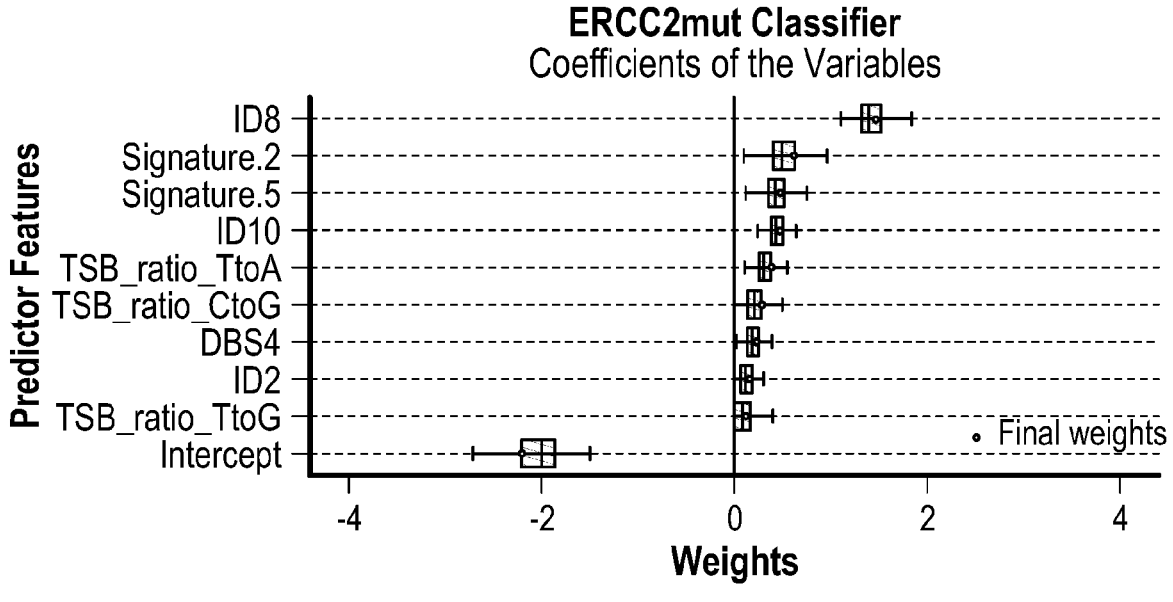
FIGS. 42A-42E show the development of the ERCC2mut logistic regression-based classifier and validation of the association between ERCC2mut scores and ERCC2 mutation status in three independent bladder cancer cohorts. Samples with an ERCC2 mutation are shown in dark gray and ERCC2 WT samples are shown in gray.
Figure 42B:
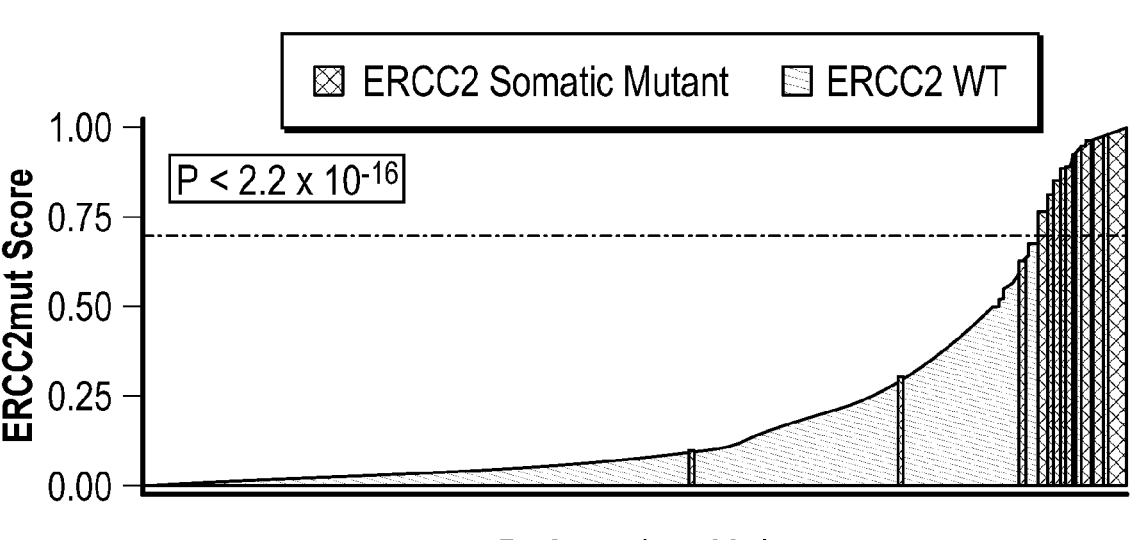
Figure 42C:
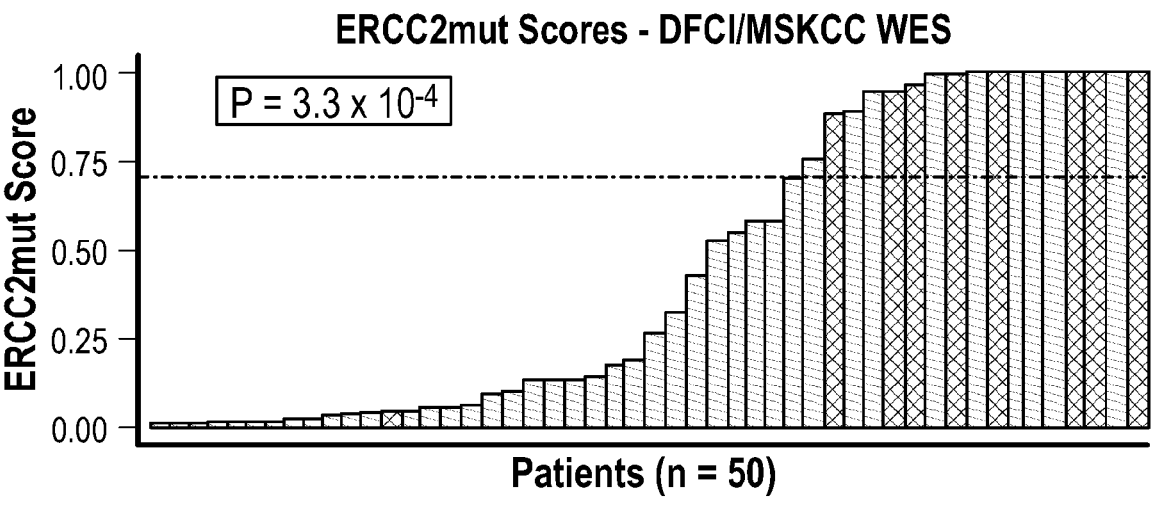
Figure 42D:
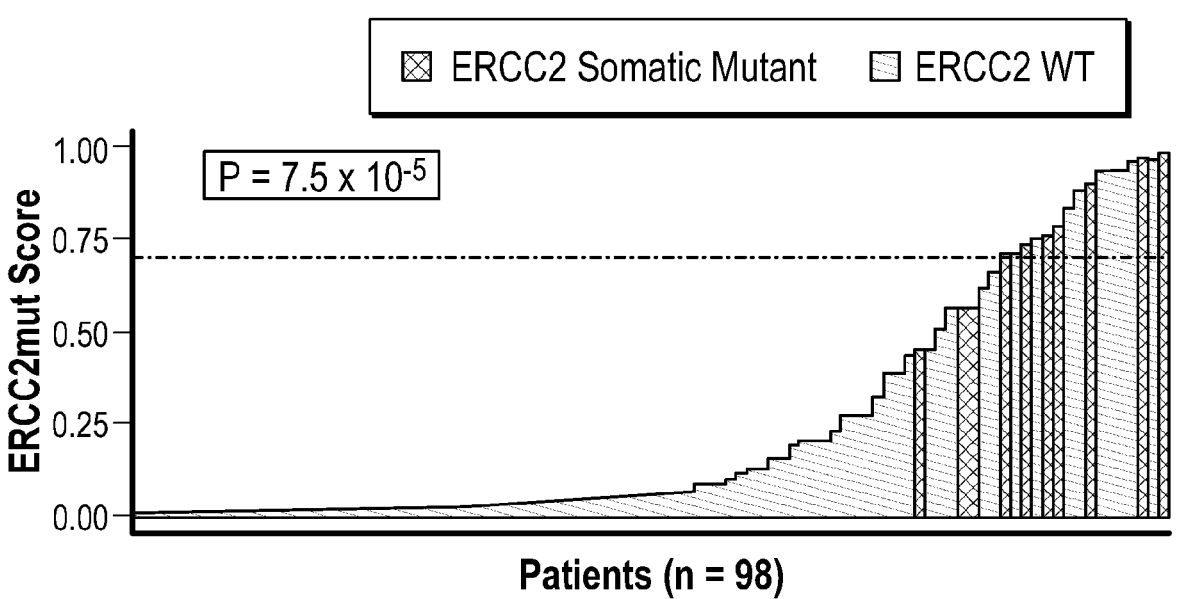
Figure 42E:
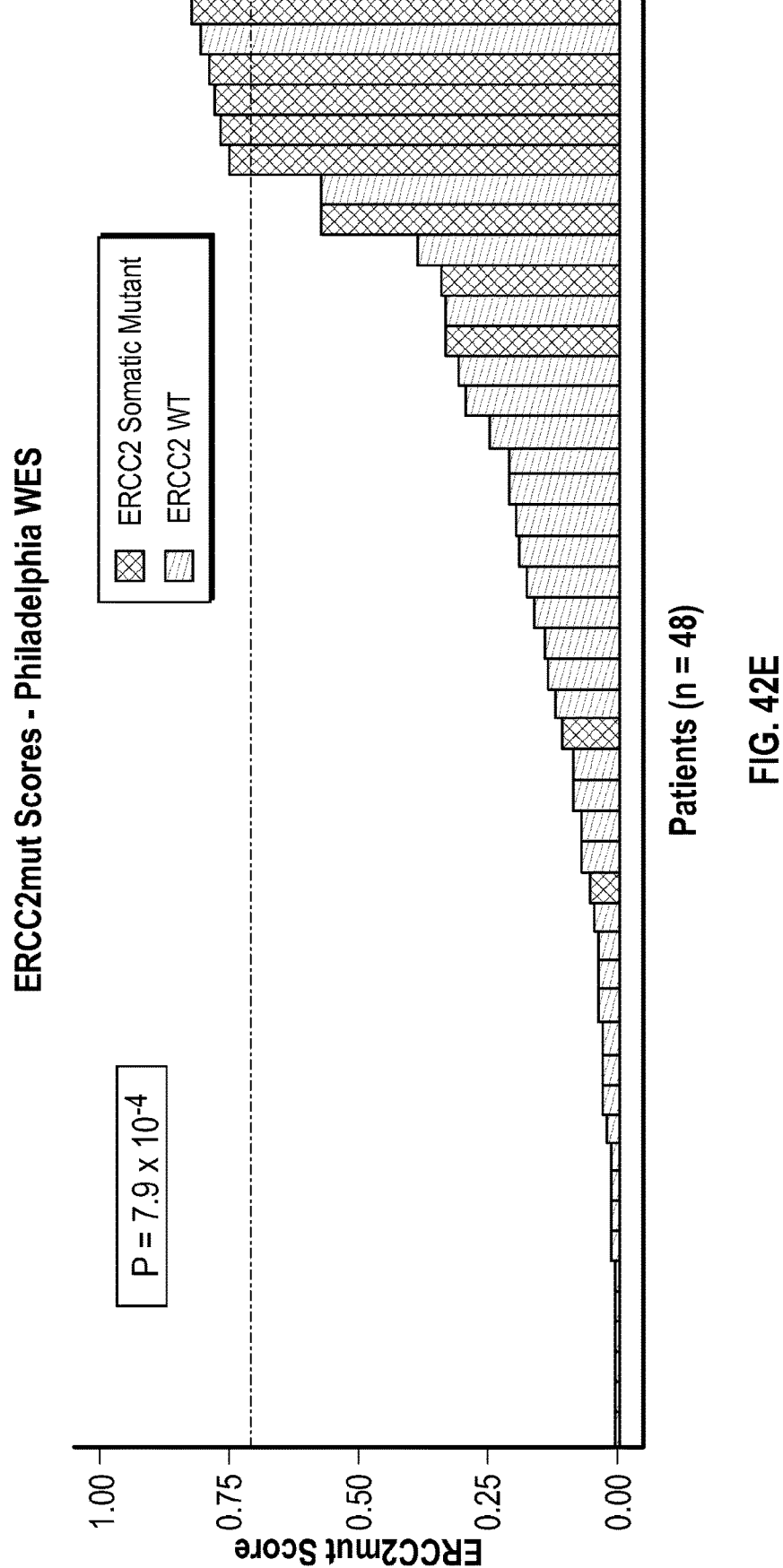
Figure 49:
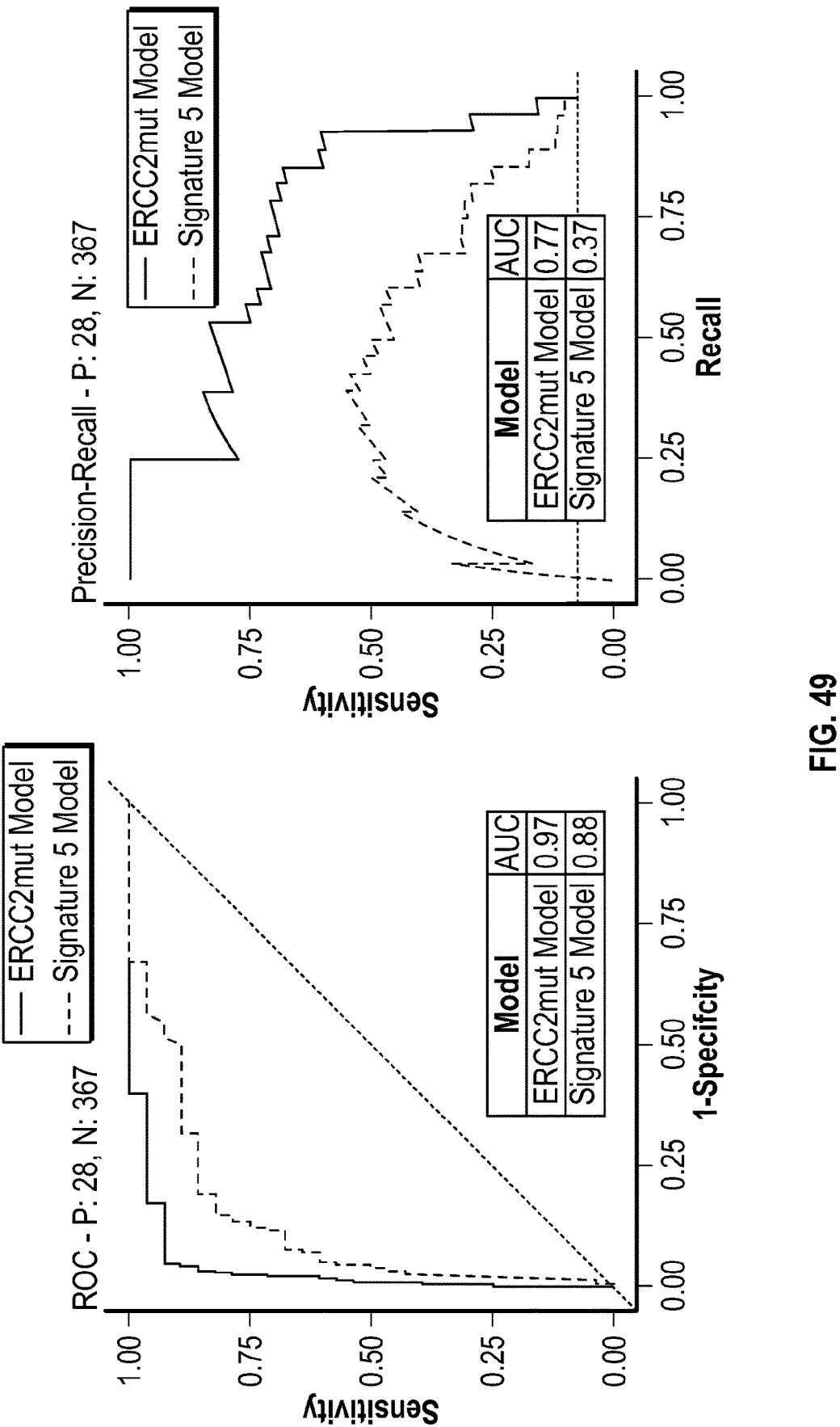
FIG. 49 shows a comparison of the performance of ERCC2mut and Signature 5 (COSMIC v2) alone as a single predictor in the TCGA WES training set.
Figures 50A, 50B, 50C:
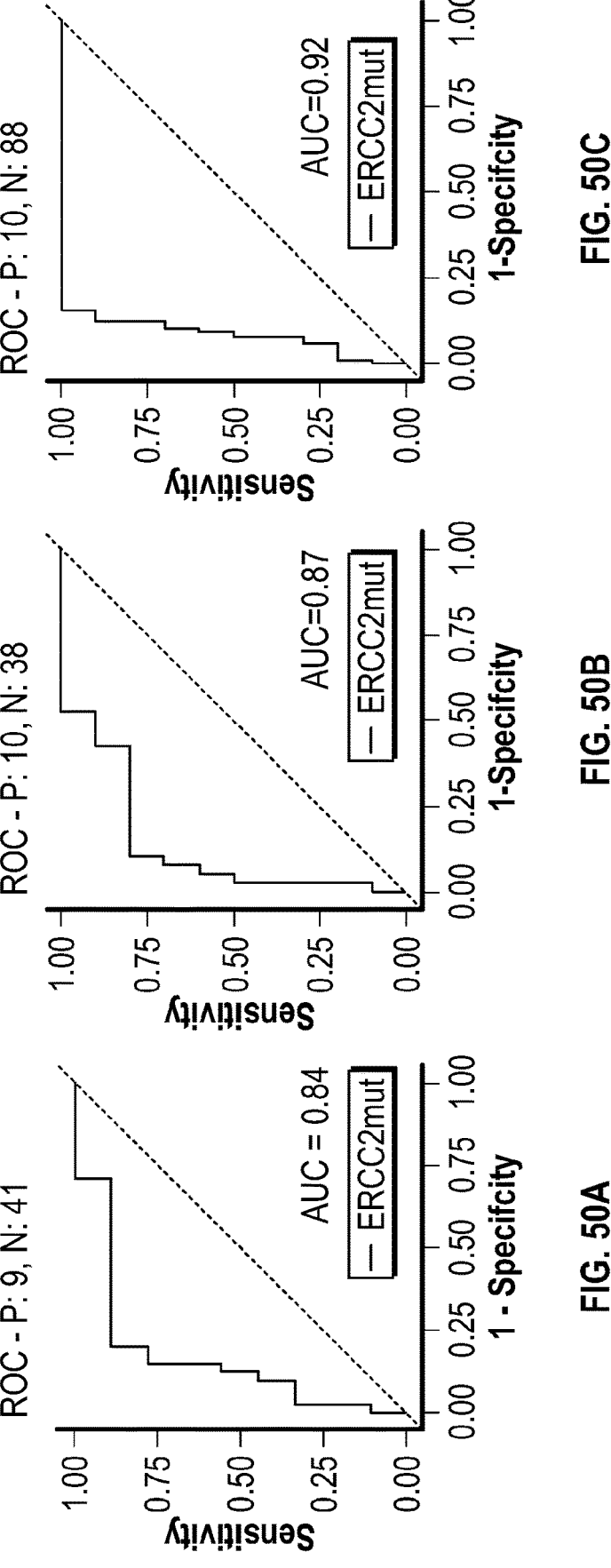
FIGS. 50A-50C show ROC curves demonstrating the performance of ERCC2mut in the DFCI/MSKCC (FIG. 50A) Philadelphia (FIG. 50B) and BGI validation cohorts (FIG. 50C).
Figure 57:
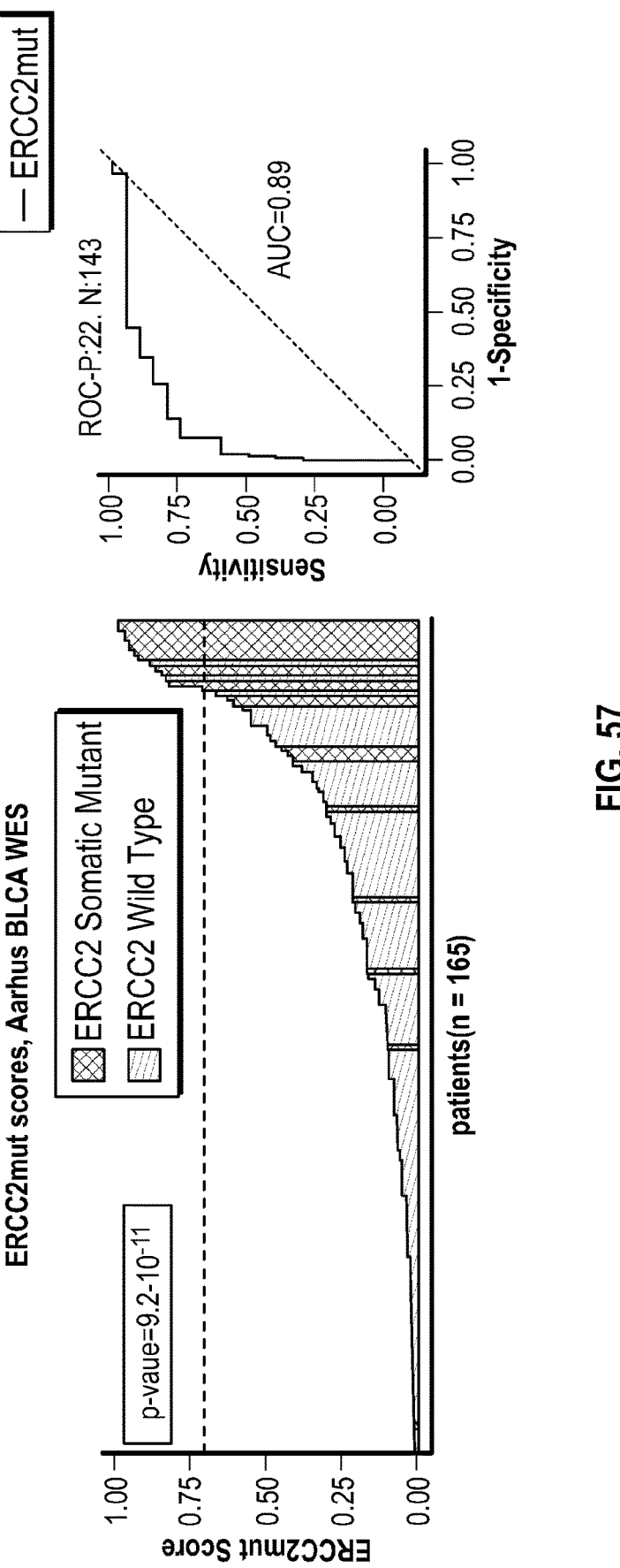
FIG. 57 shows ERCC2mut scores in the Aarhus BLCA WES cohort.

The composite ERCC2mut signature scores of the samples in the whole training set were shown in FIG. 42B demonstrating that high ERCC2mut scores ($\geq$0.7) were strongly associated with ERCC2 deficiency (p<2.2×10$^{-16}$). To validate the ability of the ERCC2mut classifier to discriminate between ERCC2 mutant and WT bladder tumors, four additional independent bladder cancer cohorts [27][20][15][15] were analyzed. In each validation cohort, ERCC2 mutant cases were significantly associated with a ERCC2mut score$\geq$0.7 (p=3.3×10$^{-4}$ in the DFCI/MSKCC, p=7.5×10$^{-5}$ in the BGI, p=7.9×10$^{-4}$ in the Philadelphia cohorts, FIGS. 42C-42E, and p=9.2×10$^{-11}$ in the Aarhus cohort (FIG. 57, See also Taber et al., "Molecular correlates of cisplatin-based chemotherapy response in muscle invasive bladder cancer by integrated multi-omics analysis." Nat Commun. 2020 Sep. 25; 11(1):4858, the contents of which is incorporated herein by reference in its entirety). ROC with the AUC values were shown for the training set (FIG. 49) and the validation sets (FIG. 50A-50C). In addition, ERCC2mut scores$\geq$0.7 were strongly associated with cisplatin response in both the DFCI/MSKCC and Philadelphia cohorts (p=2.1×10$^{-4}$ and p=0.003, FIG. 43B-43C). Importantly, there was a significant enrichment of cisplatin responders among the ERCC2 wild-type cases with high ERCC2mut scores in the DFCI/MSKCC cohort (p=0.02, FIG. 43C). In the FFPE-derived Philadelphia cohort, ERCC2mut scores were lower than in the other cohorts (which were derived from fresh frozen tissue), and there was only one WT ERCC2 case with a score$\geq$0.7 (FIG. 47). P-values were calculated by the Fisher's exact test.

Optimal Cutoff

Figure 51:
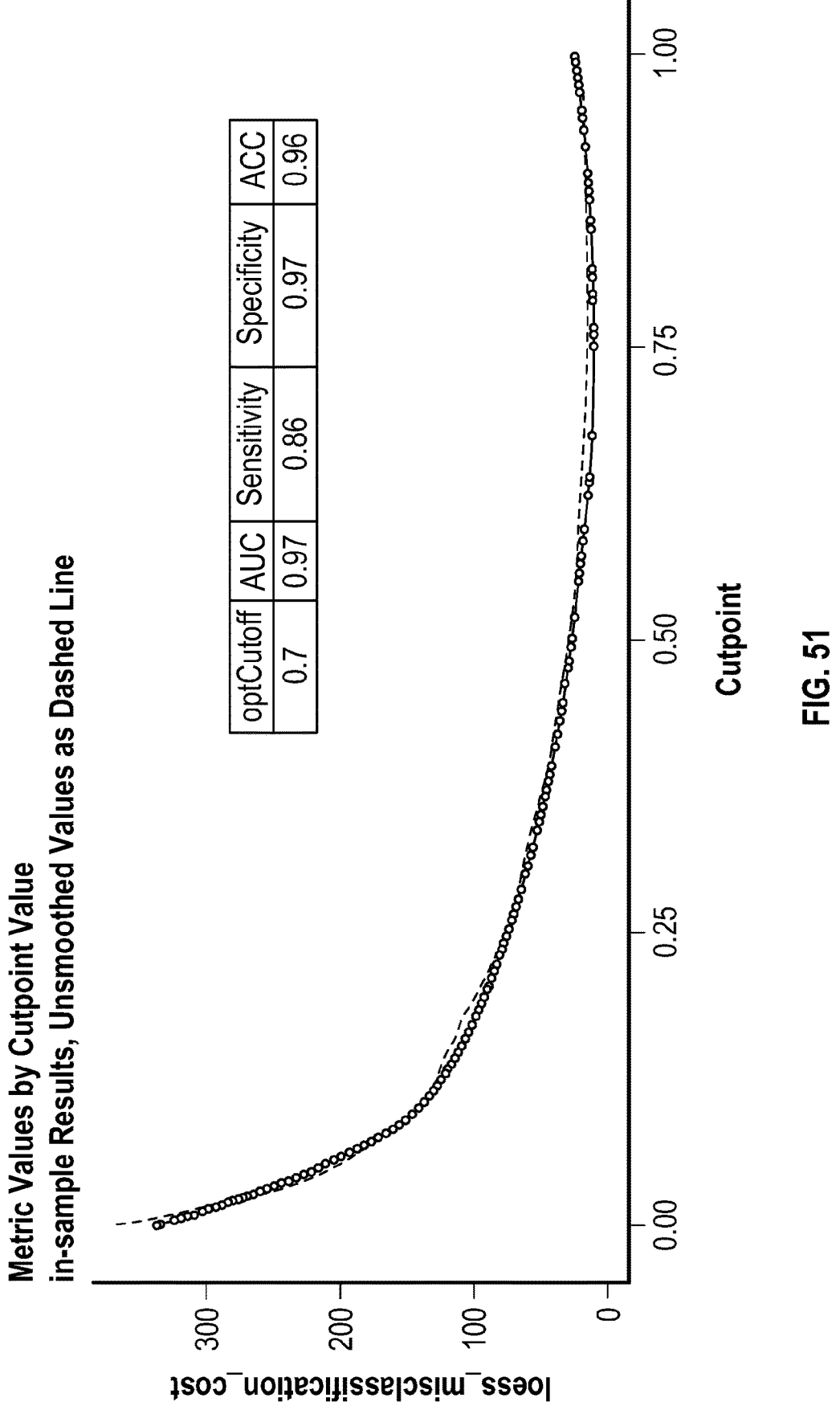
FIG. 51 shows the optimal cut-off value of 0.7 defined on the TCGA BLCA WES training set.

The optimal cut-off value was defined on the TCGA BLCA WES training set busing the cutpointr R package. The minimization of misclassification cost of ERCC2 mutation status after a loess smoothing [33] with equal weights of FP and FN errors yielded the 0.7 optimal cutoff (FIG. 51).

69

References List 1: Corresponding to Examples 1-2

1. Lord, C. J. & Ashworth, A. PARP inhibitors: Synthetic lethality in the clinic. Science 355, 1152-1158 (2017).
2. Konstantinopoulos, P. A. & Matulonis, U. A. PARP Inhibitors in Ovarian Cancer: A Trailblazing and Transformative Journey. Clin. Cancer Res. 24, 4062-4065 (2018).
3. Marteijn, J. A., Lans, H., Vermeulen, W. & Hoeijmakers, J. H. J. Understanding nucleotide excision repair and its roles in cancer and ageing. Nat. Rev. Mol. Cell Biol. 15, 465-481 (2014).
4. Cancer Genome Atlas Research Network. Comprehensive molecular characterization of urothelial bladder carcinoma. Nature 507, 315-322 (2014).
5. Van Allen, E. M. et al. Somatic ERCC2 mutations correlate with cisplatin sensitivity in muscle-invasive urothelial carcinoma. Cancer Discov 4, 1140-1153 (2014).
6. Li, Q. et al. ERCC2 Helicase Domain Mutations Confer Nucleotide Excision Repair Deficiency and Drive Cisplatin Sensitivity in Muscle-Invasive Bladder Cancer. Clin. Cancer Res. (2018). doi:10.1158/1078-0432.CCR-18-1001
7. Grivas, P. DNA Damage Response Gene Alterations in Urothelial Cancer: Ready for Practice? Clin. Cancer Res. 25, 907-909 (2019).
8. Vijai, J. et al. A Recurrent ERCC3 Truncating Mutation Confers Moderate Risk for Breast Cancer. Cancer Discov 6, 1267-1275 (2016).
9. Alexandrov, L. B. et al. Signatures of mutational processes in human cancer. Nature 500, 415-421 (2013).
10. Kim, J. et al. Somatic ERCC2 mutations are associated with a distinct genomic signature in urothelial tumors. Nat. Genet. 48, 600-606 (2016).
11. Moore, K. N. et al. Niraparib monotherapy for late-line treatment of ovarian cancer (QUADRA): a multicentre, open-label, single-arm, phase 2 trial. The Lancet Oncology 20, 636-648 (2019).
12. Zhao, E. Y. et al. Homologous Recombination Deficiency and Platinum-Based Therapy Outcomes in Advanced Breast Cancer. Clin. Cancer Res. 23, 7521-7530 (2017).
13. Davies, H. et al. HRDetect is a predictor of BRCA1 and BRCA2 deficiency based on mutational signatures. Nat. Med. 23, 517-525 (2017).
14. Jaspers, N. G. J. et al. Anti-tumor compounds illudin S and Irofulven induce DNA lesions ignored by global repair and exclusively processed by transcription- and replication-coupled repair pathways. DNA Repair (Amst.) 1, 1027-1038 (2002).
15. Koeppel, F. et al. Irofulven cytotoxicity depends on transcription-coupled nucleotide excision repair and is correlated with XPG expression in solid tumor cells. Clin. Cancer Res. 10, 5604-5613 (2004).
16. Seiden, M. V. et al. A phase II study of irofulven in women with recurrent and heavily pretreated ovarian cancer. Gynecol. Oncol. 101, 55-61 (2006).
17. Schilder, R. J. et al. A phase 2 evaluation of irofulven as second-line treatment of recurrent or persistent intermediately platinum-sensitive ovarian or primary peritoneal cancer: a Gynecologic Oncology Group trial. Int. J. Gynecol. Cancer 20, 1137-1141 (2010).
18. DePristo, M. A. et al. A framework for variation discovery and genotyping using next-generation DNA sequencing data. Nat. Genet. 43, 491-498 (2011).

19. Favero, F. et al. Sequenza: allele-specific copy number and mutation profiles from tumor sequencing data. Ann. Oncol. 26, 64-70 (2015).
20. Li, Q. & Wang, K. InterVar: Clinical Interpretation of Genetic Variants by the 2015 ACMG-AMP Guidelines. Am. J. Hum. Genet. 100, 267-280 (2017).
21. Rosenthal, R., McGranahan, N., Herrero, J., Taylor, B. S. & Swanton, C. DeconstructSigs: delineating mutational processes in single tumors distinguishes DNA repair deficiencies and patterns of carcinoma evolution. Genome Biol. 17, 31 (2016).
22. Nik-Zainal, S. et al. Landscape of somatic mutations in 560 breast cancer whole-genome sequences. Nature 534, 47-54 (2016).
23. Boot, A. et al. In-depth characterization of the cisplatin mutational signature in human cell lines and in esophageal and liver tumors. Genome Res. 28, 654-665 (2018).
24. Alexandrov, L. B., Kim, J., Haradhvala, N.J. et al. The repertoire of mutational signatures in human cancer. Nature 578, 94-101 (2020).
25. Blokzijl, F., Janssen, R., van Boxtel, R. & Cuppen, E. MutationalPatterns:
comprehensive genome-wide analysis of mutational processes. Genome Med 10, 33-11 (2018).
26. Haradhvala, N. J. et al. Mutational Strand Asymmetries in Cancer Genomes Reveal Mechanisms of DNA Damage and Repair. Cell 164, 538-549 (2016).
27. Sassa, A., Kamoshita, N., Kanemaru, Y., Honma, M. & Yasui, M. Xeroderma Pigmentosum Group A Suppresses Mutagenesis Caused by Clustered Oxidative DNA Adducts in the Human Genome. PLoS ONE 10, e0142218 (2015).
28. Rajkumar-Calkins, A. S. et al. Functional profiling of nucleotide Excision repair in breast cancer. DNA Repair (Amst.) 82, 102697 (2019).
29. Pipek, O. et al. Fast and accurate mutation detection in whole genome sequences of multiple isogenic samples with IsoMut. BMC Bioinformatics 18, 73 (2017).
30. Liu, D. et al. Clinical Validation of Chemotherapy Response Biomarker ERCC2 in Muscle-Invasive Urothelial Bladder Carcinoma. JAMA Oncol 2, 1094-1096 (2016).
31. Guo, G. et al. Whole-genome and whole-exome sequencing of bladder cancer identifies frequent alterations in genes involved in sister chromatid cohesion and segregation. Nat. Genet. 45, 1459-1463 (2013).
32. Rajkumar-Calkins, A. S. et al. Functional Profiling of Nucleotide Excision Repair in Breast. DNA Repair (Amst.)
33. Norquist, B. et al. Secondary somatic mutations restoring BRCA1/2 predict chemotherapy resistance in hereditary ovarian carcinomas. J. Clin. Oncol. 29, 3008-3015 (2011).
34. Xu, G. et al. REV7 counteracts DNA double-strand break resection and affects PARP inhibition. Nature 521, 541-544 (2015).
35. Staaf, J. et al. Whole-genome sequencing of triple-negative breast cancers in a population-based clinical study. Nat. Med. 456, 53 (2019).
36. Alexandrov, L. B. et al. Clock-like mutational processes in human somatic cells. Nat. Genet. 47, 1402-1407 (2015).
37. Sargent, R. G. et al. Recombination-dependent deletion formation in mammalian cells deficient in the nucleotide excision repair gene ERCC1. Proc. Natl. Acad. Sci. U.S.A. 94, 13122-13127 (1997).

38. Pasero, P. & Vindigni, A. Nucleases Acting at Stalled Forks: How to Reboot the Replication Program with a Few Shortcuts. Annu. Rev. Genet. 51, 477-499 (2017).

39. Lieber, M. R. The mechanism of double-strand DNA break repair by the nonhomologous DNA end-joining pathway. Annu. Rev. Biochem. 79, 181-211 (2010).

40. Jager, M. et al. Deficiency of nucleotide excision repair is associated with mutational signature observed in cancer. Genome Res. 29, 1067-1077 (2019).

41. Galsky, M. D. et al. Treatment of patients with metastatic urothelial cancer 'unfit' for Cisplatin-based chemotherapy. J. Clin. Oncol. 29, 2432-2438 (2011).

42. Ceccaldi, R. et al. A unique subset of epithelial ovarian cancers with platinum sensitivity and PARP inhibitor resistance. Cancer Res 75, 628-634 (2015).

Reference List 2: Corresponding to Examples 3-5

1. Lord C J, Ashworth A. PARP inhibitors: Synthetic lethality in the clinic. Science. 2017; 355:1152-8.
2. Konstantinopoulos P A, Matulonis U A. PARP Inhibitors in Ovarian Cancer: A Trailblazing and Transformative Journey. Clin Cancer Res. 2018; 24:4062-5.
3. Marteijn J A, Lans H, Vermeulen W, Hoeijmakers J H J. Understanding nucleotide excision repair and its roles in cancer and ageing. Nat Rev Mol Cell Biol. 2014; 15:465-81.
4. Robertson A G, Kim J, Al-Ahmadie H, Bellmunt J, Guo G, Cherniack A D, et al. Comprehensive Molecular Characterization of Muscle-Invasive Bladder Cancer. Cell. 2017; 171:540-556.e25.
5. Van Allen E M, Mouw K W, Kim P, Iyer G, Wagle N, Al-Ahmadie H, et al. Somatic ERCC2 mutations correlate with cisplatin sensitivity in muscle-invasive urothelial carcinoma. Cancer Discov. 2014; 4:1140-53.
6. Li Q, Damish A W, Frazier Z, Liu D, Reznichenko E, Kamburov A, et al. ERCC2 Helicase Domain Mutations Confer Nucleotide Excision Repair Deficiency and Drive Cisplatin Sensitivity in Muscle-Invasive Bladder Cancer. Clin Cancer Res. 2019; 25:977-88.
7. Liu D, Plimack E R, Hoffman-Censits J, Garraway L A, Bellmunt J, Van Allen E, et al. Clinical Validation of Chemotherapy Response Biomarker ERCC2 in Muscle-Invasive Urothelial Bladder Carcinoma. JAMA Oncol. 2016; 2:1094-6.
8. Grivas P. DNA Damage Response Gene Alterations in Urothelial Cancer: Ready for Practice?Clin Cancer Res. 2019; 25:907-9.
9. Plimack E R, Dunbrack R L, Brennan T A, Andrake M D, Zhou Y, Serebriiskii I G, et al. Defects in DNA Repair Genes Predict Response to Neoadjuvant Cisplatin-based Chemotherapy in Muscle-invasive Bladder Cancer. Eur Urol. 2015; 68:959-67.
10. Teo M Y, Bambury R M, Zabor E C, Jordan E, Al-Ahmadie H, Boyd M E, et al. DNA Damage Response and Repair Gene Alterations Are Associated with Improved Survival in Patients with Platinum-Treated Advanced Urothelial Carcinoma. Clin Cancer Res. 2017; 23:3610-8.
11. Hussain S A, James N D. The systemic treatment of advanced and metastatic bladder cancer. Lancet Oncol. 2003; 4:489-97.
12. Sonpavde G, Watson D, Tourtellott M, Cowey C L, Hellerstedt B, Hutson T E, et al. Administration of cisplatin-based chemotherapy for advanced urothelial carcinoma in the community. Clin Genitourin Cancer. 2012; 10:1-5.
13. Perez-Gracia J L, Loriot Y, Rosenberg J E, Powles T, Necchi A, Hussain S A, et al. Atezolizumab in Platinum-treated Locally Advanced or Metastatic Urothelial Carcinoma: Outcomes by Prior Number of Regimens. Eur Urol. 2018; 73:462-8.
14. MacDonald J R, Muscoplat C C, Dexter D L, Mangold G L, Chen S F, Kelner M J, et al. Preclinical antitumor activity of 6-hydroxymethylacylfulvene, a semisynthetic derivative of the mushroom toxin illudin S. Cancer Res. 1997; 57:279-83.
15. Jaspers N G J, Raams A, Kelner M J, Ng J M Y, Yamashita Y M, Takeda S, et al. Anti-tumor compounds illudin S and Irofulven induce DNA lesions ignored by global repair and exclusively processed by transcription- and replication-coupled repair pathways. DNA Repair (Amst). 2002; 1:1027-38.
16. Koeppel F, Poindessous V, Lazar V, Raymond E, Sarasin A, Larsen A K. Irofulven cytotoxicity depends on transcription-coupled nucleotide excision repair and is correlated with XPG expression in solid tumor cells. Clin Cancer Res. 2004; 10:5604-13.
17. Seiden M V, Gordon A N, Bodurka D C, Matulonis U A, Penson R T, Reed E, et al. A phase II study of irofulven in women with recurrent and heavily pre-treated ovarian cancer. Gynecol Oncol. 2006; 101:55-61.
18. Schilder R J, Blessing J A, Shahin M S, Miller D S, Tewari K S, Muller C Y, et al. A phase 2 evaluation of irofulven as second-line treatment of recurrent or persistent intermediately platinum-sensitive ovarian or primary peritoneal cancer: a Gynecologic Oncology Group trial. Int J Gynecol Cancer. 2010; 20:1137-41.
19. Senzer N, Arsenau J, Richards D, Berman B, MacDonald J R, Smith S. Irofulven demonstrates clinical activity against metastatic hormone-refractory prostate cancer in a phase 2 single-agent trial. Am J Clin Oncol. 2005; 28:36-42.
20. Yeo W, Boyer M, Chung H C, Ong S Y K, Lim R, Zee B, et al. Irofulven as first line therapy in recurrent or metastatic gastric cancer: a phase II multicenter study by the Cancer Therapeutics Research Group (CTRG). Cancer Chemother Pharmacol. 2007; 59:295-300.
21. Alexandrov L B, Nik-Zainal S, Wedge D C, Aparicio S A J R, Behjati S, Biankin A V, et al. Signatures of mutational processes in human cancer. Nature. 2013; 500:415-21.
22. Kim J, Mouw K W, Polak P, Braunstein L Z, Kamburov A, Kwiatkowski D J, et al. Somatic ERCC2 mutations are associated with a distinct genomic signature in urothelial tumors. Nat Genet. 2016; 48:600-6.
23. Moore K N, Secord A A, Geller M A, Miller D S, Cloven N, Fleming G F, et al. Niraparib monotherapy for late-line treatment of ovarian cancer (QUADRA): a multicentre, open-label, single-arm, phase 2 trial. Lancet Oncol. 2019; 20:636-48.
24. Zhao E Y, Shen Y, Pleasance E, Kasaian K, Leelakumari S, Jones M, et al. Homologous Recombination Deficiency and Platinum-Based Therapy Outcomes in Advanced Breast Cancer. Clin Cancer Res. 2017; 23:7521-30.
25. Ray-Coquard I, Pautier P, Pignata S, Pérol D, Gonzalez-Martin A, Berger R, et al. Olaparib plus Bevacizumab as First-Line Maintenance in Ovarian Cancer. N Engl J Med. 2019; 381:2416-28.

26. Davies H, Glodzik D, Morganella S, Yates L R, Staaf J, Zou X, et al. HRDetect is a predictor of BRCA1 and BRCA2 deficiency based on mutational signatures. Nat Med. 2017; 23:517-25.

27. Favero F, Joshi T, Marquard A M, Birkbak N J, Krzystanek M, Li Q, et al. Sequenza: allele-specific copy number and mutation profiles from tumor sequencing data. Ann Oncol. 2015; 26:64-70.

28. Li Q, Wang K. InterVar: Clinical Interpretation of Genetic Variants by the 2015 ACMG-AMP Guidelines. Am J Hum Genet. 2017; 100:267-80.

29. Rosenthal R, McGranahan N, Herrero J, Taylor B S, Swanton C. DeconstructSigs: delineating mutational processes in single tumors distinguishes DNA repair deficiencies and patterns of carcinoma evolution. Genome Biol. 2016; 17:31.

30. Boot A, Huang M N, Ng A W T, Ho S-C, Lim J Q, Kawakami Y, et al. In-depth characterization of the cisplatin mutational signature in human cell lines and in esophageal and liver tumors. Genome Res. 2018; 28:654-65.

31. Alexandrov L B, Kim J, Haradhvala N J, Huang M N, Tian Ng A W, Wu Y, et al. The repertoire of mutational signatures in human cancer. Nature. 2020; 578:94-101.

32. Nik-Zainal S, Davies H, Staaf J, Ramakrishna M, Glodzik D, Zou X, et al. Landscape of somatic mutations in 560 breast cancer whole-genome sequences. Nature. 2016; 534:47-54.

33. Blokzijl F, Janssen R, van Boxtel R, Cuppen E. MutationalPatterns: comprehensive genome-wide analysis of mutational processes. Genome Med. 2018; 10:33.

34. Haradhvala N J, Polak P, Stojanov P, Covington K R, Shinbrot E, Hess J M, et al. Mutational Strand Asymmetries in Cancer Genomes Reveal Mechanisms of DNA Damage and Repair. Cell. 2016; 164:538-49.

35. Rajkumar-Calkins A S, Szalat R, Dreze M, Khan I, Frazier Z, Reznichenkov E, et al. Functional profiling of nucleotide Excision repair in breast cancer. DNA Repair (Amst). 2019; 82:102697.

36. Pipek O, Ribli D, Molnár J, Póti Á, Krzystanek M, Bodor A, et al. Fast and accurate mutation detection in whole genome sequences of multiple isogenic samples with IsoMut. BMC Bioinformatics. 2017; 18:73.

37. Ceccaldi R, O'Connor K W, Mouw K W, Li A Y, Matulonis U A, D'Andrea A D, et al. A unique subset of epithelial ovarian cancers with platinum sensitivity and PARP inhibitor resistance. Cancer Res. 2015; 75:628-34.

38. Dreze M, Calkins A S, Gálicza J, Echelman D J, Schnorenberg M R, Fell G L, et al. Monitoring repair of UV-induced 6-4-photoproducts with a purified DDB2 protein complex. PLoS ONE. 2014; 9:e85896.

39. Tufegdzic Vidakovic A, Harreman M, Dirac-Svejstrup A B, Boeing S, Roy A, Encheva V, et al. Analysis of RNA polymerase II ubiquitylation and proteasomal degradation. Methods. 2019; 159-160:146-56.

40. Norquist B, Wurz K A, Pennil C C, Garcia R, Gross J, Sakai W, et al. Secondary somatic mutations restoring BRCA1/2 predict chemotherapy resistance in hereditary ovarian carcinomas. J Clin Oncol. 2011; 29:3008-15.

41. Cancer Genome Atlas Research Network. Comprehensive molecular characterization of urothelial bladder carcinoma. Nature. 2014; 507:315-22.

42. Guo G, Sun X, Chen C, Wu S, Huang P, Li Z, et al. Whole-genome and whole-exome sequencing of bladder cancer identifies frequent alterations in genes involved in sister chromatid cohesion and segregation. Nat Genet. 2013; 45:1459-63.

43. Galsky M D, Hahn N M, Rosenberg J, Sonpavde G, Hutson T, Oh W K, et al. Treatment of patients with metastatic urothelial cancer "unfit" for Cisplatin-based chemotherapy. J Clin Oncol. 2011; 29:2432-8.

44. Xu G, Chapman J R, Brandsma I, Yuan J, Mistrik M, Bouwman P, et al. REV7 counteracts DNA double-strand break resection and affects PARP inhibition. Nature. 2015; 521:541-4.

45. Staaf J, Glodzik D, Bosch A, Vallon-Christersson J, Reuterswird C, Hikkinen J, et al. Whole-genome sequencing of triple-negative breast cancers in a population-based clinical study. Nat Med. 2019; 25:1526-33.

Reference List 3: Corresponding to Examples 6-8

1. Alexandrov L B et al. The repertoire of mutational signatures in human cancer.

2. Alexandrov L B et al. Signatures of mutational processes in human cancer. Nature, 500(7463), 2013.

3. Alexandrov L B et al. Mutational signatures associated with tobacco smoking in human cancer. Science, 2016.

4. Blokzijl F et al. Mutationalpatterns: comprehensive genome-wide analysis of mutational processes. Genome Medicine, 10(1), 2018.

5. Bolger A M et al. Trimmomatic: a flexible trimmer for illumina sequence data. Bioinformatics, 30(15):2114-2120, 2014.

6. Bonneville R et al. Landscape of microsatellite instability across 39 cancer types. JCO Precision Oncology, 2017.

7. Boot A et al. In-depth characterization of the cisplatin mutational signature in human cell lines and in esophageal and liver tumors. Genome Research, 2018.

8. Chawla N V et al. Smote: Synthetic minority oversampling technique. Journal of Artificial Intelligence Re-search, 16:321-357, 2002.

9. Cibulskis K et al. Sensitive detection of somatic point mutations in impure and heterogeneous cancer samples. Nature Biotechnology, 31(3):213-219, 2013.

10. Costello M et al. Discovery and characterization of artifactual mutations in deep coverage targeted capture sequencing data due to oxidative dna damage during sample preparation. Nucleic Acids Research, 41(6), 2013.

11. Davies H et al. Hrdetect is a predictor of brca1 and brca2 deficiency based on mutational signatures. Nature Medicine, 23(4), 2017.

12. DePristo M A et al. A framework for variation discovery and genotyping using next-generation dna sequencing data. Nature Genetics, 43(5):491-498, 2011.

13. Favero F et al. Sequenza: allele-specific copy number and mutation profiles from tumor sequencing data.

14. Annals of Oncology, 26(1):64-70, 10 2015.

15. Freedman N D et al. Association between smoking and risk of bladder cancer among men and women.

16. JAMA, 306(7):737-45, 2011.

17. Guo G et al. Whole-genome and whole-exome sequencing of bladder cancer identifies frequent alterations in genes involved in sister chromatid cohesion and segregation. Nature Genetics, 45(12):1459-63, 2013.

18. Haradhvala N J et al. Mutational strand asymmetries in cancer genomes reveal mechanisms of dna damage and repair. Cell, 164(3):538-549, 2016.

19. Li H et al. The sequence alignment/map format and samtools. Bioinformatics, 25(16):2078-2079, 2009.

20. Li Q et al. Intervar: Clinical interpretation of genetic variants by the 2015 acmg-amp guidelines. American Journal of Human Genetics, 100(2):267-280, 2017.

21. Li Q et al. Ercc2 helicase domain mutations confer nucleotide excision repair deficiency and drive cisplatin sensitivity in muscle-invasive bladder cancer. Clinical Cancer Research, 25(3):977-988, 2018.

22. Liu D et al. Clinical validation of chemotherapy response biomarker ercc2 in muscle-invasive urothelial bladder carcinoma. JAMA Oncology, 2(8):1094-1096, 2016.

23. Nik-Zainal S et al. Landscape of somatic mutations in 560 breast cancer whole-genome sequences. Nature, 534(7605):47-54, 2016.

24. Pipek O et al. Fast and accurate mutation detection in whole genome sequences of multiple isogenic samples with isomut. BMC Bioinformatics, 18(1), 2017.

25. Poon S L et al. Genome-wide mutational signatures of aristolochic acid and its application as a screening tool. Science Translational Medicine, 2013.

26. Rajkumar-Calkins A S et al. Functional profiling of nucleotide excision repair in breast cancer. DNA Repair, 82, 2019.

27. Rosenthal R et al. deconstructsigs: delineating mutational processes in single tumors distinguishes dna repair deficiencies and patterns of carcinoma evolution. Genome Biology, 17(1), 2016.

28. Tarasov A et al. Sambamba: fast processing of ngs alignment formats. Bioinformatics, 31(12):2032-2034, 2015.

29. Van Allen E M et al. Somatic ercc2 mutations correlate with cisplatin sensitivity in muscle-invasive urothe-lial carcinoma. Cancer Discovery, 4(10):1140-53, 2014.

30. Zerbino D R et al. Velvet: algorithms for de novo short read assembly using de bruijn graphs. Genome Research, 18(5), 2008.

31. Li H. Aligning sequence reads, clone sequences and assembly contigs with bwa-mem. 2013.

32. Myrthe Jager, Francis Blokzijl, Ewart Kuijk, Johanna Bertl, Maria Vougioukalaki, Roel Janssen, Nicolle Besselink, Sander Boymans, Joep de Ligt, Jakob Skou Pedersen, Jan Hoeijmakers, Joris Pothof, Ruben van Boxtel, and Edwin Cuppen. Deficiency of nucleotide excision repair is associated with mutational signature observed in cancer. Genome Research, 29(7), 2019.

33. Tibshirani R. Regression shrinkage and selection via the lasso. Journal of the Royal Statistical Society. Series B (Methodological), 58(1):267-288, 1996.

34. Andrews S. Fastqc: a quality control tool for high throughput sequence data. available on the world wide web at bioinformatics.babraham.ac.uk/projects/fastqc, 2010.

35. Cleveland W S. Robust locally weighted regression and smoothing scatterplots. Journal of the American Statistical Association, 74(368):829-836, 1979.

36. Taber, A.; Christensen, E.; Lamy, P.; Nordentoft, I.; Prip, F.; Lindskrog, S. V.; Birkenkamp-Demtröder, K.; Okholm, T. L. H.; Knudsen, M.; Pedersen, J. S.; Steiniche, T.; AgerbØk, M.; Jensen, J. B. & Dyrskjøt, L. Molecular correlates of cisplatin-based chemotherapy response in muscle invasive bladder cancer by integrated multi-omics analysis. Nature communications, 2020, 11, 4858.

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating cancer in a subject, the method comprising:

administering an anti-cancer treatment to a subject in need thereof, wherein the subject has a nucleotide excision repair (NER) deficiency score (NERDetect score) of at least 0.70 and the anti-cancer treatment comprises an alkylating chemotherapeutic agent, and wherein the NERDetect score is a summation by logistic regression of one or more of the following mutational features of NER deficiency:

i. the number of mutations associated with a signature of insertions and deletions;

ii. the number of deletions (1-50 bp);

iii. the number of mutations associated with a signature of single base substitutions (SBS;

iv. the number of mutations associated with a signature of doublet base substitutions (DBS); and v. the ratio of the number of base substitution on the transcribed and untranscribed strand.

2. The method of claim 1, wherein the alkylating chemotherapeutic agent is a platinum-based chemotherapeutic agent.

3. The method of claim 2, wherein the platinum-based chemotherapeutic agent selected from the group consisting of cisplatin, carboplatin, dicycloplatin, eptaplatin, iproplatin, lobaplatin, miriplatin, nedaplatin, oxaliplatin, phenanthriplatin, picoplatin, satraplatin, and triplatin teranitrate.

4. The method of claim 3, wherein the platinum-based chemotherapeutic agent is cisplatin.

5. The method of claim 1, wherein the alkylating chemotherapeutic agent is selected from the group consisting of busulfan, carboplatin, carboquone, carmustine (BCNU), chlorambucil, cyclophosphamide, dacarbazine (DTIC; dimethyltriazenoimid-azolecarboxamide), hexamethylmelamine, ifosfamide, irofulven, lomustine, mechlorethamine, melphalan (L-sarcolysin), mitobronitol, nimustine, procarbazine, ranimustine, streptozocin (streptozotocin), temozolomide, thiotepa, and trofosfamide.

6. The method of claim 4, wherein the alkylating chemotherapeutic agent is irofulven.

7. The method of claim 1, wherein the cancer is selected from the group consisting of bladder cancer, breast cancer, lung cancer, ovarian cancer, thyroid cancer, pancreatic cancer, prostate cancer, uterine cancer, testicular cancer, gastric cancer, soft tissue and osteogenic sarcomas, neuroblastoma, Wim's tumor, malignant lymphoma (Hodgkin's and non-Hodgkin's lymphoma), acute myeloblastic leukemia (AMIL), acute lymphoblastic leukemia (ALL), Kaposi's sarcoma, Ewing's tumor, refractory multiple myeloma, colon cancer, and squamous cell carcinomas of the head, neck, cervix, melanoma, and vagina.

8. The method of claim 1, wherein the subject is a mammal.

9. The method of claim 1, wherein the subject is human.

10. The method of claim 1, wherein the method further comprises administering an additional anti-cancer treatment.

11. The method of claim 1, wherein the subject has previously received an anti-cancer treatment.

12. The method of claim 1, wherein the subject has not previously received an anti-cancer treatment.

13. The method of claim 1, wherein the method further comprises receiving or obtaining results of an assay indicating the subject has a NERDetect score of at least 0.70.

14. The method of claim 1, wherein the method further comprises assaying a sample from the subject to determine the NERDetect score.

15. The method of claim 14, wherein the sample is selected from the group consisting of: cells, cell lines, histological slides, frozen core biopsies, paraffin embedded tissues, formalin fixed tissues, biopsies, whole blood, nipple aspirate, serum, plasma, buccal scrape, saliva, cerebrospinal fluid, urine, stool, and bone marrow.

16. The method of claim 14, wherein the sample is obtained before the subject has received an anti-cancer treatment.

17. The method of claim 14, wherein the sample is obtained after the subject has received an anti-cancer treatment.

18. The method of claim 14, wherein the assay comprises detecting one or more of an indel signature ID8, an indel signature ID2, an indel signature ID10, a total number of 1-50 base pair deletions, a number of mutations associated with a signature of single base substitutions (SBS) signature 5 (COSIMIC signature 5 or Signature 5*), a number of mutations associated with a signature of single base substitutions signature 2 (SBS2), a number doublet base substitutions (DBS) signature 4 (DBS4), a transcriptional strand bias of one or more mutations, or any combination thereof.

19. The method of claim 14, wherein the assay comprises a step of extracting nucleic acid from the sample.

20. The method of claim 14, wherein the assay comprises one or more of whole genome sequencing, in situ hybridization, single nucleotide polymorphism (SNP) array, transcriptional arrays, array comparative genomic hybridization (aCGH), Southern blotting, molecular inversion probe (IP).

21. A method of selecting a subject for anti-cancer treatment, the method comprising:

determining or obtaining a NERDetect score for the subject and selecting the subject having a NERDetect score of at least 0.70 for anti-cancer treatment, and wherein the NERDetect score is a summation by logistic regression of one or more of the following mutational features of NER deficiency:

i. the number of mutations associated with a signature of insertions and deletions:

ii. the number of deletions (1-50 bp):

iii. the number of mutations associated with a signature of single base substitutions (SBS):

iv. the number of mutations associated with a signature of doublet base substitutions (DBS); and v. the ratio of the number of base substitution on the transcribed and untranscribed strand.

22. A method of predicting a response to anti-cancer treatment in a subject, the method comprising determining or obtaining a NERDetect score for the subject and a NERDetect score of at least 0.70 indicates the subject is responsive to the anti-cancer treatment, and wherein the NERDetect score is a summation by logistic regression of one or more of the following mutational features of NER deficiency:

i. the number of mutations associated with a signature of insertions and deletions;

ii. the number of deletions (1-50 bp):

iii. the number of mutations associated with a signature of single base substitutions (SBS), iv. the number of mutations associated with a signature of doublet base substitutions (DBS); and v. the ratio of the number of base substitution on the transcribed and untranscribed strand.

23. The method of claim 1, wherein the NERDetect score is calculated according to the following formula:

$$p = \frac{1}{1 + e^{-(\beta_0 + \Sigma \beta_i x_i)}}, \qquad \text{(Formula 1)}$$

wherein:

p is the NERDetect score;

$\beta_o$ is the intercept, i is from 1 to the number of mutational features used;

$\beta_i$ is the coefficient of the mutational feature; and $x_i$ is a mutational feature of NER deficiency.

24. The method of claim 1, wherein the NERDetect score is calculated according to the following formula:

$$p = \frac{1}{1 + e^{-(\beta_0 + \beta_1 x_1 + \beta_2 x_2 + \beta_3 x_3 + \beta_4 x_4)}} \qquad \text{(Formula 2)}$$

wherein:

p is the NERDetect score;

$\beta_o$ is the intercept;

$\beta_1$, $\beta_2$, $\beta_3$, and $\beta_4$ are the coefficients of the mutational features associated with NER deficiency; and $x_1$, $x_2$, $x_3$, and $x_4$ are the mutational features of NER deficiency.

* * * * *